(12) United States Patent
Chupak et al.

(10) Patent No.: US 7,462,600 B2
(45) Date of Patent: Dec. 9, 2008

(54) MACROLIDES

(75) Inventors: Louis S. Chupak, Old Saybrook, CT (US); Mark E. Flanagan, Gales Ferry, CT (US); Takushi Kaneko, Guilford, CT (US); Thomas V. Magee, Mystic, CT (US); Mark C. Noe, Mystic, CT (US); Usa Reilly, West Haven, CT (US)

(73) Assignee: Pfizer Inc, New York, NY (US)

( * ) Notice: Subject to any disclaimer, the term of this patent is extended or adjusted under 35 U.S.C. 154(b) by 73 days.

(21) Appl. No.: 11/313,523

(22) Filed: Dec. 21, 2005

(65) Prior Publication Data

US 2006/0135447 A1 Jun. 22, 2006

Related U.S. Application Data

(60) Provisional application No. 60/638,097, filed on Dec. 21, 2004, provisional application No. 60/717,530, filed on Sep. 14, 2005.

(51) Int. Cl.
*A61K 31/70* (2006.01)
*C07H 17/08* (2006.01)

(52) U.S. Cl. .......................................... 514/29; 536/7.4
(58) Field of Classification Search ........................ None
See application file for complete search history.

(56) References Cited

U.S. PATENT DOCUMENTS

| | | | |
|---|---|---|---|
| 2,653,899 A | 9/1953 | Bunch et al. | 167/65 |
| 2,823,203 A | 2/1958 | Clark | 260/210 |
| 4,331,803 A | 5/1982 | Watanabe et al. | 536/7.2 |
| 4,474,768 A | 10/1984 | Bright | 424/180 |
| 4,517,359 A | 5/1985 | Kobrehel et al. | 536/7.4 |
| 4,742,049 A | 5/1988 | Baker et al. | 514/29 |
| 5,075,289 A | 12/1991 | Pariza et al. | 514/29 |
| 5,523,399 A | 6/1996 | Asaka et al. | 536/7.3 |
| 5,527,780 A | 6/1996 | Agouridas et al. | 514/29 |
| 5,543,400 A | 8/1996 | Agouridas et al. | 514/29 |
| 5,614,614 A | 3/1997 | Agouridas et al. | 536/7.5 |
| 5,635,485 A | 6/1997 | Agouridas et al. | 514/29 |
| 5,747,466 A | 5/1998 | Elliott et al. | 514/29 |
| 5,747,467 A | 5/1998 | Agouridas et al. | 514/29 |
| 5,750,510 A | 5/1998 | Elliott et al. | 514/29 |
| 5,786,339 A | 7/1998 | Agouridas et al. | 519/30 |
| 5,804,565 A | 9/1998 | Asaka et al. | 514/29 |
| 5,955,440 A | 9/1999 | Sauer et al. | 514/29 |
| 6,020,521 A | 2/2000 | Randolph et al. | 560/205 |
| 6,022,965 A | 2/2000 | Benedetti et al. | 536/125 |
| 6,025,350 A | 2/2000 | Masamune et al. | 514/183 |
| 6,034,069 A | 3/2000 | Or et al. | 514/29 |
| 6,043,226 A | 3/2000 | Lundy et al. | 514/29 |
| 6,054,435 A | 4/2000 | Or et al. | 514/29 |
| 6,075,011 A | 6/2000 | Or et al. | 514/29 |
| 6,075,133 A | 6/2000 | Or et al. | 536/7.2 |
| 6,140,479 A | 10/2000 | Asaka et al. | 536/7.2 |
| 6,159,945 A | 12/2000 | Wu | 514/29 |
| 6,162,793 A | 12/2000 | Agouridas et al. | 514/29 |
| 6,162,794 A | 12/2000 | Wu | 514/29 |
| 6,191,118 B1 | 2/2001 | Asaka et al. | 514/29 |
| 6,248,719 B1 | 6/2001 | Wu | 514/29 |
| 6,262,030 B1 | 7/2001 | Wu et al. | 514/29 |
| 6,291,656 B1 | 9/2001 | Wu | 536/7.4 |
| 6,300,316 B1 | 10/2001 | Brighty et al. | 514/29 |
| 6,355,620 B1 | 3/2002 | Ma et al. | 514/29 |
| 6,387,885 B1 | 5/2002 | Dalton et al. | 514/29 |
| 6,399,582 B1 | 6/2002 | Hlasta et al. | 514/29 |
| 6,433,151 B1 | 8/2002 | Denis et al. | 536/7.2 |
| 6,437,151 B2 | 8/2002 | Leadlay et al. | 549/271 |
| 6,458,771 B1 * | 10/2002 | Hlasta et al. | 514/29 |
| 6,472,371 B1 | 10/2002 | Dirlam et al. | 514/29 |
| 6,555,524 B2 | 4/2003 | Kaneko et al. | 514/29 |
| 6,569,836 B2 | 5/2003 | Phan et al. | 514/29 |
| 6,593,302 B2 | 7/2003 | Chu et al. | 514/29 |
| 6,664,238 B1 | 12/2003 | Su et al. | 514/29 |
| 6,756,359 B2 | 6/2004 | Chu et al. | 514/29 |
| 6,777,543 B2 | 8/2004 | Wu et al. | 536/7.4 |
| 6,825,171 B2 | 11/2004 | Wu | 514/29 |
| 6,833,444 B2 | 12/2004 | McMillen et al. | 536/7.4 |
| 6,835,716 B2 | 12/2004 | Kaneko | 514/29 |

(Continued)

FOREIGN PATENT DOCUMENTS

EP 0420237 6/1996

(Continued)

OTHER PUBLICATIONS

Dutch Search report in Appln. No. 1030713.

(Continued)

*Primary Examiner*—Elli Peselev
(74) *Attorney, Agent, or Firm*—Steve T. Zelson; Jason G. Tebbutt

(57) ABSTRACT

Macrolide compounds per se, as shown below and defined herein, and their use, e.g., as antibacterial and antiprotozoal agents in animals, including humans:

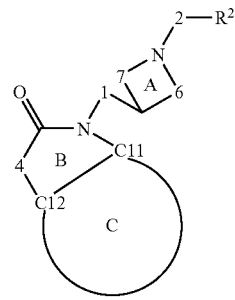

Also disclosed are methods of preparing the compounds, intermediates, and pharmaceutical compositions thereof, and methods of treating or preventing disease by administering the compounds to subjects in need. This abstract is only an excerpt and is not limiting of the invention.

30 Claims, No Drawings

U.S. PATENT DOCUMENTS

| | | | |
|---|---|---|---|
| 7,071,170 B2 | 7/2006 | Kaneko | 514/29 |
| 2002/0052328 A1 | 5/2002 | Kaneko et al. | 514/29 |
| 2002/0061856 A1 | 5/2002 | Wu | 514/29 |
| 2002/0061857 A1 | 5/2002 | Wu | 514/29 |
| 2002/0077302 A1 | 6/2002 | Wu | 514/29 |
| 2002/0115621 A1 | 8/2002 | Su et al. | 514/29 |
| 2002/0132782 A1 | 9/2002 | Ma et al. | 514/29 |
| 2002/0151507 A1 | 10/2002 | Wu | 514/29 |
| 2002/0156027 A1 | 10/2002 | McMillen et al. | 514/29 |
| 2003/0013665 A1 | 1/2003 | Kaneko | 514/29 |
| 2003/0100518 A1 | 5/2003 | Wu et al. | 514/29 |
| 2003/0100742 A1 | 5/2003 | Kaneko et al. | 536/7.4 |
| 2003/0199458 A1 | 10/2003 | Ashley et al. | 514/29 |
| 2004/0077557 A1 | 4/2004 | Ali et al. | 514/28 |
| 2004/0157787 A1 | 8/2004 | Or et al. | 514/28 |
| 2004/0171818 A1 | 9/2004 | Xu et al. | 536/7.4 |
| 2006/0142214 A1 | 6/2006 | Or et al. | 514/28 |
| 2006/0142215 A1 | 6/2006 | Tang et al. | 514/28 |
| 2006/0148731 A1 | 7/2006 | Tang et al. | 514/28 |

FOREIGN PATENT DOCUMENTS

| | | |
|---|---|---|
| EP | 1114826 | 7/2001 |
| EP | 1122261 | 8/2001 |
| WO | WO 9911651 | 3/1999 |
| WO | WO 9921869 | 5/1999 |
| WO | WO 2004094407 | 11/2004 |
| WO | WO 2006046112 | 5/2006 |
| WO | WO 2006050940 | 5/2006 |
| WO | WO 2006080954 | 8/2006 |

OTHER PUBLICATIONS

English translation of Dutch Search Report in Appln. No. 1030713.
Patent Abstracts of Japan, Publication No. 2001-072669, date of publication Mar. 21, 2001.
PCT Written Opinion for International Application No. PCT/IB2005/003829; Family member of U.S. Appl. No. 11/313,523.
PCT International Search Report for International Application No. PCT/IB2005/003829; Family member of U.S. Appl. No. 11/313,523.
Baker, W. R., et al., Modification of Macrolide Antibiotics. Synthesis of 11-Deoxy-11-(carboxyamino)-6-O-methylerythromycin A 11,12-(cyclic esters) via an Intramolecular Michael Reaction of O-Carbamates with an α,β-Unsaturated Ketone, *J. Org. Chem.*, vol. 53, pp. 2340-2345, (1988).
Cappelli, A., et al., Novel Potent 5-HT$_3$ Receptor Ligands Based on the Pyrrolidone Structure: Synthesis, Biological Evaluation, and Computational Rationalization of the Ligand-Receptor Interaction Modalities, *Bioorganic & Medicinal Chemsitry*, vol. 10, pp. 779-801, (2002).
Frigola, J., et al., 7-Azetidinylquinolones as Antibacterial Agents. Synthesis and Structure-Activity Relationships, *J. Med. Chem.*, vol. 36, pp. 801-810, (1993).
Grignon-Dubois, M, et al., Synthase de Trimethylsilyl Quinoleines, *Bull. Soc. Pharm. Bordeaux*, vol. 127, pp. 29-36 (1988).
Hamada, Y., et al., Syntheses of Nitrogen-containing Compounds: XVII. Improvement of One-Step Synthesis of Naphthyridine Derivatives and Their Methylation with Dimethyl Sulfoxide in the Presence of Base, *Chemical & Pharmaceutical Bulletin*, vol. 19, No. 9, pp. 1751-1755, (1971).
Kirst, H. A., et al., Synthesis an Structure-Activity Relationships of New 9-N-Alkyl Derivatives of 9(S)-Erythormycylamine, *J. Med. Chem.*, vol. 33, pp. 3086-3094, (1990).
Ma, Z., et al., Discovery and Development of Ketolides as a New Generation of Macrolide Antimicrobial Agents, *Current Medicinal Chemistry*, vol. 1, pp. 15-34, (2002).
Stelzer, U., et al., Preparation of (S)-2-Fluoronitriles, *Tetrahedron: Asymmetry*, vol. 4, No. 2, pp. 161-164, (1993).
Tanikawa, T., et al., Synthesis and Antibacterial Activity of a Novel Series of Acylides: 3-O-(3-Pyridyl)acetylerythromycin A Derivatives, *J. Med. Chem.*, vol. 46, pp. 2706-2715, (2003).
Wu, Y., et al., Recent Developments on Ketolides and Macrolides, *Current Medicinal Chemistry*, vol. 8, pp. 1727-1758, (2001).
Zou, X., et al., Syntheses of 4-methoxymethylbenzyl permethrinates containing fluorine and their insecticidal activity, *J. Fluorine Chemistry*, vol. 116, pp. 173-179, (2002).

* cited by examiner

MACROLIDES

This application claims priority of Appln. Nos. 60/638,097 (21 Dec. 2004) and 60/717,530 (14 Sep. 2005), both of which are incorporated herein in their entireties.

FIELD AND BACKGROUND

This invention relates to macrolide compounds and their use, e.g., as antibacterial and antiprotozoal agents in animals, including humans. The invention also relates to methods of preparing compounds, intermediates useful in preparing compounds, and pharmaceutical compositions containing compounds. The present invention further includes methods of treating and/or preventing disease, e.g., bacterial and/or protozoal infections (or for other indications, e.g., cancer, inflammation, atherosclerosis, or gastric motility reduction), by administering compounds or compositions to subjects in need of such treatment.

Erythromycin and clarithromycin are well known macrolides. Other erythromycin-based macrolide compounds have been prepared, e.g., by introducing modifications at various positions of erythromycin or clarithromycin, e.g., as in: U.S. Pat. Nos. 4,331,803; 4,474,768; 4,517,359; 5,523,399; 5,527,780; 5,635,485; 5,804,565; 6,020,521; 6,025,350; 6,075,133; 6,162,794; 6,191,118; 6,248,719; 6,291,656; 6,437,151; 6,472,371; 6,555,524; US 2002/0052328; US 2002/0061856; US 2002/0061857; US 2002/0077302; US 2002/0151507; US 2002/0156027; US 2003/0100518; US 2003/0100742; US 2003/0199458; US 2004/0077557; WO 99/11651; WO 99/21866; WO 99/21869; WO 99/35157; EP 1 114 826; and *J. Med. Chem.*, 46, 2706 (2003). Additional relevant publications are cited hereinbelow. These and all documents cited herein are fully incorporated by reference herein for all purposes, including for the teachings, modifications, and method(s) of modifying the subject positions on macrolide rings in various combinations. Thus, derivatives can include, e.g., modifications at the C-2, C-3, C-6, C-9, C-10, C-11, C-12, and C-13 erythromycin positions, etc., and corresponding azalide derivatives.

There is a desire for new macrolides in response to the increasing emergence of resistant organisms, to improve safety, and to improve activity spectrum, among other reasons.

SUMMARY OF THE INVENTION

The present invention relates to certain macrolide compounds per se, their preparation and useful intermediates, pharmaceutical compositions thereof, and methods of treating and preventing, e.g., infections therewith. In many embodiments, the compounds are active and effective against organisms that are resistant to other antibiotics, including other macrolides.

The present invention includes the compounds of the general formula:

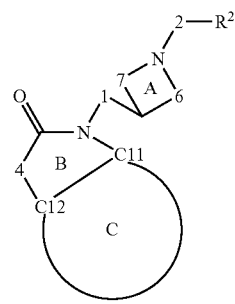

wherein C11 and C12 represent carbons at positions C-11 and C-12 of erythromycin-based macrolide Ring C by conventional macrolide numbering, and the other variables shown are defined herein; their preparation and intermediates; compositions; and use thereof to treat, e.g., bacterial infection. The structure of Ring C is not limited. Group 2-$R^2$ is a "headpiece" attached to Ring A.

In some aspects, the present invention more specifically relates to the compounds of Formula I:

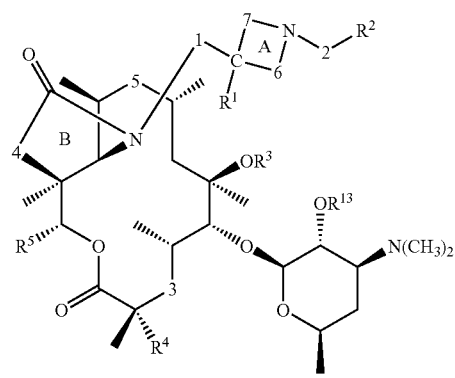

I wherein diradical 1 can be absent (absent meaning that Ring A is directly attached to Ring B by a single covalent bond), >$CH_2$, >$C(CH_3)H$, or other alkyl or substituted alkyl diradical (the ">" symbol indicating single bonds to Rings A and B; —$CH_2$— has the same meaning as >$CH_2$).

Diradical 2 can be —$C(O)(CH_2)_m$—, —$S(O)_2(CH_2)_m$—, —$SO_2N(R^6)$—, —$C(O)O(CHR^{20})_m$—, —$(C(R^6)(R^7))_m$—, or —$C(O)N(R^6)$—, wherein m is an integer from 0 to 3.

Diradical 3 represents carbon C-3 of the macrolide ring, directly bonded to C-2 and C-4, and which can be substituted, e.g., diradical 3 can be >C(O), (>CH(OC(O)$R^{14}$) the ">" symbol indicating single bonds to C-2 and C-4, meaning that C-3 is substituted by —OC(O)$R^4$), >CH(OC(O)N($R^{14}$)$R^{15}$), >CH(OC(O)O$R^{14}$), >CH(OC(O)CH(N($R^{14}$)$R^{15}$)(C$R^aR^b$)$_n$Ar), >CH(OC(O)CH(N($R^{14}$)$R^{15}$)$R^{14}$), >CH(OC(O)C(=NO$R^{14}$)(C$R^aR^b$)$_n$—Ar), >CH(OC(O)C(=NO$R^{14}$)$R^{14}$), >CH(OC(O)(C$R^aR^b$)$_n$Ar), >CH(OC(O)(C$R^aR^b$)$_n$N($R^{14}$)(C$R^aR^b$)$_n$Ar), or:

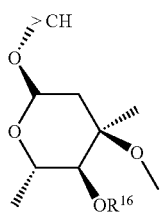

wherein n is an integer from 0 to 5.

Diradical 4 can be >O or >N($R^{10}$), preferably with the proviso that when diradical 3 is not >C(O), diradical 4 is >O.

Diradical 5, which is bonded to C-8 and C-10 of the macrolide ring and can be substituted, can be >C(O), —C(O)NH—, —N(H)C(O)—, >CH(N($R^8$)$R^9$), >C(=NC(O)$R^{19}$), or >C(=NO$R^{19}$). As an addition to this group, diradical 5 can also be >C(=N$R^{17}$).

Diradical 6 can be —(C($R^c$)($R^d$))$_x$—, wherein x is an integer from 0 to 5; diradical 7 can be —(C($R^c$)($R^e$))$_y$—, wherein y is an integer from 0 to 5; preferably with the proviso that the sum of x+y in 6 and 7 is from 1 to 5.

Group $R^1$ can be H, OH, halo (e.g., F, Cl, Br), or ($C_1$-$C_6$) alkyl, preferably with the proviso that when 1 is absent, $R^1$ is H.

Group $R^2$ can be H or Ar. In some embodiments, $R^2$ or 2-$R^2$ is a protecting group, e.g., H, Bn, Bzh, CBZ, benzyloxymethyl, or BOC, or any other suitable group.

Group $R^3$ can be ($C_1$-$C_6$)alkyl, ($C_2$-$C_6$)alkenyl, or ($C_2$-$C_6$) alkynyl, any of which can be substituted, e.g., by Ar.

Group $R^4$ can be H or halo (e.g., F, Cl, Br, preferably F), preferably with the proviso that when diradical 3 is not >C(O), $R^4$ is H.

Groups $R^5$ and $R^{20}$ can independently be ($C_1$-$C_6$)alkyl, which can be substituted, e.g., by 1 to 3 of the Group S substituents.

Each $R^6$ and $R^7$ can be independently H, ($C_1$-$C_{12}$)alkyl, ($C_2$-$C_{12}$)alkenyl, or 4-6 membered heterocyclic; wherein any of which, except H, can be substituted, e.g., by 1 to 3 of the Group S substituents; and independently wherein said ($C_1$-$C_{12}$)alkyl and ($C_2$-$C_{12}$)alkenyl can have 1 to 2 carbons independently replaced by, e.g., Group T diradicals; and independently up to one $R^6$/$R^7$ pair, together with the carbon to which they are attached, can form a 3 to 8 membered (preferably carbocyclic) ring; preferably with the proviso that no more than a total of two of the $R^6$ and $R^7$ groups are other than H.

Each $R^8$ and $R^9$ can be independently H, ($C_1$-$C_6$)alkyl, —C(O)($C_1$-$C_6$)alkyl, —S($O_2$)($C_1$-$C_6$)alkyl, any of which, except H, can be substituted, e.g., by 1 to 3 of the Group S substituents. Preferably, and especially when $R^8$ is —C(O)($C_1$-$C_6$)alkyl or —S($O_2$)($C_1$-$C_6$)alkyl, $R^9$ is H or ($C_1$-$C_6$)alkyl which, except H, can be substituted, e.g., by 1 to 3 of the Group S substituents.

Group $R^{10}$ can be H or ($C_1$-$C_6$)alkyl, which can be substituted, e.g., by 1 to 3 of the Group S substituents.

Each $R^{11}$ and $R^{12}$ is independently (a) or (b), wherein (a) is H, ($C_1$-$C_{12}$)alkyl, ($C_2$-$C_{12}$)alkenyl, ($C_2$-$C_{12}$)alkynyl, any of which, except H, can have one carbon replaced by, e.g., —NH—, —N(CH$_3$)—, —N(4-10 membered heterocyclic), —N(4-10 membered carbocyclic), —O—, —S—, —S(O)—, or —S(O)$_2$—, wherein the foregoing $R^{11}$ and $R^{12}$, together with the atom to which they are attached, can form a 3 to 8 membered ring; (b) is 9-10 membered heterocyclic, 9-10 membered carbocyclic, 4-6 membered heterocyclic, or 4-6 membered carbocyclic, wherein any of (a) or (b), except H, can be substituted by, e.g., 1 to 3 of: F, Cl, OH, ($C_1$-$C_3$) alkoxy, ($C_1$-$C_3$)alkoxy-($C_1$-$C_3$)alkoxy, oxo, ($C_1$-$C_3$)alkyl, halo-substituted ($C_1$-$C_3$)alkyl, or ($C_1$-$C_3$)alkoxy-($C_1$-$C_3$) alkyl.

Groups $R^{13}$ and $R^{16}$ can be independently H, —C(O)($C_1$-$C_6$ alkyl) which can be substituted, —C(O)Ar, —Si(phenyl)($C_1$-$C_6$ alkyl)$_2$, —Si($C_1$-$C_6$ alkyl)$_3$, or other protecting groups.

Each $R^{14}$ and $R^{15}$ can be independently H or ($C_1$-$C_{10}$)alkyl; which alkyl can be substituted, e.g., by 1 to 3 of the Group S substituents; and independently wherein 1 to 2 carbons of the alkyl can be replaced, e.g., by Group T diradicals; and independently wherein each $R^{14}$/$R^{15}$ pair can, together with the atom to which they are attached, form a 3 to 8 membered ring.

Group $R^{17}$ can be O$R^{19}$, —C(O)($C_1$-$C_6$ alkyl), or —C(O) (4-10 membered carbo- or heterocyclic), either of which can be substituted, e.g., by 1 to 3 of the Group S substituents.

Group $R^{19}$ can be H, ($C_1$-$C_6$)alkyl, —($C_1$-$C_6$ alkyl)-(4-10 membered carbo- or heterocyclic), or (4-10 membered carbo- or heterocyclic); any of which groups, except H, can be substituted, e.g., by 1 to 3 of the Group S substituents (or by F, Cl, OH, ($C_1$-$C_3$)alkoxy, ($C_1$-$C_3$)alkoxy-($C_1$-$C_3$)alkoxy, oxo, ($C_1$-$C_3$)alkyl, halo-substituted ($C_1$-$C_3$)alkyl, or ($C_1$-$C_3$)alkoxy-($C_1$-$C_3$)alkyl); independently up to 1 carbon of which groups can be replaced, e.g., by Group T diradicals (or by —NH—, —N(CH$_3$)—, —N(4-10 membered carbo- or heterocyclic), —O—, —S—, —S(O)—, or —S(O)$_2$—).

Each $R^a$ and $R^b$ can be independently H or ($C_1$-$C_6$)alkyl, which alkyl can be substituted, e.g., by 1 to 3 of the Group S substituents; and wherein 1 to 2 carbons of the alkyl can be replaced, e.g., by Group T diradicals; and each $R^a$/$R^b$ pair together with the carbon to which they are attached can form a 3 to 10 membered ring.

Each $R^c$ group can be independently H, F, Cl, ($C_1$-$C_3$)alkyl, hydroxy, ($C_1$-$C_3$)alkoxy, or CN, preferably with the proviso that when x of diradical 6 is from 2 to 5, only one $R^c$ group can be other than H.

Each $R^d$ and $R^e$ group is H, except that up to one $R^d$ group together with one $R^e$ group can form a bridging single carbon-carbon bond or bridging ($C_1$-$C_3$)alkyl diradical such that Ring A is bicyclic.

Each Ar can be independently (a) 9-10 membered heterocyclic, (b) 9-10 membered carbocyclic, (c) 4-6 membered heterocyclic, or (d) 4-6 membered carbocyclic, wherein (c) or (d) can be substituted by 4-6 membered heterocyclic or 4-6 membered carbocyclic. The Ar ring system can be substituted with 1 to 3 Group S substituents. Ar and $R^2$, however, are not limited to the ring sizes noted above and can include, e.g., larger ring systems and can be substituted by or fused to additional ring systems.

The Group S substituents include: nitro, halo, hydroxy, CF$_3$, OCF$_3$, OCHF$_2$, CHF$_2$, CN, CHO, ($C_1$-$C_{10}$)alkoxy (optionally substituted by CN), ($C_1$-$C_3$)alkoxy-($C_1$-$C_3$)alkoxy, ($C_1$-$C_3$)alkoxy-($C_1$-$C_3$)alkyl, oxo, ($C_1$-$C_{10}$)alkanoyl, ($C_1$-$C_{10}$)alkyl, ($C_2$-$C_{10}$)alkenyl, ($C_2$-$C_{10}$)alkynyl, 4-10 membered heterocyclic or carbocylic, including 9-10 and 5-6 membered, hydroxy-substituted ($C_1$-$C_6$)alkyl, —C(O)$R^{11}$, —C(O)(4-10 membered heterocyclic), —C(O)(4-10 membered carbocyclic), —C(O)$_2$(4-10 membered heterocyclic), —C(O)$_2$(4-10 membered carbocyclic), —O(4-10 membered carbocyclic), —O(4-10 membered heterocyclic), —C(O)O$R^{11}$, —OC(O)$R^{11}$, —C(O)N$R^{11}R^{12}$, —OC(O)N$R^{11}R^{12}$, —N$R^{11}R^{12}$, —SO$_2$N$R^{11}R^{12}$, and —S(O)$_p$$R^{11}$, wherein p is 0 to 2, and in cases where the Group S substituent substitutes a non-aromatic carbon, Group S can also be =N—N$R^{11}R^{12}$, =N—(4-10 membered heterocyclic), =N-(4-10 membered carbocyclic), =N—NHC(O)$R^{11}$, =N—NHC(O)N$R^{11}R^{12}$, —N(R$^{11}$)SO$_2$R$^{12}$, or =N—R$^{17}$; wherein any of the heterocyclic and carbocyclic groups can be substituted by Cl, F, (C$_1$-C$_{10}$)alkyl, (C$_1$-C$_{10}$)alkoxy, oxo, or CN.

The Group T diradicals include: —O—, —S—, —S(O)—, —S(O)$_2$—, —N((C$_1$-C$_6$)alkyl)—, —NH—, —C(O)—, —OC(O)—, —C(O)O—, —N(Ar)—, and —OC(O)O—.

Each Formula I variable definition includes any subset of that definition, and the definition of Formula I includes any combination of variable definition subsets.

In other aspects of the invention, there are provided methods for preparing compounds of the invention, and intermediates.

In other aspects of the invention, there are provided pharmaceutical compositions containing compounds of the invention.

In still other aspects of the invention, there are provided methods of treating subjects in need thereof with compounds and compositions according to the invention, including for treatment of bacterial and/or protozoal infections, and prevention.

DETAILED DESCRIPTION OF THE INVENTION

The following Detailed Description provides additional non-limiting details of the invention, including general preparations, and examples of the invention.

Compounds

As discussed above, the present invention includes erythromycin-based macrolides containing a C-11/C-12 cyclic urea or carbamate (Ring B) attached (directly or indirectly) to a cyclic amine (Ring A), which in turn can be attached to a headpiece (Group 2-R$^2$). In some aspects, the invention includes the compounds of Formula I. Furthermore, the invention includes the subgenuses and disclosed species (embodiments), including preferred embodiments, encompassed by Formula I, including in particular the following:

In some aspects of the invention, diradical 1 can be absent or methylene; or in some preferred embodiments diradical 1 is specifically absent.

Diradical 2 can in some aspects be —(C(R$^6$)(R$^7$))$_m$— (especially >CH(R$^6$)), —C(O)O—, —C(O)N(R$^6$)—, —C(O)(CH$_2$)$_m$—, or —S(O)$_2$(CH$_2$)$_m$—, wherein m is 0 to 2; or more specifically diradical 2 can be >C(O), or >S(O)$_2$, or >CH(R$^6$), or >CONR$^6$. In some embodiments, R$^6$ can be H or (C$_1$-C$_5$) alkyl which, except H, can be substituted, e.g., by OH or by (C$_1$-C$_3$)alkoxy; or more specifically, R$^6$ can be H or unsubstituted (C$_1$-C$_3$)alkyl, in particular, H or methyl.

Diradical 3 can in some aspects be >C(O). In other embodiments, diradical 3 can be cladinosyl. In other embodiments, diradical 3 can be >CHOC(O)R$^4$, >CHOC(O)NR$^{14}$R$^{15}$, >CHOC(O)OR$^{15}$, >CHOC(O)CH(NR$^{14}$R$^{15}$)((CR$^a$R$^b$)$_n$Ar, >CHOC(O)CH(NR$^{14}$R$^{15}$)R$^{14}$, >CHOC(O)C(=NOR$^{14}$)((CR$^a$R$^b$)$_n$Ar), >CHOC(O)C(=NOR$^{14}$)R$^{14}$, >CHOC(O)(CR$^a$R$^b$)$_n$Ar), or:

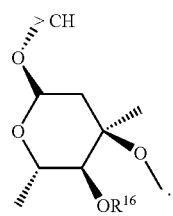

In some aspects, each R$^{14}$ and R$^{15}$ can independently be H or (C$_1$-C$_6$)alkyl of which 1 to 3 methylene units can be replaced by —O—, —S—, —S(O)—, —S(O)$_2$—, —C(O)—, or —NH—; and each R$^{14}$/R$^{15}$ pair, together with the atom to which they are both attached, can form a 3 to 8 membered ring; and said 3 to 8 membered ring can be substituted, e.g., by Ar or by 1 to 2 of the Group S substituents.

Diradical 4 can in some aspects be specifically >O.

Diradical 5 can in some aspects be >C(O) or >C(=NOR$^{19}$), or specifically, >C(O). In some embodiments, R$^{19}$ can be H or (C$_1$-C$_6$)alkyl which can be interrupted by 1 to 3 oxygen atoms and/or substituted by 4-10 membered carbo- or heterocyclic.

Diradical 6 can in some aspects be —(CH$_2$)$_x$— and diradical 7 can be —(CH$_2$)$_y$—, wherein x and y are independently integers from 0 to 4, and wherein the sum of x+y is from 2 to 4; or more specifically x and y can be integers from 0 to 3 (or 1 to 2) for a sum of 2 to 3; or more specifically, diradicals 6 and 7 can both be methylene.

In some aspects, R$^1$ can be H, OH, or methyl; or R$^1$ can be specifically H.

In some aspects, R$^2$ is preferably Ar.

In some aspects, R$^3$ can be (C$_1$-C$_6$)alkyl, (C$_2$-C$_6$)alkenyl, or (C$_2$-C$_6$)alkynyl, any of which can be substituted, e.g., by Ar; or more specifically, R$^3$ can be unsubstituted methyl.

In some aspects, R$^4$ can be H or F.

In some aspects, R$^5$ can be unsubstituted ethyl. In some embodiments, R$^{13}$ and R$^{16}$ (when present) can both be H.

In some aspects, Ar or R$^2$ ring(s) are as above and can be substituted, e.g., by 1 to 2 of: nitro, Br, Cl, F, hydroxy, (C$_1$-C$_6$)alkyl, CF$_3$, OCF$_3$, OCHF$_2$, CHF$_2$, CN, CHO, (C$_1$-C$_6$) alkoxy (optionally substituted by CN), (C$_1$-C$_3$)alkoxy-(C$_1$-C$_3$)alkoxy, (C$_1$-C$_3$)alkoxy-(C$_1$-C$_3$)alkyl, oxo, (C$_1$-C$_6$) alkanoyl, (C$_2$-C$_6$)alkenyl, (C$_2$-C$_6$)alkynyl, hydroxy-substituted (C$_1$-C$_6$)alkyl, —C(O)R$^{11}$, —OC(O)R$^{11}$, —C(O)OR$^{11}$, —C(O)NR$^{11}$R$^{12}$, —OC(O)NR$^{11}$R$^{12}$—, —NHC(O)R$^{11}$, —NR$^{11}$R$^{12}$, —NR$^{11}$SO$_2$R$^{12}$, —SO$_2$NR$^{11}$R$^{12}$, and —S(O)$_n$R$^{11}$, wherein n is 0 to 2. In some embodiments, each R$^{11}$ and R$^{12}$ can independently be H, (C$_1$-C$_6$)alkyl, (C$_3$-C$_6$) alkenyl, or (C$_3$-C$_6$)alkynyl, any of which, except H, can be substituted by one or more substituents, e.g., independently selected from Cl, F, OH, (C$_1$-C$_3$)alkoxy, (C$_1$-C$_3$)alkoxy-(C$_1$-C$_3$)alkoxy, oxo, (C$_1$-C$_3$)alkyl, halo-substituted (C$_1$-C$_3$)alkyl, or (C$_1$-C$_3$)alkoxy-(C$_1$-C$_3$)alkyl.

In some embodiments, R$^2$ can be (a) 9-10 membered heterocyclic, (b) 9-10 membered carbocyclic, (c) 4-6 membered heterocyclic, or (d) 4-6 membered carbocyclic, wherein (c) or (d) can be substituted by 4-6 membered heterocyclic or 4-6 membered carbocyclic; and the R$^2$ ring(s) described above can be substituted, e.g., by 1 to 2 of: SO$_2$R$^{11}$, hydroxy-substituted (C$_1$-C$_3$)alkyl, (C$_1$-C$_3$)alkyl, CN, CHO, F, Cl, Br, hydroxy, (C$_1$-C$_3$)alkoxy-(C$_1$-C$_3$)alkoxy, oxo, (C$_1$-C$_3$)alkanoyl, (C$_2$-C$_6$)alkenyl, (C$_2$-C$_6$)alkynyl, or (C$_1$-C$_3$)alkoxy (optionally substituted by CN). In addition, there can be substitution by nitro, CF$_3$, OCF$_3$, OCHF$_2$, or CHF$_2$. As defined and discussed herein, the foregoing rings include both aryls and heteroaryls, among others.

In some embodiments, R$^2$ can be (a) 9-10 membered heterocyclic, or (b) 5-6 membered heterocyclic or 5-6 membered carbocyclic, wherein (b) is substituted by 5-6 membered heterocyclic or by 5-6 membered carbocyclic, wherein R$^2$ can be substituted by, e.g., 1 to 2 of: SO$_2$R$^{11}$, hydroxy-substituted (C$_1$-C$_3$)alkyl, (C$_1$-C$_3$)alkyl, CN, nitro, CF$_3$, OCF$_3$, OCHF$_2$, CHF$_2$, CHO, Br, Cl, F, CF$_3$, hydroxy, (C$_1$-C$_3$)alkoxy (optionally substituted by CN), (C$_1$-C$_3$)alkoxy-(C$_1$-C$_3$)alkoxy, oxo, (C$_1$-C$_3$)alkanoyl, (C$_2$-C$_6$)alkenyl, or (C$_2$-C$_6$)alkynyl. In some preferred embodiments, the foregoing heterocyclics are heteroaryls. In some embodiments, $R^2$ can be a substituted or unsubstituted 9-10 membered heteroaryl including 1 to 3 nitrogen atoms, or other 9-10 membered heterocyclic.

In some embodiments, $R^2$ can be a 5-6 membered aryl or heteroaryl which is substituted by a 5-6 membered aryl or heteroaryl directly or with an intervening heteroatom. In some particular embodiments, $R^2$ can be selected from any of the heterocyclic radicals listed in the non-limiting general definitions section set forth in this specification, the claims, the examples, or elsewhere in the specification.

In some embodiments, $R^2$ can be phenyl, pyridinyl, naphthalenyl, quinolinyl, isoquinolinyl, 4H-quinolizinyl, quinazoliny, quinoxalinyl, 1,5-naphthyridinyl, 1,6-naphthyridinyl, 1,7-naphthyridinyl, 1,8-naphthyridinyl, cinnolinyl, phthalazinyl, pyrido[2,3-b]pyrazine, pyrido[3,4-b]pyrazine, pyrido[2,3-d]pyrimidine, pyrido[2,3-c]pyridazine, pyrido[3,2-b]pyridazine, benzimidazolyl, indolyl, indazoly, 1H-benzotriazolyl, 1H-pyrrolo[3,2-b]pyridinyl, 1H-pyrrolo[3,2-c]pyridinyl, 1H-pyrrolo[2,3-c]pyridinyl, 1H-pyrrolo[2,3-b]pyridinyl, 1H-imidazo[4,5-b]pyridinyl, 1H-imidazo[4,5-c]pyridinyl, 1H-[1,2,3]triazolo[4,5-b]pyridinyl, 1H-[1,2,3]triazolo[4,5-c]pyridinyl, pyrazolo[1,5-a]pyridinyl, imidazo[2,1-b]thiazolyl, 3H-imidazo[4,5-b]-pyridinyl, imidazo[1,5-a]pyridinyl, imidazo[1,2-a]pyridinyl, pyrrolo[1,2-a]pyridinyl, pyrrolo[1,2-a]pyrazinyl, pyrrolo[1,2-c]pyrimidinyl, pyrrolo[1,2-b]pyridazinyl, pyrrolo[1,5-a]pyrimidinyl, imidazo[1,5-a]pyrimidinyl, imidazo[1,2-a]pyrimidinyl, benzo[d]thiazolyl, benzo[c][1,2,5]oxadiazolyl, benzo[d]isooxazolyl, benzo[d][1,3]dioxolyl, benzo[d]oxazolyl, benzo[d]isothiazolyl, 5-phenylthiazolyl, 2-phenyl-1,3,4-thiadiazolyl, 4-phenylthiazolyl, 4-phenyl-1,2,3-thiadiazolyl, 5-phenyloxazolyl, 2-phenyl-1,3,4-oxadiazolyl, 5-phenyl-1,2,4-oxadiazolyl, 3-phenyl-1,2,4-oxadiazolyl, 1-phenyl-1H-pyrazolyl, 4-phenyl-4H-1,2,4-triazolyl, 1-phenyl-1H-1,2,4-triazolyl, 2-(1H-1,2,4-triazol-1-yl)pyridinyl, 2-(1H-pyrazol-1-yl)pyridinyl, 1,3-dihydrobenzo-2,2-dioxo[c]thiophene, benzo[d][1,3]dioxole, 1H-indenyl-2(3H)-sulfone, phenoxyphenyl, 4-(2-oxooxazolidin-3-yl)phenyl, 2,1,3-benzothiadiazolyl-2,2-dioxide, or 2-(4H-1,2,4-triazol4-yl)pyridinyl. Such $R^2$ groups can be substituted as discussed herein. For example, substitution can be by 1 to 2 of $(C_1-C_3)$alkyl, CN, CHO, Cl, F, $CF_3$, nitro, hydroxy, oxo, $(C_1-C_3)$alkanoyl, $(C_2-C_3)$alkenyl, $(C_2-C_3)$alkynyl, or $(C_1-C_3)$alkoxy. Other heterocyclics can also be used. See, e.g., U.S. Pat. No. 5,747,467 (cols. 2-4) or US 2004/0157787 (group $Ar_2$ therein), which are fully incorporated by reference herein. Any orientation (i.e., ring atom attached to diradical 2) of $R^2$ with respect to diradical 2 can be used, even if not specifically mentioned above or otherwise herein. For example, 1,8-naphthyridinyl is a preferred group, which in some embodiments is attached at the 4-position, and which may be substituted, for example at the 3-position (ortho to the position of attachment to the macrolide).

Thus, a first subgenus (1) is a subgroup of Formula I wherein diradical 1 is absent or >$CH_2$; diradical 2 is >$CH(R^6)$, —C(O)O—, —C(O)N($R^6$)—, —C(O)($CH_2$)$_m$—, or —S(O)$_2$($CH_2$)$_m$—, wherein m is 0 to 2; diradical 3 is >C(O); diradical 4 is >O; diradical 5 is >C(O) or >C(=$NOR^{19}$); diradical 6 is —($CH_2$)$_x$—, wherein x is an integer from 0 to 4; diradical 7 is —($CH_2$)$_y$—, wherein y is an integer of from 0 to 4; and wherein the sum of x+y is from 2 to 4; $R^1$ is H, OH, or methyl; $R^2$ is Ar; each $R^{11}$ and $R^{12}$ is independently H, $(C_1-C_6)$alkyl, $(C_3-C6)$alkenyl, or $(C_3-C_6)$alkynyl, any of which, except H, can be substituted by 1 to 2 of: Cl, F, OH, $(C_1-C_3)$alkoxy, $(C_1-C_3)$alkoxy-$(C_1-C_3)$alkoxy, oxo, $(C_1-C_3)$alkyl, halo-substituted $(C_1-C_3)$alkyl, or $(C_1-C_3)$alkoxy-$(C_1-C_3)$alkyl; $R^{13}$ is H; $R^{19}$ is H or $(C_1-C_6)$alkyl which can be interrupted by 1 to 3 oxygen atoms and can be substituted by 4-10 membered carbo- or heterocyclic; each Ar is independently (a) 9-10 membered heterocyclic, (b) 9-10 membered carbocyclic, (c) 4-6 membered heterocyclic, or (d) 4-6 membered carbocyclic, wherein (c) or (d) can be substituted by 4-6 membered heterocyclic or 4-6 membered carbocyclic; and wherein the foregoing Ar ring systems (i.e., single ring, fused rings, or nonfused bicyclic systems) can be substituted by 1 to 2 (alternatively, 3) of: nitro, Br, Cl, F, hydroxy, $(C_1-C_6)$alkyl, $CF_3$, $OCF_3$, $OCHF_2$, $CHF_2$, CN, CHO, $(C_1-C_6)$alkoxy (optionally substituted by CN), $(C_1-C_3)$alkoxy-$(C_1-C_3)$alkoxy, $(C_1-C_3)$alkoxy-$(C_1-C_3)$alkyl, oxo, $(C_1-C_6)$alkanoyl, $(C_2-C_6)$alkenyl, $(C_2-C_6)$alkynyl, hydroxy- substituted $(C_1-C_6)$alkyl, -C(O)$R^{11}$, —OC(O)$R^{11}$, —C(O)O$R^{11}$, —C(O)N$R^{11}R^{12}$, —OC(O)N$R^{11}R^{12}$—, —NHC(O)$R^{11}$, —N$R^{11}R^{12}$, —N$R^{11}SO_2R^{12}$, —SO$_2$N$R^{11}R^{12}$, or —S(O)$_p$$R^{11}$, wherein p is 0 to 2. Alternatively, $R^{13}$ can be —C(O)($C_1$-$C_6$alkyl) in the above. Independently, diradical 3 can alternatively be >CHOC(O)$R^{14}$, >CHOC(O)N$R^{14}R^{15}$, >CHOC(O)O$R^{15}$, >CHOC(O)CH(N$R^{14}R^{15}$)((CR$^a$R$^b$)$_n$Ar), >CHOC(O)CH(N$R^{14}R^{15}$)$R^{14}$, >CHOC(O)C(=NO$R^{14}$)((CR$^a$R$^b$)$_n$Ar), >CHOC(O)C(=NO$R^{14}$)$R^{14}$, >CHOC(O)(CR$^a$R$^b$)$_n$Ar), or:

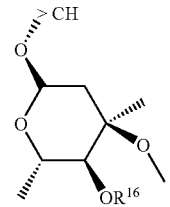

A second subgenus (2) of Formula I (meaning Formula I in its broadest sense herein) is a subgroup of Formula I or of Subgenus 1, wherein diradical 5 is >C(O); $R^3$ is methyl; $R^5$ is ethyl; and $R^6$ is H or $(C_1-C_5)$alkyl which can be substituted by OH or $(C_1-C_3)$alkoxy. In some preferred aspects thereof, diradical 2 in this subgenus can be >CH($R^6$) (Subgenus 2a) or alternatively can be >SO$_2$ (Subgenus 2b).

A third subgenus (3) of Formula I is a subgroup of any of Formula I or Subgenera 1 to 2, wherein diradical 1 is absent or methylene; $R^1$ is H; and $R^6$ (when present) is H or $(C_1-C_3)$alkyl, e.g., methyl.

A fourth subgenus (4) of Formula I is a subgroup of any of Formula I or Subgenera 1 to 3, wherein diradical 6 is —($CH_2$)$_x$—, wherein x is an integer of from 0 to 3; diradical 7 is —($CH_2$)$_y$—, wherein y is an integer from 0 to 3; and wherein the sum of x+y is 2 to 3. The invention also includes a subgenus incorporating all of the limitations of both (3) and (4) (Subgenus 4a).

A fifth subgenus (5) of Formula I is a subgroup of any of Formula I or Subgenera 1 to 4, wherein diradical 1 is absent; $R^2$ is (a) 9-10 membered heterocyclic or carbocyclic or (b) 4-6 membered heterocyclic or carbocyclic, wherein (b) can be substituted by 4-6 membered heterocyclic or carbocyclic; $R^2$ can be substituted by 1 to 2 of: $SO_2R^{11}$, hydroxy-substituted $(C_1-C_3)$alkyl, $(C_1-C_3)$alkyl, CN, nitro, $CF_3$, $OCF_3$, $OCHF_2$, $CHF_2$, CHO, F, Cl, Br, hydroxy, $(C_1-C_3)$alkoxy (optionally substituted by CN), $(C_1-C_3)$alkoxy-$(C_1-C_3)$alkoxy, oxo, $(C_1-C_3)$alkanoyl, $(C_2-C_6)$alkenyl, or $(C_2-C_6)$alkynyl; and $R^6$ (when present) is H. In some preferred embodiments thereof, $R^2$ is a substituted or unsubstituted 9-10 membered heteroaryl containing 1 to 3 nitrogen atoms. The invention also includes the subgenus incorporating all of the limitations of all of (3), (4), and (5) (Subgenus 5a).

A sixth subgenus (6) of Formula I is a subgroup of any of Formula I or Subgenera 1 to 5, wherein diradicals 6 and 7 are both methylene.

A seventh subgenus (7) of Formula I is a subgroup of any of Formula I or Subgenera 1 to 6, wherein $R^2$ is (a) 9-10 membered heterocyclic, or (b) 5-6 membered heterocyclic or carbocyclic, wherein (b) is substituted by 5-6 membered heterocyclic or carbocyclic, and wherein $R^2$ can be substituted by 1 to 2 of: —$SO_2R^{11}$, hydroxy-substituted ($C_1$-$C_3$)alkyl, ($C_1$-$C_3$)alkyl, CN, CHO, Br, Cl, F, $CF_3$, $OCF_3$, $CHF_2$, $OCHF_2$, nitro, hydroxy, ($C_1$-$C_3$)alkoxy (optionally substituted by CN), ($C_1$-$C_3$)alkoxy-($C_1$-$C_3$)alkoxy, oxo, ($C_1$-$C_3$)alkanoyl, ($C_2$-$C_6$)alkenyl, or ($C_2$-$C_6$)alkynyl. The invention also includes the subgenus combining all of the limitations of both (6) and (7) (Subgenus 7a).

A eighth subgenus (8) of Formula I is a subgroup of any of Formula I or Subgenera 1 to 6, wherein $R^2$ is 9-10 membered heterocyclic, in particular heteroaryl, containing 1 to 3 heteroatoms independently selected from N, S, or O. Alternatively, $R^2$ can be a 5-6 membered aryl or heteroaryl which is substituted by a 5-6 membered aryl or heteroaryl. $R^2$ can be substituted, e.g., by 1 to 2 of: $SO_2R^{11}$, hydroxy-substituted ($C_1$-$C_3$)alkyl, ($C_1$-$C_3$)alkyl, CN, CHO, Cl, F, $CF_3$, nitro, hydroxy, ($C_1$-$C_3$)alkoxy-($C_1$-$C_3$)alkoxy, oxo, ($C_1$-$C_3$)alkanoyl, ($C_2$-$C_6$)alkenyl, ($C_2$-$C_6$)alkynyl, or ($C_1$-$C_3$)alkoxy optionally substituted by CN. $R^2$ can also be any of the headpieces specifically disclosed herein.

In some more particular embodiments, diradical 1 is absent, 2 is >$CH_2$, >$CH(CH_3)$, or >$SO_2$, 3 is >C(O), 4 is >O, 5 is >C(O), 6 and 7 are both >$CH_2$, $R^1$ is H, $R^3$ is methyl, $R^4$ is H or F, $R^5$ is ethyl, and $R^{13}$ is H. In these and other embodiments, $R^2$ can be selected from any of the $R^2$ groups of the examples or other material herein, such as those described and listed above.

A ninth subgenus (9) is a subgroup of Formula I or Subgenus I, wherein diradical 2 is >C(O), —C(O)N($R^6$)—, or —C(O)O—; diradical 5 is >C(O); $R^3$ is methyl; $R^5$ is ethyl; and $R^6$ is H or ($C_1$-$C_5$)alkyl. More specifically, in the above, diradical 1 can be absent or methyl; diradical 6 can be —(CH$_2$)$_x$—, wherein x is from 0 to 3; diradical 7 can be —(CH$_2$)$_y$—, wherein y is from 0 to 3; and wherein the sum of x+y is 2 to 3; and $R^6$ can be H or methyl. Also, $R^2$ in the above can be (a) 9-10 membered heterocyclic or carbocyclic, or (b) 4-6 membered heterocyclic or carbocyclic, wherein (b) can be substituted by 4-6 membered heterocyclic or carbocyclic; and $R^2$ can be substituted by 1 to 2 of: $SO_2$, hydroxy-substituted ($C_1$-$C_3$)alkyl, ($C_1$-$C_3$)alkyl, CN, CHO, Br, Cl, F, $CF_3$, $OCF_3$, $OCHF_2$, $CHF_2$, nitro, hydroxy, ($C_1$-$C_3$)alkoxy (optionally substituted by CN), ($C_1$-$C_3$)alkoxy-($C_1$-$C_3$)alkoxy, oxo, ($C_1$-$C_3$)alkanoyl, ($C_2$-$C_6$)alkenyl, or ($C_2$-$C_6$)alkynyl.

The invention also includes compounds described by any subgroup of the variable definitions set forth in Formula I and any subgenera thereof.

The compounds can be further classified in terms of activity, e.g., those exhibiting an in vitro MIC of about 8 μg/mL or less, or 4 μg/mL, against *S. pyogenes*, including strains that are resistant to clarithromycin such as by an ermB mechanism, e.g., *S. pyogenes* 1079. In other aspects, the compounds may exhibit an in vitro MIC of about 0.5 μg/mL or less against *S. pneumo* including strains that are resistant to clarithromycin such as by an efflux mechanism.

Certain nonlimiting examples are named below.

3-descladinosyl-11,12-dideoxy-6-O-methyl-3-oxo-12,11-(oxycarbonyl-(1-((quinolin-5-yl)-methyl)-azetidin-3-yl)-imino)-erythromycin A. (Ex. 1.06)

3-descladinosyl-11,12-dideoxy-6-O-methyl-3-oxo-12,11-(oxycarbonyl-(1-((1H-benzoimidazol-7-yl)-methy)-azetidin-3-yl)-imino)-erythromycin A. (Ex. 1.11)

3-descladinosyl-11,12-dideoxy-6-O-methyl-3-oxo-12,11-(oxycarbonyl-(1-((quinoxalin-8-yl)-methyl)-azetidin-3-yl)-imino)-erythromycin A. (Ex. 1.12)

3-descladinosyl-11,12-dideoxy-6-O-methyl-3-oxo-12,11-(oxycarbonyl-(1-((quinolin-4-yl)-methyl)-azetidin-3-yl)-imino)-erythromycin A. (Ex. 1.16)

3-descladinosyl-11,12-dideoxy-6-O-methyl-3-oxo-12,11-(oxycarbonyl-(1-((1,8-naphthyridin-4-yl)-methyl)-azetidin-3-yl)-imino)erythromycin A. (Ex. 1.20)

3-descladinosyl-11,12-dideoxy-6-O-methyl-3-oxo-12,11-(oxycarbonyl-(1-(1S-(1,8-naphthyridin4-yl)-ethyl)-azetidin-3-yl)-imino)-erythromycin A. (Ex. 1.23)

3-descladinosyl-11,12-dideoxy-6-O-methyl-3-oxo-12,11-(oxycarbonyl-(1-((pyrido[2,3-b]pyrazin-4-yl)-methy)-azetidin-3-yl)-imino)-erythromycin A. (Ex. 1.24)

3-descladinosyl-11,12-dideoxy-6-O-methyl-3-oxo-12,11-(oxycarbonyl-(1-(1R-(1,8-naphthyridin4-yl)-ethyl)-azetidin-3-yl)-imino)-erythromycin A. (Ex. 1.25)

3-descladinosyl-11,12-dideoxy-6-O-methyl-3-oxo-12,11-(oxycarbonyl-(1-((1,5-naphthyridin4-yl)-methyl)-azetidin-3-yl)-imino)-erythromycin A. (Ex. 1.26)

3-descladinosyl-11,12-dideoxy-6-O-methyl-3-oxo-12,11-(oxycarbonyl-(1-((1,6-naphthyridin-4-yl)-methyl)-azetidin-3-yl)-imino)-erythromycin A. (Ex. 1.27)

3-descladinosyl-11,12-dideoxy-6-O-methyl-3-oxo-12,11-(oxycarbonyl-(1-((quinoxalin-6-yl)-methyl)-azetidin-3-yl)-imino)-erythromycin A. (Ex. 1.28)

3-descladinosyl-11,12-dideoxy-6-O-methyl-3-oxo-12,11-(oxycarbonyl-(1-((indazol-3-yl)-methyl)-azetidin-3-yl)-imino)-erythromycin A. (Ex. 1.29)

3-descladinosyl-11,12-dideoxy-6-O-methyl-3-oxo-12,11-(oxycarbonyl-(1-((isoquinolin-4-yl)-methyl)-azetidin-3-yl)-imino)-erythromycin A. (Ex. 1.30)

3-descladinosyl-11,12-dideoxy-2-fluoro-6-O-methyl-3-oxo-12,11-(oxycarbonyl-(1-(1R-(1,8-naphthyridin-4-yl)-ethyl)-azetidin-3-yl)-imino)-erythromycin A. (Ex. 1.32)

3-descladinosyl-11,12-dideoxy-2-fluoro-6-O-methyl-3-oxo-12,11-(oxycarbonyl-(1-((1,8-naphthyridin-4-yl)-methyl)-azetidin-3-yl)-imino)-erythromycin A. (Ex. 1.33)

3-descladinosyl-11,12-dideoxy-6-O-methyl-3-oxo-12,11-(oxycarbonyl-(1-((thiazolo[4,5-b]pyridin-7-yl)-methyl)-azetidin-3-yl)-imino)erythromycin A. (Ex. 1.35)

3-descladinosyl-11,12-dideoxy-6-O-methyl-3-oxo-12,11-(oxycarbonyl-(1-(1R-(1,5-naphthyridin-4-yl)-ethyl)-azetidin-3-yl)-imino)erythromycin A. (Ex. 1.37)

3-descladinosyl-11,12-dideoxy-6-O-methyl-3-oxo-12,11-(oxycarbonyl-(1-(1S-(1,5-naphthyridin-4-yl)-ethyl)-azetidin-3-yl)-imino)erythromycin A. (Ex. 1.38)

3-descladinosyl-11,12-dideoxy-6-O-methyl-3-oxo-12,11-(oxycarbonyl-(1-(1-(quinolin-4-yl)-propyl)-azetidin-3-yl)-imino)-erythromycin A. (Ex. 1.61)

3-descladinosyl-11,12-dideoxy-6-O-methyl-3-oxo-12,11-(oxycarbonyl-(1-(1-(quinolin-4-yl)-ethyl)-azetidin-3-yl)-imino)-erythromycin A. (Ex. 1.62)

3-descladinosyl-11,12-dideoxy-6-O-methyl-3-oxo-12,11-(oxycarbonyl-(1-(1-(quinolin-4-yl)-ethyl)-azetidin-3-yl)-imino)-erythromycin A. (Ex. 1.63)

3-descladinosyl-11,12-dideoxy-6-O-methyl-3-oxo-12,11-(oxycarbonyl-(1-(1-(quinolin4-yl)-butyl)-azetidin-3-yl)-imino)-erythromycin A. (Ex. 1.64)

3-descladinosyl-11,12-dideoxy-6-O-methyl-3-oxo-12,11-(oxycarbonyl-(1-(1-(quinolin4-yl)-butyl)-azetidin-3-yl)-imino)-erythromycin A. (Ex. 1.65)

3-descladinosyl-11,12-dideoxy-6-O-methyl-3-oxo-12,11-(oxycarbonyl-(1-(phenyl-(pyridin-4-yl)-methyl)-azetidin-3-yl)-imino)erythromycin A. (Ex. 1.69)
3-descladinosyl-11,12-dideoxy-6-O-methyl-3-oxo-12,11-(oxycarbonyl-(1-(8-methoxyquinoline-5-methyl)-azetidin-3-yl)-imino)-erythromycin A. (Ex. 1.70)
3-descladinosyl-11,12-dideoxy-6-O-methyl-3-oxo-12,11-(oxycarbonyl-(1-(3-methoxyquinoline-4-methyl)-azetidin-3-yl)-imino)-erythromycin A. (Ex. 1.71)
3-descladinosyl-11,12-dideoxy-6-O-methyl-3-oxo-12,11-(oxycarbonyl-(1-(3-methoxy-1,8-naphthyridine-4-methyl)-azetidin-3-yl)-imino)-erythromycin A. (Ex. 1.72)
3-descladinosyl-11,12-dideoxy-6-O-methyl-3-oxo-12,11-(oxycarbonyl-(1-(quinoline-3-carbonitrile-4-methyl)-azetidin-3-yl)-imino)erythromycin A. (Ex. 1.73)
3-descladinosyl-11,12-dideoxy-6-O-methyl-3-oxo-12,11-(oxycarbonyl-(1-(7-bromopyrido[3,2-b]pyrazine-8-methyl)-azetidin-3-yl)imino)-erythromycin A. (Ex. 1.74)
3-descladinosyl-11,12-dideoxy-6-O-methyl-3-oxo-12,11-(oxycarbonyl-(1-(3-bromo-1,8-naphthyridine-4-methyl)-azetidin-3-yl)-imino)-erythromycin A. (Ex. 1.75)
3-descladinosyl-11,12-dideoxy-6-O-methyl-3-oxo-12,11-(oxycarbonyl-(1-(3-chloro-1,8-naphthyridine-4-methyl)-azetidin-3-yl)-imino)-erythromycin A. (Ex. 1.76)
3-descladinosyl-11,12-dideoxy-6-O-methyl-3-oxo-12,11-(oxycarbonyl-(1-(3-bromopyridine-4-methyl)-azetidin-3-yl)-imino)-erythromycin A. (Ex. 1.77)
3-descladinosyl-11,12-dideoxy-6-O-methyl-3-oxo-12,11-(oxycarbonyl-(1-(3-fluoropyridine-4-methyl)-azetidin-3-yl)-imino)-erythromycin A. (Ex. 1.78)
3-descladinosyl-11,12-dideoxy-6-O-methyl-3-oxo-12,11-(oxycarbonyl-(1-(3-chloropyridine-4-methyl)-azetidin-3-yl)-imino)-erythromycin A. (Ex. 1.79)
3-descladinosyl-11,12-dideoxy-6-O-methyl-3-oxo-12,11-(oxycarbonyl-(1-(2-(methoxy)-1S-(1,8-napthyridin-4-yl)-ethyl)-azetidin-3-yl)-imino)-erythromycin A. (Ex. 1.80)
3-descladinosyl-11,12-dideoxy-4-O-methyl-3-oxo-12,11-(oxycarbonyl-(1-(2-(methoxy)-1R-(1,8-napthyridin-4-yl)-ethyl)-azetidin-3-yl)-imino)-erythromycin A. (Ex. 1.81)
3-descladinosyl-11,12-dideoxy-6-O-methyl-3-oxo-12,11-(oxycarbonyl-(1-(4H-quinolizin-4-one-1-methyl)-azetidin-3-yl)-imino)-erythromycin A. (Ex. 1.82)
3-descladinosyl-11,12-dideoxy-6-O-methyl-3-oxo-12,11-(oxycarbonyl-(1-(H-pyrazolo[1,5-a]pyridine-4-methyl)-azetidin-3-yl)-imino)-erythromycin A. (Ex. 1.83)
3-descladinosyl-11,12-dideoxy-6-O-methyl-3-oxo-12,11-(oxycarbonyl-(1-(8-methoxyquinoline-4-methyl)-azetidin-3-yl)-imino)erythromycin A. (Ex. 1.84)
3-descladinosyl-11,12-dideoxy-6-O-methyl-3-oxo-12,11-(oxycarbonyl-(1-(1-fluoro-3-methoxybenzene-2-methyl)-azetidin-3-yl)-imino)-erythromycin A. (Ex. 1.85)
3-descladinosyl-11,12-dideoxy-6-O-methyl-3-oxo-12,11-(oxycarbonyl-(1-(2-methoxynaphthalene-1-methyl)-azetidin-3-yl)-imino)-erythromycin A. (Ex. 1.86)
3-descladinosyl-11,12-dideoxy-6-O-methyl-3-oxo-12,11-(oxycarbonyl-(1-(1,3-difluorobenzene-2-methyl)-azetidin-3-yl)-imino)erythromycin A. (Ex. 1.87)
3-descladinosyl-11,12-dideoxy-6-O-methyl-3-oxo-12,11-(oxycarbonyl-(1-(2-(trifluoromethoxy)benzene-1-methyl)-azetidin-3-yl)-imino)-erythromycin A. (Ex. 1.88)
3-descladinosyl-11,12-dideoxy-6-O-methyl-3-oxo-12,11-(oxycarbonyl-(1-(2-cyclopropyl-3H-imidazo[4,5-b]pyridine-7-methyl)-azetidin-3-yl)-imino)-erythromycin A. (Ex. 1.89)
3-descladinosyl-11,12-dideoxy-4-O-methyl-3-oxo-12,11-(oxycarbonyl-(1-(6-methoxyquinoline-4-methyl)-azetidin-3-yl)-imino)-erythromycin A. (Ex. 1.90)
3-descladinosyl-11,12-dideoxy-6-O-methyl-3-oxo-12,11-(oxycarbonyl-(1-(naphthalene-1-methyl)-azetidin-3-yl)-imino)-erythromycin A. (Ex. 1.91)
3-descladinosyl-11,12-dideoxy-6-O-methyl-3-oxo-12,11-(oxycarbonyl-(1-(2-methylnaphthalene-1-methyl)-azetidin-3-yl)-imino)erythromycin A. (Ex. 1.92)
3-descladinosyl-11,12-dideoxy-6-O-methyl-3-oxo-12,11-(oxycarbonyl-(1-(3-methyl-3H-imidazo[4,5-b]pyridine-7-methyl)-azetidin-3-yl)-imino)-erythromycin A. (Ex. 1.93)
3-descladinosyl-11,12-dideoxy-6-O-methyl-3-oxo-12,11-(oxycarbonyl-(1-(1H-inden-2(3H)-sulfone-5-methyl-azetidin-3-yl)-imino)-erythromycin A. (Ex. 1.94)
3-descladinosyl-11,12-dideoxy-6-O-methyl-3-oxo-12,11-(oxycarbonyl-(1-(quinoline-8-carbonitrile-4-methyl)-azetidin-3-yl)-imino)-erythromycin A. (Ex. 1.95)
3-descladinosyl-11,12-dideoxy-6-O-methyl-3-oxo-12,11-(oxycarbonyl-(1-(quinoline-8-carbonitrile-5-methyl)-azetidin-3-yl)-imino)-erythromycin A. (Ex. 1.96)
3-descladinosyl-11,12-dideoxy-6-O-methyl-3-oxo-12,11-(oxycarbonyl-(1-(2-ethoxynaphthalene-1-methyl)-azetidin-3-yl)-imino)-erythromycin A. (Ex. 1.97)
3-descladinosyl-11,12-dideoxy-6-O-methyl-3-oxo-12,11-(oxycarbonyl-(1-(3-methylquinoline-4-methyl)-azetidin-3-yl)-imino)-erythromycin A. (Ex. 1.98)
3-descladinosyl-11,12-dideoxy-6-O-methyl-3-oxo-12,11-(oxycarbonyl-(1-(3-methyl-1,8-naphthyridine-4-methyl)-azetidin-3-yl)-imino)-erythromycin A. (Ex. 1.99)
3-descladinosyl-11,12-dideoxy-6-O-methyl-3-oxo-12,11-(oxycarbonyl-(1-(6-chloro-3H-imidazo[4,5-b]pyridine-7-methyl)-azetidin-3-yl)-imino)-erythromycin A. (Ex. 1.100)
3-descladinosyl-11,12-dideoxy-6-O-methyl-3-oxo-12,11-(oxycarbonyl-(1-(3-methoxy-1,5-naphthyridine-4-methyl)-azetidin-3-yl)-imino)-erythromycin A. (Ex. 1.101)
3-descladinosyl-11,12-dideoxy-6-O-methyl-3-oxo-12,11-(oxycarbonyl-(1-(6-methoxyquinoline-5-methyl)-azetidin-3-yl)-imino)-erythromycin A. (Ex. 1.102)
3-descladinosyl-11,12-dideoxy-6-O-methyl-3-oxo-12,11-(oxycarbonyl-(1-(2,4-dichlorobenzene-1-methyl)-azetidin-3-yl)-imino)-erythromycin A. (Ex. 1.103)
3-descladinosyl-11,12-dideoxy-6-O-methyl-3-oxo-12,11-(oxycarbonyl-(1-(benzo[d][1,3]dioxole-5-methyl)-azetidin-3-yl)-imino)erythromycin A. (Ex. 1.104)
3-descladinosyl-11,12-dideoxy-4-O-methyl-3-oxo-12,11-(oxycarbonyl-(1-(5-methoxyquinoxaline-8-methylazetidin-3-yl)-imino)-erythromycin A. (Ex. 1.105)
3-descladinosyl-11,12-dideoxy-6-O-methyl-3-oxo-12,11-(oxycarbonyl-(1-(3-bromo-1,5-naphthyridine-4-methyl)-azetidin-3-yl)-imino)-erythromycin A. (Ex. 1.106)
3-descladinosyl-11,12-dideoxy-6-O-methyl-3-oxo-12,11-(oxycarbonyl-(1-(3-chloroquinoline-4-methyl)-azetidin-3-yl)-imino)erythromycin A. (Ex. 1.107)
3-descladinosyl-11,12-dideoxy-6-O-methyl-3-oxo-12,11-(oxycarbonyl-(1-(3-ethoxy-1,8-naphthyridine-4-methyl)-azetidin-3-yl)-imino)-erythromycin A. (Ex. 1.108)
3-descladinosyl-11,12-dideoxy-6-O-methyl-3-oxo-12,11-(oxycarbonyl-(1-( pyridine-3-sulfonyl)-azetidin-3-yl)-imino)-erythromycin A. (Ex. 3.01)
3-descladinosyl-11,12-dideoxy-6-O-methyl-3-oxo-12,11-(oxycarbonyl-(1-(naphthalene-1-sulfonyl)-azetidin-3-yl)-imino)-erythromycin A. (Ex. 3.02)

3-descladinosyl-11,12-dideoxy-O-methyl-3-oxo-12,11-(oxycarbonyl-(1-(quinoline-8-sulfonyl)-azetidin-3-yl)-imino)-erythromycin A. (Ex. 3.03)

3-descladinosyl-11,12-dideoxy-6-O-methyl-3-oxo-12,11-(oxycarbonyl-(1-(isoquinoline-5-sulfonyl)-azetidin-3-yl)-imino)-erythromycin A. (Ex. 3.04)

3-descladinosyl-11,12-dideoxy-6-O-methyl-3-oxo-12,11-(oxycarbonyl-(1-(benzo[1,2,5]thiadiazole-4-sulfonyl)-azetidin-3-yl)-imino)erythromycin A. (Ex. 3.06)

3-descladinosyl-11,12-dideoxy-6-O-methyl-3-oxo-12,11-(oxycarbonyl-(1-(3-cyanobenzenesulfonyl)-azetidin-3-yl)-imino)-erythromycin A. (Ex. 3.10)

3-descladinosyl-11,12-dideoxy-6-O-methyl-3-oxo-12,11-(oxycarbonyl-(1-(4-cyanobenzenesulfonyl)-azetidin-3-yl)-imino)-erythromycin A. (Ex. 3.11)

3-descladinosyl-11,12-dideoxy-6-O-methyl-3-oxo-12,11-(oxycarbonyl-(1-(4-(oxazol-5-yl)-benzenesulfonyl)-azetidin-3-yl)-imino)-erythromycin A. (Ex. 3.13)

3-descladinosyl-11,12-dideoxy-6-O-methyl-3-oxo-12,11-(oxycarbonyl-(1-(H-imidazo[1,2-a]pyridine-3-sulfonyl)-azetidin-3-yl)-imino)-erythromycin A. (Ex. 3.15)

3-descladinosyl-11,12-dideoxy-6-O-methyl-3-oxo-12,11-(oxycarbonyl-(1-(6-(1H-pyrazol-1-yl)pyridine-3-sulfonyl)-azetidin-3-yl)-imino)-erythromycin A. (Ex. 3.16)

3-descladinosyl-11,12-dideoxy-6-O-methyl-3-oxo-12,11-(oxycarbonyl-(1-(imidazo[1,2-a]pyrimidine-3-sulfonyl)-azetidin-3-yl)-imino)-erythromycin A. (Ex. 3.17)

3-descladinosyl-11,12-dideoxy-6-O-methyl-3-oxo-12,11-(oxycarbonyl-(1-(2-cyanobenzenesulfonyl)-azetidin-3-yl)-imino)-erythromycin A. (Ex. 3.18)

3-descladinosyl-11,12-dideoxy-6-O-methyl-3-oxo-12,11-(oxycarbonyl-(1-(H-imidazo[1,5-a]pyridine-1-sulfonyl)-azetidin-3-yl)-imino)-erythromycin A. (Ex. 3.19)

3-descladinosyl-11,12-dideoxy-6-O-methyl-3-oxo-12,11-(oxycarbonyl-(1-(4-(2,3,4,5-tetrahydro-3,5-dioxo-1,2,4-triazin-6-yl)benzenesulfonyl)-azetidin-3-yl)-imino)-erythromycin A. (Ex. 3.20)

3-descladinosyl-11,12-dideoxy-6-O-methyl-3-oxo-12,11-(oxycarbonyl-(1-(2,3-dihydro-2-oxobenzo[d]oxazole-5-sulfonyl)-azetidin-3-yl)-imino)-erythromycin A. (Ex. 3.22)

3-descladinosyl-11,12-dideoxy-6-O-methyl-3-oxo-12,11-(oxycarbonyl-(1-(3,5-dimethyl-1H-pyrazole-4-sulfony)-azetidin-3-yl)-imino)-erythromycin A. (Ex. 3.29)

3-descladinosyl-11,12-dideoxy-6-O-methyl-3-oxo-12,11-(1-(oxycarbonyl-(2,4-dimethoxybenzenesulfonyl)-azetidin-3-yl)-imino)-erythromycin A. (Ex. 3.31)

3-descladinosyl-11,12-dideoxy-6-O-methyl-3-oxo-12,11-(1-(oxycarbonyl-(5-(isoxazol-3-yl)thiophene-2-sulfonyl)-azetidin-3-yl)-imino)-erythromycin A. (Ex. 3.33)

3-descladinosyl-11,12-dideoxy-6-O-methyl-3-oxo-12,11-(oxycarbonyl-(1-(3-(oxazol-5-yl)benzenesulfonyl)-azetidin-3-yl)-imino)-erythromycin A. (Ex. 3.35)

3-descladinosyl-11,12-dideoxy-6-O-methyl-3-oxo-12,11-(oxycarbonyl-(1-(3-(1H-pyrazol-3-yl)benzenesulfonyl)-azetidin-3-yl)-imino)-erythromycin A. (Ex. 3.36)

3-descladinosyl-11,12-dideoxy-6-O-methyl-3-oxo-12,11-(oxycarbonyl-(1-(4-(1H-pyrazol-5-yl)benzenesulfonyl)-azetidin-3-yl)-imino)-erythromycin A. (Ex. 3.39)

3-descladinosyl-11,12-dideoxy-6-O-methyl-3-oxo-12,11-(oxycarbonyl1(-(3-(3-methylisoxazol-5-yl)benzenesulfonyl)-azetidin-3-yl)-imino)-erythromycin A. (Ex. 3.40)

3-descladinosyl-11,12-dideoxy-6-O-methyl-3-oxo-12,11-(oxycarbonyl-(1-(3-(1,2,4-oxadiazol-3-yl)benzenesulfonyl)-azetidin-3-yl)-imino)-erythromycin A. (Ex. 3.41)

3-descladinosyl-11,12-dideoxy-6-O-methyl-3-oxo-12,11-(oxycarbonyl-(1-(2-oxoindoline-5-sulfonyl)-azetidin-3-yl)-imino)-erythromycin A. (Ex. 3.42)

3-descladinosyl-11,12-dideoxy-6-O-methyl-3-oxo-12,11-(oxycarbonyl-(1-(2,3-dihydro-2-oxobenzo[d]oxazole-5-sulfonyl)-azetidin-3-yl)-imino)-erythromycin A. (Ex. 3.43)

3-descladinosyl-11,12-dideoxy-6-O-methyl-3-oxo-12,11-(oxycarbonyl-(1-(4-(1H-pyrazol-1-yl)benzenesulfonyl)-azetidin-3-yl)-imino)-erythromycin A. (Ex. 3.44)

3-descladinosyl-11,12-dideoxy-6-O-methyl-3-oxo-12,11-(oxycarbonyl-(1-(4-(1,2,3-thiadiazol-4-yl)benzenesulfonyl)-azetidin-3-yl)-imino)-erythromycin A. (Ex. 3.45)

3-descladinosyl-11,12-dideoxy-6-O-methyl-3-oxo-12,11-(oxycarbonyl 1-(5-cyanonaphthalene-1-sulfonyl)-azetidin-3-yl)-imino)-erythromycin A. (Ex. 3.49)

3-descladinosyl-11,12-dideoxy-6-O-methyl-3-oxo-12,11-(oxycarbonyl 1-(3-cyano-4-(1H-pyrazol-1-yl)benzenesulfonyl)-azetidin-3-yl)-imino)-erythromycin A. (Ex. 3.50)

3-descladinosyl-11,12-dideoxy-6-O-methyl-3-oxo-12,11-(oxycarbonyl-(1-(4-(2-methyl-2H-tetrazol-5-yl)benzenesulfonyl)-azetidin-3-yl)-imino)-erythromycin A. (Ex. 3.51)

3-descladinosyl-11,12-dideoxy-6-O-methyl-3-oxo-12,11-(oxycarbonyl-(1-(4-(1H-1,2,4-triazol-1-yl)benzenesulfonyl)-azetidin-3-yl)-imino)-erythromycin A. (Ex. 3.52)

3-descladinosyl-11,12-dideoxy-4-O-methyl-3-oxo-12,11-(oxycarbonyl-(1-(4-(6-methylbenzo[d]thiazol-2-yl)benzenesulfonyl)-azetidin-3-yl)imino)-erythromycin A. (Ex. 3.54)

3-descladinosyl-11,12-dideoxy-4-O-methyl-3-oxo-12,11-(oxycarbonyl-(1-(4-(2H-1,2,3-triazol-2-yl)benzenesulfonyl)-azetidin-3-yl)-imino)erythromycin A. (Ex. 3.55)

3-descladinosyl-11,12-dideoxy-6-O-methyl-3-oxo-12,11-(oxycarbonyl-(1-(4-(1,3,4-oxadiazol-2-yl)benzenesulfonyl)-azetidin-3-yl)-imino)-erythromycin A. (Ex. 3.56)

3-descladinosyl-11,12-dideoxy-4-O-methyl-3-oxo-12,11-(oxycarbonyl-(1-(3H-benzo[d][1,2,3]triazole-5-sulfonyl)-azetidin-3-yl)-imino)erythromycin A. (Ex. 3.57)

3-descladinosyl-11,12-dideoxy-6-O-methyl-3-oxo-12,11-(oxycarbonyl-(1-(3-(1H-pyrazol-1-yl)benzenesulfonyl)-azetidin-3-yl)-imino)-erythromycin A. (Ex. 3.58)

3-descladinosyl-11,12-dideoxy-6-O-methyl-3-oxo-12,11-(oxycarbonyl-(1-(3-(5-methyl-1,3,4-oxadiazol-2-yl)benzenesulfonyl)-azetidin-3-yl)imino)erythromycin A. (Ex. 3.60)

3-descladinosyl-11,12-dideoxy-4-O-methyl-3-oxo-12,11-(oxycarbonyl-(1-(4-(5-methyl-1,3,4-oxadiazol-2-yl)benzenesulfonyl)-azetidin-3-yl)-imino)-erythromycin A. (Ex. 3.61)

3-descladinosyl-11,12-dideoxy-6-O-methyl-3-oxo-12,11-(oxycarbonyl-(1-(3-(1,3,4-oxadiazol-2-yl)benzenesulfonyl)-azetidin-3-yl)-imino)erythromycin A. (Ex. 3.62)

3-descladinosy-11,12-dideoxy-6-O-methyl-3-oxo-12,11-(oxycarbonyl-(1-(3-(1,2,3-thiadiazol-4-yl)benzenesulfonyl)-azetidin-3-yl)-imino)-erythromycin A. (Ex. 3.63)

3-descladinosyl-11,12-dideoxy-6-O-methyl-3-oxo-12,11-(oxycarbonyl-(1-(3-(oxazol-2-yl)benzenesulfonyl)-azetidin-3-yl)-imino)-erythromycin A. (Ex. 3.65)

3-descladinosyl-11,12-dideoxy-6-O-methyl-3-oxo-12,11-(oxycarbonyl-(1-(3-(pyridazin-3-yl)benzenesulfonyl)-azetidin-3-yl)-imino)erythromycin A. (Ex. 3.72)

3-descladinosyl-11,12-dideoxy-6-O-methyl-3-oxo-12,11-(oxycarbonyl-(1-(4-(1,3,4-thiadiazol-2-yl)benzenesulfonyl)-azetidin-3-yl)-imino)-erythromycin A. (Ex. 3.76)

3-descladinosyl-11,12-dideoxy-6-O-methyl-3-oxo-12,11-(oxycarbonyl-(1-(3-cyano-4-fluorobenzenesulfonyl)-azetidin-3-yl)-imino)-erythromycin A. (Ex. 3.77)

3-descladinosyl-11,12-dideoxy-6-O-methyl-3-oxo-12,11-(oxycarbonyl-(1-(benzo[d]thiazole-4-sulfonyl)-azetidin-3-yl)-imino)-erythromycin A. (Ex. 3.79)

3-descladinosyl-11,12-dideoxy-6-O-methyl-3-oxo-12,11-(oxycarbonyl-(1-(5-(1H-pyrazol-1-yl)pyridine-3-sulfonyl)-azetidin-3-yl)-imino)erythromycin A. (Ex. 3.80)

3-descladinosyl-11,12-dideoxy-4-O-methyl-3-oxo-12,11-(oxycarbonyl-(1-(3-fluoro-4-(1H-imidazol-1-yl)benzenesulfonyl)-azetidin-3-yl)-imino)-erythromycin A. (Ex. 3.81)

3-descladinosyl-11,12-dideoxy-6-O-methyl-3-oxo-12,11-(oxycarbonyl-(1-(4-(1H-imidazol-1-yl)benzenesulfonyl)-azetidin-3-yl)-imino)erythromycin A. (Ex. 3.82)

3-descladinosyl-11,12-dideoxy-6-O-methyl-3-oxo-12,11-(oxycarbonyl-(1-(1H-indazole-6-sulfonyl)-azetidin-3-yl)-imino)-erythromycin A. (Ex. 3.85)

3-descladinosyl-11,12-dideoxy-6-O-methyl-3-oxo-12,11-(oxycarbonyl-(1-(3-fluoro-4-(1H-pyrazol-1-yl)benzenesulfonyl)-azetidin-3-yl)-imino)-erythromycin A. (Ex. 3.86)

3-descladinosyl-11,12-dideoxy-6-O-methyl-3-oxo-12,11-(oxycarbonyl-(1-(1H-indazole-5-sulfonyl)-azetidin-3-yl)-imino)-erythromycin A. (Ex. 3.87)

3-descladinosyl-11,12-dideoxy-6-O-methyl-3-oxo-12,11-(oxycarbonyl-(1-(4-fluoro-3-(oxazol-5-yl)benzenesulfonyl)-azetidin-3-yl)-imino)-erythromycin A. (Ex. 3.88)

3-descladinosyl-11,12-dideoxy-6-O-methyl-3-oxo-12,11-(oxycarbonyl-(1-(quinoline-6-sulfonyl)-azetidin-3-yl)-imino)-erythromycin A. (Ex. 3.89)

3-descladinosyl-11,12-dideoxy-6-O-methyl-3-oxo-12,11-(oxycarbonyl-(1-(2-methylbenzo[d]thiazole-5-sulfonyl)-azetidin-3-yl)-imino)-erythromycin A. (Ex. 3.90)

3-descladinosyl-11,12-dideoxy-4-O-methyl-3-oxo-12,11-(oxycarbonyl-(1-(naphthalene-2-sulfonyl)-azetidin-3-yl)-imino)-erythromycin A. (Ex.3.91)

3-descladinosyl-11,12-dideoxy-6-O-methyl-3-oxo-12,11-(oxycarbonyl-(1-(phthalazine-5-sulfonyl)-azetidin-3-yl)-imino)-erythromycin A. (Ex. 3.92)

3-descladinosyl-11,12-dideoxy-4-O-methyl-3-oxo-12,11-(oxycarbonyl-(1-(quinoxaline-5-sulfonyl)-azetidin-3-yl)-imino)-erythromycin A. (Ex. 3.93)

3-descladinosyl-11,12-dideoxy-6-O-methyl-3-oxo-12,11-(oxycarbonyl-(1-(1-methyl-1H-indazole-5-sulfonyl)-azetidin-3-yl)-imino)erythromycin A. (Ex. 3.94)

3-descladinosyl-11,12-dideoxy-4-O-methyl-3-oxo-12,11-(oxycarbonyl-(1-(1,3-dihydrobenzo-2,2-dioxo[c]thiophene-5-sulfonyl)-azetidin-3-yl)-imino)-erythromycin A. (Ex. 3.95)

3-descladinosyl-11,12-dideoxy-6-O-methyl-3-oxo-12,11-(oxycarbonyl-(1-(2-methyl-2H-indazole-5-sulfonyl)-azetidin-3-yl)-imino)erythromycin A. (Ex. 3.96)

3-descladinosyl-11,12-dideoxy-6-O-methyl-3-oxo-12,11-(oxycarbonyl-(1-(6-chloroimidazo[2,1-b]thiazole-5-sulfonyl)-azetidin-3-yl)-imino)-erythromycin A. (Ex. 3.97)

3-descladinosyl-11,12-dideoxy-2-fluoro-6-O-methyl-3-oxo-12,11-(oxycarbonyl-(1-(quinoxaline-5-sulfonyl)-azetidin-3-yl)-imino)-erythromycin A. (Ex. 3.98)

3-descladinosyl-11,12-dideoxy-6-O-methyl-3-oxo-12,11-(oxycarbonyl-(1-(3-cyano-4-ethoxybenzene-1-sulfonyl)-azetidin-3-yl)-imino)-erythromycin A. (Ex. 3.99)

3-descladinosyl-11,12-dideoxy-6-O-methyl-3-oxo-12,11-(oxycarbonyl-(1-(quinoline-5-sulfonyl)-azetidin-3-yl)-imino)-erythromycin A. (Ex. 3.100)

3-descladinosyl-11,12-dideoxy-6-O-methyl-3-oxo-12,11-(oxycarbonyl-(1-(8-methoxyquinoline-5-sulfonyl)-azetidin-3-yl)-imino)-erythromycin A. (Ex. 3.101)

3-descladinosyl-11,12-dideoxy-6-O-methyl-3-oxo-12,11-(oxycarbonyl-(1-(8-ethoxyquinoline-5-sulfonyl)-azetidin-3-yl)-imino)erythromycin A. (Ex. 3.102)

3-descladinosyl-11,12-dideoxy-2-fluoro-6-O-methyl-3-oxo-12,11-(oxycarbonyl-(1-(3-cyano-4-ethoxybenzene-1-sulfonyl)-azetidin-3-yl)-imino)-erythromycin A. (Ex. 3.103)

3-descladinosyl-11,12-dideoxy-6-O-methyl-3-oxo-12,11-(oxycarbonyl-(1-(benzo[d]isothiazole-6-sulfonyl)-azetidin-3-yl)-imino)-erythromycin A. (Ex. 3.104)

3-descladinosyl-11,12-dideoxy-6-O-methyl-3-oxo-12,11-(oxycarbonyl-(1-(4-ethoxy-3-methoxybenzene-1-sulfonyl)-azetidin-3-yl)-imino)-erythromycin A. (Ex. 3.105)

3-descladinosyl-11,12-dideoxy-6-O-methyl-3-oxo-12,11-(oxycarbonyl-(1-(5-chloro-2-methoxybenzene-1-sulfonyl)-azetidin-3-yl)-imino)-erythromycin A. (Ex. 3.106)

3-descladinosyl-11,12-dideoxy-6-O-methyl-3-oxo-12,11-(oxycarbonyl-(1-(3-chlorobenzene-1-sulfonyl)-azetidin-3-yl)-imino)-erythromycin A. (Ex. 3.107)

3-descladinosyl-11,12-dideoxy-6-O-methyl-3-oxo-12,11-(oxycarbonyl-(1-(4-acetamidobenzene-1-sulfonyl)-azetidin-3-yl)-imino)-erythromycin A. (Ex. 3.108)

3-descladinosyl-11,12-dideoxy-6-O-methyl-3-oxo-12,11-(oxycarbonyl-(1-(3-(cyanomethoxy)-4-methoxybenzene-1-sulfonyl)-azetidin-3-yl)-imino)-erythromycin A. (Ex. 3.109)

3-descladinosyl-11,12-dideoxy-6-O-methyl-3-oxo-12,11-(oxycarbonyl-(1-(3-(4-fluorophenoxy)benzene-1-sulfonyl)-azetidin-3-yl)-imino)erythromycin A. (Ex. 3.110)

3-descladinosyl-11,12-dideoxy-6-O-methyl-3-oxo-12,11-(oxycarbonyl-(1-(8-methylquinoline-5-sulfonyl)-azetidin-3-yl)-imino)erythromycin A. (Ex. 3.111)

3-descladinosyl-11,12-dideoxy-6-O-methyl-3-oxo-12,11-(oxycarbonyl-(1-(8-methoxyquinoxaline-5-sulfonyl)-azetidin-3-yl)-imino)erythromycin A. (Ex. 3.112)

3-descladinosyl-11,12-dideoxy-6-O-methyl-3-oxo-12,11-(oxycarbonyl-(1-(8-(difluoromethoxy)quinoline-5-sulfonyl)-azetidin-3-yl)-imino)-erythromycin A. (Ex. 3.113)

3-descladinosyl-11,12-dideoxy-6-O-methyl-3-oxo-12,11-(oxycarbonyl-(1-(8-methylquinoxaline-5-sulfonyl)-azetidin-3-yl)-imino)-erythromycin A. (Ex. 3.114)

3-descladinosyl-11,12-dideoxy-6-O-methyl-3-oxo-12,11-(oxycarbonyl-(1-(4-(2-oxooxazolidin-3-yl)benzene-1-sulfonyl)-azetidin-3-yl)-imino)-erythromycin A. (Ex. 3.115)

3-descladinosyl-11,12-dideoxy-6-O-methyl-3-oxo-12,11-(oxycarbonyl-(1-(1,3-dimethyl-2,1,3-benzothiadiazole-2,2-dioxide-0-5-sulfonyl)-azetidin-3-yl)-imino)-erythromycin A. (Ex. 3.116)

3-descladinosyl-11,12-dideoxy-6-O-methyl-3-oxo-12,11-(oxycarbonyl-(1-(3-ethyl-1-methyl-1H-indazole-5-sulfonyl)-azetidin-3-yl)-imino)-erythromycin A. (Ex. 3.117)

3-descladinosyl-11,12-dideoxy-6-O-methyl-3-oxo-12,11-(oxycarbonyl-(1-(benzhydryl)-(azetidin-3-yl)-methyl)-imino)-erythromycin A. (Ex. 4.01)

3-descladinosyl-11,12-dideoxy-6-O-methyl-3-oxo-12,11-(oxycarbonyl-(1-((quinolin-6-yl)-methyl)-(azetidin-3-yl)-methyl)-imino)-erythromycin A. (Ex. 4.14)

3-descladinosyl-11,12-dideoxy-6-O-methyl-3-oxo-12,11-(oxycarbonyl-(1-((1H-pyrrolo[2,3-b]pyridin-3-yl)-methyl)-(azetidin-3-yl)-methyl)-imino)-erythromycin A. (Ex. 4.18)

3-descladinosyl-11,12-dideoxy-6-O-methyl-3-oxo-12,11-(oxycarbonyl-(1-((6-methyl-1H-benzo[d]imidazol-7-yl)-methyl)-(azetidin-3-yl)-methyl)-imino)-erythromycin A. (Ex. 4.44)

3-descladinosyl-11,12-dideoxy-6-O-methyl-12,11-(oxycarbonyl-(1-((1H-pyrrolo[2,3-b]pyridin-3-yl)-methyl)-(azetidin-3-yl)-methyl)-imino)-3-((2-methylpyrrolidine)-1-carbonyl)-erythromycin A. (Ex. 5.03)

3-descladinosyl-11,12-dideoxy-4-O-methyl-12,11-(oxycarbonyl-(1-((quinolin-8-ylmethyl)-(azetidin-3-yl)-methyl)-imino)-3-((2-methylpyrrolidine)-1-carbonyl)-erythromycin A. (Ex. 5.04)

3-descladinosyl-11,12-dideoxy-6-O-methyl-12,11-(oxycarbonyl-(1-((1H-pyrrolo[2,3-b]pyridin-3-yl)-methyl)-(azetidin-3-yl)-methyl)-imino)-3-((2-(3-fluorophenyl)-pyrrolidine)-1-carbonyl)-erythromycin A. (Ex. 5.05)

3-descladinosyl-11,12-dideoxy-4-O-methyl-12,11-(oxycarbonyl-(1-((1H-pyrrolo[2,3-b]pyridin-3-yl)-methyl)-(azetidin-3-yl)-methyl)-imino)-3-((2-(3-fluorophenyl)-pyrrolidine)-1-carbonyl)-erythromycin A. (Ex. 5.06)

3-descladinosyl-11,12-dideoxy-6-O-methyl-12,11-(oxycarbonyl-(1-((1H-pyrrolo[2,3-b]pyridin-3-yl)-methyl)-(azetidin-3-yl)-methyl)-imino)-3-(pyrrolidine-1-carbonyl)-erythromycin A. (Ex. 5.10)

3-descladinosyl-11,12-dideoxy-6-O-methyl-3-oxo-12,11-(oxycarbonyl-(1-((quinolin-5-yl)-methyl)-(R)-pyrrolidin-3-yl)-imino)-erythromycin A. (Ex. 9.02)

3-descladinosyl-11,12-dideoxy-6-O-methyl-3-oxo-12,11-(oxycarbonyl-(1-((1H-pyrrolo[2,3-b]pyridin-3-yl)-methyl)-(R)-pyrrolidin-3-yl)-imino)-erythromycin A. (Ex. 9.03)

3-descladinosyl-11,12-dideoxy-6-O-methyl-3-oxo-12,11-(oxycarbonyl-(1-((1,8-naphthyridin-4-yl)-methyl)-(R)-pyrrolidin-3-yl)-imino)erythromycin A. (Ex. 9.05)

3-descladinosyl-11,12-dideoxy-6-O-methyl-3-oxo-12,11-(oxycarbonyl-(1-((1H-benzo[d]imidazol-4-yl)-methyl)-(R)-pyrrolidin-3-yl)-imino)-erythromycin A. (Ex. 9.06)

3-descladinosyl-11,12-dideoxy-6-O-methyl-3-oxo-12,11-(oxycarbonyl-(1-((isoquinolin-5-yl)-methyl)-(R)-pyrrolidin-3-yl)-imino)erythromycin A. (Ex. 9.07)

3-descladinosyl-11,12-dideoxy-6-O-methyl-3-oxo-12,11-(oxycarbonyl-(1-((1H-indazol-3-yl)-methyl)-(R)-pyrrolidin-3-yl)-imino)-erythromycin A. (Ex. 9.09)

3-descladinosyl-11,12-dideoxy-2-fluoro-6-O-methyl-3-oxo-12,11-(oxycarbonyl-(1-(1H-benzo[d]imidazole-2-carboxyl)-((R)-pyrrolidin-2-yl)-methyl)-imino)-erythromycin A. (Ex. 10.27)

3-descladinosyl-11,12-dideoxy-6-O-methyl-3-oxo-12,11-(oxycarbonyl-(1-((quinoxalin-8-yl)-methyl)-((S)-pyrrolidin-3-yl)-methyl)-imino)-erythromycin A. (Ex. 11.02)

3-descladinosyl-11,12-dideoxy-6-O-methyl-3-oxo-12,11-(oxycarbonyl-(1-((1H-pyrrolo[2,3-b]pyridin-3-yl)-methyl)-((S)-pyrrolidin-3-yl)-methyl)-imino)-erythromycin A. (Ex. 11.05)

3-descladinosyl-11,12-dideoxy-6-O-methyl-3-oxo-12,11-(oxycarbonyl-(1-((quinolin-4-yl)-methyl)-((S)-pyrrolidin-3-yl)-methyl)-imino)-erythromycin A. (Ex. 11.11)

Other embodiments include the examples herein and the compounds within the scope of this document. Of note are compounds having an in vitro a MIC of about 8 µg/mL or less (preferably 4 µg/mL or less) against S. pyo. that is resistant to clarithromycin by, e.g., an erm B mechanism (e.g., S. pyogenes 1079) and/or an in vitro MIC of about 0.5 µg/mL or less against S. pneumo. that is resistant to clarithromycin by, e.g., an efflux mechanism. Examples are provided.

The present invention is not limited to the erythromycin modifications referred to above. For example, C-3 modifications referred to in US 2003/0100518 (e.g., page 1); U.S. Pat. No. 6,472,371 (e.g., column 1); U.S. Pat. No. 6,140,479 (e.g., column 2); U.S. Pat. No. 6,043,226 (e.g., column 4); and US 2002/0115621 (e.g., page 1) can be used; C-5 modifications referred to in US 2003/0100518 (e.g., page 4) can be used; C-6 modifications referred to in US 2003/0100742 (e.g., page 3); US 2003/0100518 (e.g., page 4); U.S. Pat. No. 6,075,133 (e.g., columns 4-7); and US 2002/0115621 (e.g., page 2) can be used; C-8 modification referred to in US 2003/0100518 (e.g., page 1) can be used; C-9 modifications referred to in U.S. Pat. No. 4,474,768; U.S. Pat. No. 4,517,359; and US 2003/0100518 (e.g., page 1) can be used; C-12 modifications referred to in US 2003/0013665 (e.g., pages 12-14); and WO 03/004509 can be used; C-13 modifications referred to in US 2003/0100518 (e.g., page 5); and US 2003/0013665 (e.g., page 2) can be used. The foregoing documents also refer to methods of preparing analogs. These documents are fully incorporated by reference herein.

The present invention includes intermediates. For example, the invention includes compounds wherein 2-$R^2$ is H or a protecting group such as Bzh, e.g., 3-descladinosyl-11,12-dideoxy-6-O-methyl-3-oxo-12,11-(oxycarbonyl-(azetidin-3-yl)-imino)-erythromycin A or 3-descladinosyl-11,12-dideoxy-6-O-methyl-3-oxo-12,11-(oxycarbonyl-((1-benzhydryl)-azetidin-3-yl)-imino)-erythromycin A. The invention also includes precursors of 2-$R^2$ such as 1-[1,8] napthyridinyl-4-yl ethanol or 1-[1,8]napthyridinyl-4-yl ethanone.

General Preparation Methods

The compounds of the present invention can be prepared according to the descriptions, schemes, and examples herein, which are non-limiting, in combination with the knowledge of the skilled artisan.

Erythromycin and clarithromycin compounds, many of which are known in the art and are commercially available, can be suitable starting materials for preparing compounds of the invention. See, e.g., U.S. Pat. Nos. 2,653,899; 2,823,203; and 4,331,803. These documents are fully incorporated by reference herein.

Known fermentation methods can be used to introduce various C-13 modifications (Formula I, $R^5$). For example, US 2003/0100518 describes the preparation of such compounds at pages 22-27 and refers to, e.g., U.S. Pat. No. 6,437,151 and WO 99/35157. See also U.S. Pat. No. 6,472,371 at columns 25-32. All of the above documents are fully incorporated by reference herein.

Known methods can be used to introduce variation at the C-6 position (Formula I, $R^3$). For example, U.S. Pat. No. 6,075,133, columns 55-58, describes alkylations at C-6. The above documents are fully incorporated by reference herein. Appropriate functional group protection and deprotection can be required for certain transformations.

Known methods can be used to protect at 2' and 4" (Formula I, $R^{13}$ and $R^{16}$). Incorporation of $R^{13}$ and $R^{16}$ groups can be accomplished by reaction of a compound of Formula II (Scheme I) where $R^{13}$ and $R^{16}$ are hydrogen with an acid anhydride or acid chloride containing an $R^{13}$ group in a solvent such as DCM, THF, or toluene in the presence of a base such as TEA and in the presence of an activator or catalyst such as DMAP at about RT for about 2 to 24 h. If 2 eq. of anhydride or acid chloride are used, an $R^{13}$ group will be installed at both $R^{13}$ (C-2') and $R^{16}$ (C-4"). If 1 eq. is used, only group $R^{13}$ will be installed. A group $R^{16}$ can then be installed (at C-4") in a subsequent step, thus differentiating $R^{13}$ from $R^6$. Various protecting groups ($R^{13}$ and $R^{16}$) can be used, such as those described in Greene et al., infra, including known acyl, carbamoyl, and silyl protecting groups, and the like, which can be introduced by known methods. In some preferred embodiments, the protecting reagent is acetic anhydride. Other examples of hydroxy-protecting groups include methylthiomethyl, TMS, TBDMS, TBDPS, ethers such as methoxymethyl, and esters including Ac, Bz, and the like. Examples of aprotic solvents include DCM, chloroform, DMF, THF, NMP, DMSO, diethylsulfoxide, DMF, N,N-dimethylacetamide, hexamethylphosphoric triamide, a mixture of any of the foregoing with or without any of: ether, THF, 1,2-dimethoxyethane, MeCN, EtOAc, acetone or the like. Other modifications are known in the literature and to the ordinarily skilled artisan.

Compounds can be further modified, e.g., as depicted in Schemes 1 to 3 to obtain the compounds of Formulas IV-VII, XVI, and XVII, i.e., compounds wherein diradical 3 is >C(O), 4 is —O—, and 5 is —C(O)—.

Scheme 1

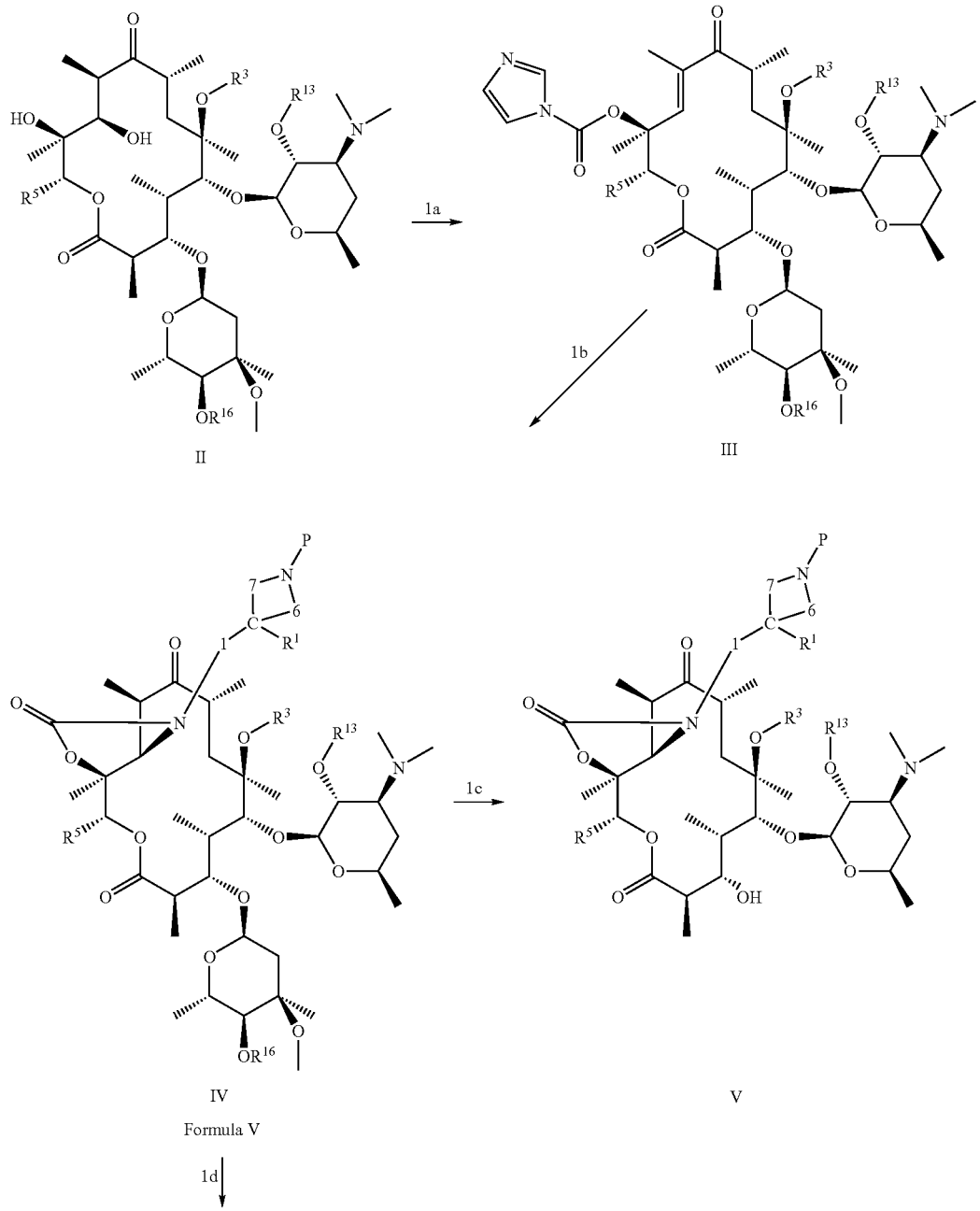

-continued

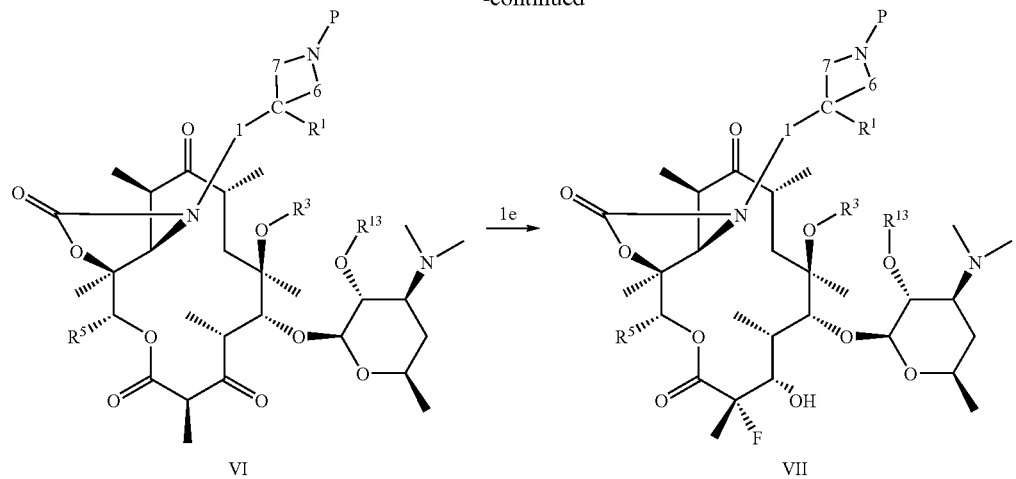

Scheme 1 illustrates preparation of compounds of Formulas III-VII. Formula III can be prepared as in Step 1a by reaction of Formula II (wherein $R^{13}$ and $R^{16}$ are not hydrogen and the $R^{13}$ and $R^{16}$ groups contain no unprotected primary alcohols or primary or secondary amines) with about 3 to 5 eq. of CDI. See, e.g., J. Org. Chem., 53, 2340 (1988), which is incorporated herein by reference in its entirety. The reaction can be carried out in an aprotic solvent such as MeCN, THF, IPE, DMF, or a mixture thereof in the presence of about 2 to 5 eq. of a base such as DBU at about 25 to 40° C. for about 2 to 12 h.

A compound of Formula IV can be prepared as in Step 1b from the corresponding compound of Formula III by reaction with the primary amine of a desired N-11 side chain in a solvent such as MeCN or DMF in the presence of a base such as TEA or DBU at about 40 to 80° C. for about 12 to 72 h. Group P in Formula IV represents a suitable protecting group or can be represent a headpiece 2-$R^2$ as defined herein for Formula I.

The cladinose moiety of Formula IV can then be removed as in Step 1c by reaction with an acid such as HCl, e.g., in a binary solvent mixture containing water and an alcohol such as EtOH at about RT to 45° C., preferably about RT to 40° C., for about 6 to 24 h, thus affording Formula V. Representative acids include dilute HCl, sulfuric acid, perchloric acid, chloroacetic acid, dichloroacetic acid, or trifluoroacetic acid. Suitable solvents for the reaction include MeOH, EtOH, IPA, butanol, or the like, and mixtures.

Step 1d illustrates oxidation of the C-3 hydroxyl group to an oxo group to obtain Formula VI. This can be accomplished using, e.g., a modified Swern oxidation. For example, a compound of Formula VI can be reacted with EDC and pyridinium trifluoroacetate in a solvent such as DCM at about RT to 50° C. for about 6 to 24 h.

When P is a protecting group, deprotection of Formula VI and introduction of a desired substituent can be accomplished by hydrogenation. For a compound of Formula VI wherein group P represents a protecting group such as Bzh, Bn, or CBZ, this group can be removed by reaction with hydrogen gas at about 1 to 4 atmospheres of pressure in the presence of a catalyst such as palladium on carbon or palladium hydroxide on carbon in a solvent such as MeOH, EtOH, EtOAc, or THF at about 25 to 60° C. for about 4 to 24 h. In the case where group P is a protecting group such as BOC, this group can be removed by reaction with TFA in a solvent such as DCM at about 0 to 25° C. for about 0.5 h, or can be removed by reaction with an acid such as HCl in, e.g., a solvent mixture containing water with MeOH, EtOH, or THF at about 25 to 50° C. for about 1 to 6 h.

Once a protecting group is removed, a new group of the structure 2-$R^2$ can be incorporated into a compound of Formula VI, e.g., in one of the following ways: 1) where diradical 2 is —C(O)(CH$_2$)$_n$—, a carboxylic acid containing a group (CH$^2$)$_n$R$^2$ can be reacted in the presence of a carbodiimide such as EDC in the presence of an activator such as HOBT and/or DMAP in a solvent such as DCM, DMF, THF or MeCN at about 25 to 40° C. for about 2 to 20 h. Alternatively, an acid chloride containing a group $R^2$ can be coupled in a solvent such as DCM, THF or MeCN in the presence of a base such as TEA, DIEA, NaHCO$_3$, or potassium carbonate at about 0 to 40° C. for about 1 to 8 h; 2) where diradical 2 is —SO$_2$(CH$_2$)$_m$— or —SO$_2$N(R$^6$)— a sulfonyl chloride or sulfamoyl chloride containing a group (CH$_2$)$_m$R$^2$ or N(R$^6$)R$^2$ can be reacted in the presence of a base such as TEA, DIEA, NaHCO$_3$, or potassium carbonate in a solvent such as DCM, DMF, THF, or MeCN at about 25 to 40° C. for about 30 min. to 4 h; 3) where diradical 2 is —(C(R$^6$)(R$^7$))$_n$—, an aldehyde containing a group $R^2$ or a ketone containing R$^6$—C(O)—(C(R$^6$)(R$^7$))$_n$—, can be similarly reacted in the presence of a base in a solvent such as MeOH, EtOH, DCM or THF, in some cases requiring the addition of 4A molecular sieves, at about 25 to 60° C. for about 2 to 18 h to form the corresponding imine, which can then be further reacted with a reducing agent such as sodium cyanoborohydride or sodium triacetoxyborohydride at about 25 to 40° C. for about 4 to 24 h; 4) where diradical 2 is —(C(R$^6$)(R$^7$))$_n$—, a halide or sulfonate containing a group —(C(R$^6$)(R$^7$))$_n$—R$^2$ can be reacted in the presence of a base at about 25 to 150° C. in a solvent such as DCM, THF, or MeCN, for about 0.1 to 12 h; 5) where diradical 2 is C(O)N(R$^6$), an isocyanate containing a group R$^2$ or a carbamoylchloride of the structure ClC(O)N(R$^2$)(R$^6$) can be reacted in the presence of a base such as TEA, DIEA, NaHCO$_3$, or potassium carbonate in a solvent such as DCM, DMF, THF, or MeCN at about 25 to 60° C. for about 2 to 8 h; and 5) where diradical 2 is C(O)O(CH$_2$)$_n$, a chloroformate containing a group (CH$_2$)$_n$—R$^2$ can be reacted in the presence of a base such as TEA, DIEA, NaHCO$_3$, or potassium carbonate in a solvent such as DCM, THF, or MeCN at about 25 to 40° C. for about 30 min. to 4 h, thus completing the inter-conversion of group 2-$R^2$. (Preparation of the reagents for introducing 2-$R^2$ to the macrolide is discussed below.)

Formula VII can be prepared as in Step 1e by first generating an anion/enolate at the C-2 carbon by reaction of VI with a base such as sodium hydride, lithium diisopropylamide, or lithium hexamethyldisilazide in a solvent such as DMF at a about −50 to −30° C. for about 10 to 30 min. This anion can then be reacted with a variety of electrophiles including an electropositive fluorinating agent such as Selectfluor® (marketed by Air Products and Chemicals, Inc). Incorporation of a group $R^4$ in this manner can be carried out before or after the inter-conversion of group 2-$R^2$ described in Step 1d, however, might be limited in some cases to the compatibility of group 2-$R^2$ to the conditions of $R^4$ installation just described. For this chemistry to proceed, group $R^{13}$ cannot be hydrogen. In a final step, a non-hydrogen $R^{13}$ group for either VI or VII can be removed (replaced by hydrogen) as known in the art by reaction in a solvent such as MeOH at about 25 to 60° C. for about 6 to 24 h to remove acyl, or TBAF in THF for silyl. Group $R^{13}$ or $R^{16}$ can be similarly removed from any final compound of the present invention.

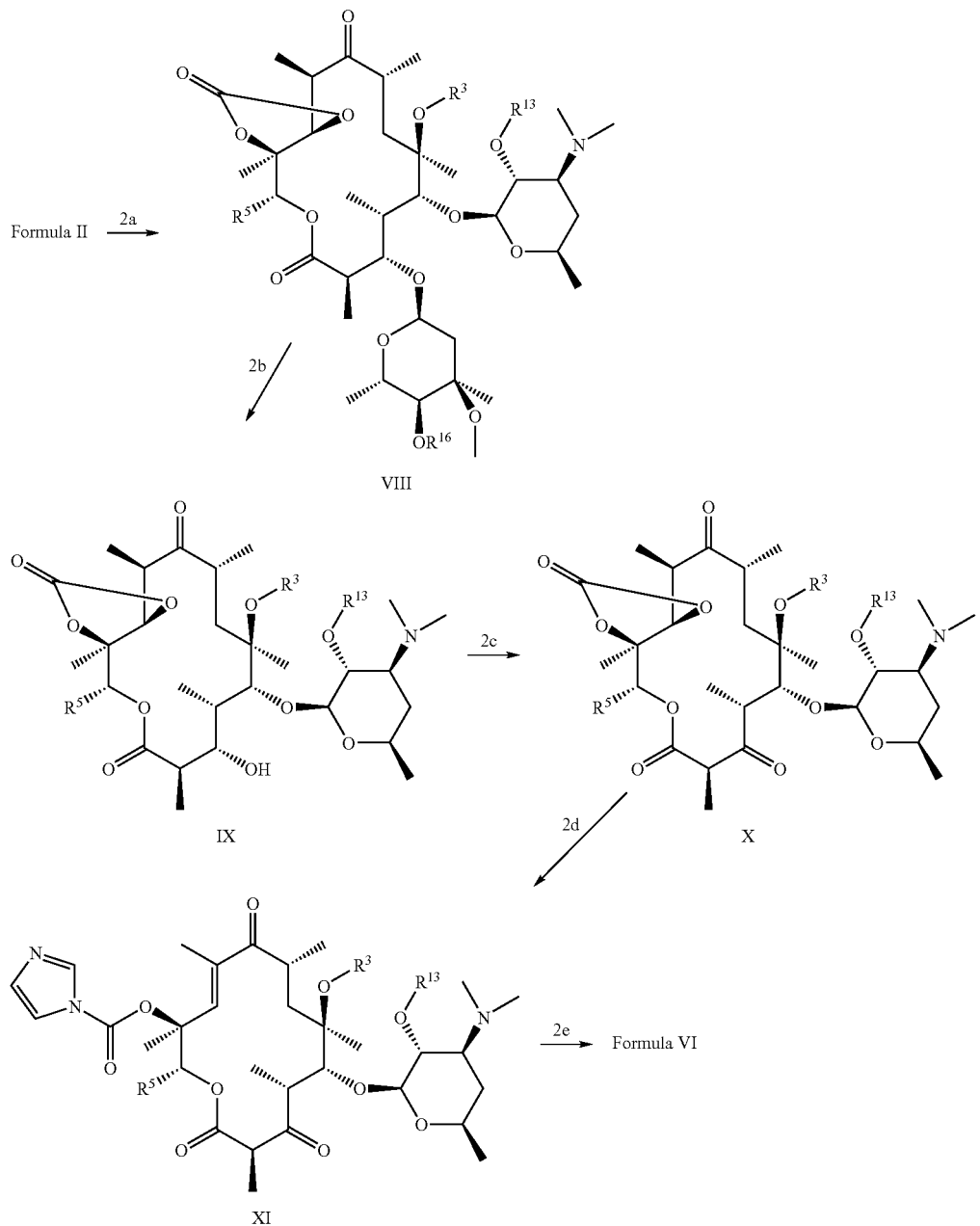

Alternatively, a compound of Formula VI wherein 3 is >C(O), 4 is —O—, and 5 is —C(O)— can be prepared as outlined in Scheme 2. As in Step 2a, Formula II can be converted to the cyclic carbonate VIII by treatment under anhydrous conditions with a phosgene equivalent such CDl, disuccinylcarbonate or ethylenecarbonate in a solvent such as DCM, MeCN, benzene, toluene, or a mixture thereof in the presence of a base such as TEA, DIEA, NaHCO$_3$, or potassium carbonate at about 25 to 50° C. for about 2 to 20 h.

The cladinose moiety can be removed as in Step 2b, either by mild aqueous acid hydrolysis or by enzymatic hydrolysis, as described in Step 1c, to afford Formula IX.

Step 2c illustrates oxidation of Formula IX to the ketone X using a modified Swern oxidation procedure, as discussed above for Scheme 1. Alternatively, this reaction can be affected by reaction of IX with the complex formed between N-chlorosuccinamide with dimethylsulfide in a solvent such as DCM at about −20 to 0° C. for about 1 h, followed by reaction with at least about 2 eq. of a base such as TEA at about −20 to 0° C. for about 1 h followed by an additional reaction time of about 1 h at about 25° C.

Formula XI can be prepared as in Step 2d by treatment under anhydrous conditions by reaction with CDl in the presence of a base such as DBU in a solvent such as DCM or DMF at about 25 to 40° C. for about 24 to 48 h. This conversion can also be done stepwise by first treating a compound of Formula X with about 1 to 3 eq. of a base such as DBU in a solvent such as benzene or toluene at about 40 to 80° C. for about 4 to 24 h. The resulting allylic alcohol can then be treated with a base such as sodium hydride in a solvent such as THF or DMF at about −40 to 0° C. for about 10 to 30 min. The anion produced can then be reacted with CDl generating the corresponding compound of Formula XI.

Formula VI can be obtained as in Step 2e by treatment with a desired primary amine, in the general manner of Scheme 1. When P is a protecting group, it can be replaced with a desired substituent, as described in Scheme 1. Moreover, Formula VI can be halogenated, etc., as discussed above for Scheme 1.

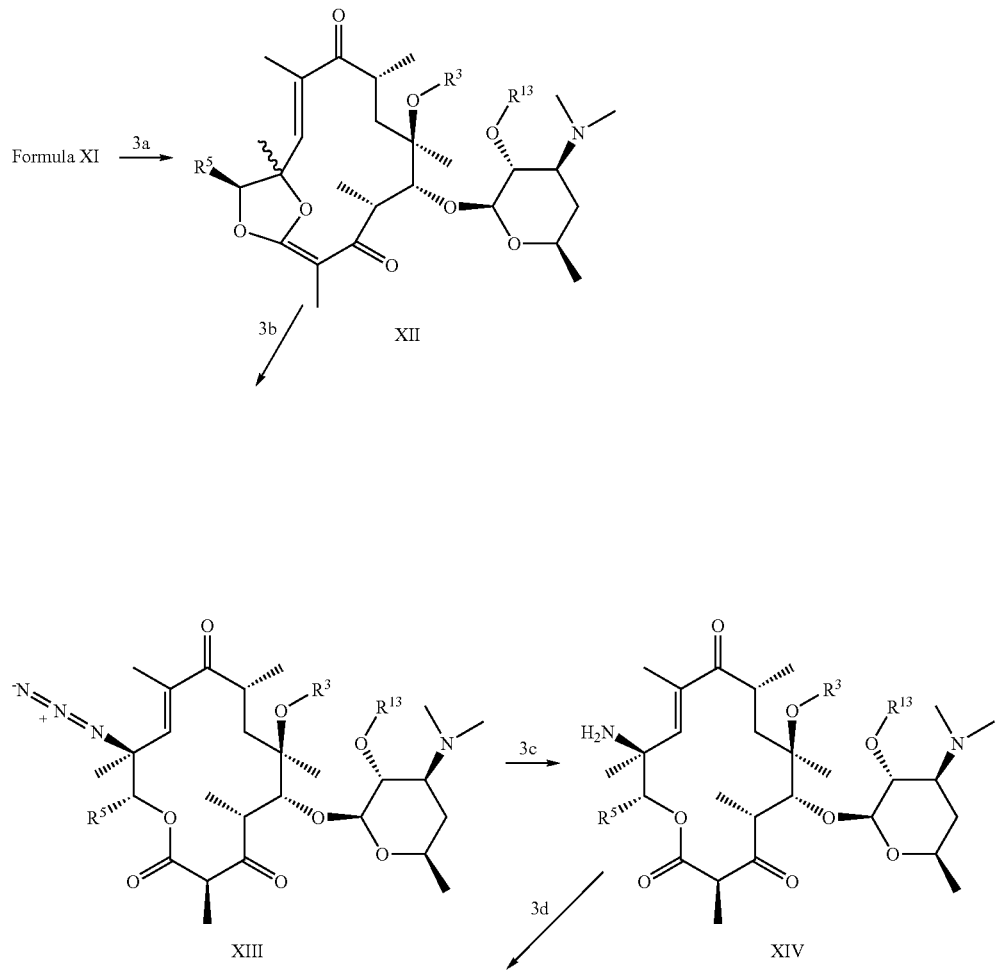

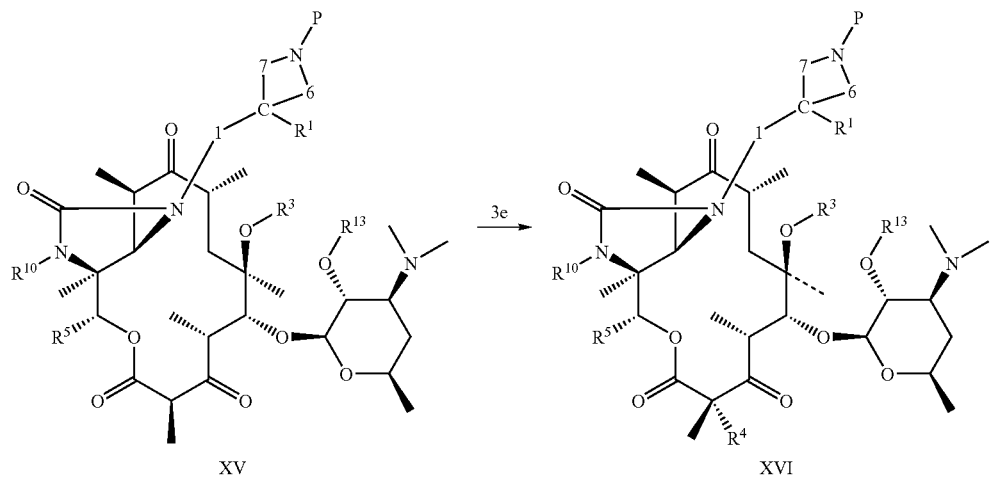

Compounds of the present invention wherein diradical 3 is >C(O), 4 is a group N—$R^{10}$, and 5 is —C(O)— can be prepared as in Scheme 3, starting from Formula XI. Similar methods are referred to in US 2003/0013665 (pages 7-14) and US 2002/0052328 (page 5), which are fully incorporated herein by reference.

Ketene acetal XII can be prepared as in Step 3a by treating XI with a base, such as DBU, 1,5-diazabicyclo[4.3.0]non-5-ene, DIEA, TEA, lithium hexamethyldisilazide, or potassium hexamethyldisilazide, preferably DBU, in the presence of a polar aprotic solvent, such as MeCN, DMF, or THF, preferably MeCN. The reaction can be stirred at about 20 to 100° C., preferably about 60 to 80° C., for about 30 min. to 3 h.

Azide XIII can be prepared as in Step 3b with about 3 eq. of an azidonation reagent such as trimethylsilylazide, sodium azide or tributyltin azide, preferably trimethylsilylazide, in the presence of a Lewis acid, such as tin-tetrachloride, titanium(IV)chloride, boron trifluoride diethyl etherate, or aluminum trichloride, preferably tin-tetrachloride, and an aprotic solvent. Suitable solvents include DCM, dichloroethane, chloroform, or carbontetrachloride, preferably DCM. The reaction can be started at about −80° C. and warmed to about 25° C. and subsequently reacted for about 4 to 24 h.

Reduction as in Step 3c of Formula XIII to obtain Formula XIV can be achieved by treatment with a reducing metal such as zinc in an acid such as acetic acid at about RT for about 30 min. to 2 h.

Amine XIV can be converted to the corresponding isocyanate by treatment with phosgene or triphosgene in the presence of a base, such as TEA or pyridine, and an aprotic solvent, such as THF or dioxane. The reaction can be carried out at about 0 to 50° C., preferably about 0° C., for about 0.5 to 12 h, preferably about 30 min.

The isocyanate can be converted to cyclic urea XV as in Step 3d by reaction with a desired primary amine in the presence of an aprotic solvent, such as THF, dioxane, or DMF to form a linear urea. The reaction can be carried out at about 0 to 100° C., preferably about 25° C., for about 0.5 to 12 h, preferably about 6 h. The resulting product can then be heated in the presence of a base such as potassium hydroxide in a solvent such as toluene at about 60 to 80° C. for about 10 to 30 min. to form the corresponding cyclic urea XV. The reaction can be carried out at about 25 to 100° C., preferably about 80° C., for about 0.5 to 12 h, preferably about 3 h.

Where $R^{10}$ is to be other than H, the compound can be treated with a strong base such as KHMDS at about −10 to 25° C., in a solvent such as THF, for about 1 to 4 h in the presence of, e.g., an alkyl or allyl halide, e.g., about at least 1 eq. of $R^{10}$-L, wherein L is a suitable leaving group such as halogen, or alternatively, mesylate or tosylate, at the time and temperature conditions noted above.

Group P of a compound of Formula XV is a protecting group, the inter-conversion of the 2-$R^2$ group can be accomplished in the same manner as Scheme 1. Incorporation of a group $R^4$ (as in Step 3e) to form a compound of Formula XVI can be carried out in a manner analogous to that described in Scheme 1.

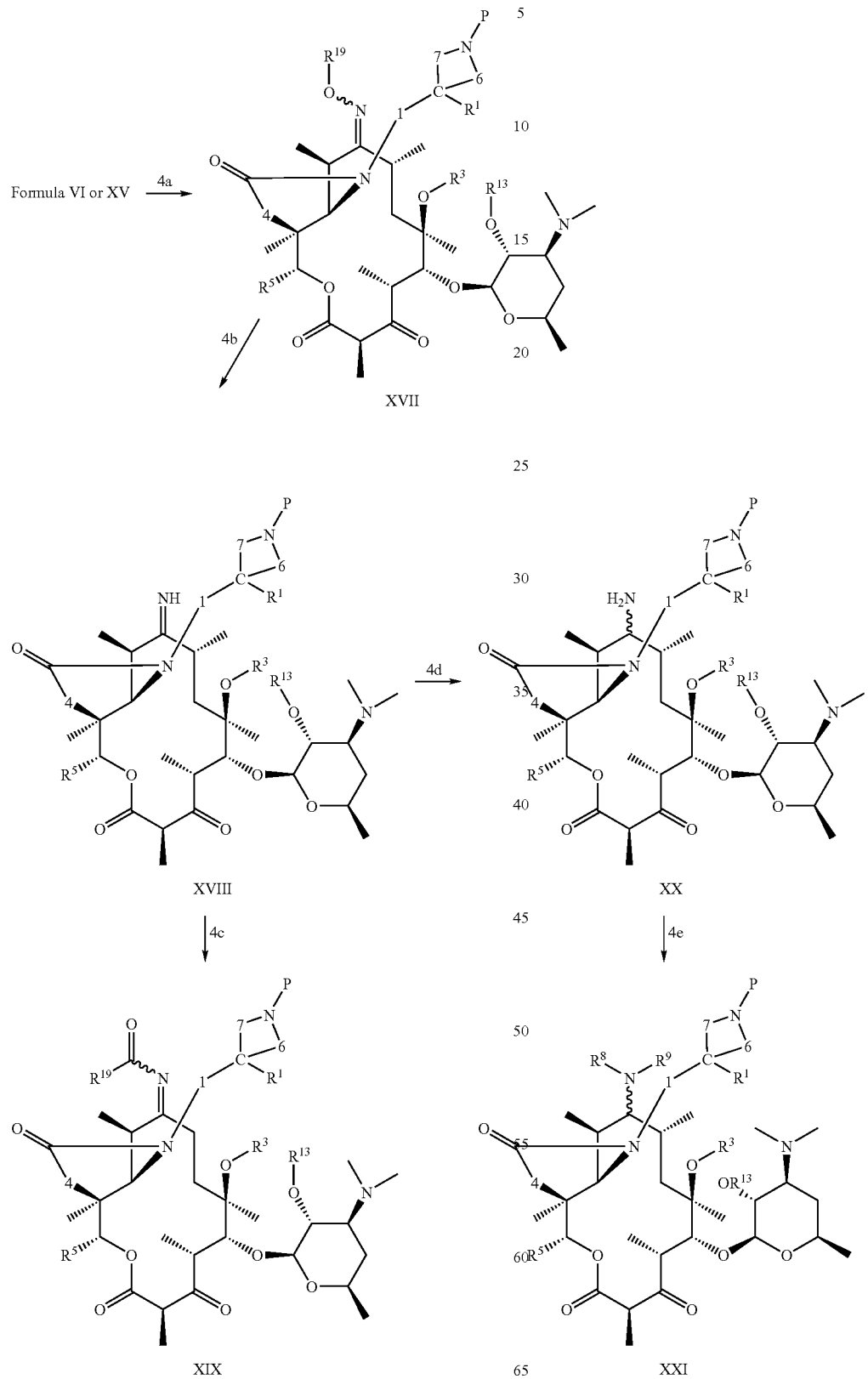

Compounds of the present invention where diradical 3 is >C(O), 4 is —O— or —N(R¹⁰)—, and 5 is other than —C(O)—, can be prepared as in Scheme 4. A starting compound of Formula VI or XV can be treated with a hydroxyl amine of structure R¹⁹—O—NH₂ as a free-base or hydrochloride salt in the presence of a base such as TEA in a solvent such as DCM or THF at about RT for about 4 to 24 h, thus providing Formula XVII as in Step 4a. Where R¹⁹ is H, a compound of Formula XVII wherein R¹⁹ is other than hydrogen can be prepared by reaction of the corresponding compound where R¹⁹ is hydrogen with an alkyl halide or substituted alkyl halide in a solvent such as DCM, MeCN, or DMF in the presence of a base such as TEA, DIEA, or NaHCO₃ at about 25 to 60° C. for about 1 to 24 h.

Where R¹⁹ of XVII is H, a compound of Formula XVIII can then be prepared as in Step 4b by reaction of XVII with a reducing agent such as TiCl₃ in a solvent such as MeOH or EtOH at about RT for about 4 to 24 h.

A compound of Formula XIX can be prepared as in Step 4c by reaction of XVIII, e.g., as described in US 2004/0171818, which is fully incorporated by reference herein, in DCM in the presence of TEA and with an acylating agent containing a desired R¹⁹ group.

A compound of Formula XX can be prepared as in Step 4d by reaction with a reducing agent such as sodium cyanoborohydride or sodium triacetoxyborohydride in a solvent such as water, MeOH, EtOH, or a mixture thereof at about RT for about 12 to 24 h.

A compound of Formula XXI can be prepared as in Step 4e by reductive amination using an aldehyde containing an R⁸ group as described in J. Med. Chem., 33, 3086 (1990), which is fully incorporated by reference herein. Alternatively, direct alkylation can be employed. In the case where R⁸ and R⁹ are both non-hydrogen, sequential reductive aminations can be performed on a compound of Formula XX using aldehydes containing groups R⁸ and R⁹. XXI can be fluorinated. According to ordinary skill in the art, modifications at C-9 (diradical 5 in Formula I) are general to the compounds of Formula I. See also, EP 0345627 and WO 02/57286, which are also fully incorporated by reference herein.

Scheme 5

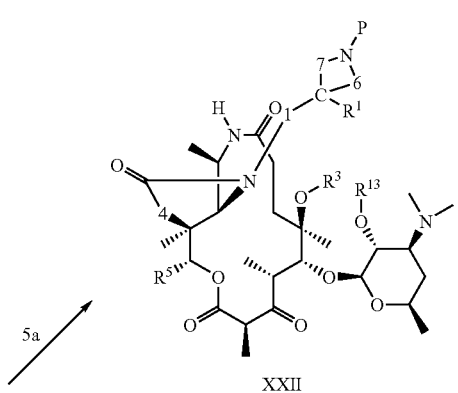

XXII

Formula XVII

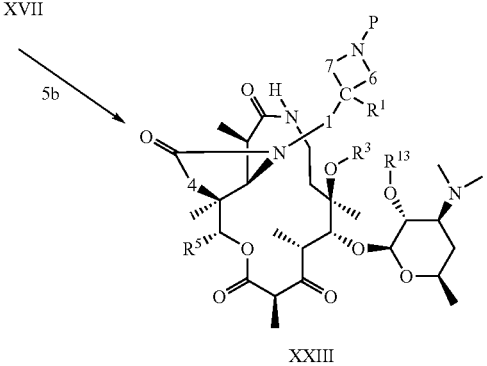

XXIII

Compounds of the present invention wherein diradical 3 is >C(O), 4 is —O— or —N(R¹⁰)—, and 5 is —C(O)NR¹⁹— or —N(R¹⁹)C(O)— can be prepared as in Scheme 5 and referred to in, e.g., U.S. Pat. No. 6,262,030, which is fully incorporated by reference herein.

Compounds wherein diradical 3 is other than >C(O) can be prepared according to Scheme 6. Similar transformations are known, e.g., as in JP2001-72669, which is fully incorporated by reference herein.

A compound of Formula V or corresponding intermediate being modified, e.g. C-9 (diradical 5) as disclosed herein or known in the art, can be reacted with a desired carboxylic acid in the presence of a carbodiimide such as EDC in the presence of an activating agent such as HOBT or DMAP in a solvent such as DCM at about 25 to 40° C. for about eight to 48 h, thus forming Formula XXIV (wherein diradical 3 is other than >C(O)— or >CHOC(O)N(R¹⁴)R¹⁵) as in Step 6a. This transformation can only be carried out on a compound of Formula V wherein group R¹³ is not hydrogen. In the cases where group P is a protecting group, the inter-conversion of group 2-R² can be accomplished in the same manner as that described in Scheme 1. At this point the protecting group R¹³ can then be removed in a similar manner to that described in Scheme 1.

A compound of Formula XXV can be formed as in Step 6b by reaction with about 1 to 3 eq. of bis-succinimidyl carbonate in a solvent such as MeCN, in the presence of a base such as TEA or DIEA at about RT for about 2 to 8 h. This transformation can only be carried out on a compound wherein group R¹³ is not hydrogen.

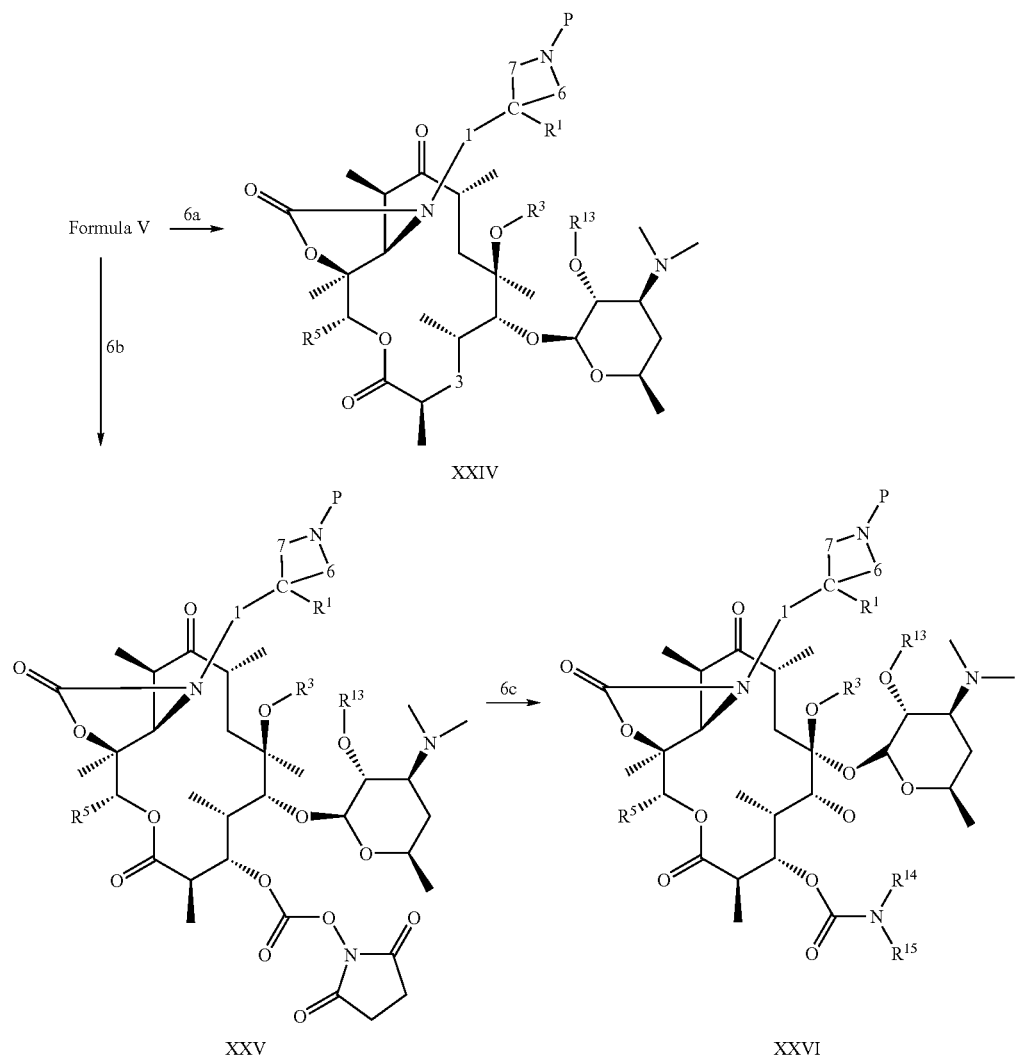

XXIV

XXV

XXVI

A compound of Formula XXVI can then be prepared as in Step 6c by reaction with an amine of the structure $HNR^{14}R^{15}$ in a solvent such as DCM, THF, DMF, or MeCN in the presence of a base such as TEA or DIEA at about RT for about 30 min. to 4 h. In the cases where group P is a protecting group, the inter-conversion of the 2-$R^2$ group can be accomplished in the same manner as that described in Scheme 1. At this point the protecting group $R^{13}$ can be removed as described in Scheme 1. See also US 2003/0100518 (e.g., page 1); U.S. Pat. No. 6,472,371 (e.g., column 1); U.S. Pat. No. 6,140,479 (e.g., column 2); U.S. Pat. No. 6,043,226 (e.g., column 4); and US 2002/0115621 (e.g., page 1), which are fully incorporated by reference herein.

A group [1-(Ring A)] for bridging N-11 to group 2-$R^2$ of Formula I can be derived from any differentially protected diamine, and can be incorporated into a macrolide as illustrated in Schemes 1-6. For illustration, preparations of some differentially protected tethering groups are described in Schemes 7-9. Alternatively, the tether and headpiece group 2-$R^2$ can be prepared as a single unit and incorporated as such into the macrolide also as in Schemes 1-6.

Scheme 7

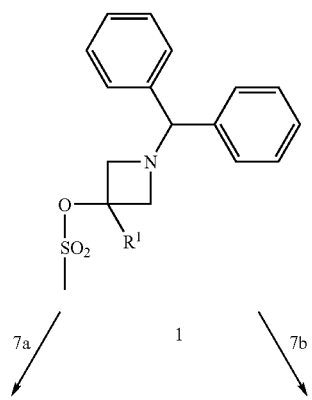

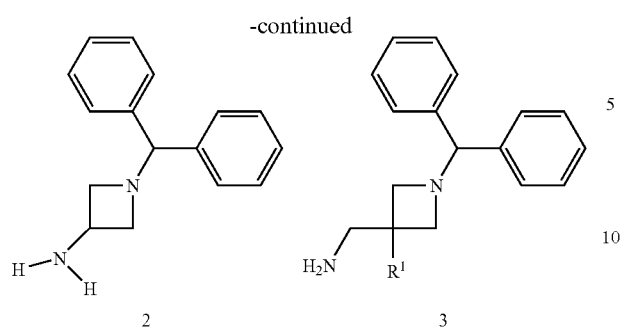
Scheme 8
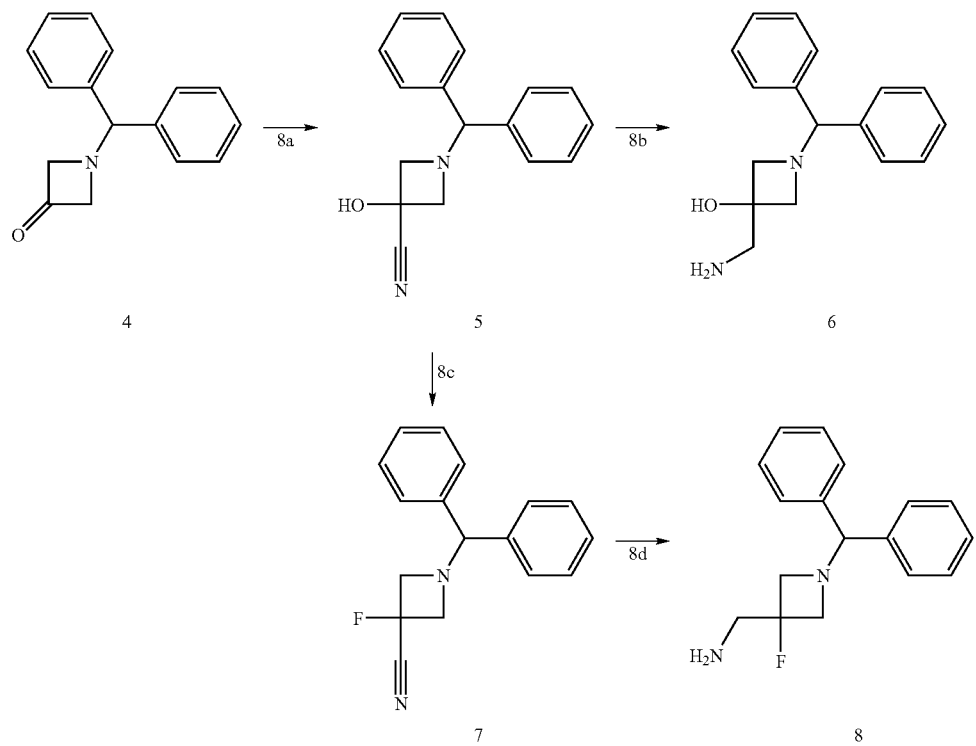
Scheme 9
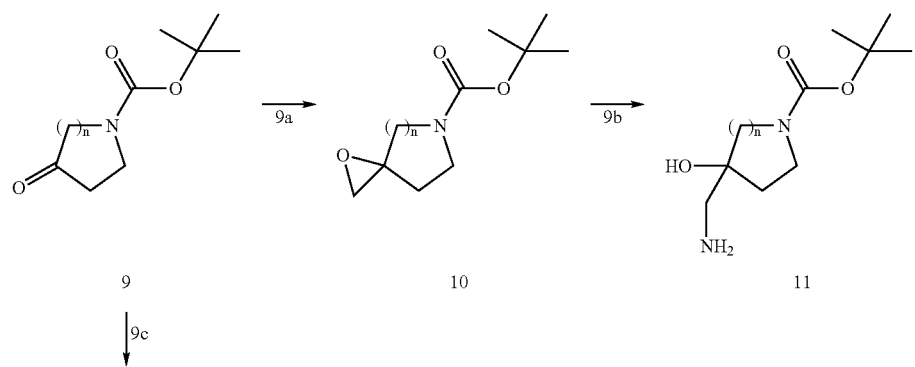

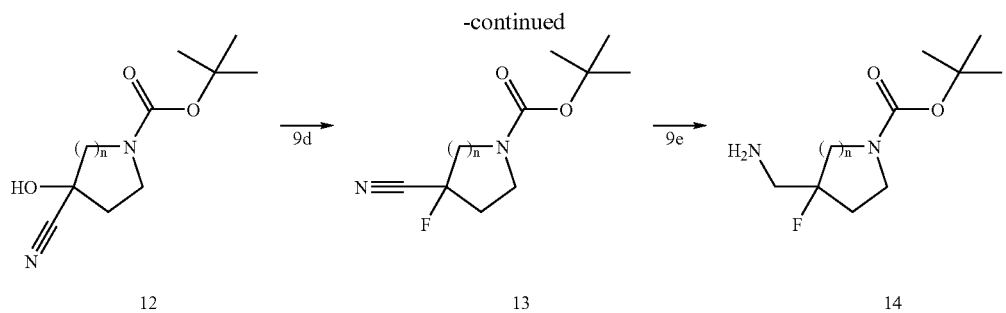

Scheme 7 illustrates the preparation of certain tether groups containing an azetidine moiety, wherein $R^1$ is H or alkyl. Methanesulfonic acid 1-benzhydryl-azetidin-3-yl ester (Compound 1 of Scheme 7, wherein $R^1$ is H) is known in the art and can be purchased from Oakwood Products. Compound 1 can be converted as in Step 7a to the corresponding azide by dissolving in an appropriate polar organic solvent, preferably DMF, adding sodium azide in excess and heating the resulting mixture to about 60-100° C., preferably about 80° C., for about 12 to 24 h. After aqueous workup, the crude azide product can then be treated with excess triphenyl phosphine and refluxed in a solvent such as THF for about 3-10 h. This mixture can be hydrolyzed by adding $NH_4OH$ and heating to about 50 to 70° C. for about 12-24 h, yielding Compound 2.

Compound 3, wherein $R^1$ is H or alkyl can be prepared as in Step 7b by displacement of the mesylate with cyanide followed by lithium aluminum hydride reduction, e.g., using the method of Frigola, J., et al., J. Med. Chem., 36(7), 801 (1993), which is fully incorporated by reference herein.

Scheme 8 illustrates preparation of certain other tether groups containing an azetidine moiety, wherein $R^1$ is OH or F. Starting ketone 4 is known and commercially available. Compound 5 can be prepared by reaction of 4 as in Step 8a with potassium cyanide in the presence of sodium bisulfite in a solvent such as dioxane, THF, or EtOAc or a combination thereof at about 0 to 25° C. for about 24 to 48 h. See also, WO 04/94407, which is fully incorporated by reference herein.

As in Step 8b, reduction of Compound 5 to amine 6 can be carried out by reaction with an excess of about 2 eq. lithium aluminum hydride in a solvent such as THF at about 0 to 25° C. for about 4 to 6 h.

Compound 7 can be prepared as in Step 8c by reaction of Compound 5 with DAST by the method of Stelzer et al., Tetrahedron Asymmetry, 4, 161 (1993), which is fully incorporated by reference herein. Reduction of Compound 7 to amine 8 can be conducted as in Step 8d in an analogous manner to that described for Step 8b.

Preparation of tether intermediates 11 and 14 can be conducted as outlined in Scheme 9. From Compound 9, wherein n is 1 to 3, epoxidation to form the corresponding Compound 10 can be achieved by reaction with trimethylsulfonium iodide in the presence of a strong base such as sodium hydride in a solvent such as DMF, DCM or DMSO, preferably DMF, at about RT for about 8 to 18 h.

Corresponding Compound 11 can be prepared by reaction with $NH_4OH$ at about 25 to 80° C. for about 1 to 6 h, as in Step 9b. Compound 15 can be prepared from 9 as in Steps 9c-e in an analogous manner to Scheme 8.

The headpiece reagents (i.e., reagents for forming Formula I, 2-$R^2$ or Scheme 1, group P) to be reacted with the cyclic amine (Formula I, Ring A) nitrogen of the macrolide template for the examples are commercially available, known in the art, within the ordinary skill in the art in view of this specification, or described or enabled herein by Scheme 10 and Preparations 9 to 26.

Sulfonylchlorides used to prepare sulfonamides can be prepared in different ways. Aromatic or heteroaromatic systems can be reacted with excess chlorosulfonic acid in a solvent such as chloroform at about 50 to 80° C. for about 12 to 48 h. After concentration, the intermediate sulfonic acid can be converted to the corresponding sulfonyl chloride by treatment with phosphorous oxychloride at reflux for about 12 to 24 h.

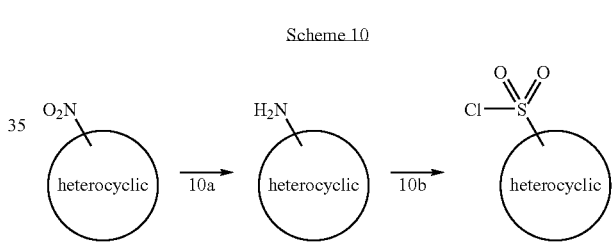

Scheme 10

Alternatively, sulfonylchlorides can be prepared from aromatic or heteroaromatic nitro- or amine-containing compounds as illustrated in Scheme 10. A nitrocompound can be converted to the corresponding amino compound as in Step 10a by a variety of known methods, including indium reduction, or catalytic hydrogenation using palladium or platinum-based catalysts. The corresponding aromatic or heteroaromatic sulfonyl chloride can then be prepared from the amine as in Step 10b by reaction with sodium nitrite in a mixture of glacial acetic acid and conc. HCl at about 0 to 5° C. for about 5 to 15 min. A satd. solution of sulfur dioxide and excess copper(II)chloride in aqueous acetic acid can then be added and stirred at about RT for about 12 to 36 h followed by basic aqueous work-up.

COMPOUND EXAMPLES

The compounds listed in Tables 1 to 16 were prepared and characterized. Specifically, macrolide intermediates (templates) were prepared, followed by coupling of the cyclic amine (Formula I, Ring A) nitrogen of the template to the desired headpiece to incorporate group 2-$R^2$ of Formula I. Described below are non-limiting macrolide template preparations, non-limiting headpiece reagent preparations, and non- limiting examples of final compounds according to the invention.

Preparation 1: 3-descladinosyl-11,12-dideoxy-6-O-methyl-3-oxo-12,11-(oxycarbonyl-(azetidin-3-yl)-imino)-erythromycin A Step 1: DBU (10 mL, 67 mmol) was added to 1-benzhydryl-azetidine-3-ylamine (9.0 g, 37.8 mmol) dissolved in anhydrous MeCN (100 mL) at RT. To this solution was added 11-deoxy-2',4"-diacetyl-10,11-didehydro-12-O((1H-imidazol-1-yl)carbonyl)-6-O-methyl-erythromycin A (32.5 g, 35.8 mmol) and the resulting mixture was heated (50° C.) for 7.5 h, then allowed to stir overnight at RT. A white precipitate was collected by filtration (21 g, 19.5 mmol). The filtrate was concentrated to about 25 mL before adding water (20 mL), satd. aq. NaHCO$_3$ solution (30 mL), and extracting the resulting mixture with DCM (50 mL). The organic layer was washed with satd. aq. NaHCO$_3$ solution, dried over Na$_2$SO$_4$, and concentrated under vacuum to a tan foam. MS (ESI+) for m/z 540 (M/2+H)$^+$.

Step 2: The product from Step 1 was dissolved in EtOH (100 mL) and 2N HCl (100 mL), heated (40° C.) for 3 h, then cooled to 30° C. and stirred overnight. The resulting mixture was concentrated under vacuum, maintaining the bath at 28° C., to about half of the original volume. To the resulting concentrate was added DCM (100 mL), followed by careful addition of solid potassium carbonate to basify the aqueous layer (to pH 10). The organic layer was separated, and the aqueous layer was re-extracted with DCM (3×100 mL). The combined organic layers were dried over Na$_2$SO$_4$ and concentrated to a white foam. MS (ESI+) for m/z 440 (M/2+H)$^+$.

Step 3: The crude product from Step 2 was re-dissolved in anhydrous DCM (200 mL) and to which were added anhydrous DMSO (20 mL, 282 mmol), pyridinium trifluoroacetate (15 g, 77.7 mmol), and finally EDC (30 g, 156.5 mmol). The mixture was stirred at RT for 3 h and then treated with satd. aq. NaHCO$_3$ solution (30 mL), water (30 mL). The reaction mixture was placed in a separatory funnel and the layers allowed to separate for several hours. The aqueous layer was re-extracted with DCM (3×75 mL) and the combined organic layers were washed with water (50 mL). After drying the organics over Na$_2$SO$_4$ the solvent was removed under vacuum to yield a yellow foam. MS (ESI+) for m/z 439 (M+H)$^+$.

Step 4: The yellow foam from Step 3 was re-dissolved in MeOH (200 mL) and heated (50° C.) for 24 h, then concentrated under vacuum to dryness. This solid material was rinsed with hexanes/diethyl ether (2/1), treated with MeOH (50 mL) and the resulting slurry heated on a steam bath up to the boiling point, then cooled to RT. The resulting white solid was filtered and dried under vacuum (10.5 g, 12.6 mmol, 35% yield over four steps). MS (ESI+) for m/z 418 (M/2+H)$^+$. $^1$H NMR (CDCl$_3$) δ 7.41 (m, 4 H), 7.21 (m, 4 H), 7.16 (m, 2 H), 4.88 (br d, 1 H), 4.60 (s, 1 H).

Step 5: The white solid from Step 4 was dissolved in MeOH and treated with conc. aq. HCl (2.4 mL, 28 mmol). To this was added Pearlman's catalyst (palladium hydroxide, 20% weight Pd, about 6 g) and the slurry was subjected to hydrogen gas (40 to 50 psi) in a Parr shaker while heating (35° C.) for up to 2 h. The Parr flask was cooled to RT, purged with nitrogen, and the solids were filtered off. The filtrate was treated with TEA (6.0 mL, 43 mmol) and concentrated under vacuum to yield the title compound along with diphenylmethane (1 eq.) and the hydrochloride salt of TEA (2.2 eq.) as a free flowing crude solid (14 g total; about 59% by weight the title compound). MS (ESI+) for m/z 335 (M/2+H)$^+$. $^1$H NMR (CD$_3$OD) δ 4.71-4.59 (m, 2 H), 4.48 (br t, 1 H), 4.33 (d, 1 H), 4.27 (d, 1 H), 4.16 (br t, 1 H).

The product of Preparation 1 corresponds to the macrolide template of Tables 1 to 3.

Preparation 2a: 2'-acetyl-3-descladinosyl-11,12-dideoxy-6-O-methyl-12,11-(oxycarbonyl-((1-(benzhydryl)-azetidin-3-yl)-methyl)-imino)-erythromycin A Step 1: To 11-deoxy-2',4"-diacetyl-10,11-didehydro-12-O-((1H-imidazol-1-yl)-carbonyl)-6-O-methyl-erythromycin A (18.8 g, 20.7 mmol) were added anhydrous MeCN (25 mL), TEA (20 mL, 144 mmol), and C—(1-benzhydryl-azetidin-3-yl)-methylamine (5.5 g, 21.8 mmol). The mixture was heated (60° C.) for 7.5 h, fitted with a reflux condenser, then concentrated under a nitrogen stream with continued heating overnight to yield a solid mass. MS (ESI+) for m/z 1093 (M+H)$^+$.

Step 2: To the crude solid from Step 1 were added EtOH (100 mL) and 2N HCl (100 mL) and the mixture was stirred at RT for 2.5 days. Due to incomplete reaction, the mixture was heated (30° C.) for 16 h, then the temperature increased slightly (to 40° C.) for an additional 24 h before cooling to RT again. The solvent was reduced (under vacuum) by one half while maintaining 28° C. The resulting concentrate was extracted with EtOAc (2×100 mL). The combined organics were back-washed with water (20 mL), the aqueous layers re-combined, and the pH was slowly raised to 10 with satd. aq. NaHCO$_3$ solution whereupon the (now basic) aqueous layer was extracted with EtOAc (4×100 mL). The combined organic layers were dried (Na$_2$SO$_4$), filtered, and concentrated under vacuum to give the title compound. MS (ESI+) for m/z 447 (M/2+H)$^+$.

Preparation 2b: 3-descladinosyl-11,12-dideoxy-6-O-methyl-3-oxo-12,11-(oxycarbonyl-((azetidin-3-yl)-methyl)-imino)-erythromycin A Step 1: 2'-Acetyl-3-descladinosyl-11,12-dideoxy-6-O-methyl-12,11-(oxycarbonyl-((1-(benzhydryl)-azetidin-3-yl)-methyl)-imino)-erythromycin A (10 g, 11.2 mmol) was dissolved in DCM (75 mL) at RT. To this stirred solution were added anhydrous DMSO (10 mL, 140.8 mmol), pyridinium trifluoroacetate (7.6 g, 39 mmol), and EDC (7.5 g, 39 mmol). The reaction mixture was stirred overnight at RT, then treated with satd. aq. NaHCO$_3$ (30 mL), water (30 mL), and the resulting mixture was extracted with DCM (4×30 mL). The combined organic layers were dried (Na$_2$SO$_4$), filtered, concentrated under vacuum, then re-dissolved in MeOH (70 mL) and heated (40° C.) for 24 h. TEA (2 mL) was added to the reaction and heating continued for another 24 h to ensure complete deacetylation. The methanolic solution was then concentrated under vacuum to a golden foam which was purified (SGC using DCM:MeOH: NH$_4$OH eluant in 93:7:0.4 ratio) to give 6.4 g (7.55 mmol) intermediate. MS (ESI+) for m/z 425 (M/2+H)$^+$.

Step 2: Intermediate from step 1 (6.2 g, 7.3 mmol) was dissolved in MeOH (100 mL) and to this was added Pearlman's catalyst (palladium hydroxide, 20% weight Pd, 3 g) and the resulting slurry shaken under hydrogen pressure (Parr system, 50 psi) while heating (40° C.). After 5 h more catalyst was added (8 g) and the reaction continued for 18 h but monitoring (LCMS) suggested moderate conversion to desired product. Subsequently conc. aq. HCl (2 mL) was added and the reaction continued as before for an additional 4 days until the conversion was complete. The slurry was then filtered to remove the solids and the filtrate concentrated to the title compound as a dihydrochloride salt (5.23 g, 7.28 mmol), which could be used for analog generation. MS (ESI+) for m/z 342 (M/2+H)+. ¹H NMR (DMSO-d₆) δ 4.59 (br d, 1 H), 4.23 (d, 1 H), 4.06 (m, 2 H).

The product of Preparation 2b corresponds to the macrolide template of Table 4.

Preparation 2c: 3-descladinosyl-11,12-dideoxy-6-O-methyl-12,11-(oxycarbonyl-((azetidin-3-yl)-methyl)-imino)-3-(pyrrolidine-1-carbonyl)-erythromycin A and 3-descladinosyl-11,12-dideoxy-6-O-methyl-12,11-(oxycarbonyl(azetidin-3-yl)-methyl)-imino)-3-(azetidine-1-carbonyl)-erythromycin A Step 1: 2'-Acetyl-3-descladinosyl-11,12-dideoxy-6-O-methyl-12,11-(oxycarbonyl-((1-(benzhydryl)-azetidin-3-yl)-methyl)-imino)-erythromycin A (3.0 g, 3.4 mmol) was dissolved in anhydrous MeCN (15 mL) and TEA (1.4 mL, 10 mmol). Bis(N-succinimidyl) carbonate (1.29, 5 mmol) was added and the solution stirred for 24 h at RT, whereupon additional TEA (1.4 mL, 10 mmol) and bis(N-succinimidyl) carbonate (1.29, 5 mmol) were added and the reaction stirred for an additional 24 h. Additional MeCN (15 mL) was added and the resulting stock solution split into two portions (Steps 2a and 2b).

Step 2a: The major portion of the stock solution from Step 1 (24 mL) was treated with pyrrolidine (1 mL, 12 mmol) and monitored by LCMS until carbamate formation deemed complete. MS (ESI+) for m/z 496 (M/2+H)+. This solution was concentrated under vacuum, re-dissolved in MeOH (80 mL), and heated (60° C.) for 20 h to remove the 2'-acetyl protecting group. Removal of the MeOH followed by purification (SGC using DCM:MeOH:NH₄OH eluant in 95:4:1 ratio) yielded purified intermediate (3.32 g). MS (ESI+) for m/z 475 (M/2+H)+.

Step 2b: The minor portion of the stock solution from Step 1 (6 mL) was treated with azetidine (1 mL, 18 mmol) and monitored as in Step 2a above. MS (ESI+) for m/z 489 (M/2+H)+. The 2'-acetyl protecting group was removed and the intermediate purified as in Step 2a above (0.32 g obtained). MS (ESI+) for m/z 468 (M/2+H)+.

Step 3a: The product from Step 2a was dissolved in MeOH (100 mL) and conc. aq. HCl (0.331 mL, 3.85 mmol). To this was added Pearlman's catalyst (palladium hydroxide, 20% weight Pd, 3.0 g). The slurry was subjected to hydrogen (40 psi) with heating (35° C.) while shaken (Parr system) for 18 h. After removal of the solids the filtrate was concentrated under vacuum to yield 3-descladinosyl-11,12dideoxy-6-O-methyl-12,11-(oxycarbonyl-((azetidin-3-yl)-methyl)-imino)-3-(pyrrolidine-1-carbonyl)-erythromycin A as a dihydrochloride salt (2.74 g). MS (ESI+) for m/z 385 (M/2+H)+.

Step 3b: The product from Step 2b was hydrogenolyzed as in Step 3a to yield 3-descladinosyl-11,12-dideoxy-6-O-methyl-12,11-(oxycarbonyl-((azetidin-3-yl)-methyl)-imino)-3-(azetidine-1-carbonyl)-erythromycin A as a dihydrochloride salt (0.25 g). MS (ESI+) for m/z 385 (M+H)+.

The product of Preparation 2c corresponds to a template of Table 5

Preparation 2d: 3-descladinosyl-11,12-dideoxy-6-O-methyl-12,11-(oxycarbonyl-((azetidin-3-yl)-methyl)-imino)-3-((2-methylpyrrolidine)-1-carbonyl)-erythromycin A was prepared according to Preparation 2c, Steps 1, 2a, and 3a, substituting 2-methylpyrrolidine for pyrrolidine in Step 2a. MS (ESI+) for m/z 399 (M/2+H)+. The product of Preparation 2d corresponds to a template of Table 5.

Preparation 2e: 3-descladinosyl-11,12-dideoxy-6-O-methyl-12,11-(oxycarbonyl-((azetidin-3-yl)-methyl)-imino)-3-((2-(3-fluorophenyl)-pyrrolidine)-1-carbonyl)-erythromycin A was prepared according to Preparation 2c, Steps 1, 2a, and 3a, substituting 2-(3-fluorophenyl)-pyrrolidine for pyrrolidine in Step 2a. MS (ESI+) for m/z 439 (M/2+H)+. The product of Preparation 2e corresponds to a template of Table 5.

Preparation 3: 3-descladinosyl-11,12-dideoxy-6-O-methyl-12,11-(oxycarbonyl-((3-methyl-azetidin-3-yl)-methyl)-imino)-erythromycin A can be prepared in analogous fashion to Preparation 1 substituting C-(1-benzhydryl-3-methyl-azetidin-3-yl)-methylamine for 1-benzhydryl-azetidine-3-ylamine. MS (ESI+) for m/z 349 (M/2+H)+. The product of Preparation 3 corresponds to the template of Table 6.

Preparation 4: 3-descladinosyl-11,12-dideoxy-6-O-methyl-12,11(oxycarbonyl-((3-hydroxy-azetidin-3-yl)-methyl)-imino)-erythromycin A can be prepared in analogous fashion to Preparation 1 substituting 3-aminomethyl-1-benzhydryl-azetidin-3-ol for 1-benzhydryl-azetidine-3-ylamine. MS (ESI+) for m/z 350 (M/2+H)+. The product of Preparation 4 corresponds to the template of Table 7.

Preparation 5a: 3-descladinosyl-11,12-dideoxy-6-O-methyl-3-oxo-12,11-(oxycarbonyl-((S)-pyrrolidin-3-yl)-imino)-erythromycin A An analogous procedure to Preparation 1, Steps 1 to 4, was followed substituting (S)-1-benzyl-pyrrolidin-3-ylamine for 1-benzhydryl-azetidine-3-ylamine, giving 3-descladinosyl-11,12-dideoxy-6-O-methyl-3-oxo-12,11-(oxycarbonyl-((S)-1-benzyl-pyrrolidin-3-yl)-imino)-erythromycin A. MS (ESI+) for m/z 387 (M/2+H)+. This product (4g, 5.2 mmol) was dissolved in 4.4% formic acid in MeOH (360 mL), treated with palladium black (0.30 g) and stirred for 4 h with heating (40° C.). The mixture was filtered and the filtrate was neutralized with satd. aq. NaHCO₃. The resulting mixture was concentrated under vacuum and extracted (3×EtOAc). The combined organic layers were dried (Na₂SO₄), filtered, and concentrated under vacuum to give the title compound (3 g, 4.4 mmol). MS (ESI+) for m/z 342 (M/2+H)+. ¹H NMR (CD₃OD) δ 1.11 (dd, 3 H), 0.87 (t, 3 H). The product of Preparation 5a corresponds to the template of Table 8.

Preparation 5b: 3-descladinosyl-11,12-dideoxy-6-O-methyl-3-oxo-12,11-(oxycarbonyl-((R)-pyrrolidin-3-yl)-imino)-erythromycin A can be prepared in analogous fashion to Preparation 5a, substituting (R)-1-benzyl-pyrrolidin-3-ylamine for (S)-1-benzyl-pyrrolidin-3-ylamine. ¹H NMR (CD₃OD) δ 1.28 (d, 3 H), 1.17 (d, 3 H), 1.07 (d, 3 H), 0.88 (t, 3 H). The product of Preparation 5b corresponds to the template of Table 9.

Preparation 6a: 2'-acetyl-3-descladinosyl-11,12-dideoxy-6-O-methyl-3-oxo-12,11-(oxycarbonyl-(((S)-pyrrolidin-2-yl)-methyl)-imino)-erythromycin A Step 1. The protected intermediate can be prepared in analogous fashion to Preparation 1, Steps 1 to 4, substituting (S)-2-aminomethyl-pyrrolidine-1-carboxylic acid tert-butyl ester for 1-benzhydryl-azetidine-3-ylamine.

Step 2. The crude product from Step 1 can be prepared with excess trifluoroacetic acid in dichloroethane at RT for 3 h, followed by concentration to dryness under vacuum to give the title compound as a trifluoroacetate salt. MS (ESI+) for m/z 370 (M/2+H)$^+$. The product of Preparation 6a corresponds to the template of Table 12.

Preparation 6b: 3-descladinosyl-11,12-dideoxy-6-O-methyl-3-oxo-12,11-(oxycarbonyl-(((R)-pyrrolidin-2-yl)-methyl)-imino)-erythromycin A can be prepared in analogous fashion to Preparation 1, Steps 1 to 4, substituting (R)-2-aminomethyl-pyrrolidine-1-carboxylic acid tert-butyl ester for 1-benzhydryl-azetidine-3-ylamine, followed by Preparation 6a, Step 2. MS (ESI+) for m/z 349 (M/2+H)$^+$. The product of Preparation 6b corresponds to the template of Table 10.

Preparation 7a: 3-descladinosyl-11,12-dideoxy-4-O-methyl-3-oxo-12,11-(oxycarbonyl-(((S)-pyrrolidin-3-yl)-methyl)-imino)-erythromycin A can be prepared in analogous fashion to Preparation 6b substituting (R)-3-aminomethyl-pyrrolidine-1-carboxylic acid tert-butyl ester for (R)-2-aminomethyl-pyrrolidine-1-carboxylic acid tert-butyl ester. MS (ESI+) for m/z 349 (M/2+H)$^+$. The product of Preparation 7a corresponds to the template of Table 11.

Preparation 7b: 3-descladinosyl-11,12-dideoxy-6-O-methyl-3-oxo-12,11-(oxycarbonyl-(((R)-pyrrolidin-3-yl)-methyl)-imino)-erythromycin A can be prepared in analogous fashion to Preparation 6b substituting (S)-3-aminomethyl-pyrrolidine-1-carboxylic acid tert-butyl ester for (R)-2-aminomethyl-pyrrolidine-1-carboxylic acid tert-butyl ester. MS (ESI+) for m/z 349 (M/2+H)$^+$. The product of Preparation 7b corresponds to the template of Table 13.

Preparation 8: 2'-acetyl-3-descladinosyl-11,12-dideoxy-6-O-methyl-12,11-(oxycarbonyl-((3-azabicyclo[3.1.0]hexane-6-yl)-methyl)-imino)erythromycin A can be made in analogous fashion to Preparation 6a, substituting 6-aminomethyl-3-aza-bicyclo[3.1.0]hexane-3-carboxylic acid tert-butyl ester for (S)-2-aminomethyl-pyrrolidine-1-carboxylic acid tert-butyl ester. MS (ESI+) for m/z 750 (M+H)$^+$.

Preparation 8.1: 2'-acetyl-3-descladinosyl-11,12-dideoxy-6-O-methyl-12,11-(oxycarbonyl-((piperidin-4-yl)-methyl)-imino)-erythromycin A can be made in analogous fashion to Preparation 6a, substituting 4-aminomethyl-piperidine-1-carboxylic acid tert-butyl ester for (S)-2-aminomethyl-pyrrolidine-1-carboxylic acid tert-butyl ester. MS (ESI+) for m/z 710 (M+H)$^+$.

Preparation 8.2: 3-descladinosyl-11,12-dideoxy-6-O-methyl-12,11-(oxycarbonyl-((4-hydroxy-piperidin-4-yl)-methyl)-imino)-erythromycin A can be made in analogous fashion to Preparation 6a, Step 1, substituting 4-aminomethyl-4-hydroxy-piperidine-1-carboxylic acid tert-butyl ester for (S)-2-aminomethyl-pyrrolidine-1-carboxylic acid tert-butyl ester. MS (ESI+) for m/z 869 (M+H)$^+$. The product was then subjected to excess MeOH at RT overnight, concentrated under vacuum to dryness, re-dissolved in DCM (1 mL), and treated with excess TFA (1 mL) for 4 h at RT. After concentrating under vacuum, the residue was used for derivatization directly. MS (ESI+) for m/z 727 (M+H)$^+$.

Preparation 9: 3-cyano-4-[1,2,4]triazol-1-yl-benzenesulfonyl chloride

The conversion of anilines to sulfonyl chlorides followed, with minor modification, the procedures given in *J. Med. Chem.* 29, 427-433 (1986), which is fully incorporated by reference herein.

Step 1. 5-Amino-2-[1,2,4]triazol-1-yl-benzonitrile (0.40 g, 2.16 mmol) in glacial acetic acid (2.16 mL) was treated with conc. aq. HCl (0.45 mL, 5 mmol) and the mixture cooled to between 0-5 °C. with an ice-water bath. Sodium nitrite (0.150 g, 2.17 mmol) was added and the slurry stirred for about 10 min.

Step 2. In a separate flask, copper(II) chloride dihydrate (1.8 g, 10.6 mmol) was treated with acetic acid (36 mL) and water (2.2 mL). Sulfur dioxide gas was then bubbled through to the saturation point (to constant mass), while keeping the system well ventilated. (The resulting mixture from this step could be used for several reactions.)

Step 3. A portion (3 mL) of the mixture from Step 2 was added to the slurry from Step 1, and the reaction flask was allowed to warm to RT overnight with constant stirring (kept ventilated). The mixture was then diluted with water and extracted with DCM repeatedly. The combined organic layers were washed with satd. aq. NaHCO$_3$, dried (Na$_2$SO$_4$), filtered, and concentrated under vacuum to yield the title compound (0.20 g) which was used without further purification. $^1$H NMR (CDCl$_3$) δ 9.06 (s, 1 H), 8.50 (s, 1 H), 8.39 (d, J=9 Hz, 1 H), 8.25(s, 1 H), 8.19 (d, J=9 Hz, 1H).

Preparation 10: imidazo[1,2-a]-pyridine-3-sulfonyl chloride

Step 1. Chlorosulfonic acid (0.170 mL, 2.55 mmol) was dissolved in chloroform (1 mL) and this solution was added dropwise to imidazo[1,2-a]-pyridine (0.100 g, 0.85 mmol) in chloroform (4 mL) over 10 min. The reaction mixture was heated to reflux for 24 h, then allowed to cool to RT and concentrated to dryness under vacuum. The crude oily product was treated with diethyl ether (10 mL) and ethanol (5 mL) resulting in a white precipitate. The solid was collected by filtration, washed with EtOH and dried to yield imidazo[1,2-a]-pyridine-3-sulfonic acid (0.128 mg). MS (ESI–) for m/z 131 (M–H)$^-$.

Step 2. The product from Step 1 (0.10 g, 0.5 mmol) was treated with phosphorus oxychloride (3 mL) and heated to reflux overnight. The reaction mixture was cooled to RT and treated with DCM (50 mL), poured into ice-water (100 mL), and then extracted with DCM (4×100 mL). The organic layers were combined and dried (Na$_2$SO$_4$), filtered, and concentrated to dryness under vacuum to give the title compound (0.10 g). $^1$H NMR (DMSO-d$_6$) δ 8.87 (m, 1 H), 8.25 (s, 1 H), 7.98 (m, 2 H), 7.57 (m, 1 H).

Preparation 11:
imidazo[1,2-a]-pyrimidine-2-carbaldehyde and Imidazo[1,2-a]-pyrimidine-3-carbaldehyde Imidazo[1,2-a]pyrimidine (0.30 g, 2.5 mmol) was dissolved in anhydrous DMF (10.0 mL) and added to a preformed solution of phosphorous oxychloride (0.26 mL, 2.8 mmol) in anhydrous DMF (10.0 mL). The solution was allowed to stir 72 h under nitrogen at RT. The solution was then poured into water (100 mL) and residual organics extracted with diethyl ether (3×30 mL). The remaining aqueous portion was concentrated to dryness under a nitrogen stream to yield a mixture of crude imidazo[1,2-a]-pyrimidine-3-carbaldehyde and imidazo[1,2-a]-pyrimidine-2-carbaldehyde (0.10 g total) that was used in the subsequent reductive amination step without further purification. MS (ESI+) for m/z 148 (M+H)$^+$. The isomers were separated by RP-HPLC after coupling to 3-descladinosyl-11,12-dideoxy-6-O-methyl-3-oxo-12,11-(oxycarbonyl-((azetidin-3-yl)-methyl)-imino)-erythromycin A.

Preparation 12:
imidazo[1,2-a]-pyrazine-3-carbaldehyde

Imidazo[1,2-a]-pyrazine (0.30 g, 2.5 mmol) was dissolved in anhydrous DMF (10.0 mL) and added to a preformed solution of phosphorous oxychloride (0.26 mL, 2.8 mmol) in anhydrous DMF (10.0 mL). The solution was allowed to stir 72 h under nitrogen at RT. The solution was then poured into water (100 mL) and residual organics extracted with diethyl ether (3×30 mL). The remaining aqueous portion was concentrated to dryness under a nitrogen stream to yield the title compound (0.050 g). MS (ESI+) for m/z 148 (M+H)$^+$.

Preparation 13:
pyrrolo[1,2-a]-pyrazine-6-carbaldehyde

Step 1. Pyrrolo[1,2-a]pyrazine (1.92 g, 16.3 mmol) was dissolved in water (16 mL) and treated with conc. aq. HCl (4 mL, 46.4 mmol) and 37% wt aqueous formaldehyde (5.6 mL, 67 mmol). The solution was heated to 60° C. for 4 h, allowed to cool to RT and the pH adjusted to 10. The solution was extracted with EtOAc (3×50 mL) and the combined fractions dried over Na$_2$SO$_4$ and concentrated to dryness under vacuum. The organic residue was purified (SGC using DCM: MeOH:NH$_4$OH eluant in 96:3:1 ratio). Recovered starting material was dissolved in water (20 mL) and conc. HCl (5 mL, 0.6 mol) and formaldehyde (7 mL, 0.9 mol). The solution was heated to 60° C. for 120 h, and then allowed to stir at RT for 240 h. The solution pH was then brought to 12 with sodium hydroxide solution (30% w/v aq) and extracted with EtOAc (4×30 mL). The organic fractions were combined, dried over Na$_2$SO$_4$, and concentrated to dryness under vacuum. The product was purified (SGC using DCM:MeOH:NH$_4$OH eluant in 95:4:1 ratio) yielding the title compound (0.46 g). MS (ESI+) for m/z 149 (M+H)$^+$. $^1$H NMR (CDCl$_3$) δ 8.46 (s, 1H), 7.85 (dd,1H), 7.19 (d, 1H), 6.72 (d, 1H), 6.63 (d, 1H), 4.83 (s, 1H), 4.78 (bs,1H).

Step 2. Pyrrolo[1,2-a]pyrazin-6-yl-methanol (0.06 g, 0.41 mmol) is dissolved in EtOAc (3 mL), treated with IBX (0.34 g, 1.2 mmol) and heated to 80° C. for 3 h. The solution was allowed to cool to RT and filtered with a syringe filter frit. The solution was concentrated under a nitrogen stream to yield the title compound (0.06 g), which was used without further purification. $^1$H NMR (CDCl$_3$) δ 9.87 (s, 1H), 9.34 (d, 1H), 9.02 (s, 1H), 7.93 (d, 1H), 7.47 (d, 1H), 6.82 (d, 1H).

Preparation 14:
imidazo[1,2-a]-pyridine-6-carbaldehyde

Step 1. 1H-Imidazo[1,2-a]pyridine-6-carboxylic acid (2.0 g, 5.1 mmol) was dissolved in anhydrous DCM (30 mL) and cooled to 0° C. Ethyl chloroformate (1.30 mL, 13.6 mmol) and TEA (4.31 mL, 30.8 mmol) were added to the solution and allowed to stir 1 h as the temperature was allowed to warm to ambient levels. Ethane thiol (2.0 mL, 27 mmol) was added, and the solution allowed to stir overnight. The material was partially converted, so TEA (2.0 mL, 14 mmol) and ethyl chloroformate (7.8 mL, 82 mmol) were added and allowed to stir for 15 min, followed by the addition of more ethane thiol (80 mL, 1.1 mol). The solution was allowed to stir for 2 h and then poured into a solution of satd. aq. NaHCO$_3$. The layer of DCM was removed, and the aqueous portion extracted with EtOAc (4×70 mL). The combined organic fractions were dried over Na$_2$SO$_4$, filtered, and concentrated under vacuum. The product was purified (SGC using acetone:hexanes gradient elution from ratios of 1:4 to 3:1) yielding the thioester intermediate (0.2 g). $^1$H NMR (CDCl$_3$) δ 8.82 (s, 1H), 7.67-7.57 (m, 4H), 3.07 (q, 2H), 1.32 (t, 3H).

Step 2. The thioester from Step 1 (0.11 g, 0.53 mmol) was dissolved in acetone (1.0 mL) and 10% palladium on carbon (0.027 g) was added, followed by triethyl silane (0.089 mL, 0.558 mmol). The mixture was allowed to stir for 1 h and another portion of triethyl silane (0.089 mL, 0.558 mmol) was added. After 1.5 h, the reaction was passed through a syringe filter and purified (SGC using acetone: hexanes gradient elution from 3:17 to 3:1) yielding the title compound (0.049 g). MS (ESI+) for m/z 147 (M+H)$^+$. $^1$H NMR (CDCl$_3$) δ 9.90 (s, 1H), 8.66 (s, 1H), 7.70 (d, 2H), 7.66-7.60 (m, 2H).

Preparation 15:
1-pyridin-2-yl-1H-pyrazole-4-carbaldehyde

A mixture of 2-bromopyridine (3.4 mmol), 3-pyrazolecarboxaldehyde (3.2 mmol), and potassium carbonate (3.4 mmol) in anhydrous DMF (6 mL) was heated to 120° C. for 24 h. The reaction was cooled to RT, diluted with water, and extracted with EtOAc (3 x). The organic layers were combined and dried (Na$_2$SO$_4$), filtered, and concentrated. The title compound was obtained upon purification (SGC using EtOAc:hexanes gradient eluant from 0% to 100% EtOAc).

Preparation 16: [1,8]naphthyridine-4-carbaldehyde

4-Methyl-[1,8]naphthyridine (0.743 g, 5.15 mmol) was dissolved in dioxane (32 mL) and water (4 mL). Selenium dioxide (1.14 g, 103 mmol) was added, and the solution was heated to 80° C. for 1 h. Subsequently more selenium dioxide (0.020 g, 1.80 mmol) was added, the solution heated for 30 min, and then allowed to cool to RT. The solution was passed through a syringe filter to remove solids, and poured into a solution of water : satd. aq. NaHCO$_3$ (1:1) (60 mL). The organic layer was separated and the remaining aqueous extracted with DCM (2×100 mL) and (1×50 mL). The organic fractions were combined, dried over Na$_2$SO$_4$, filtered, and concentrated under vacuum. The product was purified (SGC using MeCN:hexanes in 1:1 ratio) to yield the title compound (0.63 g). MS (ESI+) for m/z 159 (M+H)+. 1H NMR (CDCl3) δ 10.39 (s, 1H), 9.39-9.37 (m, 2H), 9.16 (d, 1H), 7.85 (d, 1H), 7.61 (dd, 1H).

Preparation 17: 1-[1,8]naphthyridin4-yl-ethanol

[1,8]Naphthyridine-4-carbaldehyde (0.300 g, 1.90 mmol) was dissolved in a mixture of anhydrous toluene (10 mL) and anhydrous THF (10 mL). The solution was cooled to 0° C. and methyl magnesium bromide (1.62 mL of 1.4M in THF/toluene) was added slowly and the solution stirred 1 h while allowing to warm to RT. Satd. aq. ammonium chloride was added until the solution reached a bright yellow color and precipitate was apparent. The solution was passed through a syringe filter and into water, where it was extracted with EtOAc (3×30 mL). The combined organic fractions were dried over $Na_2SO_4$, filtered, and concentrated under vacuum. The product was purified (SGC using MeCN:hexanes eluant in 1:1 ratio initially, then switching to DCM:MeOH:$NH_4OH$ eluant in 89:10:1 ratio to finish the compound elution) yielding the title compound (0.079 g). MS (ESI+) for m/z 175 (M+H)+. 1H NMR (CDCl3) δ 8.73 (m, 1H), 8.64 (d, 1H), 8.38 (m, 1H), 7.52 (d, 1H), 7.25 (dd, 1H), 6.32 (bs, 1H), 5.58 (dd, 1H), 1.48 (s, 3H).

Preparation 18: 1-[1,8]naphthyridin-4-yl-ethanone

1-[1,8]Naphthyridin-4-yl-ethanol (1.44 g, 8.26 mmol) was dissolved in EtOAc (250 mL), treated with IBX (7.8 g, 24.8 mmol) and heated to 80° C. for 6 h. The solution was cooled to RT and the solids removed by filtration. The product was purified (SGC using MeCN eluant) yielding the title compound (1.22 g). MS (ESI+) for m/z 173 (M+H)+. 1H NMR (CDCl3) δ 9.13 (d, 1H), 9.03 (dd, 1H), 8.85 (dd, 1H), 7.70 (d, 1H), 7.46 (dd, 1H), 2.64 (s, 3H).

Preparation 19:
5-nitro-2-[1,2,4]triazol-1-yl-benzonitrile

2-Fluoro-5-nitro-benzonitrile (1.0 g, 6.0 mmol) was dissolved in anhydrous DMF (6 mL), then treated with [1,2,4]-triazole (0.46 g, 6.7 mmol), cesium carbonate (2.9 g, 8.9 mmol), and heated (50° C.) overnight. After cooling to RT, the mixture was treated with water and the solid title compound collected by filtration (1.14 g). MS (ESI+) for m/z 216 (M+H)+.

Preparation 20:
2-methyl-5-(4-nitro-phenyl)-[1,3,4]oxadiazole

4-Nitro-benzoic acid hydrazide (1.0 g, 5.6 mmol) was heated to reflux in trimethyl orthoacetate for 4 days. After cooling to RT, the mixture was triturated with hexanes and the title compound collected by filtration (0.93 g). MS (ESI+) for m/z 206 (M+H)+.

Preparation 21:
5-amino-2-[1,2,4]triazol-1-yl-benzonitrile

5-Nitro-2-[1,2,4]triazol-1-yl-benzonitrile (1.14 g, 5.3 mmol) was dissolved in ethanol (23 mL) and satd. aq. ammonium chloride (5.3 mL) before adding indium powder (3.25 g, 28.2 mmol). The mixture was then refluxed for 3 h, cooled to RT, and the solids filtered (MeOH washed). The filtrate was diluted with water, basified with 1N NaOH (aq), and extracted with EtOAc. The organic layer was dried ($Na_2SO_4$), filtered, and concentrated under vacuum to yield the title compound (0.88 g). MS (ESI+) for m/z 186 (M+H)+.

Preparation 22:
2-methyl-5-(4-amino-phenyl)-[1,3,4]oxadiazole

2-Methyl-5-(4-nitro-phenyl)-[1,3,4]oxadiazole (0.930 g, 4.54 mmol) was dissolved in MeOH. To this was added 10% palladium on carbon (0.06 g) and the mixture shaken under hydrogen pressure (35 psi, Parr apparatus) until the reaction was complete (LCMS monitored). The solids were filtered off and rinsed with MeOH. The filtrate was concentrated to give the title compound (0.76 g). MS (ESI+) for m/z 176 (M+H)+.

Preparation 23:
4-(6-chloro-pyridazin-3-yl)-phenylamine 4-(4,4,5,5-Tetramethyl-[1,3,2]dioxaborolan-2-yl)-phenylamine (0.500 g, 2.28 mmol), 3,6-dichloropyridazine (0.340 g, 2.28 mmol), sodium carbonate (0.726 g, 6.85 mmol), and tetrakis(triphenylphosphine)palladium(0) (0.068 g, 0.059 mmol) were mixed in 1,2-dimethoxyethane (11 mL) and water (3.8 mL) under nitrogen. The reaction mixture was heated (110° C.) for 12 h, cooled to RT, diluted with brine, and extracted with EtOAc. The combined organic layers were dried ($Na_2SO_4$), filtered, and concentrated under vacuum to a crude solid which was dissolved in DCM and extracted into 1N HCl (aq). The DCM layer was discarded, and the aqueous layer was basified with 1N NaOH (aq) and re-extracted with EtOAc. The EtOAc layer was dried ($Na_2SO_4$), filtered, and concentrated under vacuum to give the title compound (0.395 g). MS (ESI+) for m/z 206 (M+H)+.

Preparation 24: 5-oxazol-5-yl-pyridin-3-ylamine

Step 1. 5-(3-pyridine)-oxazole (21.2 mmol) was converted to the corresponding N-oxide with m-chloroperbenzoic acid (46.9 mmol) in chloroform (40 mL) at RT (3 h). To the reaction mixture were added calcium hydroxide (109 mmol) and DCM (250 mL), and this was allowed to stir for 45 min before filtering off the solids. The filtrate was concentrated to give the N-oxide intermediate (2.9 g, 17.9 mmol).

Step 2. Tetrabutylammonium nitrate (6.54 g, 21.6 mmol) in DCM (90 mL) was cooled in an ice-water bath under nitrogen. To this solution was added trifluoroacetic anhydride (3.0 mL, 21.6 mmol), and the resulting mixture was stirred for 20 min before adding the product of Step 1 (in 90 mL DCM) and the resulting slurry stirred in the ice-water bath initially, then allowed to warm to RT for 2 h. The mixture was then heated (40° C.) for 9 h, cooled to RT, and treated with satd. aq. $NaHCO_3$. The mixture was then extracted with DCM (3×250 mL), and the combined organic layers were dried ($Na_2SO_4$), filtered, and concentrated under vacuum to give 5-(N-oxide-5-nitro-3-pyridine)-oxazole (0.73 g, 3.53 mmol) after purification (SGC using MeOH:DCM in 1:10 ratio).

Step 3. 5-(N-Oxide-5-nitro-3-pyridine)-oxazole (0.159 g, 0.77 mmol) from Step 2 were treated with MeOH (30 mL) and Raney nickel 2800 suspension (2 mL) and the mixture shaken under hydrogen (45 psi) for 6 h on a Parr apparatus. Filtration (Celite) yielded the title compound. MS (ESI+) for m/z 162 (M+H)+.

Preparation 25: quinolin-5-yl-carbamic acid phenyl ester

6-Aminoquinoline (0.5 g, 3.5 mmol) was treated with phenylchloroformate (0.597 g, 3.81 mmol) and TEA (1 mL) in DCM at RT for 4 h. To this were added satd. aq. NaHCO₃ and water, and the mixture was extracted with DCM. The combined organic layers were washed with brine, dried (Na₂SO₄), filtered, and concentrated under vacuum to give the title compound after purification (SGC using EtOAc:hexanes gradient eluant from 2:3 to 7:3 ratios). MS (ESI+) for m/z 265 (M+H)⁺.

Preparation 26: 1-benzhydryl-azetidin-3-ylamine

Methanesulfonic acid 1-benzhydryl-azetidin-3-yl ester (14.8 g, 47 mmol, Oakwood Products) was dissolved in anhydrous DMF (60 mL), and to this solution was added sodium azide (9.0 g, 138 mmol). The mixture was heated (80° C.) for 18 h, cooled to RT, then treated with water (20 mL) and satd. aq. NaHCO₃ (20 mL). The resulting mixture was extracted with DCM (4×60 mL) and the organic layer dried over Na₂SO₄. Solvent removal yielded a crude oil (11 g) that was redissolved in THF (85 mL) and treated with triphenyl phosphine (15 g, 57 mmol). After stirring at RT (30 min; gas evolution and some exotherm noted), the mixture was heated to reflux (6 h), then cooled back down to RT before adding NH₄OH (7 mL) and refluxing again (5 h). After cooling to RT, the solvent was removed and the residue treated with 3N HCl (35 mL) giving a pH 1. The resulting acidic solution was extracted with DCM (3×50 mL) and the organic layers were discarded. The aqueous layer was then basified with solid potassium hydroxide to pH 10 and then extracted again with DCM (3×75 mL). The aqueous layer was then satd. with solid sodium chloride and re-extracted with DCM (3×75 mL). The combined organic layers were dried over Na₂SO₄, filtered, and concentrated to yield crude 1-benzhydryl-azetidin-3-ylamine (9.0 g, 37.8 mmol). MS (ESI+) for m/z (M+H)⁺239.

The following Preparation Examples illustrate the preparation of the examples of Tables 1-16, including headpiece coupling methods that were used.

Preparation 27 (Example 1.20): 3-descladinosyl-11,
12-dideoxy-6-O-methyl-3-oxo-12,11-(oxycarbonyl-
(1-((1.8-naphthyridin-4-yl)-methyl)-azetidin-3-yl)-
imino)-erythromycin A The final crude solid from Preparation 1 (1.20 g, 1.06 mmol 3-descladinosyl-11,12-dideoxy-6-O-methyl-3-oxo-12,11-(oxycarbonyl-(azetidin-3-yl)-imino)-erythromycin A) was treated with anhydrous THF (10 mL), 1,8-naphthyridine-4-carbaldehyde (0.20 g, 1.3 mmol), TEA (0.44 mL, 3.2 mmol), acetic acid (0.095 mL, 1.6 mmol), powdered 4 angstrom molecular sieves (3 g), and the slurry heated with stirring for 4 h at 47° C. At this point, sodium triacetoxyborohydride (0.33 g, 1.6 mmol) was added and heating was continued for another 30-60 min before removing the heat source and allowing the reaction flask to come to RT overnight with continuous stirring. The reaction mixture was then diluted with DCM and filtered to remove solids. To the filtrate were added satd. aq. NaHCO₃ (15 mL) and water (15 mL), and the resulting mixture was extracted with DCM (5×30 mL). The solid filtrant was rinsed into a separatory funnel and extracted as the filtrate was. The combined organic layers were dried (Na₂SO₄), filtered, and concentrated under vacuum.
Purification (SGC using DCM:MeOH:NH₄OH gradient eluant in 96:4:0.5 to 93:7:0.5 ratios) yielded the title compound (0.557 g after conversion to the di-formate salt in MeOH with excess formic acid and concentration under vacuum).

Preparation 28: 3-descladinosyl-11,12-dideoxy-6-O-
methyl-3-oxo-12,11-(oxycarbonyl-(1-(1S-(1,8-naph-
thyridin-4-yl)-ethyl)-azetidin-3-yl)-imino)-erythro-
mycin A (Example 1.23); and 3-descladinosyl-11,12-
dideoxy-6-O-methyl-3-oxo-12,11-(oxycarbonyl-(1-
(1R-(1,8-naphthyridin-4-yl)-ethyl)-azetidin-3-yl)-
imino)-erythromycin A (Example 1.25)

The final crude solid from Preparation 1 (4.21 g, 3.72 mmol 3-descladinosyl-11,12-dideoxy-6-O-methyl-3-oxo-12,11-(oxycarbonyl-(azetidin-3-yl)-imino)-erythromycin A) was treated with anhydrous THF (35 mL), 1-[1,8]naphthyridin-4-yl-ethanone (0.7 g, 4.07 mmol), acetic acid (0.33 mL, 5.8 mmol), TEA (1.55 mL, 11.1 mmol), and powdered 4 angstrom molecular sieves (4.5 g), and the slurry was heated with stirring for 4 h at 49° C. At this point, sodium triacetoxyborohydride (2.35 g, 11 mmol) was added, and heating was continued for another hour before removing the heat source and allowing the reaction flask to come to RT overnight with continuous stirring. The solids were then filtered off and to the filtrate were added satd. aq. NaHCO₃ (15 mL) and water (15 mL), and the layers were separated. The aqueous layer was re-extracted with DCM (5×40 mL). The solid filtrant was rinsed into a separatory funnel and extracted as the filtrate was. The combined organic layers were dried (Na₂SO₄), filtered, and concentrated under vacuum to give 4 g of a crude mixture of diastereomers.

The diastereomers were separated portionwise (RP-HPLC using gradient from 8 to 30% A in B over 10 min). The more polar peak (Peak 1) eluted at 4.00 min (1.1 g collected) and the less polar peak (Peak 2) just after at 4.38 min (1.0 g collected). Peak 1 can be recrystallized from EtOAc, MeOH, MeOH/water, EtOH, EtOH/water, IPA, or water/water. Using EtOAc recrystallization suitable crystals were obtained for X-ray spectroscopic analysis and the structure unambiguously identified as 3-descladinosyl-11,12-dideoxy-6-O-methyl-3-oxo-12,11-(oxycarbonyl-(1-(R)-(1,8-naphthyridin-4-yl)-ethyl)-azetidin-3-yl)-imino)-erythromycin A (Example 1.25). Peak 2 was identified as 3-descladinosyl-11,12-dideoxy-6-O-methyl-3-oxo-12,11-(oxycarbonyl-(1-(S)-(1,8-naphthyridin-4-yl)-ethyl)-azetidin-3-yl)-imino)-erythromycin A (Example 1.23) by inference.

Preparation 29 (Example 1.33): 3-descladinosyl-11,
12-dideoxy-2-fluoro-6-O-methyl-3-oxo-12,11-(oxy-
carbonyl-(1-((1,8-naphthyridin4-yl)-methyl)-azeti-
din-3-yl)-imino)-erythromycin A Step 1: The free base of 3-descladinosyl-11,12-dideoxy-6-O-methyl-3-oxo-12,11-(oxycarbonyl-(1-((1,8-naphthyridin-4-yl)-methyl)-azetidin-3-yl)-imino)-erythromycin A (0.10 g, 0.12 mmol) was dissolved in anhydrous DCM (1.5 mL). TEA (0.069 mL, 0.50 mmol) and acetic anhydride (0.015 mL, 0.16 mmol) were added and the reaction allowed to sit overnight. To the mixture was added satd. aq. NaHCO₃ and water (1:1) and the organic layer separated. The aqueous layer was re-extracted with DCM (3×2 mL) and the combined organic layers were dried (Na₂SO₄), filtered, and concentrated under vacuum to give crude intermediate.

Step 2: The intermediate from Step 1 was dissolved in anhydrous DMF (3 mL) and anhydrous toluene (3 mL), and cooled in a dry ice/acetone bath while keeping under nitrogen positive pressure. Solid potassium bis(trimethylsilyl)amide (0.042 g, 0.21 mmol) was weighed under nitrogen and quickly added to the cooled solution, which was subsequently allowed to stir while cooling for 1 h. Solid [1-(chloromethyl)-4-fluoro-1,4-diazoniabicyclo[2.2.2]octane bis(tetrafluoroborate)] (0.062 g, 0.176 mmol) was then added and the reaction allowed to warm to RT for 1 h. DCM (20 mL) was added followed by satd. aq. NaHCO$_3$ (5 mL) and water (5 mL) and the layers separated. The aqueous layer was re-extracted with DCM (2×10 mL). The combined organic layers were dried over Na$_2$SO$_4$, filtered, and concentrated under vacuum.

Step 3: The crude product from Step 2 was dissolved in MeOH (100 mL) and heated (32° C.) overnight. After concentrating under vacuum, the crude mixture was purified by RP-HPLC to give the title compound (0.023 g, 0.028 mmol).

Preparation 30 (Example 2.06): 3-descladinosyl-11, 12-dideoxy-6-O-methyl-3-oxo-12,11-(oxycarbonyl-(1-(N-(quinolin-5-yl)-aminocarbonyl)-azetidin-3-yl)-imino)-erythromycin A The final crude solid from Preparation 1 (0.076 g, 0.067 mmol) was treated with TEA (1.0 mL) and quinolin-5-yl-carbamic acid phenyl ester (0.030 g, 0.113 mmol) in anhydrous MeCN and heated (50° C.) overnight. The reaction mixture was taken to dryness under vacuum and purified (RP-HPLC) to give the title compound.

Preparation 31 (Example 3.15): 3-descladinosyl-11, 12-dideoxy-6-O-methyl-3-oxo-12,11-(oxycarbonyl-(1-(imidazo[1,2-a]pyridine-sulfonyl)-azetidin-3-yl)-imino)-erythromycin A The final crude solid from Preparation 1 (0.20 g, 0.18 mmol) was treated with anhydrous MeCN (5 mL), followed by TEA (0.076 mL, 0.54 mmol), and imidazo[1,2-a]-pyridine-3-sulfonyl chloride (0.039 g, 0.18 mmol). The reaction was stirred at RT for 3 h, then treated with satd. aq. NaHCO$_3$ (15 mL), water (15 mL), and extracted with DCM (4×30 mL). The combined organic layers were dried (Na$_2$SO$_4$), filtered, and concentrated under vacuum. Purification by RP-HPLC yielded the title compound (0.055 g, 0.065 mmol).

Preparation 32 (Example 4.34): 3-descladinosyl-11, 12-dideoxy-6-O-methyl-3-oxo-12,11-(oxycarbonyl-((1-(quinoline-8-carbonyl)-azetidin-3-yl)-methyl)-imino)-erythromycin A Step 1: Quinoline-8-carboxylic acid (0.182 g, 1.05 mmol) was dissolved in anhydrous DCM (3 mL) with DMF (0.025 mL) added. To this were added oxalyl chloride (0.526 mL of 2M solution in dichloromethane, 1.05 mmol), which was allowed to stir for 15 min at RT, followed by TEA (0.550 mL, 3.9 mmol) and N-hydroxysuccinimide (0.140 g, 1.22 mmol). The reaction was stirred for an additional 30 min, then treated with water (10 mL), satd. aq. NaHCO$_3$ (10 mL), and then extracted with DCM (2×30 mL). The combined organic layers were dried (Na$_2$SO$_4$), filtered, and concentrated to dryness and re-dissolved in anhydrous THF (8 mL) and TEA (0.550 mL, 3.9 mmol) to be used as a stock solution for Step 2 below.

Step 2: 3-Descladinosyl-11,12-dideoxy-6-O-methyl-3-oxo-12,11-(oxycarbonyl-((azetidin-3-yl)-methyl)-imino)-erythromycin A dihydrochloride salt from Preparation 2a (0.050 g, 0.073 mmol) was treated directly with the stock solution prepared in Step 1 above (2 mL) and allowed to react for 15 min at RT before treating with water (15 mL), satd. aq. NaHCO$_3$ (10 mL), and subsequently extracting with DCM (3×30 mL). The combined organic layers were dried (Na$_2$SO$_4$) and purified (SGC using DCM:MeOH eluant in 9:1 ratio) to give the title compound (0.022 g, 0.026 mmol). MS (ESI+) for m/z 420 (M/2+H)$^+$. $^1$H NMR (CD$_3$OD) δ 8.94 (br d, 1 H), 8.37 (br t, 1 H), 8.02 (br d, 1 H), 7.76 (br d, 1 H), 7.64 (t, 1 H), 7.56 (m, 1 H).

Preparation 33 (Example 10.14): 3-descladinosyl-11, 12-dideoxy-6-O-methyl-3-oxo-12,11-(oxycarbonyl-((1-(pyrazolo[1,5-a]pyridine-2-carbonyl)-(R)-pyrrolidin-2-yl)-methyl)-imino)-erythromycin A Step 1. Pyrazolo[1,5-a]pyridine-2-carboxylic acid (0.228 g, 1.41 mmol), EDC (0.455 g, 2.38 mmol), HOBT (0.328 g, 2.38 mmol), and 2'-acetyl-3-descladinosyl-11,12-dideoxy-6-O-methyl-3-oxo-12,11-(oxycarbonyl-(((S)-pyrrolidin-2-yl)-methyl)-imino)-erythromycin A trifluoroacetate salt from Preparation 6a (0.80 g) were mixed in anhydrous DMF (7 mL) at RT overnight, then heated (45° C.) for 2 days. The reaction mixture was treated with satd. aq. NaHCO$_3$, water, and extracted with DCM repeatedly. The combined organic layers were dried (Na$_2$SO$_4$) and concentrated under vacuum to dryness.

Step 2. The crude product from Step 1 was re-dissolved in MeOH and heated (40° C.) for 3 h to remove the 2'-acetyl group and give the title compound after RP-HPLC purification.

Preparation 34 (Example 12.11): 3-descladinosyl-11, 12-dideoxy-6-O-methyl-3-oxo-12,11-(oxycarbonyl-((1-(quinoline-5-carbonyl)-(S)pyrrolidin-2-yl)-methyl)-imino)-erythromycin A Step 1. Quinoline-5-carboxylic acid (0.04 g, 0.23 mmol) was placed in anhydrous MeCN (1.5 mL) and treated with TEA (0.078 mL, 0.56 mmol) followed by O—(N-succinimidyl)-N,N,N',N'-tetramethyluronium tetrafluoroborate (0.056 g, 0.185 mmol) and the mixture allowed to stir for 3 h.

Step 2. 3-Descladinosyl-11,12-dideoxy-6-O-methyl-3-oxo-12,11-(oxycarbonyl-(((R)-pyrrolidin-2-yl)-methyl)-imino)-erythromycin A trifluoroacetate salt from Preparation 6b (0.075 g, 0.081 mmol) in anhydrous MeCN was added to the mixture from Step 1 and the resulting mixture stirred overnight.

Step 3. To ensure the cleavage of any undesired 2'-esters during Step 2, the reaction mixture (from Step 2) was taken to dryness under a nitrogen stream and re-dissolved in MeOH, then heated (60° C.) for 1.5 h. Purification (RP-HPLC) gave the title compound (0.006 g).

Preparation 35 (Example 1.107): 3-descladinosyl-11, 12-dideoxy-6-O-methyl-3-oxo-12,11-(oxycarbonyl-(1-((3-chloro-quinolin-4-yl)-methyl)-azetidin-3-yl)-imino)-erythromycin A Step 1: 3-Chloro-4-methylquinoline (0.10 g, 0.56 mmol; *Bull. Soc. Pharm. Bordeaux* 1988, 127, 29), N-bromosuccinimide (0.200 g, 1.13 mmol), and benzoyl peroxide (0.040 g, 0.168 mmol) in 3 mL carbon tetrachloride were heated in a sealed tube at 85° C. for 2.5 h. Water (3 mL) was added and the product was extracted with DCM (3×3 mL). The organic layer was dried over Na$_2$SO$_4$ and the solvent was evaporated. The LC-MS of the remaining solid indicated it was approximately a 60:40 mixture of 3-chloro-4-bromomethylquinoline and the starting material. MS (ESI+) for m/z 257 (M+H)$^+$.

Step 2: This crude product (0.34 mmol), the final crude solid from Preparation 1 (0.22 g, 0.34 mmol), TEA (0.087 mL, 0.67 mmol) in 2 mL MeCN were heated in a microwave reactor at 90° C. for 6 min. The reaction mixture was concentrated and the residue was purified (RP-HPLC) to give the title compound (0.050 g, 0.059 mmol).

Preparation 36:
4-bromomethyl-3-methoxy-[1,5]naphthyridine

Step 1: 3,5-Dibromo-4-methylpyridine (100 mg) was placed in a microwave tube, followed by CuI (0.01 eq.), cesium carbonate (2 eq.) and 1,10-phenanthroline (0.02 eq.) in 2 ml MeOH. The mixture was heated at 160° C. for 2 h under microwave irradiation. The reaction mixture was partitioned between aqueous satd. NaHCO$_3$ and EtOAc, and the EtOAc layer dried over Na$_2$SO$_4$. The crude intermediate was 3-bromo-5-methoxy-4-methylpridine purified by SGC (EtOAc/Hexanes). MS (ESI+) for m/z 201 [M+H]$^+$.

Step 2: 3-Bromo-5-methoxy-4-methylpridine (0.76 g) was placed in a single neck round bottom flask with NaOtBu (1.4 eq), BINAP (0.8 eq), Pd$_2$(dba)$_3$ (0.25 eq), and benzhydrylideneamine (1 eq) in toluene 20 ml, and refluxed at 150° C. for 4 h. The reaction was partitioned between water and EtOAc, and the EtOAc layer dried over Na$_2$SO$_4$. The product was purified by SGC (EtOAc/ Hexane) affording 5-methoxy-4-methyl-N-(diphenylmethylene)pyridine-3-amine. MS (ESI+) for m/z 302 [M+H]$^+$.

Step 3: To 5-methoxy-4-methyl-N-(diphenylmethylene)pyridine-3-amine (0.7g) in a single neck round bottle flask, was added 14 ml of 1N HCl/THF (1:1) and the resulting mixture heated at 55° C. for 1 h. The reaction was basified with 1N NaOH to pH9, extracted with DCM, dried over Na$_2$SO$_4$, and concentrated to dryness under vacuum affording 5-methoxy-4-methyl-pyridin-3-ylamine. MS (ESI+) for m/z 139 [M+H]$^+$.

Step 4: To 3-methoxy-4-methyl-1,5-naphthyridine (0.26 g) dissolved in carbontetrachloride (6 ml) was added N-bromosuccinimide (1.2 eq) and benzoyl peroxide (0.3 eq) and heated at 80° C. for 4 h. The reaction was partitioned between satd. NaHCO$_3$ and DCM, and the DCM layer then dried over Na$_2$SO$_4$ to give the title compound (120 mg) after concentration. MS (ESI+) for m/z 252 [M+H]$^+$.

Preparation 37: 8-methoxyquinoxaline-5-sulfonyl chloride

Step 1: 2,3-Diaminophenol (2 g) in 10 ml acetic acid and 20 ml 4M sodium acetate and a solution of oxalaldehyde (4.8 g) dissolved in 20 ml water were combined and the resulting mixture was heated at 60° C. for 1.5 h. After cooling to RT water (100 ml) was added and the mixture extracted with EtOAc. The organic layer was dried over Na$_2$SO$_4$, and concentrated to give quinoxalin-5-ol. MS (ESI+) for m/z 147 [M+H]$^+$.

Step 2: To quinoxalin-5-ol (0.43 g) dissolved in DMF (6 ml) was added K$_2$CO$_3$ (2.5 eq.) and KI (0.2 eq.). To this mixture was then added dropwise iodomethane (1.2 eq.). The resulting mixture then heated to 50° C. overnight. The reaction mixture was subsequently partitioned between satd. NaHCO$_3$ and EtOAc, the EtOAc layer backwashed with water and brine, dried over Na$_2$SO$_4$, and concentrated to dryness under vacuum. The crude material was then purified by SGC (MeOH:DCM) affording 5-methoxyquinoxaline. MS (ESI+) for m/z 160 [M+H]$^+$.

Step 3: 5-Methoxyquinoxaline was converted to the title compound by the method of Preparation 10. MS (ESI+) for m/z 259 [M+H]$^+$.

Preparation 38:
7-bromo-pyrido[2,3-b]pyrazine-8-carbaldehyde

2-Amino-5-bromo-4-methyl-3-nitropyridine (1.63 g, 7.0 mmol; Combi-Blocks) was partially dissolved in MeOH (240 mL) in a Parr shaker flask, and to this was added PtO$_2$ catalyst (29 mg) before subjecting it to H$_2$ (45 psi) with shaking at RT for 1 h. More catalyst was added (30 mg) and hydrogenolysis continued for an additional 2 h before removal of the solids by filtration. The filtrate was concentrated to yield crude 5-bromo-2,3-diamino-4-methyl-3-nitropyridine (1.5 g). MS (ESI+) for m/z 203 (M+H)$^+$. This was subsequently converted to the title compound following analogous methods in Preparation 37 Step 1 and Preparation 16. MS (ESI+) for m/z 239 (M+H)$^+$.

Preparation 39:
3-chloro-[1,8]naphthyridine-4-carbaldehyde

Step 1: 4-Methyl-pyridin-2-ylamine (30 g, 0.28 mol) was dissolved in DCM (300 mL) and treated with TEA (41 mL) followed by trimethylacetyl chloride (38 mL) via a dropping funnel over 30 min. The mixture was allowed to stir overnight at RT, then poured into a separatory funnel with water (100 mL) and satd. aq. NaHCO$_3$ (75 mL). The organic layer was extracted, washed with satd. aq. NaHCO$_3$ (75 mL), dried over Na$_2$SO$_4$, and concentrated to give solid 2,2-dimethyl-N-(4-methyl-pyridin-2-yl)-propionamide (42 g, 0.22 mol). $^1$H NMR (CDCl$_3$) δ 8.09 (m, 2 H), 7.93 (br s, 1 H), 6.83 (m, 1 H), 2.33 (s, 3H), 1.29 (s, 9H).

Step 2: 2,2-Dimethyl-N-(4-methyl-pyridin-2-yl)-propionamide (42 g, 0.22 mol) from Step 1 was placed in a 3-neck 3 L flask fitted with an overhead stirrer. To this was added water (650 mL), then Na$_2$HPO$_4$ (78 g, 0.55 mol), followed by DCM (220 mL). The mixture was stirred and cooled in an ice-bath to 0° C., then chlorine gas was bubbled slowly through a sparge-frit. The reaction was monitored by TLC (EtOAc/hexanes 1/1), and found to be complete after 80 min. The reaction mixture was poured into a separatory funnel and extracted. The aqueous layer was re-extracted with DCM (2×100 mL). The combined layers were dried over Na$_2$SO$_4$ and concentrated to a crude solid product which was recrystallized from hexanes to yield the purified N-(5-chloro-4-methyl-pyridin-2-yl)-2,2-dimethyl-propionamide (41 g, 0.18 mol). $^1$H NMR (CDCl$_3$) δ 8.18 (s, 1 H), 8.12 (s, 1 H), 7.94 (br s, 1 H), 2.35 (s, 3H), 1.29 (s, 9H).

Step 3: N-(5-chloro-4-methyl-pyridin-2-yl)-2,2-dimethyl-propionamide (18.3 g, 0.081 mol) from Step 2 was placed in a flame-dried three-neck 1 L flask fitted with an overhead stirrer, under nitrogen. To this solid was added anhydrous diethyl ether (170 mL) and the mixture stirred until a solution, whereupon it was cooled in a dry ice/acetone bath for 20 min (slurry formed). To the resulting slurry was dropped in tert-butyl lithium (1.7 M in pentane, 100 mL) via cannula over an 8 min period. The flask was removed from the cooling bath and allowed to stir until it reached RT, at which time 3-dimethylamino-propenal (10 mL, 0.10 mol) was added neat. The resulting mixture was stirred overnight at RT under a nitrogen stream; by morning a dry powder resulted. To this was added water (80 mL) followed by slow addition of conc. HCl (40 mL) while cooling the flask in an ice/water bath. After the acid addition, the ice bath was removed and the flask was heated to 80° C. for 1 h, cooled in an ice/water bath and treated with NaOH (solid pellets) until basic. The basic aqueous mixture was subsequently extracted with DCM (4×100 mL)—patience and brine were required to help break the resulting emulsions. The combined extracts were dried over Na$_2$SO$_4$ and concentrated under vacuum to yield crude product, which was further purified by SGC (EtOAc eluant) to yield pure 3-chloro-4-methyl-[1,8]naphthyridine (10 g, 0.056 mol). Note: owing to weak UV activity, it was found more efficacious to monitor column fractions with MS rather than UV.

MS (ESI+) for m/z 179 (M+H)+. ¹H NMR (CDCl₃) δ 9.06 (m, 1 H), 8.96 (s, 1 H), 8.34 (d, 1 H), 7.51 (m, 1H), 2.72 (s, 3H).

Step 4: 3-Chloro4-methyl-[1,8]naphthyridine (3.0 g, 16.7 mmol) from Step 3 was dissolved in 4:1 dioxane:water (30 mL) and selenium dioxide (5.9 g, 50.4 mmol) was added. The reaction mixture was heated (110° C.) for 2.5 h, cooled to RT, poured into satd. aq. NaHCO₃ (30 mL) and water (10 mL). The mixture was subsequently treated with DCM (80 mL) and the solids filtered off through Celite and rinsing the filter cake with DCM. After separating the aqueous and organic layers, the aqueous phase was re-extracted with DCM (4×80 mL) and the combined organics were dried (Na₂SO₄) and concentrated. The crude product was chromatographed by SGC (MeCN eluant) to yield the title compound 3-chloro-[1,8]naphthyridine-4-carbaldehyde (1.0 g, 5.2 mmol). Note: owing to weak UV activity, it was found more efficacious to monitor column fractions with MS rather than UV, as in Step 3. MS (ESI+) for m/z 193 (M+H)+. ¹H NMR(CDCl₃)δ 10.79 (s, 1H), 9.28 (dd, 1H), 9.17 (s, 1H), 9.14 (dd, 1H), 7.63(dd. 1H).

Preparation 40: 2-cyclopropyl-3H-imidazo[4,5-b]pyridine-7-carbaldehyde

2-Cyclopropyl-7-methyl-3H-imidazo[4,5-b]pyridine (100 mg, 0.58 mmol; from EP0420237 A1) was treated with SeO₂ (160 mg, 1.44 mmol) in 6 ml of dioxane:water (4:1) and subjected to microwave irradiation (300 W, normal absorbance) at 180° C. for three 20 min intervals. The mixture was subsequently treated with satd. aq. NaHCO₃ (25 ml) and water (25 ml) and the solids were removed by filtration through Celite, rinsing with DCM. The filtrate was extracted with DCM (4×50 mL) and the combined organic extracts were dried (Na₂SO₄), filtered, and concentrated to dryness to yield the crude title compound. MS (ESI+) for m/z 188 (M+H)+.

Preparation 41: 3-methyl-3H-imidazo[4,5-b]pyridine-7-carbaldehyde

Step 1: 4-Methyl-pyridine-2,3-diamine (1.0 g, 8.12 mmol) was treated with formic acid (15 mL) and heated to reflux for 3 h. After cooling to RT, the solution was concentrated under a nitrogen stream over 48 h, then diluted with DCM (30 mL) before filtering out the solids in a Buechner funnel. The filtrate was concentrated and the crude product chromatographed by SGC (DCM:MeOH:NH₄OH=90:10:1 as eluant) to yield purified 7-methyl-3H-imidazo[4,5-b]pyridine (0.325 g, 2.44 mmol). MS (GCMS) for m/z 133 (M)+.

Step 2: 7-Methyl-3H-imidazo[4,5-b]pyridine (2.0 g, 15 mmol) was dissolved in acetone (60 ml) and treated with freshly ground KOH (4.21 g) followed by dropwise addition of iodomethane (10 ml). After 10 min, the reaction mixture was poured into satd. aq. NaHCO₃ (25 ml) in water (25 ml) and extracted with DCM (4×80 ml). The organic layers were combined and dried over Na₂SO₄, filtered, and concentrated. SGC (DCM:MeOH:NH₄OH =96:4:1 as eluant) yielded 3,7-dimethyl-3H-imidazo[4,5-b]pyridine (1.05 g). ¹H NMR (CDCl₃) δ 7.94 (s, 1H), 7.83 (d, 1H), 6.48 (s, 1H), 3.04 (s, 3H), 2.07 (s, 3H).

Step 3: Oxidation with SeO₂ as described in Preparation 16 yielded the title compound. MS (ESI+) for m/z 162 (M+H)+.

Preparation 42: 6-chloro-3H-imidazo[4,5-b]pyridine-7-carbaldehyde

Step 1: N-(5-chloro-4-methyl-pyridin-2-yl)-2,2-dimethyl-propionamide (3.0 g, 13.2 mmol) from Preparation 39 Step 2 was treated with concentrated sulfuric acid (19 ml) and allowed to stir for 30 min before cooling in an ice-water bath to between 0-10° C. and adding fuming red nitric acid (0.67 ml) over a 10 min period. The reaction mixture was heated (35° C.) overnight, then diluted with water (40 ml) and extracted with DCM (6×50 ml). The DCM was removed under vacuum and the residue was re-dissolved in conc. HCl (20 ml) and heated to 40° C. for 18 h, then 100° C. for 4 h, and finally 50° C. for 18 h. The mixture was cooled to RT, diluted with water (50 ml), and extracted with DCM (5×40 ml). The aqueous layer was treated with 30% (w/v) NaOH aq. until the pH=12, then extracted with DCM (6×60 ml). These latter extracts were combined, dried over Na₂SO₄, filtered, and concentrated to yield 5-chloro-4-methyl-3-nitro-pyridin-2-ylamine (1.0 g). ¹H NMR (CDCl₃) δ 8.15 (s, 1H), 5.93 (br s, 2H), 2.49 (s, 3H).

Step 2: The material from Step 1 (1.0 g) was dissolved in MeOH (300 ml) and PtO₂ (40 mg) was added. The mixture was subjected to hydrogen (50 psi) in a Parr shaker for 3.5 h, then filtered through Celite and to the filtrate was added conc. HCl (1 ml) before concentrating to yield 5-chloro-4-methyl-pyridine-2,3-diamine hydrochloride (1 g). NMR (CDCl₃) δ 7.39 (s, 1H), 2.29 (s, 3H).

Step 3: The material from Step 2 (1 g) was dissolved in phosphoric acid (20 ml), then added to formic acid (10 ml) and heated (130° C.) for 1 h, and then cooled to RT for 3 d. The reaction mixture was then poured into ice (200 g) and the pH adjusted with 30% (w/v) aq. NaOH until solids formed. The solids were removed via filtration and rinsed with water. The filtrate (aqueous) was concentrated to dryness and extracted with hot EtOH repeatedly. The EtOH extracts were combined and concentrated to solids (3 g). The solids were extracted with hot MeCN (4×80 ml); the combined MeCN extracts were cooled to RT and solids precipitated. The precipitates were filtered (Celite) and the filtrate was concentrated to yield 6-chloro-7-methyl-3H-imidazo[4,5-b]pyridine (0.278 g). MS (ESI+) for m/z 168 (M+H)+.

Step 4: The product from Step 3 (0.278 g) was subjected to SeO₂ oxidation as in Preparation 16, yielding the title compound (69 mg). MS (ESI+) for m/z 182 (M+H)+.

Preparation 43: 4-bromomethyl-quinoline-3-carbonitrile

4-Methyl-quinoline-3-carbonitrile (*Arch. Pharm.* 1989, 322, 511) was brominated according to the procedure used in Preparation 36, Step 4. MS (ESI+) for m/z 249 (M+2)+.

Preparation 44: 3-methyl-quinoline-4-carbaldehyde

Step 1: 2-Chloro-3-methyl-quinoline-4-carbonyl chloride (200 mg) was synthesized as reported (*Bioorg. Med. Chem.* 2002, 10, 779) and dissolved in THF (4 ml) and treated with sodium borohydride (189 mg, 5.0 mmol) under nitrogen. The reaction mixture was stirred for 1 h, diluted with water, extracted three times with DCM, dried over Na₂SO₄, filtered and evaporated under vacuum to provide 174 mg of crude alcohol. ¹H NMR (CDCl₃) δ 8.12 (d, 1H), 7.97 (d, 1H), 7.65 (m, 1H) 7.57 (m, 1H), 5.16 (s, 2H), 2.62 (s, 3H). LCMS (ESI+) for m/z 208 (M)+, 210 (M+2)+.

Step 2: A mixture of 170 mg of the alcohol from Step 1 (0.819 mmol), 30 mL of EtOH, 0.35 mL of TEA (2.5 mmol)

and 100 mg of 10% Pd/C was shaken under 15 psi of hydrogen for 30 min, filtered through Celite with MeOH and evaporated under vacuum. The resulting residue was partitioned between water and DCM, extracted three more times with DCM, washed with brine, dried over $Na_2SO_4$, filtered and evaporated under vacuum to provide 128 mg of the title compound. $^1H$ NMR ($CDCl_3$) δ 8.60 (s, 1H), 8.19 (d, 1H), 8.04 (d, 1H), 7.63 (m, 1H), 7.56 (m, 1H), 5.13 (s, 2H), 2.51 (s, 3H). LCMS (ESI+) for m/z 174 (M+H)+.

Preparation 45: 8-methoxyquinoline-5-carbaldehyde

Step 1: 5-(Hydroxymethyl) quinolinol (6.7 g, 38 mmol) was dissolved in DMF (38 mL) and treated with potassium carbonate (16 g, 116 mmol) followed by methyl iodide (2.9 mL, 6.8 g, 48 mmol). The mixture was allowed to stir overnight at RT, then poured into a separatory funnel with water and extracted 3x DCM. The organic layer was dried over $Na_2SO_4$, and concentrated to give solid 5-hydroxymethyl-8-methoxyquinoline (6.5 g). $^1H$ NMR ($CDCl_3$) δ 8.97 (d, 1H), 8.51 (d, 1H) 7.49 (m, 2H), 6.99 (d, 1H), 5.05 (s, 2H), 4.09 (s, 3H).

Step 2: 5-Hydroxymethyl-8-methoxyquinoline (6.5 g, 34 mmol) from Step 1 was dissolved in 250 mL of DCM and treated with 24 g of manganese dioxide. After stirring for 24 h, the mixture was treated with an additional 6 g of manganese dioxide and stirred for 24 h. The mixture was filtered through a pad of Celite, and the filtrate was concentrated under vacuum to afford 6 g of the title compound as a brown solid. $^1H$ NMR ($CDCl_3$) δ 10.2 (s, 1 H), 9.69 (d, 1 H), 9.01 (d, 1 H), 8.01 (d, 1H), 7.61 (dd, 1H), 7.16 (d, 1H), 4.19 (s, 3H).

Preparation 46: 3-methoxyquinoline-4-carbaldehyde

Step 1: Methyl 3-hydroxycinchoninate, (J. Org. Chem. 1953, 18, 552) (1.53 g, 7.54 mmol), potassium carbonate (1.15 g, 8.29 mmol) in acetone (11 ml) was treated with methyl iodide (470 uL, 7.54 mmol) was stirred at RT under nitrogen overnight. The mixture diluted with water and extracted into DCM and washed with satd. sodium thiosulfate solution. The organics were dried over $Na_2SO_4$ and concentrated. Material purified by SGC (Combi flash, 10-50% EtOAc-hexanes over 40 minutes) gave methyl 3-methoxycinchoninate. $^1H$ NMR ($CDCl_3$) δ 8.85 (s, 1H), 8.07 (d, 1H), 7.72 (d, 1H), 7.61 (m, 2H), 4.08 (s, 3H), 4.03 (s, 1H). MS (ESI+) for m/z 218 (M+H)+.

Step 2: Methyl 3-methoxycinchoninate (427 mg, 1.96 mmol) in toluene (3.9 ml) cooled to −78° C. under nitrogen atmosphere. DiBAL-H 1M in toluene (5.9 ml, 5.9 mmol) added dropwise over 5 min. Reaction quenched with water (3.9 ml and warmed to RT, alternating portions of magnesium sulfate and $NaHCO_3$ added and EtOAc added. Solids filtered and washed with EtOAc then concentrated gave intermediate alcohol (339 mg). $^1H$ NMR($CDCl_3$): δ 8.67 (s, 1H), 8.10 (d,1H), 8.00 (d, 1H), 7.55 (m, 2H), 5.14 (s, 2H), 3.98 (s,3H).

Step 3: The product from Step 2 (339 mg, 1.79 mmol) was dissolved in DCM (1.8 ml) and treated with Dess-Martin periodinane (760 mg, 1.79 mmol) at RT. After completion the mixture was diluted with DCM and washed with sat. $NaHCO_3$ solution. Organics were then dried over $Na_2SO_4$ and concentrated. Material was purified by SGC (0-100% EtOAc: hexanes over 45 minutes) yielding yellow solid (264 mg). MS (ESI+) for m/z 188 (M+H)+. $^1H$ NMR ($CDCl_3$) δ 10.90 (s, 1H), 9.02 (m, 2H), 8.08 (d, 1H), 7.65 (m, 2H), 4.21 (s, 3H).

Preparation 47: 3-methoxy-[1,8]-naphthyridine-4 carbaldehyde

Step 1: N-(5-amino-4-methyl-pyridin-2-yl)-2,2-dimethyl-proprionamide (WO 9614844) (5.38 g, 25.96 mmol) dissolved in tetrafluoroboric acid 48% in water (90 ml) and cooled to −10° C. in a brine/ice bath. Sodium nitrite (2.33 g, 33.74 mmol) in water 40 ml was added dropwise to the solution over 25 min. The solids were collected by filtration and washed with cold diethyl ether. Solids were then transferred to flask and heated in MeOH (85 ml) open to air at 55-60° C. overnight. Solvent was removed under vacuum and the crude material dissolved in EtOAc and washed with $NaHCO_3$ solution. The organics were dried over $Na_2SO_4$ and concentrated after filtration. The intermediate was purified by SGC and eluted with EtOAc:hexanes 0 to 25% over 30 minutes furnished 3.16 g N-(5-methoxy-4-methyl-pyridin-2-yl)-2,2-dimethyl-proprionamide. MS (ESI+) for m/z (M+H)+ 223. $^1H$ NMR ($CDCl_3$) δ 8.08 (s, 1H), 7.74 (s, NH), 7.68 (s, 1H), 3.84 (s, 3H), 2.22 (s, 3H), 1.62 (s, $NH_2$), 1.30 (s, 9H).

Step 2: The material from Step 1 was converted to 3-methoxy-4-methyl-[1,8]naphthyridine by the method in Preparation 39 Step 3. $^1H$ NMR ($CDCl_3$) δ 8.98 (d, 1H), 8.92 (s, 1H), 8.32 (d, 1H), 7.45 (m,1H), 4.07 (s, 3H), 2.54 (s, 3H).

Step 3: The material from Step 2 was converted to 3-methoxy-[1,8]naphthyridine-4-carbaldehyde by the method in Preparation 16. $^1H$ NMR ($CDCl_3$) δ 10.84 (s, 1H), 9.42 (d, 1H0, 9.22(s, 1H), 9.03 (m, 1H), 7. 57 (m, 1H) 4. 25 (s,3H).

Preparation 48: 4-methyl-[1,8]naphthyridine

4-Methyl-pyridin-2-ylamine was converted to 4-methyl-[1,8]naphthyridine according to known methods (Chem. Pharm. Bull. 1971, 19, 1751). m-Nitrobenzene sodium sulfonate (202 g, 897 mmol) was weighed into a 3 L 3-necked flask equipped with an overhead stirrer, and the flask immersed in an ice-water bath before adding conc. sulfuric acid (260 ml), glycerol (145 ml, 1987 mmol), 4-methyl-pyridin-2-ylamine (50 g, 463 mmol), and finally water (260 ml). The mixture was heated to 120° C. for 8 h, then cooled to RT to yield a chocolate brown slurry. Sodium hydroxide (20 N aq) was added slowly with cooling (such that the temperature did not exceed 40° C.) until pH approximated 10. The resulting sludge was filtered through Celite and the filtrate extracted with DCM (3×100 ml). The organic layers were dried over $Na_2SO_4$, filtered, and concentrated under vacuum to a black oil. The desired product (7.32 g, 50.8 mmol) was isolated by SGC (DCM:MeOH 95:5).

Preparation 49:
3-bromo-[1,8]naphthyridine-4-carbaldehyde

Step 1: 2-Amino-5-bromo-4-methylpyridine furnished 3-bromo-4-methyl-[1,8]-naphthyridine using the analogous method in Preparation 48. $^1H$ NMR ($CDCl_3$) δ 9.11 (m, 2H), 8.43 (d, 1H), 7.54 (m, 1H), 2.79 (s, 3H).

Step 2: A mixture of 3-bromo-4-methyl-[1,8]-naphthyridine (1.5 g, 6.7 mmol), dioxane (16 mL) and water (0.6 mL) was treated with selenium dioxide (3.0 g, 27 mmol) and stirred at 80° C. for 1 h. The mixture was cooled to RT, diluted with satd. aq. $NaHCO_3$, extracted 3× with EtOAc, and the combined organic phases were dried over $Na_2SO_4$, filtered and concentrated under vacuum. Filtration through a pad of silica gel eluting with EtOAc gave 0.70 g of the title compound as a yellow solid. $^1H$ NMR ($CDCl_3$) δ 10.62 (s, 1H), 9.32 (s, 1H), 9.28 (d, 1H), 1.18 (d, 1H), 7.66 (dd, 1H).

Preparation 50: 2-methoxy-1-[1,8]naphthyridin-4-yl-ethanone

Step 1: 1-[1,8]Naphthyridin-4-yl-ethanone from Preparation 18 (250 mg, 1.45 mmol), 2,6-lutidine (0.254 ml, 2.18 mmol) in DCM (3.6 ml) was treated with trimethylsilyl triflate (0.276 ml, 1.53 mmol) and allowed to stir at RT overnight. Mixture diluted with DCM and washed with satd. NaHCO$_3$. Organics dried over Na$_2$SO$_4$ and concentrated, furnished 350 mg 4-(1-trimethylsilanyloxy-vinyl)-[1,8]-naphthyridine as an oil. MS (ESI+) for m/z 245 (M+H)$^+$.

Step 2: To a suspension of iodosobenzene (347 mg, 1.57 mmol), in MeOH (7.2 ml) in an ice bath was added borontrifluoride diethyletherate (0.200 ml, 1.57 mmol) followed by 4-(1-trimethylsilanyloxy-vinyl)-[1,8]-naphthyridine from Step 1 (350 mg, 1.43 mmol) in minimum amount of MeOH. The reaction mixture was warmed to RT overnight and then quenched with solid NaHCO$_3$ and diluted with water. Iodobenzene was extracted with EtOAc and the desired material re-extracted with DCM 2×. The organic layers were dried over Na$_2$SO$_4$ and concentrated to an orange oil (110 mg), which consisted of a 2:3 mixture of starting material and desired title compound. MS (ESI+) for m/z 203 (M+H)$^+$.

Preparation 51: 5-bromomethyl-quinoline-8-carbonitrile

Step 1: 5-Bromo-2-methylbenzenamine (*J. Fluorine Chem.* 2002, 116, 173) (8.9 g, 48 mmol) was treated with water (27 mL), concentrated sulfuric acid (27 mL), glycerol (19 g, 206 mmol), 3-nitrobenzenesulfonic acid sodium salt (21 g, 23 mmol) and was heated to 120° C. for 8 h, then to 150° C. for 4 h. The mixture was cooled to RT, quenched with ice, cautiously basified with solid sodium hydroxide and buffered with solid NaHCO$_3$. The mixture was extracted twice with EtOAc, and the organic layers dried over Na$_2$SO$_4$, and concentrated. Purification by SGC (Combiflash, 5-40% EtOAc-hexanes over 40 minutes) gave 5.33 g of 5-methyl-8-bromoquinoline. $^1$H NMR (CDCl$_3$) δ 9.05 (d, 1H), 8.34 (d, 1H), 7.94 (d, 1H), 7.49 (dd, 1H), 7.24 (d, 1H), 2.65 (s, 3H).

Step 2: 5-Methyl-8-bromoquinoline (01.5 g, 6.78 mmol) was treated with Pd$_2$(dba)$_3$ (0.62 g 0.67 mmol), diphenylphosphinoferrocene (0.752 g, 1.36 mmol), zinc cyanide (2.77 g, 23.7 mmol), cuprous iodide (0.064 g, 0.34 mmol) and degassed DMF (45 mL, purged with nitrogen prior to use) in a Schlenk flask under nitrogen. The mixture was heated to 80° C. overnight. After cooling to RT, the mixture was poured into 4:1:4 sat ammonium chloride:ammonium hydroxide(37%):water (90 ml), extracted 3× with EtOAc, and the organic layers dried over Na$_2$SO$_4$, and concentrated. The material was purified by SGC and eluted with 5-45% EtOAc:hexanes over 30 minutes to afford 1.05 g of 5-methylquinoline-8-carbonitrile. $^1$H NMR (CDCl$_3$) δ 9.10 (d, 1H), 8.39 (d, 1H), 8.01 (d, 1H), 7.58 (m, 1H), 7.43 (m, 1H), 2.76 (s, 3H).

Step 3: The material from Step 2 was brominated according to the method of Preparation 36 Step 4, yielding the title compound. $^1$H NMR (CDCl$_3$) δ 9.16 (m, 1H), 8.55 (d, 1H), 8.08 (d, 1H), 7.66 (m, 1H), 4.88 (s, 2H).

Preparation 52: 4-formyl-quinoline-8-carbonitrile

Step 1: 2-Bromoaniline (5.16 g, 30 mmol) dissolved in acetic acid and conc. sulfuric acid was treated with a solution of methyl vinyl ketone in acetic acid. The reaction mixture heated to 90° C. for 14 h. The cooled mixture was poured into water and basified with sodium hydroxide and extracted into EtOAc. The organics were dried over Na$_2$SO$_4$, and concentrated the purified by SGC (Combiflash 0-100% EtOAc: hexanes over 30 minutes) followed by recrystallization from hot hexanes furnished 4-methyl-8-bromoquinoline (2.3 g). $^1$H NMR (CDCl$_3$) δ 8.92 (d, 1H), 8.08 (d,1H), 8.01 (d,1H), 7.45 (t,1H), 7.32 (d,1H), 2.71 (s, 3H).

Step 2: 4-Methyl-8-bromoquinoline (0.1 g, 0.47 mmol) was treated with Pd$_2$(dba)$_3$ (0.049 g, 0.047 mmol), diphenylphosphinoferrocene (0.052 g, 0.094 mmol), zinc cyanide (0.19 g, 1.6 mmol), cuprous iodide (0.005 g, 0.024 mmol) and degassed DMF (2.3 mL, purged with nitrogen prior to use) in a Schlenk flask under nitrogen. The mixture was heated to 80° C. for 2 h. After cooling to RT, the mixture was diluted with water, extracted 3× with EtOAc, and the organic layers dried over Na$_2$SO$_4$, and concentrated to afford 0.1 g of 5-methylquinoline-8-carbonitrile. $^1$H NMR (CDCl$_3$) δ 8.89 (d, 1H), 8.04 (d, 1H), 8.02 (d, 1H), 7.41 (m, 1H), 7.27 (m, 1H), 2.70 (s, 3H).

Step 3: The material from Step 2 was converted using Preparation 16 to the title compound. $^1$H NMR (CDCl$_3$) δ 10.43 (s, 1H), 9.40 (d, 1H, 9.38 (d, 1H), 8.24 (d,1H), 7.94 (d,1H), 7.80 (t, 1H).

Preparation 53: 2,2-dioxo-2,3-dihydro-1H-2λ$^6$-benzo[c]thiophene-5-carbaldehyde Step 1: A solution of methyl 3,4-bis(bromomethyl)benzoate (997 mg, 3.10 mmol) in EtOH (16 ml) and water (4 ml) was treated with sodium sulfide nonahydrate (745 mg, 3.10 mmol). The solution was heated to reflux for 2 h with rapid stirring, then cooled to RT. The mixture was then concentrated to dryness under vacuum, and the residue was suspended in DCM (50 ml). The slurry was filtered and the solid washed with additional DCM. The filtrate was dried over Na$_2$SO$_4$, filtered and concentrated under vacuum to afford methyl 2,1-dihydrobenzothiophene-5-carboxylate (581 mg) as a yellow oil. $^1$H NMR (CDCl$_3$) δ 7.88-7.94 (m, 2H), 7.31 (d, 1H), 4.29 (s, 4H), 3.92 (s, 3H). MS (ESI+) for m/z 197 [M+H]$^+$.

Step 2: A solution of sulfide from Step 1 (577 mg, 2.97 mmol) in DCM (24 ml), MeOH (24 ml) and water (16 ml) was treated with oxone (2.37 g, 3.85 mmol, 1.3 equiv), and the reaction stirred at RT overnight. The mixture was then filtered through a pad of Celite, and the pad washed with additional DCM (2×20 ml). The filtrate layers were separated, and the aqueous layer extracted with DCM (2×25 ml). The combined organic extracts were dried over Na$_2$SO$_4$, filtered, and concentrated under vacuum. The resulting crude residue was purified by SGC (gradient 80:20 to 50:50 hexanes/EtOAc) to afford methyl 2,2-dioxo-2,1-dihydrobenzothiophene-5-carboxylate (288 mg) as an off-white solid: $^1$H NMR (CDCl$_3$) δ 8.05 (d, 1H), 8.01 (s, 1H), 7.41 (d, 1H), 4.42 (d, 4H), 3.94 (s, 3H). MS (ESI+) for m/z 227 [M+H]$^+$.

Step 3: A solution of ester from Step 2 (288 mg, 1.27 mmol) in DCM (10 ml) was cooled to −78° C. under nitrogen and treated with LiAlH$_4$ (1.0 M in hexanes, 1.50 ml, 1.50 mmol) dropwise over 5 min. The mixture was then stirred at −78° C. for 90 min., then warmed to RT and stirred for an additional 1 h. Water (1 ml) was then added, and vigorous gas evolution was observed. The mixture was stirred for 10 min. and 2 N NaOH (1 ml) was then added, followed by additional water (3 ml). The mixture was stirred for 30 min, diluted with EtOAc (50 ml) and dried over Na$_2$SO$_4$. Subsequent filtration and concentration of the filtrate under vacuum afforded the desired alcohol intermediate (310 mg), which was used directly. This alcohol was dissolved in DCM (13 ml), and the solution treated with MnO$_2$ (463 mg, 5.33 mmol). After stirring at RT for 1.75 h, the slurry was filtered through a pad of Celite, and the pad repeatedly washed with DCM. The filtrate was then concentrated under vacuum, and the residue purified by SGC (gradient 75:25 to 50:50 hexanes/EtOAc) to afford the title compound (25 mg) as a light yellow solid: $^1$H NMR (CDCl$_3$) δ 10.02 (s, 1H), 7.85-7.92 (m, 2H), 7.53 (d, 1H), 4.45 (d, 4H). $^{13}$C NMR (CDCl$_3$) δ 190.8, 137.8, 136.8, 132.6, 130.3, 127.0, 126.9, 56.9, 56.6. MS (ESI+) for m/z 197 [M+H]$^+$.

Preparation 54: benzothiazole-5-sulfonyl chloride

Step 1: A solution of 2-bromo-5-nitroaniline (5.27 g, 24.3 mmol) in 98% formic acid (30 ml) was heated to reflux for 90 min under nitrogen. The cooled reaction mixture was then poured into cold water (600 ml) which afforded a yellow precipitate. The solid was isolated by filtration and the cake washed with cold water (2×200 ml). Subsequent drying overnight under vacuum overnight afforded N-formyl-2-bromo-5-nitroaniline (5.84 g, 98%) as a yellow solid: $^1$H NMR (DMSO-d$_6$) δ 10.14 (br s, 1H), 9.01 (d, J=2.4 Hz, 1H), 8.46 (s, 1H), 7.98 (d, J=8.8 Hz, 1H), 7.91 (dd, J=8.8, 2.5 Hz, 1H); $^{13}$C NMR (DMSO-d$_6$) δ 161.2, 146.9, 136.6, 134.0, 120.6, 119.8, 116.7.

Step 2: A solution of formamide from Step 1 (5.83 g, 23.8 mmol) and sodium sulfide nonahydrate (8.60 g, 35.8 mmol) in EtOH (120 ml) was heated to reflux for 2 h under nitrogen. After this time the reaction was cooled to RT then poured into cold water (600 ml). The resulting solution was cooled in an ice bath and acidified to pH 1 with 37% HCl. The solution was cooled in an ice bath for a further 1 h, during which time an orange precipitate formed. This solid was isolated by filtration and dried under vacuum to afford 5-nitrobenzothiazole as an orange solid (2.28 g). The above filtrate was extracted with EtOAc (3×200 ml), and the combined organic extracts dried over Na$_2$SO$_4$, filtered and concentrated under vacuum to afford additional 5-nitrobenzothiazole (0.89 g) as an orange solid. NMR and TLC analysis indicated that both crops of product were identical; the combined yield was 3.17 g. $^1$H NMR (CDCl$_3$) δ 9.19 (s, 1H), 9.02 (d, 1H), 8.35 (dd, 1H), 8.12 (d, 1H); $^{13}$C NMR (CDCl$_3$) δ 157.3, 153.1, 147.0, 140.2, 122.5, 120.1, 119.3. MS (ESI+) for m/z 181 [M+H]$^+$.

Step 3: A solution of material from Step 2 (1.17 g, 6.47 mmol) in 37% HCl (15 mL) was heated to 40° C., treated with tin(II) chloride dihydrate (4.39 g, 19.4 mmol), and stirred at this temperature for 30 min. The reaction was then poured into satd. aqueous NaHCO$_3$ (250 mL) and extracted with EtOAc (3×100 mL). The combined organic extracts was dried over Na$_2$SO$_4$, filtered, and concentrated under vacuum. The resulting crude residue was purified by SGC (gradient 75:25 to 0:100 hexanes/EtOAc) to afford 4 (0.214 g) as an orange solid: $^1$H NMR (CDCl$_3$) δ 8.91 (s, 1H), 7.69 (d, J=8.5 Hz, 1H), 7.41 (d, J=2.2 Hz, 1H), 6.87 (dd, J=8.5, 2.2 Hz, 1H), 4.12 (br s, 2H); MS (ESI+) for m/z 151 [M+H]$^+$.

Step 4: A solution of the aniline from Step 3 (0.217 g, 1.45 mmol) in glacial acetic acid (2 ml) was added dropwise to 37% HCl (2 ml). The mixture was cooled to −10° C. by an ice/salt bath and a solution of sodium nitrite (0.110 g, 1.59 mmol) in water (1.1 ml) added dropwise. The mixture was then stirred for 60 min at −10° C. While this diazotization reaction was in progress, a second flask containing glacial acetic acid (2 ml) and cuprous chloride (0.029 g, 0.293 mmol) was treated with sulfur dioxide gas until the mixture became a blue-green color. This mixture was cooled to 10° C. and the above diazotization reaction was added in portions over 15 min. Vigorous gas evolution was observed. The mixture was warmed to RT and stirred overnight. The reaction was then poured into cold water (100 ml) and the aqueous layer extracted with EtOAc (3×50 ml). The combined organic extracts were washed with water (2×50 ml), satd. aqueous NaHCO$_3$ (3×25 ml), and brine (3×25 ml), then dried over Na$_2$SO$_4$, filtered and concentrated under vacuum. Purification of the resulting crude solid by SGC (90:10 hexanes/EtOAc) afforded the title compound (0.123 g) as an off-white solid: mp 110-112° C.; $^1$H NMR (CDCl$_3$) δ 9.24 (s, 1H), 8.83 (d, 1H), 8.23 (d, 1H), 8.11 (dd, 1H). $^{13}$C NMR (CDCl$_3$) δ 157.5, 152.7, 142.6, 141.0, 123.4, 123.1, 122.8. MS (ESI+) for m/z 234, 236 [M+H]$^+$.

Preparation 55:
4-ethoxy-3-methoxy-benzenesulfonyl chloride

Step 1: Iodoethane (1.93 mL, 38.4 mmol) was added dropwise over 15 min. to a stirred mixture of 4-nitroguaiacol 1 (5.00 g, 29.6 mmol) and K$_2$CO$_3$ (6.21 g, 44.3 mmol) in DMF (30 ml) at 60° C. under nitrogen. After 2 h the reaction was cooled to RT and diluted with water (100 ml) and methyl tert-butyl ether (250 ml). The organic layer was washed with water (25 ml), brine (2×20 ml), dried over Na$_2$SO$_4$, filtered and concentrated under vacuum to afford 2-ethoxy-5-nitroanisole (5.74 g) as a pale yellow solid. mp 88-90° C. $^1$H NMR (DMSO-d$_6$) δ 7.89 (dd, 1H), 7.73 (d, 1H), 7.16 (d, 1H), 4.17 (q, 2H), 3.88 (s, 3H), 1.37 (t, 3H). $^{13}$C NMR (DMSO-d$_6$) δ 153.9, 148.6, 140.5, 117.6, 111.5, 106.4, 64.6, 55.9, 14.4. MS (ESI+) for m/z 198 [M+H]$^+$.

Step 2: A suspension of 2-ethoxy-5-nitroanisole from Step 1 (5.50 g, 27.9 mmol) and 10% Pd/C (1.0 g) in 1:1 EtOH:EtOAc (50 ml) was shaken under an atmosphere of H$_2$ (35-40 psi) for 30 min. The reaction mixture was filtered through Celite and concentrated under vacuum to afford 4-ethoxy-3-methoxyaniline (4.82 g, 100%) as a brown solid: mp 54-56° C. $^1$H NMR (DMSO-d$_6$) δ 6.61 (d, 1H), 6.25 (d, 1H), 6.03 (dd, 1H), 4.65 (s, 2H), 3.82 (q, 2H), 3.66 (s, 3H), 1.22 (t, 3H); $^{13}$C NMR (DMSO-d$_6$) δ 143.6, 138.8, 116.6, 105.1, 99.9, 65.0, 55.1, 15.1; MS (ESI+) for m/z 168 [M+H]$^+$.

Step 3: To a solution of 4-ethoxy-3-methoxyaniline from Step 2 (2.35 g, 14.05 mmol) in glacial acetic acid (5 ml) was added concentrated HCl (15 ml). The mixture was cooled to −10° C. in an ice/salt bath and a solution of sodium nitrite (1.06 g, 15.36 mmol) in water (2.5 mL) added dropwise. The mixture was then stirred for 90 min at −10° C. While this diazotization reaction was in progress, a second flask containing glacial acetic acid (16 ml) was satd. with sulfur dioxide gas for 10 min, then cuprous chloride (0.278 g, 2.81 mmol) was added, followed by additional sulfur dioxide gas until the mixture became a blue-green color. This mixture was cooled to 10° C. and the above diazotization reaction mixture added portionwise over 25 min. The resulting mixture was allowed to warm to RT overnight. The reaction mixture was then poured into ice-cold water (100 ml) and the aqueous layer extracted with EtOAc (4×50 ml). The combined organic extracts were washed with water (2×50 ml), satd. aqueous NaHCO$_3$ (4×50 ml), and brine (3×50 ml), then dried over Na$_2$SO$_4$, filtered and concentrated under vacuum. Purification of the resulting dark red oil by chromatography (Biotage, gradient 100:0 to 80:20 hexanes/EtOAc over 850 ml) afforded 48 mg of impure product as an orange-yellow semi-solid. Trituration of this semi-solid with hexanes afforded the title compound (34 mg) as a light yellow solid. mp 72-73° C. $^1$H NMR (CDCl$_3$) δ 7.66 (dd, 1H), 7.44 (d, 1H), 6.97 (d, 1H), 4.21 (q, 2H), 3.96 (s, 3H), 1.52 (t, 3H). $^{13}$C NMR (CDCl$_3$) δ 154.3, 149.5, 135.7, 121.7, 111.3, 109.3, 65.1, 56.4, 14.5.

Additional non-limiting examples are given in Tables 1-16. Atop each table, the macrolide template structure of the examples thereunder is shown. Template variable(s) are defined for each example within the tables. The tables list (1) the example number, (2) the variable name(s) (Compounds that are C-2 fluorinated are indicated with a 2-F in the name window of a Table entry. See Preparation 29) (Compounds listed with an asterisk (*) in the name window are single diastereomers of unidentified absolute configuration.), (3) M+1 or M/2 ([M+2]/2) MS data (unless otherwise indicated), (4) $^1$H NMR spectral data run in $CD_3OD$ (unless otherwise indicated), and (5) the preparation method of coupling the headpiece reagent with the template is given as the Preparation number which describes conditions used to prepare the subject compound. In cases where a 2'-acetate protecting group exists, the group is removed as a final step as in Preparation 34, Step 3. The compounds were prepared as formate salts unless otherwise indicated.

Chromatographic purifications were typically carried out using reverse-phase high performance liquid chromatography (RP-HPLC, Shimadzu instruments) using gradient elution with acetonitrile (0.1% formic acid) and water (0.1% formic acid) solvent systems. An evaporative light scattering detection system was used to assist the compound visualization and collection process for RP-HPLC. Other purifications were carried out by normal-phase medium pressure SGC.

TABLE 1

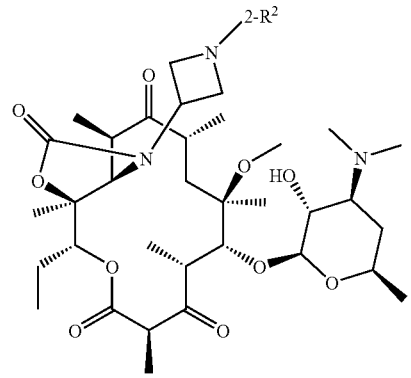

| Ex. # | 2-R$^2$ Name | MS | $^1$H NMR | Prep # |
|---|---|---|---|---|
| 1.01 | benzyl | m-1 757 | 7.43 (m, 5H) | 1 |
| 1.02 | (pyridin-2-yl)methyl | m-1 758 | 8.58 (d, 1H); 7.84 (m, 1H); 7.42 (d, 1H); 7.38 (m, 1H) | 27 |
| 1.03 | (pyridin-3-yl)methyl | m-1 758 | 8.58 (s, 1H); 8.53 (d, 1H); 7.88 (d, 1H); 7.46 (m, 1H) | 27 |
| 1.04 | (pyridin-4-yl)methyl | m-1 758 | 8.48 (dd, 2H); 7.41 (d, 2H) | 27 |
| 1.05 | (quinolin-8-yl)methyl | 810 | 8.98 (d, 1H); 8.41 (d, 1H); 8.03 (d, 1H); 7.87 (d, 1H) | 27 |
| 1.06 | (quinolin-5-yl)methyl | m-1 808 | 8.90 (d, 1H); 8.72 (d, 1H); 8.08 (d, 1H); 7.78 (m, 1H) | 27 |
| 1.07 | (quinolin-6-yl)methyl | M/2 406 | 8.85 (d, 1H); 8.38 (d, 1H); 8.03 (d, 1H); 7.98 (bs, 1H); 7.79 (d, 1H); 7.57 (m, 1H) | 27 |
| 1.08 | 3,4-difluorobenzyl | m-1 793 | 7.36-7.24 (m, 2H); 7.20 (bs, 1H) | 27 |
| 1.09 | (1H-benzo[d]imidazo-2-yl)methyl | m-1 797 | 7.52 (dd, 2H); 7.20 (dd, 2H) | 27 |
| 1.10 | (1-[pyrid-2-yl]-pyrazol-3-yl)methyl | m-1 824 | CDCl$_3$: 8.62 (bs, 1H); 8.41 (bs, 1H); 8.01-7.92 (m, 2H); 7.31 (bs, 1H); 6.61 (bs, 1H) | 27 |
| 1.11 | (1H-benzoimidazol-7-yl)methyl | M/2 400 | 8.27 (s, 1H); 7.65 (dd, 1H); 7.36-7.32 (m, 2H) | 27 |
| 1.12 | (quinoxalin-8-yl)methyl | m-1 809 | 9.01-8.96 (m, 2H); 8.20 (d, 1H); 7.99 (d, 1H); 7.91 (m, 1H) | 27 |
| 1.13 | (benzooxazol-7-yl)methyl | M/2 401 | 8.53 (s, 1/2H); 8.18 (s, 1/2H); 7.75 (d, 1/2H); 7.45 (m, 1H); 7.36 (d, 1/2H) | 27 |
| 1.14 | 4-cyanobenzyl | 784 | 7.76 (d, 2H); 7.58 (d, 2H) | 27 |
| 1.15 | 3-cyanobenzyl | m-1 782 | 7.76 (bs, 1H); 7.74-7.68 (m, 2H); 7.56 (t, 1H) | 27 |
| 1.16 | (quinolin-4-yl)methyl | m-1 808 | CDCl$_3$: 8.80 (d, 1H); 8.20 (d, 1H); 803 (d, 1H); 7.79 (t, 1H); 7.76 (t, 1H) | 27 |
| 1.17 | (1,8-naphthyridin-3-yl)methyl | m-1 809 | 9.08 (dd, 1H); 8.53-8.48 (m, 2H); 7.70 (dd, 1H); 7.63 (d, 1H) | 27 |
| 1.18 | (1H-pyrazol-5-yl)methyl | m-1 747 | 7.69 (d, 1H); 6.43 (d, 1H) | 27 |
| 1.19 | (1H-pyrazol-4-yl)methyl | m-1 747 | 7.80 (s, 2H) | 27 |
| 1.20 | (1,8-naphthyridin-4-yl)methyl | M/2 406 | 9.05 (dd, 1H); 9.00 (d, 1H); 8.75 (dd, 1H); 7.68 (m, 1H); 7.61 (d, 1H) | 27 |
| 1.21 | 1R-(pyridin-4-yl)ethyl | m-1 772 | 8.50 (dd, 2H); 7.48-7.40 (m, 2H) | 28 |
| 1.22 | 1S-(pyridin-4-yl)ethyl | m-1 772 | 8.46 (dd, 2H); 7.40 (d, 2H) | 28 |
| 1.23 | 1S-(1,8-naphthyridin-4-yl)ehtyl | 825 | 9.06 (d, 1H); 9.03 (d, 1H); 8.90 (d, 1H); 7.73 (d, 1H); 768 (m, 1H) | 28 |
| 1.24 | (pyrido[2,3-b]pyrazin-8-yl)methyl | M/2 407 | 9.14-9.11 (m, 2H); 9.04 (d, 1H); 7.88 (d, 1H) | 27 |
| 1.25 | 1R-(1,8-naphthyridin-4-yl)ethyl | 825 | 9.08 (d, 1H); 9.02 (d, 1H); 8.91 (d, 1H); 7.71-7.68 (m, 2H) | 28 |

TABLE 1-continued

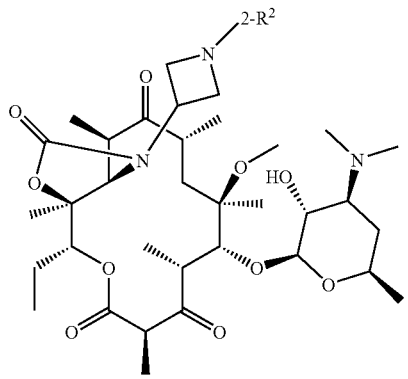

| Ex. # | 2-R² Name | MS | ¹H NMR | Prep # |
|---|---|---|---|---|
| 1.26 | (1,5-naphthyridin-4-yl)methyl | m-1 809 | 9.05 (dd, 1H); 8.99 (d, 1H); 8.48 (dd, 1H); 7.88-7.82 (m, 2H) | 27 |
| 1.27 | (1,6-naphthyridin-4-yl)methyl | 811 | 9.13 (m, 1H), 8.67 (d, 1H), 8.41 (d, 1H), 7.91 (d, 1H), 7.60 (m, 1H) | 27 27 |
| 1.28 | (quinoxalin-6-yl)methyl | 811 | 8.84 (d, 2H) 8.1 (m, 2H) 7.84 (d, 1H) | 27 |
| 1.29 | (indazol-3-yl)methyl | 799 | 7.20 (t, 1H); 7.42 (t, 1H); 7.54 (d, 1H); 7.83 (d, 1H) | 27 |
| 1.30 | (isoquinolin-4-yl)methyl | 811 | 7.76 (t, 1H); 7.92 (t, 1H); 8.18 (d, 1H); 8.28 (d, 1H); 8.49 (s, 1H); 9.26 (s, 1H) | 27 |
| 1.31 | (isoquinolin-3-yl)methyl | 811 | 7.73 (t, 1H); 7.80 (t, 1H); 7.83 (s, 1H); 7.95 (d, 1H); 8.12 (d, 1H); 9.29 (s, 1H) | 27 |
| 1.32 | 1R-(1,8-naphthyridin-4-yl)ethyl (2F template | 843 | 9.05 (m, 1H); 8.99 (d, 1H); 8.91 (d, 1H); 7.69-7.65 (m, 2H) | 28 |
| 1.33 | (1,8-naphthyridin-4-yl)methyl (2F template) | M/2 415 | 9.04 (dd, 1H); 8.99 (d, 1H); 8.74 (dd, 1H); 7.66 (dd, 1H); 7.59 (d, 1H) | 27 |
| 1.34 | (2-methyl-thiazolo[5,4-b]pyridin-5-yl)methyl | 831 | 8.10 (d, 1H) 7.46 (d, 1H) | 27 |
| 1.35 | (thiazolo[4,5-b]pyridin-7-yl)methyl | 831 | 9.64 (s, 1H); 8.82 (s, 1H); 7.74 (s, 1H) | 27 |
| 1.36 | (6-chloro-1H-quinolin-2-on-4-yl)methyl | 860 | 7.90 (s, 1H); 7.56 (d, 1H); 7.37 (d, 1H); 6.67 (s, 1H) | 27 |
| 1.37 | 1R-(1,5-naphthyridin-4-yl)ethyl | M/2 413 | 9.03 (dd, 1H); 8.96 (dd, 1H); 8.44 (m, 1H); 7.84-7.79 (m, 2H) | 28 |
| 1.38 | 1S-(1,5-naphthyridin-4-yl)ethyl | M/2 413 | 9.05 (m, 1H); 8.99 (m, 1H); 8.49 (m, 1H); 7.87-7.81 (m, 2H) | 28 |
| 1.39 | (2-methoxyquinolin-4-yl)methyl | 840 | 6.96 (s, 1H); 7.45 (t, 1H); 7.63 (t, 1H); 7.82 (d, 1H); 8.00 (d, 1H) | 27 |
| 1.40 | (2-hydroxyquinolin-4-yl)methyl | 827 | 7.87 (d, 1H); 7.57 (t, 1H); 7.39 (d, 1H); 7.32 (t, 1H); 6.64 (s, 1H) | 27 |
| 1.41 | (1-[3-fluorophenyl]-pyrazol-4-yl)methyl | 843 | 7.09 (t, 1H); 7.53 (m, 1H); 7.65 (m, 2H); 7.80 (s, 1H); 8.52 (s, 1H) | 27 |
| 1.42 | (1H-3-[4-fluorophenyl]-pyrazol-4-yl)methyl | 843 | 7.25 (t, 2H); 7.64 (m, 2H); 7.88 (s, 1H) | 27 |
| 1.43 | 3-(pyridin-2-yl)-benzyl | 836 | 7.45 (m, 1H); 7.56 (m, 2H); 7.92 (m, 2H); 8.05 (d, 1H); 8.08 (s, 1H); 8.68 (s, 1H) | 27 |
| 1.44 | 3-(3-ethyl-[1,2,4]oxadiazol-5-yl)benzyl | 855 | 7.68 (t, 1H); 7.72 (d, 1H); 8.16 (d, 1H); 8.22 (s, 1H) | 27 |
| 1.45 | (6-[pyrazol-1-yl]pyridin-3-yl)methyl | 826 | 6.51 (t, 1H); 7.75 (d, 1H); 7.95 (d, 2H); 8.43 (s, 1H); 8.58 (d, 1H) | 27 |
| 1.46 | (2-[3-methyl-(1,2,4)oxadiazol-5-yl]pyridin-4-yl)methyl | 842 | 7.56 (d, 1H); 8.14 (s, 1H); 8.67 (d, 1H) | 27 |
| 1.47 | 3-(oxazol-5-yl)benzyl | 826 | 7.46 (d, 1H); 7.53 (t, 1H); 7.60 (s, 1H); 7.80 (d, 1H); 7.85 (s, 1H); 8.30 (s, 1H) | 27 |
| 1.48 | 4-(pyridin-2-yl)benzyl | 836 | 7.42 (m, 1H); 7.60 (d, 2H); 7.92 (m, 2H); 8.06 (d, 2H); 8.64 (d, 1H) | 27 |
| 1.49 | 4-(pyridin-3-yl)benzyl | 836 | 7.58 (m, 1H); 7.62 (d, 2H); 7.78 (d, 2H); 8.14 (d, 1H); 8.59 (s, 1H); 8.86 (s, 1H) | 27 |
| 1.50 | 4-(pyrazin-2-yl)benzyl | 837 | 7.55 (m, 2H); 8.10 (d, 1H); 8.14 (s, 1H); 8.58 (d, 1H); 8.72 (m, 1H); 9.16 (m, 1H) | 27 |
| 1.51 | (2-[phenyl]-thiazol-5-yl)methyl | 842 | 7.50 (m, 3H); 7.79 (s, 1H); 7.94 (m, 2H) | 27 |
| 1.52 | (1H-2-[phenyl]-imidazol-5-yl)methyl | 825 | 7.31 (s, 1H); 7.42 (m, 1H); 7.48 (t, 2H); 7.90 (d, 2H) | 27 |
| 1.53 | 3-([1,2,4]triazol-1-yl)benzyl | 825 | 6.56 (m, 1H); 7.38 (d, 1H); 7.54 (1, 1H); 7.76 (m, 1H); 7.82 (s, 1H); 8.26 (d, 1H) | 27 |
| 1.54 | (2-[phenyl]-thiazol-3-yl)methyl | M/2 422 | 7.42 (m, 3H); 7.52 (s, 1H); 7.94 (m, 2H) | 27 |
| 1.55 | 1-(4-[imidazol-1-yl]phenyl)ethyl | 839 | 7.13 (s, 1H); 7.49-7.56 (m, 5H); 8.12 (m, 1H) | 28 |

TABLE 1-continued

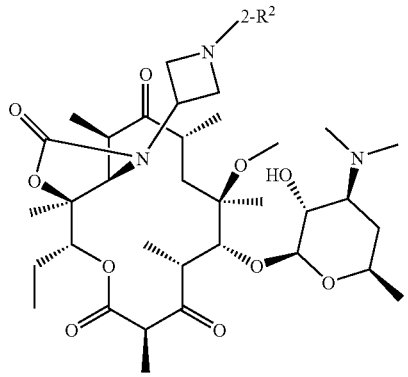

| Ex. # | 2-R² Name | MS | ¹H NMR | Prep # |
|---|---|---|---|---|
| 1.56 | 3-([1,2,3]triazol-1-yl)benzyl | 826 | 7.44 (d, 1H); 7.55 (t, 1H); 7.78 (d, 1H); 7.90 (d, 1H); 8.54 (d, 1H) | 27 |
| 1.57 | 4-(imidazol-1-yl)benzyl | 825 | 7.16 (s, 1H); 7.54-7.64 (m, 5H); 8.18 (s, 1H) | 27 |
| 1.58 | 4-(isoxazol-5-yl)benzyl | 826 | 7.55 (d, 2H); 7.58 (s, 1H); 7.80 (d, 2H); 8.28 (s, 1H) | 27 |
| 1.59 | 3-(imidazol-1-yl)benzyl | 825 | 7.24 (bs, 1H); 7.50 (d, 1H); 7.60 (t, 1H); 7.66 (d, 1H); 7.74 (s, 1H) | 27 |
| 1.60 | 3-(pyrazol-1-yl)benzyl | 825 | 6.54 (t, 1H); 7.38 (d, 1H); 7.54 (t, 1H); 7.72-7.76 (m, 2H); 7.82 (s, 1H); 8.25 (d, 1H) | 27 |
| 1.61 | 1-(quinolin-4-yl)propyl | 838 | CDCl₃: 7.62 (t, 1H); 7.85 (d, 1H) | 28 |
| 1.62 | 1-(quinolin-4-yl)ethyl (*) | 824 | CDCl₃: 8.26 (t, 1H); 8.90 (q, 1H) | 28 |
| 1.63 | 1-(quinolin-4-yl)ethyl (*) | 824 | CDCl₃: 8.90 (q, 1H); 9.00 (d, 1H) | 28 |
| 1.64 | 1-(quinolin-4-yl)butyl (*) | 852 | CDCl₃: 7.77 (t, 1H); 8.25 (d, 1H) | 28 |
| 1.65 | 1-(quinolin-4-yl)butyl (*) | 852 | CDCl₃: 7.62 (t, 1H); 7.80 (t, 1H) | 28 |
| 1.66 | phenyl-(pyridin-3-yl)methyl (*) | 836 | CDCl₃: 7.56 (t, 1H); 8.66 (s, 1H) | 28 |
| 1.67 | phenyl-(pyridin-3-yl)methyl (*) | 836 | CDCl₃: 8.48 (t, 1H); 8.62 (s, 1H) | 28 |
| 1.68 | phenyl-(pyridin-4-yl)methyl (*) | 836 | CDCl₃: 7.58 (d, 1H); 8.66 (d, 1H) | 28 |
| 1.69 | phenyl-(pyridin-4-yl)methyl (*) | 836 | CDCl₃: 7.47 (q, 2H); 8.55(d, 1H) | 28 |
| 1.70 | 8-methoxyquinoline-5-methyl | 839.7 | 7.22 (d, 1H), 7.67 (m, 2H), 866 (d, 1H), 8.86 (d, 2H) | 27 |
| 1.71 | 3-methoxyquinoline-4-methyl | 839.7 | 8.92 (s, 1H), 8.21 (d, 1H), 8.03 (d, 1H), 7.68 (t, 2H) | 27 |
| 1.72 | 3-methoxy-1,8-naphthyridine-4-methyl | 841.0 | 7.59 (m, 1H), 8.71 (d, 1H), 9.03 (d, 1H), 9.06 (s, 1H) | 27 |
| 1.73 | quinoline-3-carbonitrile-4-methyl | 835 (M + 1) | 8.95 (s, 1H), 8.39 (d, 1H), 8.10 (d, 1H), 7.82 (t, 1H), 7.67 (t, 1H) | 35 |
| 1.74 | 7-bromopyrido[3,2-b]pyrazine-8-methyl | 892 | 9.26 (s, 1H), 9.09 (d, 1H), 9.05 (d, 1H) | 27 |
| 1.75 | 3-bromo-1,8-naphthyridine-4-methyl | 888.8 | 7.71 (m, 1H), 8.86 (dd, 1H), 9.06 (m, 1H), 9.14 (s, 1H) | 27 |
| 1.76 | 3-chloro-1,8-naphthyridine-4-methyl | 845 | CDCl₃: 9.06 (dd, 1H), 8.99 (s, 1H), 8.73 (dd, 1H), 7.52 (dd, 1H) | 27 |
| 1.77 | 3-bromopyridine-4-methyl | 839 | 8.61 (br s, 1H), 8.44 (dd, 1H), 7.45 (d, 1H) | 27 |
| 1.78 | 3-fluoropyridine-4-methyl | 778 | 8.46 (s, 1H), 8.40 (br s, 1H), 8.34 (d, 1H), 7.46 (t, 1H) | 27 |
| 1.79 | 3-chloropyridine-4-methyl | M/2 398 | 8.51 (s, 1H), 8.44 (d, 1H), 8.37 (s, 1H), 7.47 (d, 1H). | 27 |
| 1.80 | 2-(methoxy)-1S-(1,8-napthyridin-4-yl)-ethyl | 854.7 | 7.66 (d, 1H), 7.68 (d, 1H), 8.94 (d, 1H), 9.02 (d, 1H), 9.06 (m, 1H) | 27 |
| 1.81 | 2-(methoxy)-1S-(1,8-napthyridin-4-yl)-ethyl | 854.3 | 7.65 (dd, 1H), 7.76 (d, 1H), 8.96 (d, 1H), 9.04 (d, 1H), 9.08 (m, 1H) | 27 |
| 1.82 | 4H-quinolizin-4-one-1-methyl | 825.8 | 6.70 (d, 1H), 7.34 (t, 1H), 7.76 (t, 1H), 7.72 (d, 1H), 8.14 (d, 1H) | 27 |
| 1.83 | H-pyrazolo[1,5-a]pyridine-4-methyl | 799.0 | 6.83 (d, 1H), 6.92 (t, 1H), 7.32 (d, 1H), 8.01 (d, 1H) | 27 |
| 1.84 | 8-methoxyquinoline-4-methyl | 840.1 | 7.26 (d, 1H), 7.56 (d, 1H), 7.63 (t, 1H), 7.74 (d, 1H) | 27 |
| 1.85 | 1-fluoro-3-methoxybenzene-2-methyl | 806 (M + 1) | — | 27 |
| 1.86 | 2-methoxynaphthalene-1-methyl | 839 (M + 1) | 8.16 (d, 1H), 7.89 (d, 1H), 7.77 (d, 1H), 7.56 (t, 1H), 7.34 (t, 1H), 7.26 (d, 1H) | 27 |
| 1.87 | 1,3-difluorobenzene-2-methyl | 398 (M/2 + 1) | — | 27 |
| 1.88 | 2-(trifluoromethoxy)benzene-1-methyl | 422 (M/2 + 1) | — | 27 |
| 1.89 | 2-cyclopropyl-3H-imidazo[4,5-b]pyridine-7-methyl | 840 | 8.26 (d, 1H), 7.27 (d, 1H) | 27 |

TABLE 1-continued

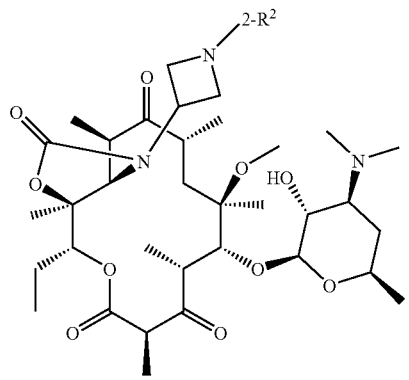

| Ex. # | 2-R² Name | MS | ¹H NMR | Prep # |
|---|---|---|---|---|
| 1.90 | 6-methoxyquinoline-4-methyl | 839.6 | 7.48 (d, 1H), 7.53 (m, 2H), 8.00 (d, 1H), 8.70 (m, 1H) | 27 |
| 1.91 | naphthalene-1-methyl | 809 (M + 1) | 8.22 (d, 1H), 7.83 (m, 2H), 7.71 (d, 1H), 7.57 (t, 1H), 7.47 (m, 2H) | 27 |
| 1.92 | 2-methylnaphthalene-1-methyl | 823 (M + 1) | 8.30 (d, 1H), 7.76 (t, 2H), 7.56 (t, 1H), 7.42 (t, 1H), 7.32 (d, 1H) | 27 |
| 1.93 | 3-methyl-3H-imidazo[4,5-b]pyridine-7-methyl | M/2 408 | 8.41 (br s, 1H), 8.31 (d, 1H), 8.28 (s, 1H), 7.23 (d, 1H) | 27 |
| 1.94 | 1H-inden-2(3H)-sulfone-5-methyl | 849 | 7.4 (m, 1H), 7.3 (m, 2H) | 27 |
| 1.95 | quinoline-8-carbonitrile-4-methyl | 834.7 | 7.62 (d, 1H), 7.74 (t, 1H), 8.24 (d, 1H), 8.96 (d, 1H) | 27 |
| 1.96 | quinoline-8-carbonitrile-5-methyl | 834.7 | 7.70 (m, 2H), 8.20 (d, 1H), 8.76 (d, 1H), 9.20 (d, 1H) | 35 |
| 1.97 | 2-ethoxynaphthalene-1-methyl | 852.8 | 7.46 (t, 1H), 7.48 (d, 1H), 7.62 (t, 1H), 7.90 (d, 1H), 8.04 (d, 1H) | 27 |
| 1.98 | 3-methylquinoline-4-methyl | 824 (M + 1) | 8.72 (s, 1H), 8.33 (d, 1H), 8.03 (d, 1H), 7.59 (m, 2H) | 27 |
| 1.99 | 3-methyl-1,8-naphthyridine-4-methyl | 825 (M + 1) | 9.03 (d, 1H), 8.93 (s, 1H), 8.82 (d, 1H), 7.52 (dd, 1H) | 27 |
| 1.100 | 6-chloro-3H-imidazo[4,5-b]pyridine-7-methyl | M/2 418 | 8.41 (s, 1H), 8.39 (s, 1H), 8.33 (s, 2H) | 27 |
| 1.101 | 3-methoxy-1,5-naphthyridine-4-methyl | M + 1 841 | CDCl₃: 8.40 (m, 2H); 8.98 (d, 1H) | 35 |
| 1.102 | 6-methoxyquinoline-5-methyl | 839 | CDCl₃: 8.78 (d, 1H); 8.61 (d, 1H); 1.15 (d, 1H), 7.48 (d, 1H), 7.46 (m, 1H) | 27 |
| 1.103 | 2,4-dichlorobenzene-1-methyl | 826 | 7.52 (s, 1H); 7.45 (dd, 1H); 7.36 (dd, 1H) | 27 |
| 1.104 | benzo[d][1.3]dioxole-5-methyl | M + 1 802 | 6.68-6.93 (m 3H) | 27 |
| 1.105 | 5-methoxyquinoxaline-8-methyl | 840 | 7.84 (d, 1H); 7.30 (d, 1H) | 27 |
| 1.106 | 3-bromo-1,5-naphthyridine-4-methyl | M + 2 890 | 9.09 (s, 1H); 9.00 (d, 1H); 8.38 (dd, 1H); 7.79 (m, 1H) | 27 |
| 1.107 | 3-chloroquinoline-4-methyl | M + 1 844 | 8.52 (d, 1H); 8.03 (d, 1H); 7.64 (t, 1H); 7.57 (t, 1H); 7.24 (s, 1H) | 35 |
| 1.108 | 3-ethoxy-1,8-naphthyridine-4-methyl | M + 1 855 | 8.24 (s, 3H), 8.96 (d, 1H), 9.10 (s, 1H) | 27 |

TABLE 2

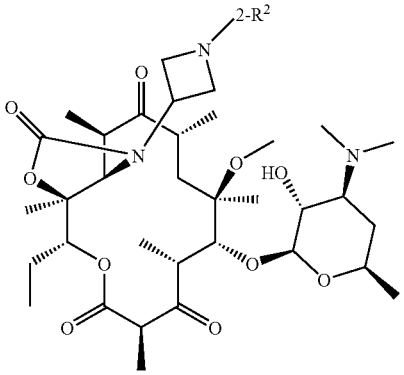

| Ex. # | 2-R² Name | MS | ¹H NMR | Prep. # |
|---|---|---|---|---|
| 2.01 | isoquinoline-4-carboxyl | m-1 822 | 9.31 (d, 1H); 8.52 (d, 1H); 8.24-8.12 (m, 2H); 7.89 (t, 1H); 7.75 (t, 1H) | 33 |
| 2.02 | 2-methyl-3H-benzo[b]imidazole-4-carboxyl | M/2 414 | 7.63 (bs, 1H); 7.38 (m, 1H); 7.24 (m, 1H) | 33 |
| 2.03 | N-(naphthalen-1-yl)aminocarbonyl | 838 | 7.88 (d, 1H); 7.80 (m, 2H); 7.60 (d, 1H); 7.50 (m, 3H) | 30 |
| 2.04 | N-(naphthalen-2-yl)aminocarbonyl | 838 | 7.98 (s, 1H); 7.71 (m, 3H); 7.40 (m, 2H); 7.33 (dd, 1H) | 30 |
| 2.05 | N-(quinolin-6-yl)aminocarbonyl | 839 | CDCl$_3$: 7.98 (d, 1H); 8.05 (d, 1H) | 30 |
| 2.06 | N-(quinolin-5-yl)aminocarbonyl | 839 | CDCl$_3$: 7.98 (d, 1H); 8.39 (d, 1H) | 30 |
| 2.07 | N-(3-(4-fluorophenyl)-1H-pyrazol-5-yl) aminocarbonyl | 872 | CDCl$_3$: 7.75 (t, 2H); 8.05 (s, 1H) | 30 |
| 2.08 | N-(3-(5-methylpyridin-3-yl)-1H-pyrazol-5-yl) aminocarbonyl | 867 | CDCl$_3$: 7.90 (t, 1H); 8.39 (s, 1H) | 30 |
| 2.09 | N-(quinoxalin-8-yl) aminocarbonyl | 839 | CDCl$_3$: 7.62 (d, 1H); 7.65 (t, 1H) | 30 |
| 2.10 | N-((quinolin-6-yl)inethyl) aminocarbonyl | 853 | CDCl$_3$: 7.66 (t, 1H); 7.98 (t, 1H) | 30 |
| 2.11 | N-((quinolin-3-)methyl) aminocarbonyl | 853 | CDCl$_3$: 7.72 (t, !H); 7.80 (d, 1H) | 30 |
| 2.12 | 4-(5-methyl-1,2,4-oxadiazol-3-yl)benzoyl | 855 | CDCl$_3$: 7.78 (m, 2H); 8.12 (m, 2H) | 33 |
| 2.13 | 4-(1H-pyrazol-1-yl)benzoyl | 839 | 6.54 (s, 1H); 7.74-7.87 (m, 5H); 8.31 (s, 1H) | 33 |
| 2.14 | 4-(1H-imidazol-1-yl)benzoyl | 839 | 7.16 (s, 1H); 7.65-7.71 (m, 3H); 7.79-7.84 (m, 2H); 8.23 (m, 1H) | 33 |
| 2.15 | 4-(1H-1,2,4-triazol-1-yl)benzoyl | 841 | 7.88-9.30 (m, 2H); 7.97-8.03 (m, 2H); 9.86 (d, 1H) | 33 |
| 2.16 | 3-(5-methyl-1,2,4-oxadiazol-3-yl)benzoyl | 855 | 7.60 (m, 1H); 7.82 (m, 1H); 8.17 (m, 1H); 8.25 (d, 1H) | 33 |
| 2.17 | 3-(3,5-dimethyl-1H-pyrazol-1-yl)benzoyl | 867 | 6.08 (s, 1H); 7.58-7.60 (m, 4H) | 33 |
| 2.18 | 2-(5-methyl-1,2,4-oxadiazol-3-yl)pyridine-4-carboxyl | 856 | 7.78 (m, 1H); 8.26 (d, 1H); 8.82 (m, 1H) | 33 |
| 2.19 | 2-(1H-tetrazol-1-yl)pyridine-4-carboxyl | 842 | 7.73 (m, 1H); 8.25 (d, 1H); 8.72 (m, 1H); 9.96 (s, 1H) | 33 |
| 2.20 | 6-(1H-pyrazol-1-yl)pyridine-3-carboxyl | 840 | 6.54 (s, 1H); 7.78 (s, 1H); 8.04 (m, 1H); 8.22 (m, 1H); 8.65 (m, 1H); 8.73 (m, 1H) | 33 |
| 2.21 | 2-phenylacetyl | 787 | 7.32-7.23 (m, 5H) | 33 |
| 2.22 | (S)-2-phenylpropanoyl | 801 | 7.32-7.21 (m, 5H) | 33 |

TABLE 3

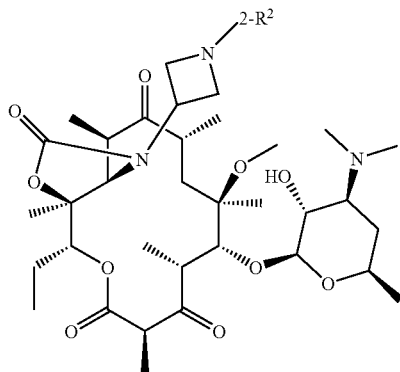

| Ex. # | 2-R² Name | MS | ¹H NMR | Prep # |
|---|---|---|---|---|
| 3.01 | pyridine-3-sulfonyl | 810 | 8.96 (d, 1H); 8.81 (dd, 1H); 8.25 (m, 1H0; 7.76 (dd, 1H) | 31 |
| 3.02 | naphthalene-1-sulfonyl | 859 | 8.73 (d, 1H); 8.24-8.16 (m, 2H); 7.99 (d, 1H); 7.68-7.57 (m, 3H) | 31 |
| 3.03 | quinoline-8-sulfonyl | 860 | 9.04 (dd, 1H); 8.44-8.39 (m, 2H); 8.21 (dd, 1H); 7.70 (t, 1H); 7.61 (dd, 1H) | 31 |
| 3.04 | isoquinoline-5-sulfonyl | M/2 431 | 9.36 (s, 1H); 8.62-8.58 (m, 2H); 8.48-8.41 (m, 2H); 7.84 (t, 1H) | 31 |
| 3.05 | benzo[1,2,5]oxadiazole-4-sulfonyl | 851 | 8.21 (d, 1H); 8.08 (d, 1H); 7.68 (t, 1H) | 31 |
| 3.06 | benzo[1,2,5]thiadiazole-4-sulfonyl | 867 | 8.31 (dd, 1H); 8.24 (dd, 1H); 7.82 (t, 1H) | 31 |
| 3.07 | 2-fluorobenzenesulfonyl | 827 | 7.82 (m, 1H); 7.69 (m, 1H); 7.37 (m, 2H) | 31 |
| 3.08 | 3-fluorobenzenesulfonyl | 827 | 7.65 (m, 2H); 7.57 (m, 1H); 7.44 (m, 1H) | 31 |
| 3.09 | 4-fluorobenzenesulfonyl | 827 | 7.89 (m, 2H); 7.35 (m, 2H) | 31 |
| 3.10 | 3-cyanobenzenesulfonyl | 834 | 8.21 (s, 1H); 8.11 (m, 1H); 8.03 (m, 1H); 7.81 (t, 1H) | 31 |
| 3.11 | 4-cyanobenzenesulfonyl | 834 | 7.99 (s, 4H) | 31 |
| 3.12 | 5-methyl-1-phenyl-1H-pyrazole-4-sulfonyl | 889 | 7.53-7.57 (m, 5H); 7.96 (s, 1H) | 31 |
| 3.13 | 4-(oxazol-5-yl)benzenesulfonyl | 876 | 7.74 (s, 1H); 7.93 (d, 2H); 8.01 (d, 2H); 8.36 (s, 1H) | 31 |
| 3.14 | 4-(4,5-dihydro-6-methyl-3,5-dioxo-1,2,4-triazin-2(3H)-yl)benzenesulfonyl | 934 | 7.91-7.96 (m, 4H) | 31 |
| 3.15 | H-imidazo[1,2-a]pyridine-3-sulfonyl | 849 | 8.89 (d, 1H); 8.51 (s, 1H); 7.72 (d, 1H); 7.58 (m, 1H); 7.18 (m, 1H) | 31 |
| 3.16 | 6-(1H-pyrazol-1-yl)pyridine-3-sulfonyl | 876 | 8.70 (s, 1H) 8.60 (m, 1H) 7.74 (m, 1H) 6.46 (m, 1H) | 31 |
| 3.17 | imidazo[1,2-a]pyrimidine-3-sulfonyl | 850 | 9.28 (dd, 1H); 8.78 (dd, 1H); 8.42 (s, 1H); 7.30 (dd, 1H) | 31 |
| 3.18 | 2-cyanobenzenesulfonyl | 834 | 8.03 (m, 2H); 7.84 (m, 2H) | 31 |
| 3.19 | H-imidazo[1,5-a]pyridine-1-sulfonyl | 849 | 8.88 (d, 1H); 8.45 (s, 1H); 7.72 (d, 1H); 7.58 (m, 1H) | 31 |
| 3.20 | 4-(2,3,4,5-tetrahydro-3,5-dioxo-1,2,4-triazin-6-yl)benzenesulfonyl | 920 | 7.65-8.65 (m, 4H) | 31 |
| 3.21 | 1-(pyridin-2-yl)-1H-pyrazole-4-sulfonyl | 876 | 9.0 (s, 1H) 8.37 (s, 1H) 8.08 (s, 1H) 8.04 (d, 1H) 7.85 (m, 1H) 7.29 (m, 1H) | 31 |
| 3.22 | 2,3-dihydro-2-oxobenzo[d]oxazole-5-sulfonyl | 866 | 7.73 (m, 2H) 7.17 (d, 1H) | 31 |
| 3.23 | 4-(methylsulfonyl)benzenesulfonyl | 887 | 8.16 (d, 2H) 8.07 (d, 2H) 3.09 (s, 3H) | 31 |
| 3.24 | 2,3-dihydrobenzo[b][1,4]dioxine-6-sulfonyl | 876 | — | 31 |
| 3.25 | 2-(methylsulfonyl)benzenesulfonyl | 887 | — | 31 |
| 3.26 | 4-(pyridin-4-yloxy)benzenesulfonyl | 902 | — | 31 |
| 3.27 | 4-(pyridin-3-yloxy)benzenesulfonyl | 902 | — | 31 |
| 3.28 | 1,2-dimethyl-1H-imidazole-4-sulfonyl | 827 | — | 31 |
| 3.29 | 3,5-dimethyl-1H-pyrazole-4-sulfonyl | 827 | — | 31 |
| 3.30 | 1,2,3,4-tetrahydro-2,4-dioxopyrimidine-5-sulfonyl | 843 | — | 31 |

TABLE 3-continued

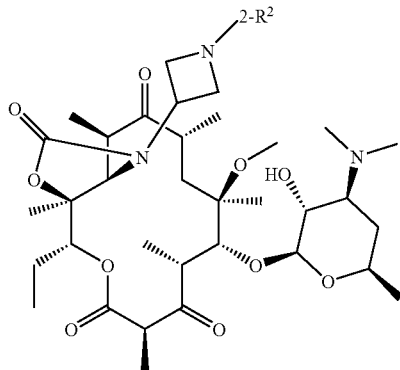

| Ex. # | 2-R² Name | MS | ¹H NMR | Prep # |
|---|---|---|---|---|
| 3.31 | 2,4-dimethoxybenzenesulfonyl | 869 | — | 31 |
| 3.32 | 3,5-dimethylisoxazole-4-sulfonyl | 828 | — | 31 |
| 3.33 | 5-(isoxazol-3-yl)thiophene-2-sulfonyl | 882 | 8.30 (d, 1H) 7.65 (d, 1H) 7.59 (d, 1H) 6.54 (d, 1H) | 31 |
| 3.34 | 4-(pyridin-2-yloxy)benzenesulfonyl | 902 | 8.22 (m, 1H) 7.87 (d, 2H) 7.69 (dd, 1H) 7.28 (d, 2H) 7.06 (dd, 1H) 6.95 (d, 1H) | 31 |
| 3.35 | 3-(oxazol-5-yl)benzenesulfonyl | 876 | CDCl₃: 7.80 (d, 1H); 7.82 (d, 1H) | 31 |
| 3.36 | 3-(1H-pyrazol-3-yl)benzenesulfonyl | 875 | CDCl₃: 7.80 (d, 1H); 7.98 (d, 1H) | 31 |
| 3.37 | 2-methoxypyridine-3-sulfonyl | 840 | 8.35 (m, 1H), 8.19 (m, 1H), 7.01 (m, 1H) | 31 |
| 3.38 | 6-methoxypyridine-3-sulfonyl | 840 | 8.63 (d, 1H), 7.96 (dd, 1H), 6.85 (d, 1H) | 31 |
| 3.39 | 4-(1H-pyrazol-5-yl)benzenesulfonyl | 875 | CDCl₃: 7.95 (d, 2H), 7.88 (d, 2H), 7.60 (m, 1H), 6.66 (dd, 1H) | 31 |
| 3.40 | 3-(3-methylisoxazol-5-yl)benzenesulfonyl | 890 | CDCl₃: 7.96 (m, 2H), 7.65 (dd,1H), 7.41 (m, 2H) | 31 |
| 3.41 | 3-(1,2,4-oxadiazol-3-yl)benzenesulfonyl | 877 | CDCl₃: 7.60 (t, 1H); 7.80 (d, 1H) | 31 |
| 3.42 | 2-oxoindoline-5-sulfonyl | 864 | CDCl₃: 7.73 (d, 1H) 7.68 (s, 1H) 6.93 (d, 1H) | 31 |
| 3.43 | 2,3-dihydro-2-oxobenzo[d]oxazole-5-sulfonyl | 866 | CDCl₃: 7.68 (m, 2H) 7.1 2 (d,1H) | 31 |
| 3.44 | 4-(1H-pyrazol-1-yl)benzenesulfonyl | 875 | 6.55 (t, 1H); 7.75 (d, 1H); 7.94 (d, 2H); 8.09 (d, 2H) | 31 |
| 3.45 | 4-(1,2,3-thiadiazol-4-yl)benzenesulfonyl | 893 | 8.02 (d, 2H); 8.43 (d, 2H); 9.49 (s, 1H) | 31 |
| 3.46 | 3-fluoro-4-morpholinobenzenesulfonyl | 911 | 7.53 (dd, 1H), 7.47 (dd, 1H), 6.97 (t, 1H) | 31 |
| 3.47 | 4-(3,5-dimethyl-1H-pyrazol-1-yl)benzenesulfonyl | 903 | 7.92 (d, 2H), 7.65 (d, 2H), 6.00 (s, 1H) | 31 |
| 3.48 | 6-cyanopyridine-3-sulfonyl | 835 | 8.12 (d, 2H); 8.42 (d, 2H); 9.11 (s, 1H) | 31 |
| 3.49 | 5-cyanonaphthalene-1-sulfonyl | 884 | 9.06 (d, 1H) 8.50 (d, 1H) 8.41 (d, 1H) 8.0 (d, 1H) 7.77 (dd, 1H) 7.70 (dd, 1H) | 31 |
| 3.50 | 3-cyano-4-(1H-pyrazol-1-yl)benzenesulfonyl | 900 | 8.36 (d, 1H) 8.26 (s, 1H) 8.14 (d, 1H) 8.09 (d, 1H) 7.85 (d, 1H) 6.59 (dd, 1H) | 31 |
| 3.51 | 4-(2-methyl-2H-tetrazol-5-yl)benzenesulfonyl | 891 | 8.34 (d, 2H) 8.0 (d, 2H) 4,42 (s, 3H) | 31 |
| 3.52 | 4-(1H-1,2,4-triazol-1-yl)benzenesulfonyl | 876 | 8.73 (s, 1H) 8.13 (s, 1H) 8.05 (d, 2H) 7.95 (d, 2H) | 31 |
| 3.53 | 4-(1H-imidazol-1-yl)-3-methylbenzenesulfonyl | 889 | 7.86 (s, 1H) 7.80 (d, 1H) 7.75 (bs, 1H) 7.43 (d, 1H) 7.24 (bs, 1H) 7.1 5 (bs, 1H) 2.33 (s, 3H) | 31 |
| 3.54 | 4-(6-methylbenzo[d]thiazol-2-yl)benzenesulfonyl | 956 | 8.25 (d, 2H) 7.95 (m, 3H) 7.69 (s, 1H) 7.30 (d, 1H) | 31 |
| 3.55 | 4-(2H-1,2,3-triazol-2-yl)benzenesulfonyl | 876 | 8.29 (d, 2H) 7.95 (d, 2H) 7.81 (s, 2H) | 31 |
| 3.56 | 4-(1,3,4-oxadiazol-2-yl)benzenesulfonyl | 877 | 8.05 (d, 2H); 8.35 (d, 2H); 9.10 (s, 1H) | 31 |
| 3.57 | 3H-benzo[d][1,2,3]triazole-5-sulfonyl | 850 | 7.84 (d, 2H); 8.05 (d, 2H); 8.43 (s, 1H) | 31 |
| 3.58 | 3-(1H-pyrazol-1-yl)benzenesulfonyl | 875 | 8.11 (m, 1H); 8.04-8.02 (m, 2H); 7.74 (m, 1H); 7.70 (m, 1H); 7.63 (m, 1H); 6.47 (m, 1H) | 31 |
| 3.59 | 3-(1,2,4-oxadiazol-5-yl)benzenesulfonyl | 877 | CDCl₃: 7.60 (t, 1H); 7.94 (d, 1H) | 31 |
| 3.60 | 3-(5-methyl-1,3,4-oxadiazol-2-yl)benzenesulfonyl | 891 | CDCl₃: 7.92 (t, 1H); 8.04 (d, 1H) | 31 |
| 3.61 | 4-(5-methyl-1,3,4-oxadiazol-2-yl)benzenesulfonyl | 891 | CDCl₃: 8.03 (d, 2H); 8.28 (d, 2H) | 31 |

TABLE 3-continued

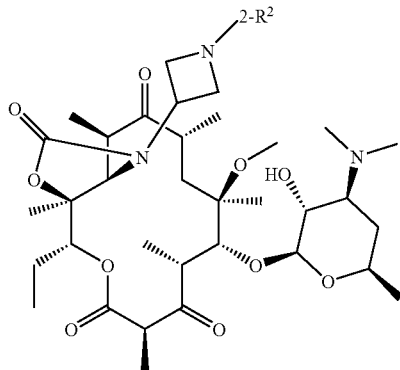

| Ex. # | 2-R² Name | MS | ¹H NMR | Prep # |
|---|---|---|---|---|
| 3.62 | 3-(1,3,4-oxadiazol-2-yl)benzenesulfonyl | 877 | CDCl₃: 7.70 (t, 1H); 7.95 (d, 1H) | 31 |
| 3.63 | 3-(1,2,3-thiadiazol-4-yl)benzenesulfonyl | 893 | CDCl₃: 7.75 (t, 1H); 7.95 (d, 1H) | 31 |
| 3.64 | 3-cyano-4-(1H-imidazol-1-yl)benzenesulfonyl | 899 | 7.25 (s, 1H); 7.70 (s, 1H); 7.89 (d, 1H); 8.24 (d, 1H) | 31 |
| 3.65 | 3-(oxazol-2-yl)benzenesulfonyl | 876 | CDCl₃: 7.63 (t, 1H); 7.95 (d, 1H) | 31 |
| 3.66 | 3-(2-methylpyrimidin-4-yl)benzenesulfonyl | 901 | CDCl₃: 8.70 (d, 1H), 8.38 (dd, 1H), 8.27 (m, 1H), 7.97 (m, 1H), 7.69 (dd, 1H), 7.59 (d, 1H) | 31 |
| 3.67 | 3-pyrimidin-4-yl)benzenesulfonyl | 887 | CDCl₃: 9.27 (s, 1H), 8.81 (m, 1H), 8.53 (s, 1H), 8.40 (dd, 1H), | 31 |
| 3.68 | 3-(2-methyloxazol-5-yl)benzenesulfonyl | 890 | CDCl₃: 7.60 (t, 1H); 7.80 (d, 1H) | 31 |
| 3.69 | 4-(1H-1,2,3-triazol-1-yl)benzenesulfonyl | 876 | 8.77 (s, 1H) 8.25 (d, 2H) 8.09 (d, 2H) 7.97 (s, 1H) | 31 |
| 3.70 | 3-cyano-4-(2H-1,2,3-triazol-2-yl)benzenesulfonyl | 901 | 8.11 (s, 2H); 8.25 (dd, 1H); 8.38 (s, 1H); 8.47 (d, 1H) | 31 |
| 3.71 | 3-cyano-4-(2H-1,2,4-triazol-1-yl)benzenesulfonyl | 901 | 8.13 (d, 1H); 8.28 (m, 2H); 8.45 (s, 1H); 9.24 (s, 1H) | 31 |
| 3.72 | 3-(pyridazin-3-yl)benzenesulfonyl | M/2 444 | CDCl₃, 9.20 (m, 1H), 8.51 (d, 1H), 8.44 (s, 1H), 7.99 (d, 2H), 7.74 (dd, 1H), 7.61 (m, 1H) | 31 |
| 3.73 | 4-methoxy-3-(oxazol-5-yl)benzenesulfonyl | 906 | CDCl₃: 7.10 (d, 1H); 7.90 (d, 1H) | 31 |
| 3.74 | 3-(1-methyl-1H-pyrazol-5-yl)benzenesulfonyl | 889 | CDCl₃: 7.50 (d, 1H); 7.65 (d, 1H) | 31 |
| 3.75 | 5-(oxazol-5-yl)pyridine-3-sulfonyl | 877 | CDCl₃: 9.11 (s, 1H), 8.99 (s, 1H), 8.34 (s, 1H), 8.01 (s, 1H), | 31 |
| 3.76 | 4-(1,3,4-thiadiazol-2-yl)benzenesulfonyl | 893 | 9.13 (s, 1H) 8.20 (d, 2H) 7.98 (d, 2H) | 31 |
| 3.77 | 3-cyano-4-fluorobenzenesulfonyl | 852 | 8.14 (dd, 1H), 8.1 (m, 1H), 7.41 (m, 1H) | 31 |
| 3.78 | 4-(6-chloropyridazin-3-yl)benzenesulfonyl | 921 | 7.95 (d, 1H); 8.06 (d, 2H); 8.37 (d, 1H); 8.45 (d, 2H) | 31 |
| 3.79 | benzo[b]thiazole-6-sulfonyl | 866 | 8.04 (d, 1H); 8.32 (d, 1H); 8.72 (s, 1H); 9.51 (s, 1H) | 31 |
| 3.80 | 5-(1H-pyrazol-1-yl)pyridine-3-sulfonyl | 876 | CDCl₃: 9.24 (s, 1H), 8.94 (s, 1H), 8.43 (d, 1H), 8.05 (d, 1H), 7.77 (s, 1H), 6.53 (dd, 1H) | 31 |
| 3.81 | 3-fluoro-4-(1H-imidazol-1-yl)benzenesulfonyl | 893 | 8.0 (bs, 1H), 7.77 (m, 2H), 7.61 (m, 1H), 7.4 (bs, 1H), 5.2 (bs, 1H) | 31 |
| 3.82 | 4-(1H-imidazol-1-yl)benzenesulfonyl | 875 | 8.0 (bs, 1H), 7.98 (d, 2H), 7.60 (d, 2H), 7.4 (bs, 1H), 7.3 (bs, 1H) | 31 |
| 3.83 | 2,3-dihydro-1H-indene-5-sulfonyl | 849 | 7.44 (d, 1H); 7.59 (d, 1H); 7.65 (s, 1H) | 31 |
| 3.84 | 4-(1H-tetrazol-5-yl)benzenesulfonyl | 877 | 7.96 (d, 2H); 8.33 (d, 2H) | 31 |
| 3.85 | 1H-indazole-6-sulfonyl | 849 | 7.58 (d, 1H); 8.02 (d, 1H); 8.09 (s, 1H); 8.17 (s, 1H) | 31 |
| 3.86 | 3-fluoro-4-(1H-pyrazol-1-yl)benzenesulfonyl | 893 | 8.23 (m, 1H), 8.15 (t, 1H), 7.74 (m, 3H), 6.49 (dd, 1H) | 31 |
| 3.87 | 1H-indazole-5-sulfonyl | 849 | 8.37 (s, 1H), 8.20 (s, 1H), 7.86 (d, 1H), 7.57 (d, 1H) | 31 |
| 3.88 | 4-fluoro-3-(oxazol-5-yl)benzenesulfonyl | 894 | CDCl₃: 7.39 (t, 1H); 7.80 (q, 1H) | 31 |
| 3.89 | quinoline-6-sulfonyl | 861 | 8.21 (m, 2H); 8.32 (d, 1H); 8.58 (s, 1H); 9.03 (m, 2H) | 31 |
| 3.90 | 2-methylbenzo[d]thiazole-5-sulfonyl | 880 | 7.84 (d, 1H); 8.20 (d, 1H); 8.33 (s, 1H) | 31 |

TABLE 3-continued

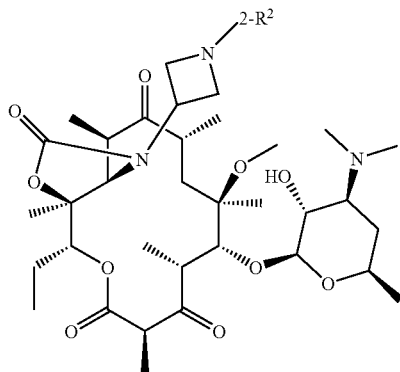

| Ex. # | 2-R² Name | MS | ¹H NMR | Prep # |
|---|---|---|---|---|
| 3.91 | naphthalene-2-sulfonyl | 859 | 8.44 (s, 1H), 8.0 (m, 2H), 7.9 (m, 2H), 7.6 (m, 2H) | 31 |
| 3.92 | phthalazine-5-sulfonyl | 861 | CDCl₃: 10.43 (s, 1H), 9.60 (s, 1H), 8.54 (d, 1H), 8.20 (d, 1H), 8.03 (dd, 1H) | 31 |
| 3.93 | quinoxaline-5-sulfonyl | 861 | CDCl₃: 9.01 (d, 1H), 8.91 (d, 1H), 8.50 (d, 1H), 8.30 (d, 1H), 7.84 (dd, 1H) | 31 |
| 3.94 | 1-methyl-1H-indazole-5-sulfonyl | 863 | 8.33 (s, 1H), 8.12 (s, 1H), 7.85 (d, 1H), 7.52 (d, 1H) | 31 |
| 3.95 | 1,3-dihydrobenzo-2,2-dioxo[c]thiophene-5-sulfonyl | 899 | 7.85 (d, 1H), 7.79 (s, 1H), 7.50 (d, 1H) | 31 |
| 3.96 | 2-methyl-2H-indazole-5-sulfonyl | 863 | 8.32 (s, 1H) 8.11 (s, 1H) 7.83 (d, 1H) 7.52 (d, 1H) 4.08 (s) | 31 |
| 3.97 | 6-chloroimidazo[2,1-b]thiazole-5-sulfonyl | 888.8 | 8.02 (d, 1H), 7.43 (d, 1H) | 31 |
| 3.98 | quinoxaline-5-sulfonyl (2-F template) | 879 (M + 1) | 9.01 (d, 1H), 8.91 (d, 1H), 8.51 (d, 1H), 8.31 (d, 1H), 7.84 (t, 1H) | 31 |
| 3.99 | 3-cyano-4-ethoxybenzene-1-sulfonyl | 876 (M − 1) | 8.01 (s, 1H), 8.03 (d, 1H), 7.38 (dd, 1H) | 31 |
| 3.100 | quinoline-5-sulfonyl | M + 1 859 | 9.18 (dd, 1H); 8.39 (t, 2H) | 31 |
| 3.101 | 8-methoxyquinoline-5-sulfonyl | M + 1 889 | 8.15 (d, 1H); 9.00 (d, 1H) | 31 |
| 3.102 | 8-ethoxyquinoline-5-sulfonyl | M + 1 903 | 7.59 (m, 1H); 8.12 (d, 1H) | 31 |
| 3.103 | 3-cyano-4-ethoxybenzene-1-sulfonyl (2-F template) | 896 | 8.43 (s, 1H), 8.11 (br s, 1H), 8.04 (dd, 1H), 7.38 (d, 1H) | 31 |
| 3.104 | benzo[d]isothiazole-6-sulfonyl | 865 | 9.01 (s, 1H), 8.54 (s, 1H), 8.25 (d, 1H), 7.91 (d, 1H) | 31 |
| 3.105 | 4-ethoxy-3-methoxybenzene-1-sulfonyl | 882 | 7.43 (d, 1H), 7.31 (s, 1H), 6.94 (d, 1H) | 31 |
| 3.106 | 5-chloro-2-methoxybenzene-1-sulfonyl | 873 | 7.90 (s, 1H), 7.48 (d, 1H), 7.00 (d, 1H) | 31 |
| 3.107 | 3-chlorobenzene-1-sulfonyl | 843 | 7.88 (s, 1h), 7.78 (d, 1h), 7.60 (d, 1h), 7.5 (m, 1h) | 31 |
| 3.108 | 4-acetamidobenzene-1-sulfonyl | 865 | — | 31 |
| 3.109 | 3-(cyanomethoxy)-4-methoxybenzene-1-sulfonyl | 894 M + 1 | 7.59 (d, 1H); 7.49 (s, 1H); 7.25 (d, 1H) | 31 |
| 3.110 | 3-(4-fluorophenoxy)benzene-1-sulfonyl | 918 | 7.84 (d, 2H), 7.1 (m, 6H) | 31 |
| 3.111 | 8-methylquinoline-5-sulfonyl | 874 | 9.00 (d, 2H); 8.34 (d, 1H); 7.8 (d, 1H) | 31 |
| 3.112 | 8-methoxyquinoxaline-5-sulfonyl | M + 1 890 | 7.10 (d, 1H); 8.50 (d, 1H) | 31 |
| 3.113 | 8-(difluoromethoxy)quinoline-5-sulfonyl | M + 1 926 | 8.35 (d, 1H); 9.00 (d, 1H) | 31 |
| 3.114 | 8-methylquinoxaline-5-sulfonyl | M + 1 894 | 7.57 (d, 1H); 7.49 (s, 1H); 7.24 (d, 1H) | 31 |
| 3.115 | 4-(2-oxooxazolidin-3-yl)benzene-1-sulfonyl | 894 | 7.89 (d, 2H), 7.79 (d, 2H) | 31 |
| 3.116 | 1,3-dimethyl-2,1,3-benzothiadiazole-2,2-dioxide0-5-sulfonyl | M + 1 929 | 7.12 (d, 1H); 7.31 (s, 1H); 7.53 (d, 1H) | 31 |
| 3.117 | 3-ethyl-1-methyl-1H-indazole 5-sulfonyl | 890 | 7.82 (d, 1H); 7.69 (d, 1H) | 31 |

TABLE 4

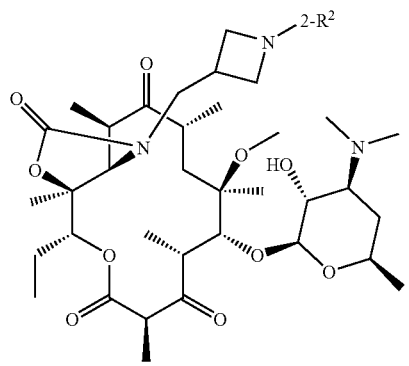

| Ex. # | 2-R² Name | MS | ¹H NMR | Prep. # |
|---|---|---|---|---|
| 4.01 | benzhydryl | 849 | CDCl₃: 7.34 (d, 2H); 7.56 (t, 2H) | 2a |
| 4.02 | 2,5-difluorobenzoyl | 822 | CDCl₃: 8.76 (s, 1H); 7.89 (d, 1H) | 33 |
| 4.03 | nicotinoyl | 787 | CDCl₃: 8.86 (s, 1H); 7.89 (s, 1H) | 33 |
| 4.04 | (pyridin-3-yl)methyl | 773 | CDCl₃: 8.76 (s, 1H); 7.65 (d, 1H) | 27 |
| 4.05 | isonicotinoyl | 787 | CDCl₃: 8.65 (d, 1H); 7.88 (d, 1H) | 33 |
| 4.06 | 3-cyanobenzoyl | 811 | CDCl₃: 8.56 (s, 1H); 7.54 (d, 1H) | 33 |
| 4.07 | 3-cyanobenzenesulfonyl | 848 | 8.10 (dt, 2H); 7.84 (t, 1H) | 31 |
| 4.08 | 3-cyanobenzyl | M/2 400 | 7.77 (s, 1H); 7.58 (t, 1H) | 27 |
| 4.09 | (1H-pyrazol-5-yl)methyl | M/2 382 | 7.66 (s, 1H); 6.39 (s, 1H) | 27 |
| 4.10 | (quinolin-3-yl)methyl | | 8.83 (s, 1H); 8.41 (s, 1H); 8.03 (d, 1H); 7.98 (d, 1H) | 27 |
| 4.11 | (1H-indol-3-yl)methyl | M/2 407 | 7.70 (d, 1H); 7.52 (s, 1H); 7.41 (d, 1H); 7.18 (t, 1H); 7.16 (t, 1H) | 27 |
| 4.12 | (quinoxalin-2-yl)methyl | M/2 413 | 8.83 (s, 1H); 8.15-8.09 (m, 2H); 7.86-7.82 (m, 2H) | 27 |
| 4.13 | (quinolin-4-yl)methyl | M/2 413 | 8.78 (bs, 1H); 8.17 (d, 1H); 8.01 (d, 1H); 7.78 (t, 1H); 7.62 (t, 1H); 7.48 (bs, 1H) | 27 |
| 4.14 | (quinolin-6-yl)methyl | M/2 413 | 8.91 (bs, 1H); 8.41 (d, 1H); 8.10-8.05 (m, 2H); 7.80 (d, 1H); 7.59 (m, 1H) | 27 |
| 4.15 | (quinolin-5-yl)methyl | 824 | 8.91 (bs, 1H); 8.72 (d, 1H); 8.18 (d, 1H); 7.79 (d, 1H); 7.72 (d, 1H); 7.62 (m, 1H) | 27 |
| 4.16 | (1H-benzo[d]imidazo-2-yl)methyl | M/2 407 | 7.53 (bd, 2H); 7.21 (bd, 2H) | 27 |
| 4.17 | (quinoxalin-8-yl)methyl | M/2 413 | 8.99 (bs, 2H), 8.20 (d, 1H); 7.99 (d, 1H); 7.90 (t, 1H) | 27 |
| 4.18 | (1H-pyrrolo[2,3-b]pyridin-3-yl)methyl | | 8.18 (d, 1H); 8.11 (d, 1H); 7.44 (s, 1H); 7.12 (dd, 1H) | 27 |
| 4.19 | (1H-pyrrolo[2,3-c]pyridin-3-yl)methyl | 813 | 8.96 (s, 1H); 8.24 (d, 1H); 8.15 (s, 1H); 8.08 (d, 1H); 7.95 (s, 1H) | 27 |
| 4.20 | (1H-benzoimidazoi-7-yl)methyl | M/2 407 | 8.56 (s, 1H); 7.59 (d, 1H); 7.30-7.20 (m, 2H) | 27 |
| 4.21 | (1-(3-fluorophenyl)-1H-pyrazol-4-yl)methyl | M/2 429 | 7.66 (s, 1H); 7.60-7.43 (m, 3H); 7.03 (t, 1H) | 27 |
| 4.22 | (1H-indazol-3-yl)methyl | m-1 811 | 7.81 (d, 1H); 7.54 (d, 1H); 7.40 (t, 1H); 7.20 (t, 1H) | 27 |
| 4.23 | (6-chloro-1H-indazol-3-yl)methyl | m-1 845 | 7.79 (d, 1H); 7.57 (s, 1H); 7.18 (dd, 1H) | 27 |
| 4.24 | (H-pyrrolo[1,2-a]pyrazin-6-yl)methyl | 813 | 8.81 (bs, 1H); 7.52 (bs, 1H); 7.11 (d, 1H); 6.98 (d, 1H) | 27 |
| 4.25 | (H-imidazo[1,2-a]pyridin-6-yl)methyl | m-1 811 | 8.63 (s, 1H); 7.91 (s, 1H); 7.63-7.57 (m, 2H); 7.37 (d, 1H) | 27 |
| 4.26 | (imidazo[1,2-a]pyrimidin-3-yl)methyl | 814 | 8.94 (dd, 1H); 8.61 (dd, 1H); 7.83 (s, 1H); 7.14 (dd, 1H) | 27 |
| 4.27 | (imidazo[1,2-a]pyrimidin-2-yl)methyl | 814 | 8.80 (d, 1H); 8.60 (bs, 1H); 7.95 (d, 1H); 7.05 (m, 1H) | 27 |
| 4.28 | (imidazo[1,2-a]pyrazin-3-yl)methyl | M/2 408 | 9.00 (s, 1H); 8.53 (dd, 1H); 7.95 (d, 1H); 7.86 (s, 1H) | 27 |
| 4.29 | (naphthalen-2-yl)methyl | M/2 412 | 8.15 (d, 1H); 8.00-7.92 (m, 2H); 7.65 (m, 1H); 7.60-7.49 (m, 2H) | 27 |
| 4.30 | (1-(pyridin-3-yl)-1H-pyrazol-3-yl)methyl | M/2 421 | 9.02 (s, 1H); 8.53 (s, 1H); 8.51 (m, 1H); 8.24 (m, 1H); 7.88 (s, 1H); 7.57 (m, 1H) | 27 |

TABLE 4-continued

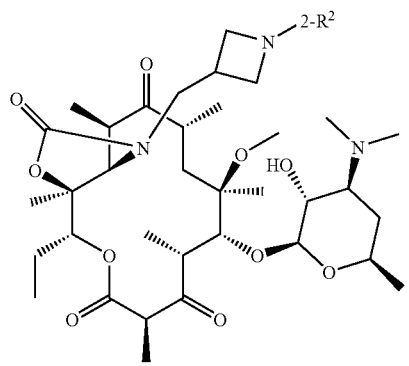

| Ex. # | 2-R² Name | MS | ¹H NMR | Prep. # |
|---|---|---|---|---|
| 4.31 | (1-(pyridin-2-yl)-1H-pyrazol-3-yl)methyl | M/2 421 | 8.61 (d, 1H); 8.42 (bs, 1H); 8.00-7.90 (m, 2H); 7.31 (bs, 1H); 6.58 (d, 1H) | 27 |
| 4.32 | quinoline-5-carboxyl (free base) | M/2 420 | CDCl3: 8.93 (bs, 1H); 8.57 (bd, 1H); 8.14 (d, 1H); 7.64 (t, 1H); 7.58 (dd, 1H); 7.44 (m, 1H) | 33 |
| 4.33 | quinoline-6-carboxyl (free base) | M/2 420 | CDCl3: 8.96 (bs, 1H); 8.14 (bs, 1H); 7.42 (bs, 1H) | 33 |
| 4.34 | quinoline-8-carboxyl (free base) | M/2 420 | 8.96 (bd, 1H); 8.39 (bt, 1H); 8.01 (bd, 1H); 7.79 (bs, 1H); 7.63 (bt, 1H); 7.58 (m, 1H) | 32 |
| 4.35 | H-pyrazolo[1,5-a]pyridine-3-carboxyl (free base) | M/2 414 | 8.61 (bd, 1H); 8.23-8.19 (m, 2H); 7.42 (bt, 1H); 7.02 (bt, 1H) | 33 |
| 4.36 | (quinolin-8-yl)methyl | 824 | 8.98 (dd, 1H); 8.38 (dd, 1H); 8.03 (m, 1H); 7.89 (d, 1H); 7.65-7.56 (m, 2H) | 27 |
| 4.37 | quinoline-4-carboxyl | 838 | 8.90 (d, 1H); 8.09-8.04 (m, 2H); 7.82 (t, 1H); 7.71 (m, 1H); 7.54 (dd, 1H) | 33 |
| 4.38 | quinoline-3-carboxyl | 838 | 9.06 (bt, 1H); 8.62 (m, 1H); 8.10 (d, 1H); 8.05 (d, 1H); 7.87 (m, 1H); 7.76 (m, 1H) | 33 |
| 4.39 | isoquinoline-3-carboxyl | 838 | 9.22 (d, 1H); 8.40 (d, 1H); 8.12 (m, 1H); 8.02 (m, 1H); 7.84-7.72 (m, 2H) | 33 |
| 4.40 | 1,8-naphthyridine-2-carboxyl | 839 | 9.10 (m, 1H); 8.60-8.48 (m, 2H); 8.18 (m, 1H); 771 (m, 1H) | 33 |
| 4.41 | 1,6-naphthyridine-2-carboxyl | 839 | 9.36 (s, 1H); 8.74 (d, 1/2H); 8.70 (d, 1/2H); 8.64 (dd, 1H); 8.21-7.92 (m, 2H) | 33 |
| 4.42 | (H-pyrazolo[1,5-a]pyridin-3-yl)methyl | M/2 407 | 8.55 (d, 1H); 8.10 (s, 1H); 7.83 (d, 1H); 7.35 (t, 1H); 6.97 (t, 1H) | 27 |
| 4.43 | (1H-pyrazolo[3,4-b]pyridin-3-yl)methyl | M/2 812 | 8.53 (dd, 1H); 8.30 (m, 1H); 7.26 (dd, 1H) | 27 |
| 4.44 | (6-methyl-1H-benzo[d]imidazol-7-yl)methyl | m-1 825 | 8.21 (d, 1H); 7.51 (d, 1H); 7.20 (d, 1H) | 27 |
| 4.45 | 1H-imidazo[4,5-b]pyridine-7-carboxyl | M/2 415 | 8.52-8.44 (m, 2H); 7.74 (d, 1H) | 33 |
| 4.46 | benzo[d]oxazole-7-carboxyl | M/2 415 | 8.67-6.83 (m, 4H) | 33 |
| 4.47 | isoquinoline-4-carboxyl | 838 | 9.31 (bs, 1H); 8.52 (d, 1H); 8.19 (m, 1H); 8.11 (bt, 1H); 7.89 (t, 1H); 7.78 (t, 1H) | 33 |

TABLE 5

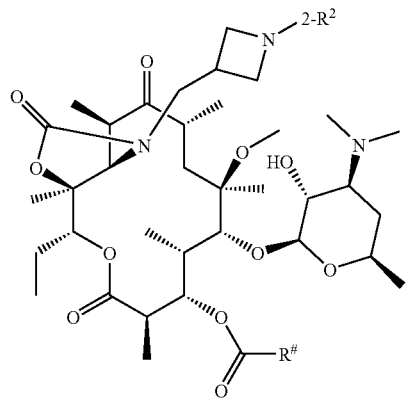

| Ex. # | 2-R² Name | R# Name | MS | ¹H NMR | Prep. # |
|---|---|---|---|---|---|
| 5.01 | quinoline-4-carboxyl | pyrrolidin-1-yl | M/2 469 | 8.92 (m, 1H); 8.10-8.04 (m, 2H); 7.83 (m, 1H); 7.72 (m, 1H); 7.56 (m, 1H) | 33 |
| 5.02 | quinoline-4-carboxyl | pyrrolidin-1-yl | M/2 469 | 8.89 (bs, 1H); 8.57 (m, 1H); 8.13 (d, 1H); 7.82 (m, 1H); 7.75 (m, 1H) | 33 |
| 5.03 | (1H-pyrrolo[2,3-b]pyridin-3-yl)methyl | 2-methyl pyrrolidinyl | M/2 464 | 8.21 (d, 1H); 8.15 (d, 1H); 7.53 (s, 1H); 7.15 (dd, 1H) | 27 |
| 5.04 | (quinolin-8-yl)methyl | 2-methyl pyrrolidinyl | M/2 469 | 8.99 (dd, 1H); 8.39 (dd, 1H); 8.05 (d, 1H); 7.90 (d, 1H) | 27 |
| 5.05 | (1H-pyrrolo[2,3-b]pyridin-3-yl)methyl | 2-(3-fluorophenyl) pyrrolidinyl | M/2 504 | 8.25 (dd, 1H); 8.17 (dd, 1H); 7.65 (s, 1H); 7.34 (m, 1H); 7.19 (m, 1H) | 27 |
| 5.06 | (1H-pyrrolo[2,3-b]pyridin-3-yl)methyl | 2-(3-fluorophenyl) pyrrolidinyl | M/2 504 | 8.21-8.14 (m, 2H); 7.66 (m, 1H); 7.32 (m, 1H); 7.21-7.18 (m, 2H); 7.01 (d, | 27 |
| 5.07 | quinoline-8-carboxyl | pyrrolidin-1-yl | M/2 469 | 8.95 (m, 1H); 8.36 (m, 1H); 8.02 (m, 1H); 7.78 (m, 1H); 7.65 (m, 1H) | 33 |
| 5.08 | (quinolin-8-yl)methyl | pyrrolidin-1-yl | 923 | 8.99 (dd, 1H); 8.39 (dd, 1H); 8.04 (d, 1H); 7.90 (d, 1H); 7.66-7.59 (m, 2H) | 27 |
| 5.09 | (isoquinolin-1-yl)methyl | pyrrolidin-1-yl | M/2 462 | 8.45 (d, 1H); 8.07 (d, 1H); 7.97 (d, 1H); 7.82-7.73 (m, 3H) | 27 |
| 5.10 | (1H-pyrrolo[2,3-b]pyridin-3-yl)methyl | pyrrolidin-1-yl | M/2 457 | 8.26 (dd, 1H); 8.20 (dd, 1H); 7.68 (s, 1H); 7.20 (m, 1H) | 27 |
| 5.11 | (1H-benzo[d]imidazol-2-yl)methyl | pyrrolidin-1-yl | M/2 (457 | 7.52 (dd, 2H); 7.20 (m, 2H) | 27 |
| 5.12 | (1H-pyrazolo[3,4- | pyrrolidin-1- | m-1 911 | 8.56 (d, 1H); 8.31 (d, 1H); 7.29 (m, 1H) | 27 |
| 5.13 | (quinolin-8-yl)methyl | azetidin-1-yl | M/2 + 41 474 | 9.00 (bs, 1H); 8.05 (bd, 1H); 7.91 (m, 1H); 7.66-7.60 (m, 2H) | 27 |
| 5.14 | (benzo[d]thiazol-2-yl)methyl | pyrrolidin-1-yl | M/2 465 | 7.96 (d, 1H); 7.90 (d, 1H); 7.47 (t, 1H); 7.39 (t, 1H) | 27 |

TABLE 6

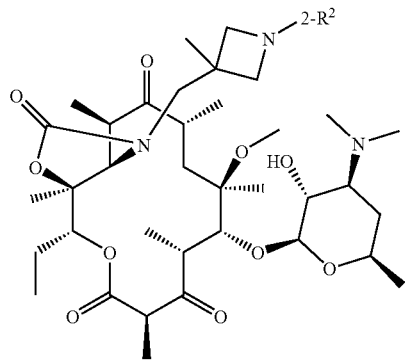

| Ex. # | 2-R² Name | MS | ¹H NMR | Prep. # |
|---|---|---|---|---|
| 6.01 | (quinolin-6-yl)methyl | 419 | CDCl₃: 8.95 (d, 1H); 8.12 (d, 1H) | 27 |
| 6.02 | (quinolin-5-yl)methyl | 838 | CDCl₃: 8.35 (s, 1H); 8.40 (d, 1H) | 27 |
| 6.03 | (1H-pyrrolo[2,3-b]pyridin-3-yl)methyl | 827 | CDCl₃: 6.80 (s, 1H); 7.38 (s, 1H) | 27 |
| 6.04 | (quinoxalin-7-yl)methyl | 839 | CDCl₃: 7.95 (d, 1H); 8.38 (s, 2H) | 27 |
| 6.05 | (quinoxalin-8-yl)methyl | 839 | CDCl₃: 7.90 (t, 1H); 8.20 (q, 2H) | 27 |
| 6.06 | (quinolin-7-yl)methyl | 838 | CDCl₃: 7.78 (d, 1H); 8.18 (d, 1H) | 27 |
| 6.07 | (quinoxalin-2-yl)methyl | 839 | CDCl₃: 7.78 (d, 2H); 8.25 (q, 2H) | 27 |
| 6.08 | (5-fluoro-1H-indol-3-yl)methyl | 844 | CDCl₃: 7.36 (q, 2H); 7.60 (s, 1H) | 27 |
| 6.09 | (3-phenyl-1H-pyrazol-4-yl)methyl | 853 | CDCl₃: 7.48 (q, 3H); 8.00 (s, 1H) | 27 |
| 6.10 | (1H-indol-5-yl)methyl | 826 | CDCl₃: 7.40 (d, 1H); 7.62 (s, 1H) | 27 |
| 6.11 | (1H-benzo[d]imidazol-2-yl)methyl | 827 | CDCl₃: 7.60 (d, 2H); 8.38 (s, 3H) | 27 |
| 6.12 | quinoline-3-carboxyl | 852 | CDCl₃: 7.80 (t, 1H); 8.14 (d, 1H) | 33 |
| 6.13 | quinoline-4-carboxyl | 852 | CDCl₃: 8.10 (q, 2H); 8.25 (s, 1H) | 33 |
| 6.14 | quinoline-5-carboxyl | 852 | CDCl₃: 8.60 (t, 1H); 8.20 (t, 1H) | 33 |
| 6.15 | quinoline-6-carboxyl | 852 | CDCl₃: 7.50 (q, 1H0; 8.39 (d, 1H) | 33 |
| 6.16 | quinoline-7-carboxyl | 852 | CDCl₃: 8.20 (d, 1H); 8.20 (s, 1H) | 33 |
| 6.17 | quinoline-8-carboxyl | 852 | CDCl₃: 7.40 (q, 1H); 8.18 (d, 1H) | 33 |
| 6.18 | 1H-benzo[d]imidazole-2-carboxyl | 841 | CDCl₃: 7.40 (q, 1H); 8.60 (d, 1H) | 33 |
| 6.19 | benzo[d]thiazole-6-carboxyl | 858 | CDCl₃: 8.20 (s, 1H); 8.24 (d, 1H) | 33 |
| 6.20 | isoquinoline-4-carboxyl | 852 | CDCl₃: 7.62 (t, 1H); 8.03 (t, 1H) | 33 |
| 6.21 | 6-(1H-pyrazol-1-yl)pyridine-2-carboxyl | 868 | CDCl₃: 7.79 (s, 1H); 8.00 (d, 1H) | 33 |
| 6.22 | H-pyrazolo[1,5-a]pyridine-2-carboxyl | 843 | CDCl₃: 7.58 (s, 1H); 7.80 (d, 1H) | 33 |
| 6.23 | 1H-pyrrolo[2,3-b]pyridine-2-carboxyl | 841 | CDCl₃: 7.15 (q, 1H); 8.00 (d, 1H) | 33 |
| 6.24 | H-pyrazolo[1,5-a]pyridine-3-carboxyl | 843 | CDCl₃: 7.38 (t, 1H); 8.40 (d, 1H) | 33 |

TABLE 7

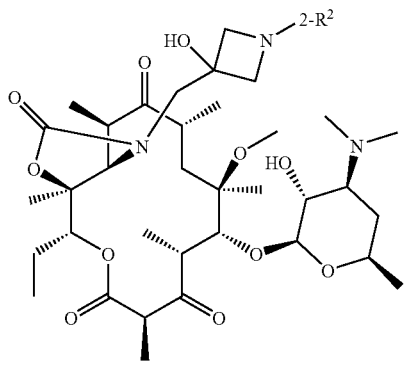

| Ex. # | 2-R² Name | MS | ¹H NMR | Prep. # |
|---|---|---|---|---|
| 7.01 | (quinolin-5-yl)methyl | M/2 421 | CDCl₃: 8.90 (d, 1H); 8.53 (d, 1H); 8.03 (d, 1H); 7.64 (dd, 1H); 7.52 (d, 1H) | 27 |
| 7.02 | (quinolin-6-yl)methyl | M/2 421 | CDCl₃: 8.91 (d, 1H); 8.21 (d, 1H); 8.09 (d, 1H); 7.92 (s, 1H); 7.74 (d, 1H) | 27 |
| 7.03 | (quinoxalin-6-yl)methyl | M/2 421 | CDCl₃: 8.84 (d, 2H); 8.13 (s, 1H); 8.10 (d, 1H); 7.93 (d, 1H) | 27 |
| 7.04 | (1H-pyrrolo[2,3-b]pyridin-3-yl)methyl | M/2 415 | CDCl₃: 8.60 (d, 1H); 8.24 (m, 1H); 7.96 (s, 1H); 7.64 (d, 1H) | 27 |
| 7.05 | quinoline-6-carboxyl | M/2 428 | CDCl₃: 9.21 (d, 1H); 8.55 (d, 1H); 8.36 (d, 1H); 8.36 (d, 1H); 8.13 (d, 1H); 8.04 (s, 1H) | 33 |
| 7.06 | quinoline-8-sulfonyl | M/2 446 | CDCl₃: 9.09 (d, 1H); 8.41 (d, 1H); 8.20 (d, 1H); 8.01 (d, 1H); 7.60 (dd, 1H) | 31 |
| 7.07 | (2,5-dimethyl-1H-imidazol-4-yl)methyl | M/2 404 | CDCl₃: 2.47 (s, 3H); 2.29 (s, 3H) | 27 |
| 7.08 | (1H-benzo[d]imidazol-7-yl)methyl | M/2 415 | CDCl₃: 8.19 (s, 1H); 7.78 (d, 1H); 7.23 (dd, 1H); 7.16 (d, 1H) | 27 |
| 7.09 | 1,2,3,4-tetrahydro-2,4-dioxopyrimidine-5-methyl | M/2 412 | CDCl₃: 7.15 (s, 1H) | 27 |
| 7.10 | (4-(pyrimidin-2-yl)phenyl)methyl | M/2 434 | CDCl₃: 8.79 (d, 2H); 8.42 (d, 2H); 7.47 (d, 2H); 7.18 (dd, 1H) | 27 |
| 7.11 | (isoxazol-5-yl)methyl | M/2 391 | CDCl₃: 8.16 (s, 1H); 6.18 (s, 1H) | 27 |
| 7.12 | (4-(pyrimidin-5-yl)phenyl)methyl | M/2 434 | CDCl₃: 9.20 (s, 1H); 8.95 (s, 2H); 7.55 (d, 2H); 7.47 (d, 2H) | 27 |
| 7.13 | (1-(pyridin-3-yl)-1H-pyrazol-3-yl)methyl | M/2 429 | CDCl₃: 9.03 (s, 1H); 8.56 (d, 1H); 8.24 (s, 1H); 8.06 (d, 1H); 7.79 (s, 1H); 7.42 (dd, 1H) | 27 |
| 7.14 | isoquinoline-5-sulfonyl | M/2 446 | CDCl₃: 9.34 (s, 1H); 8.70 (d, 1H); 8.50 (d, 1H); 8.42 (d, 1H); 8.23 (d, 1H) | 31 |
| 7.15 | 3,5-dimethyl-1H-pyrazole-4-sulfonyl | 857 | CDCl₃: 2.50 (s, 6H) | 31 |
| 7.16 | 2,3-dihydro-2-oxobenzo[d]oxazole-6-sulfonyl | 896 | CDCl₃: 7.65 (d, 1H); 7.64 (s, 1H); 7.24 (d, 1H) | 31 |
| 7.17 | 1,8-naphthyridine-2-carboxyl | M/2 428 | CDCl₃: 9.15 (m, 1H); 8.27 (m, 3H); 7.53 (m, 1H) | 33 |
| 7.18 | quinoxaline-6-carboxyl | 855 | CDCl₃: 8.88 (d, 2H); 8.36 (s, 1H); 8.14 (d, 1H); 8.06 (d, 1H) | 33 |
| 7.19 | quinoline-5-carboxyl | M/2 428 | CDCl₃: 8.93 (d, 1H); 8.60 (dd, 1H); 8.14 (d, 1H); 7.66 (m, 2H); 7.48 (dd, 1H) | 33 |
| 7.20 | quinoline-8-carboxyl | M/2 428 | CDCl₃: 9.15 (d, 1H); 8.16 (d, 1H); 7.85 (d, 1H); 7.78 (d, 1H); 7.55 (dd, 1H) | 33 |
| 7.21 | quinoline-7-carboxyl | M/2 428 | CDCl₃: 9.01 (d, 1H); 8.18 (m, 2H); 7.90 (s, 1H); 7.87 (d, 1H); 7.51 (dd, 1H) | 33 |
| 7.22 | quinoline-2-carboxyl | M/2 428 | CDCl₃: 9.22 (s, 1H); 8.44 (s, 1H); 8.13 (d, 1H); 8.02 (d, 1H); 7.79 (dd, 1H) | 33 |
| 7.23 | isoquinoline-4-carboxyl | M/2 428 | CDCl₃: 9.27 (s, 1H); 8.58 (s, 1H); 8.20 (d, 1H); 8.00 (d, 1H); 7.79 (dd, 1H) | 33 |
| 7.24 | isoquinoline-8-carboxyl | M/2 428 | CDCl₃: 9.64 (s, 1H); 8.57 (dd, 1H); 7.86 (d, 1H); 7.66 (m, 3H) | 33 |
| 7.25 | 1,8-naphthyridine-3-carboxyl | M/2 428 | CDCl₃: 9.17 (s, 1H); 8.28 (m, 3H); 7.53 (m, 1H) | 33 |
| 7.26 | 1H-pyrrolo[2,3-b]pyridine-2-carboxyl | M/2 422 | CDCl₃: 8.43 (d, 1H); 8.01 (m, 1H); 7.13 (m, 1H); 6.91 (s, 1H) | 33 |
| 7.27 | 1H-pyrrolo[2,3-c]pyridine-2-carboxyl | M/2 422 | CDCl₃: 9.02 (s, 1H); 8.31 (m, 1H); 7.71 (m, 1H); 7.02 (s, 1H) | 33 |
| 7.28 | 1H-benzo[d]imidazole-2-carboxyl | M/2 422 | CDCl₃: 7.68 (m, 2H); 7.31 (m, 2H) | 33 |

TABLE 7-continued
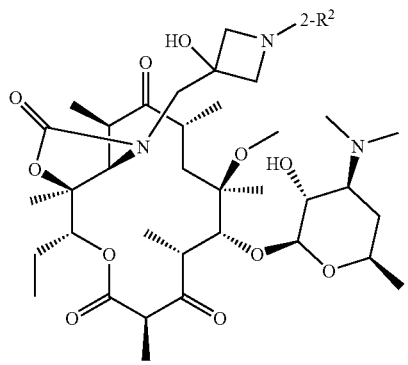
| Ex. # | 2-R² Name | MS | ¹H NMR | Prep. # |
|---|---|---|---|---|
| 7.29 | H-imidazo[1,2-a]pyridine-2-carboxyl | M/2 422 | CDCl₃: 8.13 (m, 1H); 8.11 (s, 1H); 7.61 (dd, 1H); 7.19 (d, 1H); 6.81 (dd, 1H) | 33 |
| 7.30 | H-pyrazolo[1,5-a]pyridine-2-carboxyl | M/2 422 | CDCl₃: 8.37 (d, 1H); 7.55 (dd, 1H); 6.97 (m, 3H) | 33 |
| 7.31 | 6-(1H-pyrazol-1-yl)pyridine-3-carboxyl | 870 | CDCl₃: 8.69 (d, 1H); 8.58 (s, 1H); 8.11 (d, 1H); 8.00 (d, 1H); 7.75 (s, 1H) | 33 |
| 7.32 | 1H-pyrrolo[3,2-b]pyridine-2-carboxyl | M/2 422 | CDCl₃: 8.52 (d, 1H); 7.80 (d, 1H); 7.23 (m, 1H); 6.97 (d, 1H) | 33 |
TABLE 8
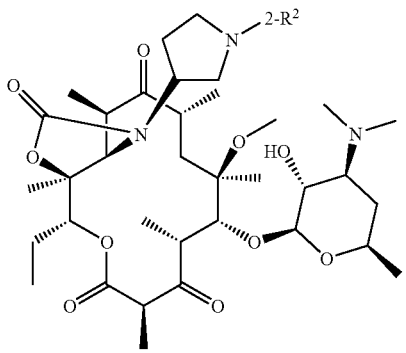
| Ex. # | 2-R² Name | MS | ¹H NMR | Prep. # |
|---|---|---|---|---|
| 8.01 | (1H-benzo[d]imidazo-4-yl)methyl | 813 | 7.30 (m, 2H); 7.62 (m, 1H); 8.22 (s, 1H); 9.06 (d, 1H) | 27 |
| 8.02 | (benzo[d]thiazol-2-yl)methyl | 831 | 7.93 (t, 1H); 7.50 (t, 1H); 7.94 (d, 1H); 8.00 (d, 1H) | 27 |

TABLE 9

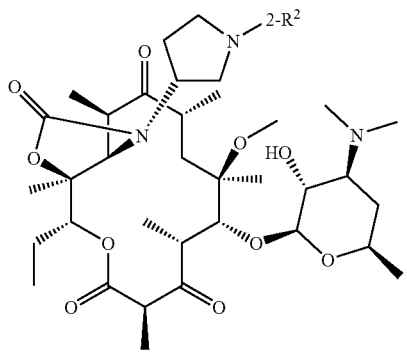

| Ex. # | 2-R² Name | MS | ¹H NMR | Prep. # |
|---|---|---|---|---|
| 9.01 | (quinolin-4-yl)methyl | M/2 413 | 7.56 (d, 1H); 7.60 (t, 1H); 7.76 (t, 1H); 8.02 (d, 1H); 8.28 (d, 1H); 8.78 (d, 1H) | 27 |
| 9.02 | (quinolin-5-yl)methyl | M/2 413 | 7.52 (m, 1H); 7.62 (d, 1H); 7.72 (t, 1H); 7.96 (d, 1H) | 27 |
| 9.03 | (1H-pyrrolo[2,3-b]pyridin-3-yl)methyl | 813 | 7.22 (m, 1H); 7.68 (s, 1H); 8.22 (d, 1H); 8.28 (d, 1H) | 27 |
| 9.04 | (quinolin-3-yl)methyl | M/2 413 | 7.64 (t, 1H); 7.80 (t, 1H); 7.96 (d, 1H); 8.04 (t, 1H); 8.40 (s, 1H); 8.90 (s, 1H) | 27 |
| 9.05 | (1,8-naphthyridin-4-yl)methyl | 825 | 7.61 (m, 2H); 8.86 (d, 1H); 8.98 (d, 1H) | 27 |
| 9.06 | (1H-benzo[d]imidazol-4-yl)methyl | 814 | 7.38 (m, 2H); 7.70 (t, 1H); 8.31 (s, 1H) | 27 |
| 9.07 | (isoquinolin-5-yl)methyl | 824 | 7.72 (t, 1H); 7.92 (d, 1H); 8.20 (m, 2H); 8.52 (d, 1H) | 27 |
| 9.08 | isoquinoline-5-sulfonyl | 874 | 7.88 (t, 1H); 8.48 (m, 2H); 8.64 (d, 1H); 8.68 (d, 1H) | 31 |
| 9.09 | (1H-indazol-3-yl)methyl | 813 | 7.24 (t, 1H); 7.46 (m, 2H); 7.56 (d, 1H); 7.88 (d, 1H) | 27 |
| 9.10 | (isoquinolin-4-yl)methyl | 824 | 7.76 (t, 1H); 7.85 (t, 1H); 8.16 (d, 1H); 8.32 (d, 1H); 8.45 (s, 1H) | 27 |

TABLE 10

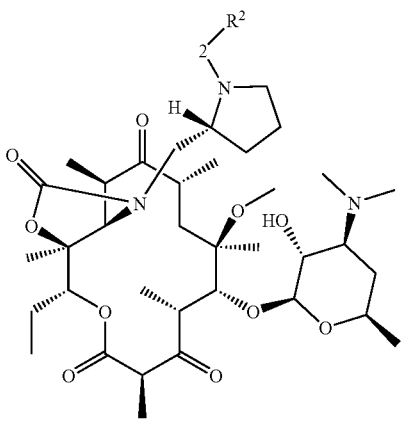

| Ex. # | 2-R² Name | MS | ¹H NMR | Prep. # |
|---|---|---|---|---|
| 10.01 | (isoxazol-5-yl)methyl | 777 | 8.3 (s, 1H); 6.37 (s, 1H) | 27 |
| 10.02 | (1H-1,2,3-triazol-4-yl)methyl | 777 | 7.95 (s, 1H) | 27 |
| 10.03 | (isoquinolin-5-yl)methyl | 837 | 9.4 (s, 1H); 8.61 (d, 1H); 8.3 (d, 1H); 8.21 (d, 1H); 7.9 (m, 2H) | 27 |
| 10.04 | (quinolin-4-yl)methyl | 837 | 8.79 (d, 1H); 8.3 (d, 1H); 8.02 (d, 1H); 7.75 (m, 2H); 7.64 (m, 1H) | 27 |
| 10.05 | (quinolin-8-yl)methyl | 837 | 9.03 (d, 1H); 8.5 (d, 1H); 8.09 (d, 1H); 7.66 (m, 2H) | 33 |
| 10.06 | quinoline-6-carboxyl | 851 | 8.89 (d, 1H); 8.48 (s, 1H); 8.44 (d, 1H); 8.11 (s, 1H); 7.59 (dd, 1H) | 33 |
| 10.07 | quinoline-3-carboxyl | 852 | 8.98 (s, 1H); 8.03 (m, 2H); 7.89 (t, 1H); 7.67 (t, 1H) | 33 |

TABLE 10-continued

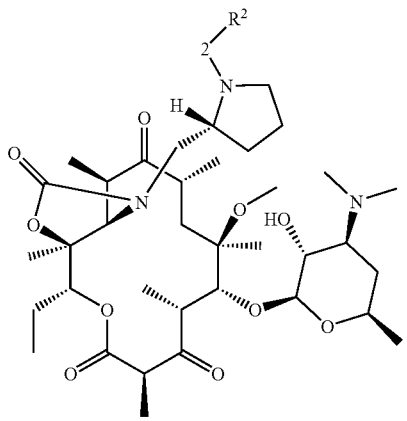

| Ex. # | 2-R² Name | MS | ¹H NMR | Prep. # |
|---|---|---|---|---|
| 10.08 | quinoline-2-carboxyl | 852 | CDCl₃: 7.58 (t, 1H); 7.96 (d, 1H) | 33 |
| 10.09 | isoquinoline-3-carboxyl | 852 | CDCl₃: 7.60 (t, 1H); 8.11 (d, 1H) | 33 |
| 10.10 | quinoline-4-carboxyl | 852 | CDCl₃: 7.88 (d, 1H); 7.98 (t, 1H) | 33 |
| 10.11 | quinoline-8-carboxyl | 852 | CDCl₃: 7.76 (t, 1H); 8.10 (q, 4H) | 33 |
| 10.12 | quinoxaline-6-carboxyl | 853 | CDCl₃: 8.05 (d, 1H); 8.18 (d, 1H) | 33 |
| 10.13 | 6-(1H-pyrazol-1-yl)pyridine-3-carboxyl | 868 | CDCl₃: 7.70 (s, 1H); 8.00 (t, 1H) | 33 |
| 10.14 | H-pyrazolo[1,5-a]pyridine-2-carboxyl | 841 | CDCl₃: 7.98 (d, 1H); 7.50 (q, 1H) | 33 |
| 10.15 | quinoline-7-carboxyl | 852 | CDCl₃: 7.48 (q, 1H); 7.82 (d, 1H) | 33 |
| 10.16 | 1,8-naphthyridine-2-carboxyl | 853 | CDCl₃: 7.58 (q, 1H); 7.80 (d, 1H) | 33 |
| 10.17 | isoquinoline-1-carboxyl | 852 | CDCl₃: 7.62 (t, 1H); 7.80 (t, 1H) | 33 |
| 10.18 | 1H-benzo[d]imidazole-2-carboxyl | 843 | CDCl₃: 7.25 (t, 2H); 8.36 (d, 1H) | 33 |
| 10.19 | 2-(trifluoromethyl)-1,6- | 921 | CDCl₃: 8.10 (t, 1H); 8.98 (d, 1H) | 33 |
| 10.20 | isoquinoline-4-carboxyl | 852 | CDCl₃: 7.80 (t, 1H); 8.05 (d, 1H) | 33 |
| 10.21 | quinoxaline-2-carboxyl | 853 | CDCl₃: 7.80 (t, 1H); 8.05 (t, 1H) | 33 |
| 10.22 | benzo[d]thiazole-7-carboxyl | 858 | CDCl₃: 7.52 (t, 1H); 7.70 (t, 1H) | 33 |
| 10.23 | benzo[d]oxazole-7-carboxyl | 842 | CDCl₃: 7.60 (d, 1H); 8.40 (d, 1H) | 33 |
| 10.24 | 3H-imidazo[4,5-c]pyridine-2-carboxyl | M/2 422 | CDCl₃: 7.60 (d, 1H); 8.42 (d, 1H) | 33 |
| 10.25 | 3H-imidazo[4,5-b]pyridine-2-carboxyl | M/2 422 | CDCl₃: 6.89 (t, 1H); 7.10 (t, 1H) | 33 |
| 10.26 | 9H-purine-8-carboxyl | M/2 421 | CDCl₃: 8.79 (s, 1H); 8.40 (s, 1H) | 33 |
| 10.27 | 1H-benzo[d]imidazole-2-carboxyl (2-F template) | 859 | CDCl₃: 7.30 (q, 2H); 7.60 (t, 2H) | 33 |
| 10.28 | H-pyrazolo[1,5-a]pyridine-2-carboxyl (2-F template) | 859 | CDCl₃: 6.88 (t, 1H); 7.05 (t, 1H) | 33 |
| 10.29 | isoquinoline-1-carboxyl (2-F template) | 870 | CDCl₃: 8.00 (d, 1H); 8.21 (d, 1H) | 33 |
| 10.30 | 1,8-naphthyridine-2-carboxyl (2-F template) | 871 | CDCl₃: 7.51 (q, 1H); 8.03 (d, 1H) | 33 |
| 10.31 | 1H-benzo[d]imidazole-2-carboxyl | 859 | CDCl₃: 7.30 (q, 2H); 7.60 (t, 2H) | 33 |
| 10.32 | 1H-indazole-5-carboxyl | 841 | CDCl₃: 7.42 (d, 1H); 7.60 (d, 1H) | 33 |
| 10.33 | quinoxaline-5-carboxyl | 853 | CDCl₃: 7.80 (m, 4H); 8.18 (d, 1H) | 33 |
| 10.34 | 1H-pyrrolo[2,3-c]pyridine-2-carboxyl | 841 | CDCl₃: 7.40 (d, 1H); 8.20 (q, 1H) | 33 |
| 10.35 | 2-methyl-4-oxo-4H-pyrido[1,2-a]pyrimidine-7-carboxyl | 884 | CDCl₃: 7.50 (d, 1H); 7.98 (d, 1H) | 33 |
| 10.36 | 1-benzyl-1,2-dihydro-2-oxopyridine-3-carboxyl | 908 | CDCl₃: 7.38 (t, 2H); 7.50 (q, 2H) | 33 |
| 10.37 | isoquinoline-8-carboxyl | 852 | CDCl₃: 7.60 (m, 4H); 8.50 (q, 2H) | 33 |
| 10.38 | 1,8-naphthyridine-3-carboxyl | 853 | CDCl₃: 7.50 (m, 2H); 7.80 (d, 1H) | 33 |
| 10.39 | 2-methyl-1,8-naphthyridine-3-carboxyl | 867 | CDCl₃: 7.40 (q, 1H); 8.20 (s, 1H) | 33 |
| 10.40 | 2-(trifluoromethyl)-1,8-naphthyridine-3-carboxyl | 921 | CDCl₃: 7.40 (m, 2H); 8.35 (d, 1H) | 33 |
| 10.41 | 2-methyl-1,6-naphthyridine-3-carboxyl | 867 | CDCl₃: 8.40 (s, 1H); 8.70 (d, 1H) | 33 |
| 10.42 | 1H-pyrrolo[3,2-b]pyridine-2-carboxyl | 841 | CDCl₃: 7.80 (q, 1H); 8.51 (t, 2H) | 33 |

TABLE 10-continued

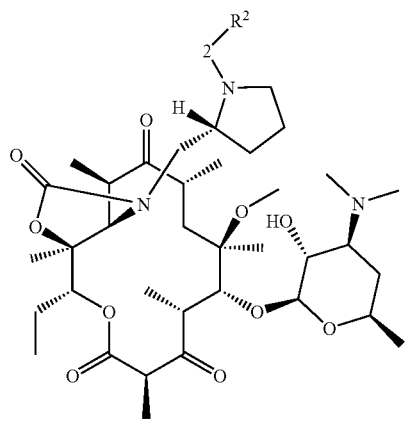

| Ex. # | 2-R² Name | MS | ¹H NMR | Prep. # |
|---|---|---|---|---|
| 10.43 | imidazo[1,2-a]pyrimidine-2-carboxyl | 842 | CDCl$_3$: 7.00 (q, 2H); 8.61 (t, 1H) | 33 |
| 10.44 | thiazolo[4,5-b]pyridine-7-carboxyl | 859 | CDCl$_3$: 7.58 (q, 1H); 8.80 (q, 1H) | 33 |
| 10.45 | H-pyrazolo[1,5-a]pyridine-3-carboxyl | M/2 421 | CDCl$_3$: 7.28 (t, 1H); 8.40 (d, 1H) | 33 |
| 10.46 | isoquinoline-5-sulfonyl | 888 | CDCl$_3$: 7.86 (t, 1H); 8.20 (d, 1H) | 31 |
| 10.47 | quinoline-8-sulfonyl | 888 | CDCl$_3$: 7.62 (t, 1H); 8.00 (d, 1H) | 31 |
| 10.48 | 1,2-dihydro-6-methyl-2-oxopyridine-3-carboxyl | M/2 416 | CDCl$_3$: 7.80 (d, 1H); 8.40 (s, 1H) | 33 |
| 10.49 | 1,6-naphthyridine-2-carboxyl | M/2 472 | CDCl$_3$: 9.28 (s, 1H); 8.76 (d, 1H); 8.36 (m, 1H); 8.04 (m, 1H) | |
| 10.50 | 3H-imidazo[4,5-b]pyridine-7-carboxyl | 842 | CDCl$_3$: 6.96 (d, 1H); 7.45 (d, 1H) | 33 |
| 10.51 | pyrazolo[1,5-a]pyrimidine-3-carboxyl | 842 | CDCl$_3$: 6.80 (q, 2H); 8.00 (s, 1H) | 33 |
| 10.52 | 1H-benzo[d]imidazole-4-carboxyl | 841 | CDCl$_3$: 7.80 (q, 2H); 8.20 (s, 1H) | 33 |
| 10.53 | pyrazolo[1,5-a]pyrimidine-2-carboxyl | 842 | CDCl$_3$: 6.81 (q, 2H); 8.45 (d, 1H) | 33 |
| 10.54 | H-imidazo[1,2-a]pyridine-2-carboxyl | M/2 421 | CDCl$_3$: 7.19 (t, 1H); 7.58 (d, 1H) | 33 |
| 10.55 | 1H-pyrrolo[2,3-b]pyridine-2-carboxyl | 841 | CDCl$_3$: 7.02 (q, 2H); 7.96 (d, 1H) | 33 |

TABLE 11

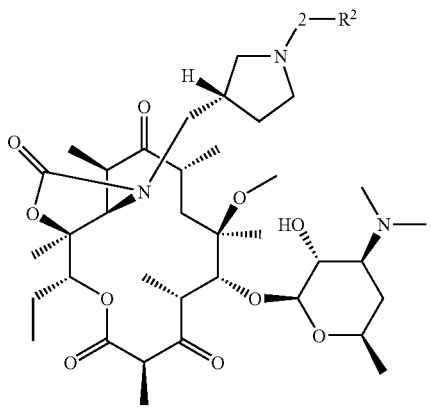

| Ex. # | 2-R² Name | MS | ¹H NMR | Prep. # |
|---|---|---|---|---|
| 11.01 | (quinolin-5-yl)methyl | 839 | 8.89-8.87 (m, 2H); 7.98 (d, 1H); 7.73 (dd, 1H); 7.64-7.62 (m, 2H) | 27 |
| 11.02 | (quinoxalin-8-yl)methyl | 839 | 8.87 (d, 2H); 8.09-8.07 (m, 2H); 7.96 (d, 1H) | 27 |

TABLE 11-continued

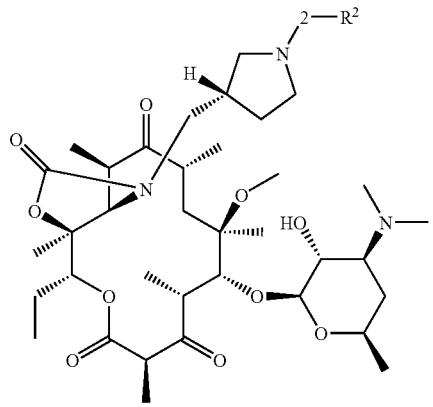

| Ex. # | 2-R² Name | MS | ¹H NMR | Prep. # |
|---|---|---|---|---|
| 11.03 | (quinolin-3-yl)methyl | 837 | 8.2 (s, 1H); 8.4 (s, 1H); 8.0 (d, 1H); 7.9 (d, 1H); 7.7 (t, 1H); 7.6 (t, 1H) | 27 |
| 11.04 | (quinolin-2-yl)methyl | 837 | 8.3 (d, 1H); 8.1 (d, 1H); 7.9 (d, 1H); 7.8 (t, 1H); 7.6 (m, 2H) | 27 |
| 11.05 | (1H-pyrrolo[2,3-b]pyridin-3-yl)methyl | 826 | 8.3 (d, 1H); 8.2 (d, 1H); 7.7 (s, 1H); 7.2 (t, 1H) | 27 |
| 11.06 | (1-methyl-1H-benzo[d]imidazol-2-yl)methyl | 840 | 7.53 (d, 1H); 7.45 (d, 1H); 7.29 (t, 1H); 7.2 (t, 1H); 3.92 (s, 3H) | 27 |
| 11.07 | (6-methoxypyridin-3-yl)methyl | 817 | 8.2 (s, 1H); 7.75 (d, 1H); 6.82 (d, 1H); 3.9 (s, 3H) | 27 |
| 11.08 | (6-methoxypyridin-2-yl)methyl | m-1 816 | 7.7 (t, 1H); 7.0 (d, 1H); 6.8 (d, 1H); 3.95 (s, 3H) | 27 |
| 11.09 | (2-methoxypyridin-3-yl)methyl | 817 | 8.0 (d, 1H); 7.7 (d, 1H); 6.9 (m, 1H); 3.92 (s, 3H) | 27 |
| 11.10 | (isoquinolin-1-yl)methyl | m-1 835 | 8.48 (d, 1H); 8.12 (d, 1H); 7.97 (d, 1H); 7.7 (m, 3H) | 27 |
| 11.11 | (quinolin-4-yl)methyl | m-1 835 | 8.23 (d, 1H); 8.3 (d, 1H); 8.0 (d, 1H); 7.8 (t, 1H); 7.65 (t, 1H); 7.6 (d, 1H) | 27 |
| 11.12 | (quinolin-8-yl)methyl | 837 | 9.0 (m, 1H); 8.41 (d, 1H); 8.0 (d, 1H); 7.87 (d, 1H); 7.62 (m, 1H) | 27 |
| 11.13 | (isoquinolin-5-yl)methyl | 837 | 9.29 (s, 1H); 8.59 (d, 1H); 8.2 (m, 2H); 7.9 (d, 1H); 7.7 (t, 1H) | 27 |
| 11.14 | (1-(pyridin-2-yl)-1H-pyrazol-4-yl)methyl | 853 | 8.63 (s, 1H), 8.42 (d, 1H); 7.94 (m, 2H); 7.3 (m, 1H); 6.6 (d, 1H) | 27 |
| 11.15 | (1-(pyridin-3-yl)-1H-pyrazol-4-yl)methyl | 853 | 9.0 (s, 1H); 8.5 (m, 2H); 8.3 (d, 1H); 7.9 (s, 1H); 7.6 (m, 1H) | 27 |
| 11.16 | H-pyrazolo[1,5-a]pyridine-2-carboxyl | M/2 421 | 7.88 (m, 2H); 7.20 (m, 1H); 7.64 (m, 1H); 8.51 (s, 1H) | 33 |
| 11.17 | quinoline-3-carboxyl | M/2 427 | 7.64 (m, 1H); 7.81 (m, 1H); 8.00 (d, 2H); 8.52 (s, 1H); 8.96 (s, 1H) | 33 |
| 11.18 | quinoline-6-carboxyl | M/2 427 | 7.56 (m, 1H); 7.84 (m, 1H); 8.04-8.10 (m, 2H); 8.44 (d, 1H); 8.88 (s, 1H) | 33 |

TABLE 12

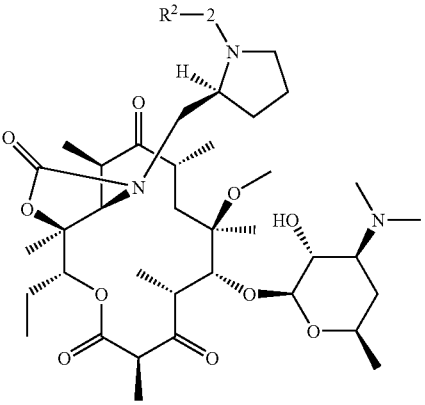

| Ex. # | 2-R² Name | MS | ¹H NMR | Prep. # |
|---|---|---|---|---|
| 12.01 | (6-methoxypyridin-2-yl)methyl | 817 | 7.7 (1, 1H); 7.1 (d, 1H); 6.8 (d, 1H); 3.94 (s, 3H) | 27 |
| 12.02 | (2-methoxypyridin-3-yl)methyl | 818 | 8.2 (d, 1H); 7.86 (d, 1H); 7.03 (m, 1H); 4.01 (s, 3H); | 27 |
| 12.03 | (6-methoxypyridin-3-yl)methyl | 817 | 8.1 (s, 1H); 7.0 (d, 1H); 6.8 (d, 1H); 3.88 (s, 3H) | 27 |
| 12.04 | (isoxazol-5-yl)methyl | 777 | 8.3 (s, 1H); 6.36 (s, 1H) | 27 |
| 12.05 | quinoline-3-carboxyl | M/2 427 | 8.97 (bs, 1h); 8.55 (bs, 1H); 8.07-8.00 (m, 2H); 7.83 (t, 1H); 7.66 (1, 1H) | 33 |
| 12.06 | quinoline-6-carboxyl | 852 | 8.90 (m, 1H); 8.43 (d, 1H); 8.14 (d, 1H); 8.08 (m, 1H); 7.88 (d, 1H); 7.58 (dd, 1H) | 33 |
| 12.07 | 1,8-naphthyridine-2-carboxyl | M/2 427 | 9.14 (d, 1H); 8.61 (m, 1H); 8.53 (d, 1H); 8.32 (m, 1H); 7.72 (m, 1H) | 33 |
| 12.08 | quinoline-4-carboxyl | 852 | 8.90 (d, 1H); 8.08 (d, 1H); 7.83 (m, 1H); 7.70 (m, 1H); 7.58 (d, 1H) | 33 |
| 12.09 | isoquinoline-3-carboxyl | 852 | 9.24 (bs, 1H); 8.13 (bs, 2H); 8.01 (m, 1H); 7.82 (t, 1H); 7.74 (m, 1H) | 33 |
| 12.10 | quinoline-8-carboxyl | 852 | 8.86 (bs, 1/2H); 8.80 (bs, 1/2H); 8.35 (d, 1H); 7.98 (d, 1H); 7.82 (m, 1H); 7.63 (m, 1H) | 33 |
| 12.11 | quinoline-5-carboxyl | 852 | 8.89 (dd, 1H); 8.34 (d, 1H); 8.09 (d, 1H); 7.82 (m, 1H); 7.69 (m, 1H) | 34 |
| 12.12 | quinoline-7-carboxyl | 852 | 8.91 (m, 1H); 8.43 (m, 1H); 8.14 (bs, 1H); 8.05 (d, 1H); 7.72 (d, 1H); 7.61 (dd, 1H) | 33 |

TABLE 13

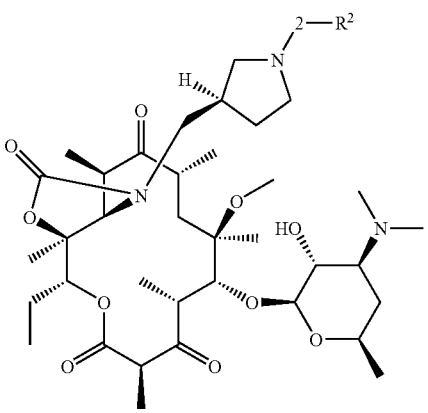

| Ex. # | 2-R² Name | MS | ¹H NMR | Prep. # |
|---|---|---|---|---|
| 13.01 | (1H-pyrrolo[2,3-b]pyridin-3-yl)methyl | 827 | 8.2 (dd, 2H); 7.6 (s, 1H); 7.2 (m, 1H) | 27 |
| 13.02 | 3-(aminomethyl)-1H-pyrrolo[3,2-c]pyridin-6 (5H)-one | 842 | 7.9 (s, 1H); 7.8 (s, 1H); 7.7 (s, 1H) | 27 |
| 13.03 | (1H-pyrrolo[2,3-c]pyridin-3-yl)methyl | 827 | 8.9 (s, 1H); 8.2 (s, 1H); 8.0 (d, 2H) | 27 |

TABLE 13-continued

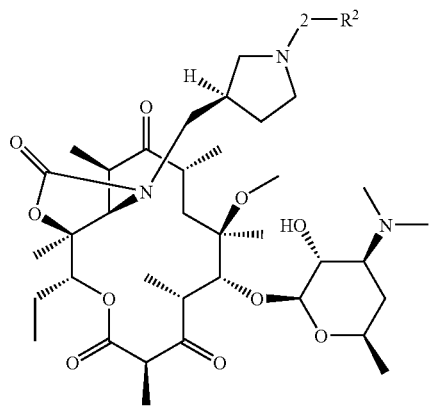

| Ex. # | 2-R² Name | MS | ¹H NMR | Prep. # |
|---|---|---|---|---|
| 13.04 | 2-(aminomethyl)quinolin-8-ol | 853 | 8.25 (d, 1H); 7.47 (d, 1H); 7.38 (t, 1H); 7.36 (d, 1H); 7.1 (d, 1H) | 27 |
| 13.05 | (4-(pyridin-2-yl)phenyl)methyl | 863 | 8.71 (d, 1H); 8.03 (d, 2H); 7.9 (m, 2H); 7.61 (d, 2H); 7.4 (m 1H) | 27 |
| 13.06 | (isoxazol-5-yl)methyl | 777 | 8.3 (s, 1H); 6.39 (s, 1H) | 27 |
| 13.07 | (1H-1,2,3-triazol-4-yl)methyl | 777 | 7.8 (s, 1H) | 27 |
| 13.08 | (2-phenyl-1H-imidazol-4-yl)methyl | m-1 850 | 7.8 (d, 2H); 7.41 (m, 2H); 7.39 (1, 1H); 7.1 (s, 1H) | 27 |
| 13.09 | 1,6-naphthyridine-2-carboxyl | 853 | 7.93-8.00 (m, 2H); 8.68 (m, 1H); 8.73 (m, 1H); 9.37 (s, 1H) | 33 |
| 13.10 | quinoline-3-carboxyl | 852 | 7.70 (t, 1H); 7.82 (t, 1H); 8.07-8.10 (m, 2H); 8.52 (s, 1H); 9.01 (s, 1H) | 33 |
| 13.11 | quinoline-8-carboxyl | 851 | 8.9 (s, 1H); 8.39 (d, 1H); 8.0 (d, 2H); 7.79 (d, 1H); 7.6 (m, 1H) | 33 |
| 13.12 | quinoline-6-carboxyl | M/2 427 | 7.60 (m, 1H); 7.88 (m, 1H); 8.08 (m, 1H); 8.14 (m, 1H); 8.45 (m, 1H); 8.92 (m, 1H) | 33 |
| 13.13 | quinoxaline-2-carboxyl | 853 | 7.89 (m, 2H); 8.12 (m, 2H); 9.22 (s, 1H) | 33 |
| 13.14 | benzo[d]thiazole-7-carboxyl | 858 | 7.64 (t, 1H); 7.77 (d, 1H); 8.16 (d, 1H); 9.31 (s, 1H) | 33 |
| 13.15 | 1H-pyrrolo[2,3-b]pyridine-2-carboxyl | M/2 421 | 7.07 (d, 1H); 7.15 (m, 1H); 8.12 (d, 1H); 8.33 (m, 1H) | 33 |
| 13.16 | H-pyrazolo[1,5-a]pyridine-2-carboxyl | 841 | 6.95 (m, 2H); 7.21 (m, 1H); 7.66 (d, 1H); 8.61 (dd, 1H) | 33 |
| 13.17 | isoquinoline-4-carboxyl | 852 | 7.76-7.90 (m, 3H); 8.20 (m, 1H); 8.47 (s, 1H); 9.31 (d, 1H) | 33 |

TABLE 14

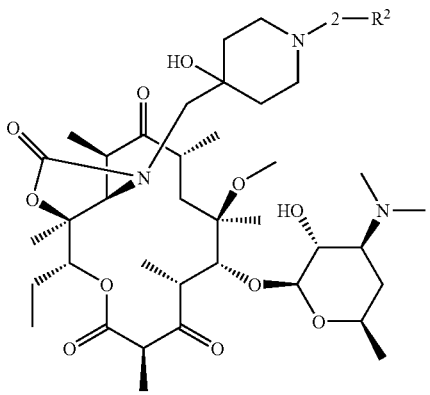

| Ex. # | 2-R² Name | MS | ¹H NMR | Prep. # |
|---|---|---|---|---|
| 14.01 | (1H-pyrrolo[2,3-b]pyridin-3-yl)methyl | 857 | 8.22 (s, 1H); 8.19 (d, 1H); 7.21 (m, 2H) | 27 |

TABLE 15

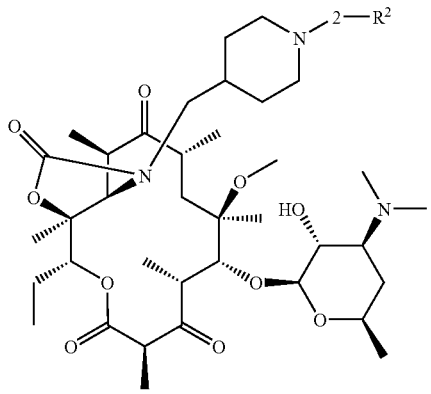

| Ex. # | 2-R² Name | MS | ¹H NMR | Prep. # |
|---|---|---|---|---|
| 15.01 | (quinoxalin-8-yl)methyl | 852 | 8.92 (s, 1H); 8.86 (s, 1H); 8.1 (d, 1H); 7.9 (d, 1H); 7.82 (m, 1H) | 27 |
| 15.02 | (quinolin-4-yl)methyl | M/2 426 | 8.75 (d, 1H); 8.32 (d, 1H); 8.0 (d, 1H); 7.73 (1, 1H); 7.62 (t, 1H); 7.55 (d, 1H) | 27 |
| 15.03 | (quinolin-3-yl)methyl | m-1 849 | 8.83 (s, 1H); 8.27 (s, 1H); 8.0 (d, 1H); 7.92 (d, 1H); 7.74 (t, 1H); 7.61 (1, 1H) | 27 |
| 15.04 | (6-methoxypyridin-3-yl)methyl | 831 | 8.0 (s, 1H); 7.8 (d, 1H); 6.9 (d, 1H); 3.9 (s, 3H) | 27 |
| 15.05 | (6-methoxypyridin-2-yl)methyl | M/2 416 | 7.72 (t, 1H); 7.04 (d, 1H); 6.83 (d, 1H); 3.97 (s, 3H) | 27 |
| 15.06 | (2-methoxypyridin-3-yl)methyl | 831 | 7.29 (d, 1H); 7.8 (d, 1H); 7.1 (m, 1H); 4.03 (s, 3H) | 27 |
| 15.07 | (4- (pyridin-2-yl)phenyl)methyl | 878 | 8.6 (d, 1H); 7.87 (m, 4H); 7.45 (d, 2H); 7.38 (t, 1H) | 27 |
| 15.08 | (2-phenyl-1H-imidazol-5-yl)methyl | 866 | 7.83 (d, 2H); 7.42 (m, 2H); 7.36 (1, 1H); 7.1 (s, 1H) | 27 |
| 15.09 | (isoxazol-5-yl)methyl | 791 | 8.51 (s, 1H); 6.70 (s, 1H) | 27 |
| 15.10 | (1H-1,2,3-triazol-4-yl)methyl | 791 | 7.82 (s, 1H) | 27 |

TABLE 16

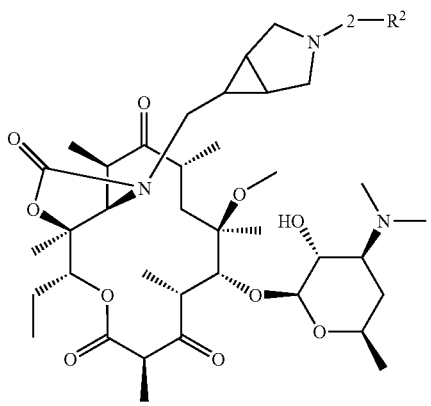

| Ex.# | 2-R² Name | MS | ¹H NMR | Prep. # |
|---|---|---|---|---|
| 16.01 | tert-butyl-oxycarbonyl | 808 | CDCl₃: 4.28 (t, 2H); 3.82 (t, 1H) | 8 |
| 16.02 | nicotinoyl | 814 | CDCl₃: 8.69 (s, 1H); 8.23 (d, 1H) | 33 |
| 16.03 | 2,5-difluorobenzoyl | 849 | CDCl₃: 8.28 (s, 1H); 7.89 (d, 2H) | 33 |
| 16.04 | (pyridin-3-yl) methyl | 800 | CDCl₃: 8.34 (s, 1H); 7.98 (d, 1H) | 27 |
| 16.05 | 3-cyanobenzoyl | 838 | CDCl₃: 8.57 (s, 1H); 8.68 (d, 1H) | 33 |

Biological Properties

As noted above, macrolides, including ketolides, are generally known as a class to possess antibacterial activity in many instances. Although not limiting to the present invention, it is believed that the macrolide binds to a subunit of the bacterial ribosome, resulting in protein synthesis inhibition. Thus, at least in general terms, the activity of and mechanism of action of erythromycin, clarithromycin, and other macrolides are known, although the present invention is not bound or limited by any theory.

In some embodiments, compounds of the invention exhibit a broad spectrum of antibacterial activity and/or are effective against a variety of infectious strains of interest. For example, using a standard microtiter broth serial dilution test, compounds of the invention have been found to exhibit useful levels of activity against a wide range of pathogenic microorganisms, including strains of *Staphylococcus aureus* (*S. aureus*), *Streptococcus pneumoniae* (*S. pneumo.*), *Moraxella catarrhalis*, *Streptococcus pyogenes* (*S. pyo.*), and *Haemophilus influenzae* (*H. inf.*), including resistant strains. Compounds of the invention can therefore be used, e.g., for treating and/or preventing a variety of diseases caused by pathogenic bacteria in human beings and animals.

Bacterial strains that contain the gene with the designation of ermA, ermB, or ermC are resistant to some macrolides, lincosamides, and streptogramin B antibiotics due to modifications (methylation) of 23S rRNA molecules by an Erm methylase, thereby generally attenuating binding by members of all three antibiotic classes. Other strains containing macrolide efflux genes have also been described. For example, msrA encodes a component of an efflux system in staphylococci that prevents entry of some macrolides and streptogramins, while mefA/E encodes a transmembrane protein that appears to efflux only macrolides.

Inactivation of macrolide antibiotics can occur and can be mediated by either a phosphorylation of the 2'-hydroxyl (mph) or by cleavage of the macrocyclic lactone (esterase). "AcrAB" or "AcrAB-like" indicates that an intrinsic multi-drug efflux pump exists in the strain.

Activity against bacterial and protozoa pathogens can be demonstrated by a compound's ability to inhibit growth of defined strains of pathogens. The assay described herein includes a panel of bacterial strains assembled to include a variety of target pathogenic species, including representatives of macrolide resistance mechanisms that have been characterized. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. The assay is performed in microtiter trays and interpreted according to Performance Standards for Antimicrobial Susceptibility Testing; 14th Informational Supplement (M100-S14), published by The National Committee for Clinical Laboratory Standards (NCCLS) guidelines; the MIC is used to compare strains. Compounds are initially dissolved in DMSO as 40 mg/ml stock solutions. Table 17 lists data obtained for compounds of Tables 1 to 16.

| Strain Designation | Macrolide Resistance Mechanism(s) |
|---|---|
| *Streptococcus pyogenes* 1079 | ermB |
| *Streptococcus pneumoniae* 1016 | (susceptible) |
| *Streptococcus pneumoniae* 1095 | ermB |
| *Streptococcus pneumoniae* 1175 | mefA |
| *Haemophilus influenzae* 1218 | (susceptible) |

TABLE 17

| Ex. # | S. pneumo. 1016 (μg/mL) | S. pneumo. 1095 (μg/mL) | S. pneumo. 1175 (μg/mL) | S. pyogenes 1079 (μg/mL) | H. influenzae 1218 (μg/mL) |
|---|---|---|---|---|---|
| 1.01 | <0.06 | <0.06 | 0.12 | >64.00 | 0.5 |
| 1.02 | <0.06 | 0.12 | 0.12 | >64.00 | 0.25 |
| 1.03 | <0.06 | <0.06 | 2 | >64.00 | 0.5 |
| 1.04 | <0.06 | 0.12 | 0.5 | >64.00 | 0.25 |
| 1.05 | <0.06 | <0.06 | 0.12 | 64 | 0.25 |
| 1.06 | <0.06 | <0.06 | <0.06 | 4 | 1 |
| 1.07 | <0.06 | <0.06 | 0.25 | 16 | — |
| 1.08 | <0.06 | 0.5 | 0.25 | >64.00 | — |
| 1.09 | <0.06 | <0.06 | 0.25 | >64.00 | — |
| 1.10 | <0.06 | <0.06 | 0.12 | >64.00 | — |
| 1.11 | <0.06 | <0.06 | 0.5 | 4 | <0.06 |
| 1.12 | <0.06 | <0.06 | <0.06 | 2 | 0.25 |
| 1.13 | <0.06 | 0.12 | 1 | 64 | 0.25 |
| 1.14 | <0.06 | 1 | 0.5 | >64.00 | 0.25 |
| 1.15 | <0.06 | <0.06 | 0.25 | >64.00 | 0.25 |
| 1.16 | <0.06 | <0.06 | 0.25 | 4.25 | 0.5 |
| 1.17 | <0.06 | <0.06 | 0.25 | >64.00 | 0.12 |
| 1.18 | <0.06 | 1 | 2 | >64.00 | 0.25 |
| 1.19 | <0.06 | 0.12 | 4 | >64.00 | 0.5 |
| 1.20 | <0.06 | <0.06 | 0.12 | 1 | 0.25 |
| 1.21 | <0.06 | <0.06 | 0.5 | 32 | 2 |
| 1.22 | <0.06 | 1 | 1 | >64.00 | 16 |
| 1.23 | <0.06 | <0.06 | 0.25 | 16 | 0.5 |
| 1.24 | <0.06 | <0.06 | 0.25 | 4 | 1 |
| 1.25 | <0.06 | <0.06 | 0.25 | 1 | 0.5 |
| 1.26 | <0.06 | <0.06 | <0.06 | 1 | 0.38 |
| 1.27 | <0.06 | <0.06 | 0.5 | 2 | 0.5 |
| 1.28 | <0.06 | <0.06 | 4 | 8 | 0.5 |
| 1.29 | <0.06 | <0.06 | 1 | 2 | 0.5 |
| 1.30 | <0.06 | <0.06 | <0.06 | 4 | 1 |
| 1.31 | <0.06 | <0.06 | 2 | 64 | 1 |
| 1.32 | <0.06 | <0.06 | 0.25 | 0.12 | 0.5 |
| 1.33 | <0.06 | <0.06 | <0.06 | 0.25 | 0.25 |
| 1.34 | <0.06 | <0.06 | 0.12 | 32 | 0.5 |
| 1.35 | <0.06 | <0.06 | 0.12 | 4 | 1 |
| 1.36 | <0.06 | <0.06 | 0.12 | 8 | 0.5 |
| 1.37 | <0.06 | <0.06 | 0.25 | 4 | 1 |
| 1.38 | <0.06 | <0.06 | 0.25 | 4 | 1 |
| 1.39 | <0.06 | <0.06 | 0.25 | 16 | 1 |
| 1.40 | <0.06 | <0.06 | 0.25 | 32 | 0.5 |
| 1.41 | <0.06 | <0.06 | <0.06 | >64.00 | 0.12 |
| 1.42 | <0.06 | <0.06 | 0.25 | >64.00 | 2 |
| 1.43 | <0.06 | <0.06 | <0.06 | 16 | 2 |
| 1.44 | <0.06 | <0.06 | 0.5 | >64.00 | 16 |
| 1.45 | <0.06 | <0.06 | 0.5 | 16 | 4 |
| 1.46 | <0.06 | <0.06 | 0.25 | >64.00 | 8 |
| 1.47 | <0.06 | <0.06 | <0.06 | 64 | 0.25 |
| 1.56 | — | <0.06 | <0.06 | >64.00 | 1 |
| 1.57 | — | <0.06 | <0.06 | 64 | 1 |
| 1.61 | <0.06 | <0.06 | 0.25 | 8 | 4 |
| 1.62 | <0.06 | <0.06 | <0.06 | 2 | 0.5 |
| 1.63 | <0.06 | <0.06 | 0.12 | 2 | 1 |
| 1.64 | <0.06 | <0.06 | <0.06 | 1 | 1 |

TABLE 17-continued

| Ex. # | S. pneumo. 1016 (µg/mL) | S. pneumo. 1095 (µg/mL) | S. pneumo. 1175 (µg/mL) | S. pyogenes 1079 (µg/mL) | H. influenzae 1218 (µg/mL) |
|---|---|---|---|---|---|
| 1.65 | <0.06 | <0.06 | <0.06 | 8 | 1 |
| 1.66 | <0.06 | 0.5 | <0.06 | 64 | 2 |
| 1.67 | <0.06 | <0.06 | <0.06 | 16 | 0.5 |
| 1.68 | <0.06 | 4 | <0.06 | 32 | 4 |
| 1.69 | <0.06 | <0.06 | <0.06 | 8 | 1 |
| 1.70 | <0.063 | <0.063 | <0.063 | 2 | 1 |
| 1.71 | <0.063 | <0.063 | <0.063 | <0.063 | 1 |
| 1.72 | <0.063 | <0.063 | <0.063 | <0.063 | 1 |
| 1.73 | <0.063 | <0.063 | <0.063 | 0.125 | 2 |
| 1.74 | <0.063 | <0.063 | <0.063 | 0.5 | 1 |
| 1.75 | <0.063 | <0.063 | <0.063 | <0.063 | 1 |
| 1.76 | <0.063 | <0.063 | <0.063 | 0.125 | 0.5 |
| 1.77 | <0.063 | <0.063 | <0.063 | 1 | 0.5 |
| 1.78 | <0.063 | <0.063 | <0.063 | 4 | 1 |
| 1.79 | <0.063 | <0.063 | <0.063 | 4 | 1 |
| 1.80 | <0.063 | 1 | 0.125 | 16 | 4 |
| 1.81 | <0.063 | 0.5 | <0.063 | 4 | 4 |
| 1.82 | <0.063 | <0.063 | <0.063 | 4 | 0.5 |
| 1.83 | <0.063 | <0.063 | <0.063 | 4 | 1 |
| 1.84 | <0.063 | <0.063 | <0.063 | 8 | 2 |
| 1.85 | <0.063 | — | — | 16 | 2 |
| 1.86 | <0.063 | 0.125 | <0.063 | 1 | 1 |
| 1.87 | <0.063 | — | — | 8 | 0.5 |
| 1.88 | <0.063 | — | — | 8 | 0.5 |
| 1.89 | <0.063 | 0.5 | <0.063 | 1 | 4 |
| 1.90 | <0.063 | 0.125 | <0.063 | 2 | 2 |
| 1.91 | <0.063 | 0.125 | <0.063 | 8 | 1 |
| 1.92 | <0.063 | 0.125 | <0.063 | 2 | 2 |
| 1.93 | <0.063 | <0.063 | 1 | 1 | 2 |
| 1.94 | <0.063 | 0.5 | 0.25 | 4 | 1 |
| 1.95 | <0.063 | 1 | <0.063 | 1 | 2 |
| 1.96 | <0.063 | <0.063 | <0.063 | 1 | 1 |
| 1.97 | <0.063 | <0.063 | <0.063 | 2 | 0.5 |
| 1.98 | <0.063 | <0.063 | <0.063 | 0.25 | 2 |
| 1.99 | <0.063 | <0.063 | <0.063 | 0.5 | 1 |
| 1.100 | <0.063 | <0.063 | <0.063 | 0.125 | 0.5 |
| 1.101 | <0.063 | 0.125 | <0.063 | 0.25 | 2 |
| 1.102 | <0.063 | <0.063 | <0.063 | 1 | 2 |
| 1.103 | <0.063 | <0.063 | 0.125 | 16 | 0.25 |
| 1.104 | <0.063 | <0.063 | 0.125 | >64 | 0.25 |
| 1.105 | <0.063 | <0.063 | 0.125 | 8 | 1 |
| 1.106 | <0.063 | <0.063 | <0.063 | 0.25 | 1 |
| 1.107 | <0.063 | <0.063 | <0.063 | 0.25 | 1 |
| 1.108 | <0.063 | <0.063 | 0.125 | 0.5 | 1 |
| 2.01 | <0.06 | 32 | 0.25 | >64.00 | 4 |
| 2.02 | <0.06 | >64.00 | 2 | >64.00 | 2 |
| 2.03 | <0.06 | 8 | <0.06 | >64.00 | 2 |
| 2.04 | <0.06 | 8 | <0.06 | 32 | 8 |
| 2.05 | <0.06 | 16 | <0.06 | 64 | 0.5 |
| 2.06 | <0.06 | 16 | 0.25 | >64.00 | 0.5 |
| 2.07 | <0.06 | 4 | 32 | 16 | 16 |
| 2.08 | <0.06 | 1 | 16 | 32 | 8 |
| 2.09 | <0.06 | 16 | 0.25 | >64.00 | 8 |
| 2.10 | <0.06 | 8 | 0.25 | >64.00 | 2 |
| 2.11 | <0.06 | 2 | 0.12 | >64.00 | 0.5 |
| 2.12 | <0.06 | 2 | 0.25 | >64.00 | 32 |
| 2.13 | <0.06 | 2 | 0.12 | >64.00 | 8 |
| 2.14 | <0.06 | 2 | 0.25 | >64.00 | 4 |
| 2.15 | <0.06 | 8 | 0.5 | >64.00 | 8 |
| 2.16 | <0.06 | 16 | 0.25 | >64.00 | 64 |
| 2.17 | <0.06 | >64.00 | 0.25 | >64.00 | >64.00 |
| 2.18 | <0.06 | >64.00 | 0.5 | >64.00 | 32 |
| 2.19 | <0.06 | >64.00 | 0.5 | >64.00 | 32 |
| 2.20 | <0.06 | 1 | 0.12 | >64.00 | 16 |
| 3.01 | <0.06 | <0.06 | <0.06 | 4 | 0.25 |
| 3.02 | <0.06 | <0.06 | <0.06 | 0.5 | 0.12 |
| 3.03 | <0.06 | <0.06 | <0.06 | 1 | 0.12 |
| 3.04 | <0.06 | <0.06 | <0.06 | 0.12 | 0.25 |
| 3.05 | <0.06 | 2 | <0.06 | 16 | 0.25 |
| 3.06 | <0.06 | <0.06 | <0.06 | 1 | 0.12 |
| 3.07 | <0.06 | <0.06 | <0.06 | 16 | 0.5 |
| 3.08 | <0.06 | <0.06 | <0.06 | 16 | 0.5 |
| 3.09 | <0.06 | <0.06 | 0.25 | 16 | 0.25 |
| 3.10 | <0.06 | <0.06 | <0.06 | 4 | 0.25 |
| 3.11 | <0.06 | <0.06 | 0.5 | 8 | 0.25 |
| 3.12 | <0.06 | 1 | <0.06 | 64 | 4 |

TABLE 17-continued

| Ex. # | S. pneumo. 1016 (µg/mL) | S. pneumo. 1095 (µg/mL) | S. pneumo. 1175 (µg/mL) | S. pyogenes 1079 (µg/mL) | H. influenzae 1218 (µg/mL) |
|---|---|---|---|---|---|
| 3.13 | <0.06 | 0.12 | <0.06 | 4 | 0.25 |
| 3.14 | <0.06 | 1 | 1 | >64.00 | 1 |
| 3.15 | <0.06 | <0.06 | <0.06 | 1 | 0.25 |
| 3.16 | <0.06 | <0.06 | <0.06 | 1 | 0.5 |
| 3.17 | <0.06 | <0.06 | 0.12 | 4 | 0.5 |
| 3.18 | <0.06 | 1 | <0.06 | 2 | 0.12 |
| 3.19 | <0.06 | <0.06 | <0.06 | 1 | 0.25 |
| 3.20 | <0.06 | <0.06 | 2 | 8 | 0.5 |
| 3.21 | <0.06 | <0.06 | <0.06 | >64.00 | 1 |
| 3.22 | <0.06 | 4 | 0.5 | 1 | 0.25 |
| 3.23 | <0.06 | 0.25 | <0.06 | >64.00 | 1 |
| 3.24 | <0.06 | 1 | <0.06 | 32 | 0.25 |
| 3.25 | <0.06 | <0.06 | 0.25 | >64.00 | 1 |
| 3.26 | <0.06 | <0.06 | 8 | 64 | 4 |
| 3.27 | <0.06 | <0.06 | <0.06 | 32 | 1 |
| 3.28 | <0.06 | <0.06 | 4 | >64.00 | 1 |
| 3.29 | <0.06 | <0.06 | 0.5 | 8 | 0.25 |
| 3.30 | 1 | >64.00 | 32 | >64.00 | 32 |
| 3.31 | <0.06 | 2 | 0.12 | 4 | 0.5 |
| 3.32 | <0.06 | 0.5 | 0.12 | 32 | 2 |
| 3.33 | <0.06 | <0.06 | <0.06 | 8 | 0.5 |
| 3.34 | <0.06 | 1 | 0.12 | 64 | 16 |
| 3.35 | <0.06 | <0.06 | <0.06 | 1 | 0.12 |
| 3.36 | <0.06 | <0.06 | <0.06 | 1 | 0.25 |
| 3.37 | <0.06 | 4 | <0.06 | 16 | 0.5 |
| 3.38 | <0.06 | 1 | <0.06 | 64 | 0.5 |
| 3.39 | <0.06 | <0.06 | <0.06 | 0.25 | 0.5 |
| 3.40 | <0.06 | <0.06 | <0.06 | 4 | 2 |
| 3.41 | <0.06 | <0.06 | <0.06 | 8 | 0.25 |
| 3.42 | <0.06 | <0.06 | 0.5 | 2 | 2 |
| 3.43 | <0.06 | <0.06 | 0.5 | 1 | 0.5 |
| 3.44 | <0.06 | <0.06 | <0.06 | 0.12 | 0.25 |
| 3.45 | <0.06 | <0.06 | <0.06 | 0.12 | 0.25 |
| 3.46 | <0.06 | 0.5 | <0.06 | 32 | 2 |
| 3.47 | <0.06 | 0.5 | <0.06 | 64 | 8 |
| 3.48 | <0.06 | 1 | <0.06 | >64.00 | 0.5 |
| 3.49 | <0.06 | <0.06 | <0.06 | 0.5 | 0.5 |
| 3.50 | <0.06 | <0.06 | <0.06 | 0.25 | 1 |
| 3.51 | <0.06 | <0.06 | <0.06 | 0.5 | 2 |
| 3.52 | <0.06 | 0.12 | 0.12 | 4 | 2 |
| 3.53 | <0.06 | <0.06 | 0.25 | 64 | 4 |
| 3.54 | <0.06 | 4 | 4 | 8 | >64.00 |
| 3.55 | <0.06 | <0.06 | <0.06 | <0.06 | 1 |
| 3.56 | <0.06 | <0.06 | <0.06 | 0.5 | 1 |
| 3.57 | <0.06 | <0.06 | 8 | 4 | 1 |
| 3.58 | <0.06 | <0.06 | <0.06 | 4 | 1 |
| 3.59 | <0.06 | 8 | 8 | 64 | 16 |
| 3.60 | <0.06 | <0.06 | 0.12 | 4 | 2 |
| 3.61 | <0.06 | 2 | 0.12 | 2 | 2 |
| 3.62 | <0.06 | <0.06 | 0.5 | 8 | 2 |
| 3.63 | <0.06 | <0.06 | <0.06 | 0.25 | <0.06 |
| 3.64 | <0.06 | <0.06 | <0.06 | 32 | 0.5 |
| 3.65 | <0.06 | <0.06 | <0.06 | 1 | 0.12 |
| 3.72 | <0.06 | <0.06 | <0.06 | 1 | 1 |
| 3.75 | <0.06 | <0.06 | <0.06 | 16 | 1 |
| 3.76 | <0.06 | <0.06 | <0.06 | 0.12 | 0.5 |
| 3.77 | <0.06 | <0.06 | <0.06 | 8 | 1 |
| 3.78 | <0.06 | <0.06 | <0.06 | 64 | 4 |
| 3.79 | <0.06 | <0.06 | <0.06 | 1 | 0.25 |
| 3.80 | <0.06 | <0.06 | <0.06 | 4 | >64.00 |
| 3.81 | <0.06 | <0.06 | <0.06 | 4 | 1 |
| 3.82 | <0.06 | <0.06 | <0.06 | 2 | 0.25 |
| 3.83 | <0.06 | <0.06 | <0.06 | 32 | 1 |
| 3.84 | 1 | >64.00 | 16 | >64.00 | 32 |
| 3.85 | <0.06 | <0.06 | <0.06 | 1 | 0.25 |
| 3.86 | <0.06 | <0.06 | <0.06 | 1 | 1 |
| 3.87 | <0.06 | <0.06 | <0.06 | 0.19 | 0.19 |
| 3.88 | <0.06 | <0.06 | <0.06 | 8 | 2 |
| 3.89 | <0.06 | <0.06 | <0.06 | 8 | 1 |
| 3.90 | <0.06 | <0.06 | <0.06 | 8 | 0.25 |
| 3.91 | <0.06 | <0.06 | <0.06 | 4 | 0.12 |
| 3.92 | <0.06 | <0.06 | <0.06 | 4 | 1 |
| 3.93 | <0.06 | <0.06 | <0.06 | 1 | 0.25 |
| 3.94 | <0.06 | 0.12 | <0.06 | 0.25 | 0.25 |
| 3.95 | <0.06 | <0.06 | <0.06 | 0.12 | 0.5 |
| 3.96 | <0.06 | 0.12 | 2 | 1 | 1 |

TABLE 17-continued

| Ex. # | S. pneumo. 1016 (µg/mL) | S. pneumo. 1095 (µg/mL) | S. pneumo. 1175 (µg/mL) | S. pyogenes 1079 (µg/mL) | H. influenzae 1218 (µg/mL) |
|---|---|---|---|---|---|
| 3.97 | — | 0.25 | <0.063 | 1 | 0.125 |
| 3.98 | <0.063 | <0.063 | <0.063 | 0.25 | 0.25 |
| 3.99 | <0.063 | <0.063 | <0.063 | 0.25 | 1.41 |
| 3.100 | <0.063 | <0.063 | <0.063 | 0.125 | 0.5 |
| 3.101 | <0.063 | <0.063 | <0.063 | <0.063 | 0.125 |
| 3.102 | <0.063 | <0.063 | <0.063 | <0.063 | 1 |
| 3.103 | <0.063 | <0.063 | <0.063 | 0.5 | 2 |
| 3.104 | <0.063 | <0.063 | <0.063 | 1 | <0.063 |
| 3.105 | <0.063 | <0.063 | <0.063 | 1 | 0.25 |
| 3.106 | <0.063 | <0.063 | <0.063 | 0.5 | 0.5 |
| 3.107 | <0.063 | <0.063 | <0.063 | 1 | 025 |
| 3.108 | <0.063 | <0.063 | 0.5 | 0.25 | 1 |
| 3.109 | <0.063 | <0.063 | <0.063 | 0.125 | <0.063 |
| 3.110 | <0.063 | <0.063 | <0.063 | 4 | 2 |
| 3.111 | <0.063 | <0.063 | <0.063 | 1 | 0.5 |
| 3.112 | <0.063 | <0.063 | 0.25 | 0.125 | 2 |
| 3.113 | <0.063 | <0.063 | <0.063 | 0.5 | 1 |
| 3.114 | <0.063 | 0.125 | <0.063 | 1 | 0.25 |
| 3.115 | <0.063 | <0.063 | 0.125 | 0.25 | 1 |
| 3.116 | <0.063 | <0.063 | <0.063 | 0.5 | 0.5 |
| 3.117 | <0.063 | <0.063 | <0.063 | 1 | 1 |
| 4.01 | <0.00 | 0.39 | 0.39 | 6.25 | 6.25 |
| 4.02 | 0.01 | 0.5 | 0.5 | 100 | 3.12 |
| 4.03 | 0.02 | 0.39 | 0.78 | >100.00 | 1.56 |
| 4.04 | <0.06 | 16 | 0.25 | >64.00 | 0.5 |
| 4.05 | 0.02 | 2 | 1 | >64.00 | 4 |
| 4.06 | 0.02 | 12.5 | 0.39 | >100.00 | 3.12 |
| 4.07 | <0.06 | 24 | 0.19 | >64.00 | 1 |
| 4.08 | <0.06 | 32 | <0.06 | >64.00 | 0.12 |
| 4.09 | <0.06 | 32 | 0.5 | >64.00 | 0.12 |
| 4.10 | <0.06 | 1 | <0.06 | 16 | <0.06 |
| 4.11 | <0.06 | 4 | 2 | 64 | 1 |
| 4.12 | <0.06 | 8 | 0.12 | 64 | 1 |
| 4.13 | <0.06 | 0.5 | <0.06 | 32 | 1 |
| 4.14 | <0.06 | <0.06 | <0.06 | 8 | 0.5 |
| 4.15 | <0.06 | <0.06 | <0.06 | 32 | 0.25 |
| 4.16 | <0.06 | 2 | 0.25 | >64.00 | 0.5 |
| 4.17 | <0.06 | 0.5 | 0.12 | 64 | 0.25 |
| 4.18 | <0.06 | 0.12 | 0.5 | 8 | 0.25 |
| 4.19 | <0.06 | <0.06 | 1 | 64 | 0.5 |
| 4.20 | <0.06 | 0.12 | 0.25 | 16 | 0.25 |
| 4.21 | <0.06 | 2 | <0.06 | 64 | 0.5 |
| 4.22 | <0.06 | 2 | 0.25 | 32 | 0.12 |
| 4.23 | <0.06 | 4 | 0.12 | 16 | <0.06 |
| 4.24 | <0.06 | 0.5 | <0.06 | 64 | 0.5 |
| 4.25 | <0.06 | 0.38 | 0.31 | 64 | 0.62 |
| 4.26 | <0.06 | 2 | 2 | >64.00 | 0.25 |
| 4.27 | <0.06 | >64.00 | 4 | >64.00 | 1 |
| 4.28 | <0.06 | 8 | 1 | >64.00 | 0.25 |
| 4.29 | <0.06 | 2 | <0.06 | 16 | 0.12 |
| 4.30 | <0.06 | >64.00 | 0.25 | >64.00 | 0.5 |
| 4.31 | <0.06 | 32 | <0.06 | >64.00 | 0.5 |
| 4.32 | <0.06 | 0.5 | <0.06 | 64 | 1 |
| 4.33 | <0.06 | 1 | 0.25 | 64 | 1 |
| 4.34 | <0.06 | 1 | 1 | — | 0.25 |
| 4.35 | <0.06 | 1 | 0.12 | >64.00 | 1 |
| 4.36 | <0.06 | 0.25 | <0.06 | >64.00 | <0.06 |
| 4.37 | <0.06 | 0.25 | <0.06 | >64.00 | 0.5 |
| 4.38 | <0.06 | 2 | <0.06 | >64.00 | 2 |
| 4.39 | <0.06 | 8 | <0.06 | >64.00 | 4 |
| 4.40 | <0.06 | 8 | 0.5 | >64.00 | 4 |
| 4.41 | <0.06 | 0.25 | <0.06 | >64.00 | 2 |
| 4.42 | <0.06 | 0.5 | <0.06 | >64.00 | 0.12 |
| 4.43 | <0.06 | 0.12 | 1 | >64.00 | 0.25 |
| 4.44 | <0.06 | 0.5 | <0.06 | 8 | 0.25 |
| 4.45 | <0.06 | >64.00 | 4 | >64.00 | 16 |
| 4.46 | <0.06 | 0.5 | <0.06 | 64 | 1 |
| 4.47 | <0.06 | 0.19 | 0.12 | >64.00 | 0.75 |
| 5.01 | <0.06 | 0.5 | <0.06 | 64 | 2 |
| 5.02 | <0.06 | 0.25 | <0.06 | 16 | 4 |
| 5.03 | <0.06 | <0.06 | <0.06 | 0.5 | 2 |
| 5.04 | <0.06 | <0.06 | <0.06 | 4 | 1 |
| 5.05 | <0.06 | 2 | 0.5 | 4 | 8 |
| 5.06 | <0.06 | <0.06 | <0.06 | 0.25 | 2 |
| 5.07 | <0.06 | 0.25 | <0.06 | 16 | 4 |
| 5.08 | <0.06 | 0.25 | <0.06 | 16 | 2 |

TABLE 17-continued

| Ex. # | S. pneumo. 1016 (µg/mL) | S. pneumo. 1095 (µg/mL) | S. pneumo. 1175 (µg/mL) | S. pyogenes 1079 (µg/mL) | H. influenzae 1218 (µg/mL) |
|---|---|---|---|---|---|
| 5.09 | <0.06 | 1 | <0.06 | 64 | 2 |
| 5.10 | <0.06 | <0.06 | <0.06 | 2 | 1 |
| 5.11 | <0.06 | 1 | <0.06 | 32 | 1 |
| 5.12 | <0.06 | 2 | 0.5 | 64 | 8 |
| 5.13 | <0.06 | 16 | 0.12 | >64.00 | 1 |
| 5.14 | <0.06 | 4 | <0.06 | 32 | 4 |
| 6.01 | <0.06 | 0.5 | 0.5 | >64.00 | 1 |
| 6.02 | <0.06 | <0.06 | 0.25 | 32 | 2 |
| 6.03 | <0.06 | <0.06 | 0.12 | 16 | 0.5 |
| 6.04 | <0.06 | 0.25 | 0.25 | >64.00 | 1 |
| 6.05 | <0.06 | <0.06 | 0.12 | >64.00 | 1 |
| 6.06 | <0.06 | 0.5 | 0.5 | >64.00 | 1 |
| 6.07 | <0.06 | 1 | 0.5 | >64.00 | 4 |
| 6.08 | <0.06 | <0.06 | 0.25 | 16 | 0.5 |
| 6.09 | <0.06 | <0.06 | 0.25 | >64.00 | 0.5 |
| 6.10 | <0.06 | 0.25 | 0.12 | >64.00 | 1 |
| 6.11 | <0.06 | 0.25 | <0.06 | >64.00 | 1 |
| 6.12 | <0.06 | 0.25 | 0.12 | >64.00 | — |
| 6.13 | <0.06 | 8 | <0.06 | >64.00 | — |
| 6.14 | <0.06 | 8 | 0.25 | >64.00 | — |
| 6.15 | <0.06 | 8 | 2 | >64.00 | — |
| 6.16 | <0.06 | 0.12 | 0.12 | >64.00 | — |
| 6.17 | <0.06 | >64.00 | 0.12 | >64.00 | — |
| 6.18 | <0.06 | 0.25 | 0.25 | >64.00 | — |
| 6.19 | <0.06 | 1 | 0.5 | >64.00 | — |
| 6.20 | <0.06 | 64 | 0.5 | >64.00 | — |
| 6.21 | <0.06 | 16 | 0.5 | >64.00 | — |
| 6.22 | <0.06 | 4 | 0.5 | >64.00 | — |
| 6.23 | <0.06 | <0.06 | 0.25 | 64 | — |
| 6.24 | <0.06 | 4 | 0.25 | >64.00 | — |
| 7.01 | <0.06 | <0.06 | <0.06 | >64.00 | 1 |
| 7.02 | <0.06 | 0.12 | 0.12 | >64.00 | 0.5 |
| 7.03 | <0.06 | 0.12 | 0.12 | >64.00 | 0.5 |
| 7.04 | <0.06 | <0.06 | 1 | 32 | 0.5 |
| 7.05 | <0.06 | 2 | 1 | >64.00 | 1 |
| 7.06 | <0.06 | 32 | 0.5 | >64.00 | 0.5 |
| 7.07 | 0.12 | 8 | 4 | >64.00 | 16 |
| 7.08 | <0.06 | <0.06 | 0.25 | >64.00 | 0.25 |
| 7.09 | 0.5 | 64 | 16 | >64.00 | 16 |
| 7.10 | <0.06 | 64 | 1 | >64.00 | 2 |
| 7.11 | <0.06 | 4 | 0.5 | >64.00 | 2 |
| 7.12 | <0.06 | >64.00 | 0.5 | >64.00 | 2 |
| 7.13 | <0.06 | 1 | 1 | >64.00 | 2 |
| 7.14 | <0.06 | 1 | 0.12 | >64.00 | 0.25 |
| 7.15 | <0.06 | >64.00 | 4 | >64.00 | 2 |
| 7.16 | <0.06 | 64 | 4 | >64.00 | 1 |
| 7.17 | <0.06 | <0.06 | 0.5 | >64.00 | 1 |
| 7.18 | <0.06 | 0.25 | 0.25 | >64.00 | 2 |
| 7.19 | <0.06 | 0.12 | 0.25 | >64.00 | 1 |
| 7.20 | <0.06 | 2 | 1 | >64.00 | 0.5 |
| 7.21 | <0.06 | 0.5 | 1 | >64.00 | 2 |
| 7.22 | <0.06 | <0.06 | 0.12 | >64.00 | 1 |
| 7.23 | <0.06 | 0.5 | 0.5 | >64.00 | 2 |
| 7.24 | <0.06 | 2 | 1 | >64.00 | 2 |
| 7.25 | <0.06 | <0.06 | 2 | >64.00 | 1 |
| 7.26 | <0.06 | 0.12 | 0.25 | >64.00 | 0.5 |
| 7.27 | <0.06 | <0.06 | 1 | >64.00 | 1 |
| 7.28 | <0.06 | <0.06 | 0.25 | >64.00 | 2 |
| 7.29 | <0.06 | 0.25 | 8 | >64.00 | 1 |
| 7.30 | <0.06 | 0.25 | 0.25 | >64.00 | 8 |
| 7.31 | <0.06 | 4 | 0.12 | >64.00 | 8 |
| 7.32 | <0.06 | <0.06 | 2 | >64.00 | 2 |
| 8.01 | <0.06 | >64.00 | 0.25 | >64.00 | 8 |
| 8.02 | <0.06 | 8 | 0.5 | 32 | 16 |
| 9.01 | <0.06 | 0.5 | 0.12 | 32 | 1 |
| 9.02 | <0.06 | <0.06 | 0.12 | 8 | 0.5 |
| 9.03 | <0.06 | <0.06 | 0.5 | 1 | 0.12 |
| 9.04 | <0.06 | <0.06 | <0.06 | 32 | 0.5 |
| 9.05 | <0.06 | 0.5 | 0.5 | 8 | 8 |
| 9.06 | <0.06 | <0.06 | <0.06 | 4 | 0.25 |
| 9.07 | <0.06 | <0.06 | 0.12 | 2 | 1 |
| 9.08 | <0.06 | 4 | 0.12 | 16 | 0.25 |
| 9.09 | <0.06 | 0.25 | 0.12 | 2 | 0.12 |
| 9.10 | <0.06 | 8 | 0.25 | 64 | 0.5 |
| 10.01 | <0.06 | 0.25 | 0.5 | >64.00 | 1 |
| 10.02 | <0.06 | 0.25 | 2 | >64.00 | 1 |

TABLE 17-continued

| Ex. # | S. pneumo. 1016 (μg/mL) | S. pneumo. 1095 (μg/mL) | S. pneumo. 1175 (μg/mL) | S. pyogenes 1079 (μg/mL) | H. influenzae 1218 (μg/mL) |
|---|---|---|---|---|---|
| 10.03 | <0.06 | 0.25 | 0.25 | 64 | 8 |
| 10.04 | <0.06 | <0.06 | <0.06 | 16 | 0.5 |
| 10.05 | <0.06 | <0.06 | 0.12 | >64.00 | 4 |
| 10.06 | <0.06 | <0.06 | 0.12 | 64 | 2 |
| 10.07 | <0.06 | <0.06 | 0.25 | >64.00 | 2 |
| 10.08 | <0.06 | <0.06 | 2 | >64.00 | 2 |
| 10.09 | <0.06 | <0.06 | 1 | >64.00 | 2 |
| 10.10 | <0.06 | <0.06 | 1 | >64.00 | 4 |
| 10.11 | <0.06 | 0.5 | 4 | >64.00 | 16 |
| 10.12 | <0.06 | <0.06 | 0.12 | 32 | 2 |
| 10.13 | <0.06 | 0.5 | 0.5 | >64.00 | 16 |
| 10.14 | <0.06 | <0.06 | 0.12 | 32 | 0.25 |
| 10.15 | <0.06 | <0.06 | 0.25 | >64.00 | 2 |
| 10.16 | <0.06 | <0.06 | 0.25 | >64.00 | 0.25 |
| 10.17 | <0.06 | <0.06 | 0.12 | >64.00 | 0.5 |
| 10.18 | <0.06 | <0.06 | <0.06 | 16 | 0.25 |
| 10.19 | <0.06 | <0.06 | 0.12 | >64.00 | 8 |
| 10.20 | <0.06 | <0.06 | 0.12 | 64 | 2 |
| 10.21 | <0.06 | <0.06 | 0.12 | >64.00 | 2 |
| 10.22 | <0.06 | 0.12 | 2 | 64 | 2.5 |
| 10.23 | <0.06 | <0.06 | 1 | >64.00 | 8 |
| 10.24 | <0.06 | <0.06 | 1 | >64.00 | 2 |
| 10.25 | <0.06 | <0.06 | 0.5 | >64.00 | 4 |
| 10.26 | <0.06 | <0.06 | 1 | >64.00 | 2 |
| 10.27 | <0.06 | <0.06 | 0.25 | 8 | 2 |
| 10.28 | <0.06 | <0.06 | 0.12 | 16 | 1 |
| 10.29 | <0.06 | <0.06 | 0.12 | 16 | 2 |
| 10.30 | <0.06 | <0.06 | 0.12 | 32 | 2 |
| 10.31 | <0.06 | <0.06 | <0.06 | 16 | 0.25 |
| 10.32 | <0.06 | <0.06 | 0.5 | >64.00 | 1 |
| 10.33 | <0.06 | <0.06 | 0.25 | >64.00 | 2 |
| 10.34 | <0.06 | 0.12 | 0.12 | >64.00 | 2 |
| 10.35 | <0.06 | 0.25 | 1 | >64.00 | 32 |
| 10.36 | <0.06 | 4 | 0.5 | >64.00 | 16 |
| 10.37 | <0.06 | <0.06 | <0.06 | 16 | 0.5 |
| 10.38 | <0.06 | <0.06 | 0.5 | >64.00 | 1 |
| 10.39 | <0.06 | <0.06 | 0.5 | >64.00 | 2 |
| 10.40 | <0.06 | <0.06 | <0.06 | >64.00 | 2 |
| 10.41 | <0.06 | <0.06 | <0.06 | >64.00 | 2 |
| 10.42 | <0.06 | <0.06 | <0.06 | 64 | 0.5 |
| 10.43 | <0.06 | <0.06 | 0.25 | >64.00 | 1 |
| 10.44 | <0.06 | <0.06 | 0.12 | >64.00 | 1 |
| 10.45 | <0.06 | <0.06 | <0.06 | >64.00 | 1 |
| 10.46 | <0.06 | <0.06 | <0.06 | 64 | 1 |
| 10.47 | <0.06 | 0.12 | <0.06 | 64 | 2 |
| 10.48 | <0.06 | 4 | 0.5 | >64.00 | 1 |
| 10.49 | <0.06 | 2 | 2 | >64.00 | 8 |
| 10.50 | <0.06 | 0.5 | 2 | >64.00 | 8 |
| 10.51 | <0.06 | <0.06 | 0.5 | >64.00 | 1 |
| 10.52 | <0.06 | <0.06 | <0.06 | 64 | 0.25 |
| 10.53 | <0.06 | <0.06 | 0.12 | >64.00 | 1 |
| 10.54 | <0.06 | <0.06 | 0.25 | 64 | 1 |
| 10.55 | <0.06 | <0.06 | <0.06 | 32 | 1 |
| 11.01 | <0.06 | <0.06 | 0.25 | 16 | 1 |
| 11.02 | <0.06 | <0.06 | 0.25 | 4 | 0.5 |
| 11.03 | <0.06 | <0.06 | 0.5 | 64 | 2 |
| 11.04 | <0.06 | <0.06 | 0.12 | 64 | 1 |
| 11.05 | <0.06 | <0.06 | 0.5 | 4 | 0.5 |
| 11.06 | <0.06 | 2 | 2 | >64.00 | 4 |
| 11.07 | <0.06 | <0.06 | 0.25 | 16 | 1 |
| 11.08 | <0.06 | <0.06 | 0.25 | >64.00 | 0.5 |
| 11.09 | <0.06 | 4 | 16 | >64.00 | 4 |
| 11.10 | <0.06 | <0.06 | <0.06 | 64 | 0.12 |
| 11.11 | <0.06 | 0.12 | 0.12 | 8 | 1 |
| 11.12 | <0.06 | <0.06 | <0.06 | — | <0.06 |
| 11.13 | <0.06 | <0.06 | <0.06 | — | 0.25 |
| 11.14 | <0.06 | 0.25 | 0.25 | 32 | 2 |
| 11.15 | <0.06 | <0.06 | 0.5 | 64 | 2 |
| 11.16 | <0.06 | 8 | 0.5 | >64.00 | 8 |
| 11.17 | <0.06 | 8 | 2 | >64.00 | 4 |
| 11.18 | <0.06 | 8 | 2 | >64.00 | 2 |
| 12.01 | <0.06 | 2 | 1 | >64.00 | 8 |
| 12.02 | <0.06 | 8 | 8 | >64.00 | 16 |
| 12.03 | <0.06 | >64.00 | 0.5 | >64.00 | 4 |
| 12.04 | <0.06 | 4 | 1 | >64.00 | 2 |
| 12.05 | <0.06 | 1 | 1 | >64.00 | 4 |

TABLE 17-continued

| Ex. # | S. pneumo. 1016 (µg/mL) | S. pneumo. 1095 (µg/mL) | S. pneumo. 1175 (µg/mL) | S. pyogenes 1079 (µg/mL) | H. influenzae 1218 (µg/mL) |
|---|---|---|---|---|---|
| 12.06 | <0.06 | 0.25 | 1 | >64.00 | 2 |
| 12.08 | <0.06 | 1 | 2 | >64.00 | 16 |
| 12.09 | <0.06 | 1 | 1 | >64.00 | 2 |
| 12.10 | <0.06 | 0.5 | 2 | >64.00 | 8 |
| 12.11 | <0.06 | 0.5 | 1 | >64.00 | 8 |
| 12.12 | <0.06 | <0.06 | 1 | >64.00 | 2 |
| 13.01 | <0.06 | 0.25 | 1 | >64.00 | 1 |
| 13.02 | 0.12 | 16 | 4 | 64 | 16 |
| 13.03 | <0.06 | 1 | 4 | >64.00 | 2 |
| 13.04 | <0.06 | 1 | 0.25 | 64 | 1 |
| 13.05 | <0.06 | 16 | 0.5 | >64.00 | 4 |
| 13.06 | <0.06 | >64.00 | 0.5 | >64.00 | 2 |
| 13.07 | <0.06 | >64.00 | 4 | >64.00 | 2 |
| 13.08 | <0.06 | 4 | 0.5 | 64 | 2 |
| 13.09 | <0.06 | >64.00 | 1 | >64.00 | 4 |
| 13.10 | <0.06 | >64.00 | 0.25 | >64.00 | 4 |
| 13.11 | <0.06 | 16 | 4 | >64.00 | 4 |
| 13.12 | <0.06 | >64.00 | 0.5 | >64.00 | 4 |
| 13.13 | <0.06 | >64.00 | 0.5 | >64.00 | 16 |
| 13.14 | <0.06 | 2 | <0.06 | >64.00 | 1 |
| 13.15 | <0.06 | 2 | 0.12 | >64.00 | 4 |
| 13.16 | <0.06 | >64.00 | 1 | >64.00 | 16 |
| 13.17 | <0.06 | >64.00 | 0.25 | >64.00 | 4 |
| 14.01 | <0.06 | 32 | 1 | >64.00 | 4 |
| 15.01 | <0.06 | >64.00 | 0.25 | >64.00 | 32 |
| 15.02 | <0.06 | >64.00 | 0.5 | >64.00 | 32 |
| 15.03 | <0.06 | >64.00 | 0.25 | >64.00 | 8 |
| 15.04 | <0.06 | >64.00 | 0.5 | >64.00 | 16 |
| 15.05 | <0.06 | >64.00 | 0.5 | >64.00 | 8 |
| 15.06 | <0.06 | >64.00 | 0.5 | >64.00 | 32 |
| 15.07 | <0.06 | >64.00 | 1 | >64.00 | 32 |
| 15.08 | <0.06 | >64.00 | 1 | >64.00 | 2 |
| 15.09 | <0.06 | >64.00 | 0.5 | >64.00 | 16 |
| 15.10 | <0.06 | >64.00 | 8 | >64.00 | 4 |
| 16.01 | 0.25 | 50 | 25 | >100.00 | 1.56 |
| 16.02 | 0.02 | 3.12 | 0.78 | >100.00 | 0.78 |
| 16.03 | 0.01 | 1.56 | 0.5 | 50 | 0.5 |
| 16.04 | 0.03 | 3.12 | >100.00 | >100.00 | 0.5 |
| 16.05 | 0.01 | 1.56 | 1.56 | 3.12 | 0.5 |

In some embodiments, compounds according to the present invention also exhibit favorable properties with respect to predicted drug-drug interaction (e.g., predicted statin DDI) as observed by MBI, which in some embodiments of this invention predicts about a four-fold or less, about three-fold or less, or about a two-fold or less increase in AUC of a co-administered CYP3A4 object drug midazolam. Furthermore, the lung/plasma distribution ratio can be greater than about 10, 15, or 20 according to the present invention. The muscle/plasma distribution ratio can be about 1 or greater, about 2 or greater, or about 2.4 or greater.

In some embodiments, compounds of the invention can be used against macrolide-resistant or multi-drug resistant bacterial strains. For example, in some embodiments, compounds of the invention exhibit favorable activity against resistant S. pyo. strains, including methylation-based resistance such as ermB. Moreover, in some embodiments, this activity is better than that of some known ketolides. For instance, clarithromycin-resistant (e.g., ermB mechanism) S. pyo in vitro MICs can be about 8 µg/mL or less, 4 µg/mL or less, 2 µg/mL, or 1 µg/mL or less (i.e., generally the lower the better). Clarithromycin-resistant (e.g., efflux mechanism) S. pneumo. in vitro MICs can be about 0.5 µg/mL or less. In some embodiments, compounds of the present invention are useful or effective against H. inf, S. aureus, and macrolide-resistant S. pneumo. In at least these aspects, compounds of the present invention can be at least about 8, 16, 32-fold, or more, more potent than telithromycin. Thus, the invention includes using the compounds to take advantage of such favorable properties.

Pharmaceutical Compositions and Use

The present invention includes methods of treatment of the human or non-human animal body, e.g., to combat or treat (including prevention) bacterial or protozoal infections, comprising administering to subjects a useful or effective amount of a compound of the invention, including a physiologically acceptable salt or solvate thereof, and including compositions.

For systemic administration the daily dose as employed for adult human treatment can range from about 2 to 100 mg/kg body weight, preferably about 5 to 60 mg/kg body weight, which can be administered in 1 to 4 daily doses, for example, depending on the route of administration, the condition of the patient, and other factors known to the skilled artisan. When the composition comprises dosage units, each unit can contain about 200 mg to 1 g of active ingredient. In some embodiments, dosage can be in the range of about 300 to 430 mg QD. The duration of treatment can in some aspects of the invention be dictated by the rate of response.

The compounds of the invention can be formulated for administration in any way for use in human or veterinary medicine and the invention therefore includes within its scope pharmaceutical compositions comprising a compound of the invention adapted for use in human or veterinary medicine.

Such compositions can be presented for use in conventional manner with or without the aid of one or more suitable carriers or excipients. The compositions of the invention include those in a form formulated for parenteral, intravenous, oral, buccal, rectal, topical, implant, ophthalmic, nasal or genitourinary use. In some preferred embodiments, oral administration can be convenient and effective. Dosage forms, e.g. oral, can include any immediate, modified, extended, controlled, or delayed release formulations, including osmotic pumps and the like.

The compounds of the invention can also be combined with other active ingredients as desired to attain combination therapy for more than one condition or biological target. For example, the compounds can be combined with other antiinfectives, or agents that increase the efficacy or other properties of antiinfectives, e.g., efflux inhibitors.

General Definitions and Descriptions

It is to be understood that any section headings and subheadings herein are for the convenience of the reader and are non-limiting. For example, the subject matter the Summary of the Invention has no special status solely as a result of its placement in that section.

Unless otherwise indicated, the language and terms used in this document are to be given their broadest reasonable interpretation as understood by the relevant skilled artisan. In addition, in descriptions and claims in which the subject matter (e.g., substitution at a given molecular position) is recited as being selected from a group of possibilities, the recitation is specifically intended to include any subset of the recited group. In the case of multiple variable positions or substituents, any combination of group or variable subsets is also contemplated.

Unless otherwise noted herein, erythromycin-based macrolide carbons are identified by the numbering convention shown below:

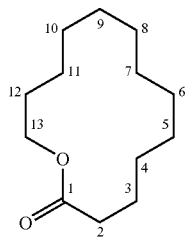

Unless otherwise apparent or indicated, the compounds of the invention and term "compound" in the claims includes any pharmaceutically acceptable salts or solvates, and any amorphous or crystal forms, or tautomers, whether or not specifically recited in context. Similarly, a recitation is open to any material or composition containing the recited compound (e.g., a composition containing a salt of a racemic mixture of compounds, tautomers, epimers, stereoisomers, impure mixtures, etc.).

The term "pharmaceutically acceptable salt(s)", as used herein, unless otherwise indicated, includes salts of acidic or basic groups which can be present in the compounds. Compounds that are basic in nature are capable of forming a wide variety of salts with various inorganic and organic acids. The acids that can be used to prepare pharmaceutically acceptable acid addition salts of such basic compounds are those that form non-toxic acid addition salts. The compounds can form, e.g., sulfates, phosphates, citrates, acetates, tosylates, succinates, besylates, mesylates, lactates, and hydrochlorides. Basic salts can be mono or dibasic.

Compounds of the present invention have asymmetric centers and therefore can exist in different enantiomeric and diastereomeric forms. The invention includes all optical isomers and stereoisomers, and mixtures thereof in all ratios, and to all pharmaceutical compositions and methods of treatment that can employ or contain them. Although specific compounds exemplified in this application can be depicted in a particular stereochemical configuration, compounds having either the opposite stereochemistry at chiral center or mixtures thereof are also envisioned. The invention further includes all E and Z configurations of the compounds. The foregoing can be present as mixtures or enriched in any component to any degree. Where stereochemistry at a position is not specified, such is intended to encompass either configuration or a mixture of any ratio.

Compounds of this invention include pharmaceutically acceptable derivatives or prodrugs thereof. A "pharmaceutically acceptable derivative or prodrug" means any pharmaceutically acceptable salt, ester, salt of an ester or other derivative of a compound that, upon administration to a recipient, is capable of providing (directly or indirectly) a compound of this invention or a metabolite or residue thereof. Particularly favored derivatives and prodrugs of the invention are those that increase the bioavailability of the compounds when such compounds are administered to a patient (e.g., by allowing an orally administered compound to be more readily absorbed into the blood), enhance delivery of the parent compound to a given biological compartment, increase solubility to allow administration by injection, alter metabolism or alter rate of excretion.

The present invention includes compounds wherein one or more hydrogen, carbon or other atoms are replaced by different isotopes thereof. Such compounds can be useful as research and diagnostic tools in metabolism pharmacokinetic studies and in binding assays.

The term "substituted" and substitutions contained in formulas of this invention refers to the replacement of one or more hydrogen radicals in a given structure with a specified radical, or, if not specified, to the replacement with any chemically feasible radical. When more than one position in a given structure can be substituted with more than one substituent selected from specified groups, the substituents can be either the same or different at every position (independently selected) unless otherwise indicated. In some cases, two positions in a given structure can be substituted with one shared substituent. It is understood that chemically impossible or highly unstable configurations are not desired or intended, as the skilled artisan would appreciate.

Unless indicated otherwise, a substituent, diradical or other group referred to herein can be bonded through any suitable position to a referenced subject molecule. For example, the term "indolyl" includes 1-indolyl, 2-indolyl, 3-indolyl, etc.

The convention for describing the carbon content of certain moieties is "$(C_a\text{-}C_b)$" or "$C_a\text{-}C_b$" meaning that the moiety can contain any number of from "a" to "b" carbon atoms.

The term "absent," as used herein to describe a structural variable (e.g., "—R— is absent") means that diradical R has no atoms, and merely represents a single bond between adjoining atoms, unless otherwise indicated.

The term "alkyl", as used herein, unless otherwise indicated, means a satd. monovalent hydrocarbon radical having cyclic ("cycloalkyl" at least three ring atoms), straight and/or branched moieties. The term "Me", as used herein, unless otherwise indicated, refers to methyl. The term "Et", as used herein, unless otherwise indicated, refers to ethyl. The term "Pr", as used herein, unless otherwise indicated, refers to propyl including isopropyl.

The term "alkenyl", as used herein, unless otherwise indicated, means straight-chain, cyclic in the case of four or more ring atoms, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like.

The term "alkynyl", as used herein, unless otherwise indicated, means straight-chain or branched-chain hydrocarbon radicals containing at least one carbon-carbon triple bond. Examples of alkynyl radicals include ethynyl, E- and Z-propynyl, isopropynyl, E- and Z-butynyl, E- and Z-isobutynyl, E- and Z-pentynyl, E, Z-hexynyl, and the like.

The term "alkoxy", as used herein, unless otherwise indicated, means —O-alkyl, —O-alkenyl, or —O-alkynyl.

The term "alkanoyl", as used herein, unless otherwise indicated, means —C(O)-alkyl, —C(O)-alkenyl, or —C(O)-alkynyl.

The term "aromatic," includes planar ring systems containing 4n+2 pi electrons, wherein n is an integer.

The term "aryl", as used herein, unless otherwise indicated, means a fully aromatic radical containing only carbon atoms in its ring system. Non-limiting examples include phenyl, napthyl, and anthracenyl.

The term "carbocyclic," as use herein, unless otherwise indicated, means a ring system containing only carbon atoms in the ring(s) without regard to aromaticity. A carbocyclic moiety can be aryl or non-aryl, wherein non-aryl includes satd. and unsatd. rings, and ring systems having aromatic and/or non-aromatic portions. Examples of carbocyclics include phenyl, naphthyl, cyclohexenyl, and indenyl. The term "4-10 membered carbocyclic" means chemically feasible monocyclic and fused bicyclic carbocyclics having from 4 to 10 ring atoms. This includes, e.g., cyclopentanyl, and the carbocyclics noted above. Similarly, "4-6 membered carbocyclic" means monocyclic carbocyclic ring systems having 4 to 6 ring carbons, and "9-10 membered carbocyclic" means fused bicyclic carbocyclic ring systems having 9 to 10 ring carbons.

The term "heteroaryl," as used herein, unless otherwise indicated, means a fully aromatic radical containing at least one heteroatom in its ring system. Heteroaryls include, e.g., 5 and 6 membered monocyclics such as pyrazinyl and pyridinyl, and 9 and 10 membered fused bicyclic ring systems, such as quinolinyl. Other examples of heteroaryl include quinolin-4-yl, 7-methoxy-quinolin-4-yl, pyridin-4-yl, pyridin-3-yl, and pyridin-2-yl. Other examples of heteroaryl include pyridinyl, imidazolyl, pyrimidinyl, pyrazolyl, triazolyl, pyrazinyl, tetrazolyl, furanyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. Examples of 5-6 membered heteroaryls include, thiophenyl, isoxazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazolyl, 1,2,5-triazinyl, 1,3,5-triazinyl, and the like.

The term "heterocyclic," as used herein, unless otherwise indicated, means any ring system containing at least one of N, O, or S, and can be heteroaryl or otherwise. Non-aryl heterocyclic groups include satd. and unsatd. systems and can include groups having only 4 atoms in their ring system. The heterocyclic groups include benzo-fused ring systems and ring systems substituted with one or more oxo moieties. Recitation of ring sulfur is understood to include the sulfide, sulfoxide or sulfone where feasible. The heterocyclic groups also include partially unsatd. or fully satd. 4-10 membered ring systems, e.g., single rings of 4 to 8 atoms in size and bicyclic ring systems, including aromatic 6-membered aryl or heteroaryl rings fused to a non-aromatic ring. Also included are 4-6 membered ring systems ("4-6 membered heterocyclic"), which include 5-6 membered heteroaryls, and include groups such as azetidinyl and piperidinyl. Heterocyclics can be heteroatom-attached where such is possible. For instance, a group derived from pyrrole can be pyrrol-1-yl (N-attached) or pyrrol-3-yl (C-attached). Other heterocyclics include imidazo(4,5-b)pyridin-3-yl and benzoimidazol-1-yl.

Examples heterocyclic groups include pyrrolidinyt, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyt, imidazolinyl, imidazolidinyt, 3-azabicyclo[3.1.0]hexanyl, 3-azabicyclo[4.1.0]heptanyt, 3H-indolyl, quinolizinyl, and the like.

Heterocyclic or carbocyclic-substituted rings include, e.g., 2-phenyl-thiazol-5-yl, 2-pyridin-3-yl-thiazol-4-yl, 4-phenyl-imidazol-1-yl, and 4-pyridin-3-yl-imidazol-1-yl.

The term "9-10 membered heterocyclic" means a fused 5,6 or 6,6 bicyclic heterocyclic ring system, which can be satd., unsatd. or aromatic. The term "9-10 membered fused bicyclic heterocyclic" also refers to a phenyl fused to one 5 or 6 membered heterocyclic group. Examples include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3 benzo[1,3]dioxolyl, 2H-chromanyl, isochromanyl, 5-oxo-2,3 dihydro-5H-[1,3]thiazolo[3,2-a]pyrimidyl, 1,3-benzothiazolyl, 1,4,5,6 tetrahydropyridaziyl, 1,2,3,4,7,8 hexahydropteridinyl, 2-thioxo-2,3,6,9-tetrahydro-1H-purin-8-yl, 3,7-dihydro-1H-purin-8-yl, 3,4-dihydropyrimidin-1-yl, 2,3-dihydro-1,4-benzodioxinyl, benzo[1,3]dioxolyl, 2H-chromenyl, chromanyl, 3,4-dihydrophthalazinyl, 2,3-ihydro-1H-indolyl, 1,3-dihydro-2H-isoindol-2-yl, 2,4,7-trioxo-1,2,3,4,7,8-hexahydropteridin-yl, thieno[3,2-d]pyrimidinyl, 4-oxo-4,7-dihydro-3H-pyrrolo[2,3-d]pyrimidin-yl, 1,3-dimethyl-6-oxo-2-thioxo-2,3,6,9-tetrahydro-1H-purinyl, 1,2-dihydroisoquinolinyl, 2-oxo-1,3-benzoxazolyl, 2,3-dihydro-5H-1,3-thiazolo-[3,2-a]pyrimidinyl, 5,6,7,8-tetrahydro-quinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4-dihydropyrimidin-1-yl imidazolylpyridyl, quinoliyl, isoquinolinyl, quinazolinyl, quinoxalinyl, naphthyridinyl, pyrazolyl[3,4]pyridine, 1,2-dihydroisoquinolinyl, cinnolinyl, 2,3-dihydro-benzo[1,4]dioxin4-yl, 4,5,6,7-tetrahydrobenzo[b]-thiophenyl-2-yl, 1,8-naphthyridinyl, 1,5-napthyridinyl, 1,6-naphthyridinyl, 1,7-napthyridinyl, 3,4-dihydro-2H-1,4-benzothiazine, 4,8-dihydroxy-quinolinyl, 1-oxo-1,2-dihydro-isoquinolinyl, 4-phenyl-[1,2,3]thiadiazolyl, and the like.

The size of ring systems can be described according to the number of ring atoms using the format "x-y membered," meaning that the ring system in questions can have from x to y atoms in the ring system. Ring systems can include fused rings. For example, the term "9-10 membered carbocyclic" refers to a 5,6 or 6,6 fused bicyclic carbocyclic ring system which can be satd., unsatd. or aromatic. It also refers to a phenyl fused to one 5 or 6 membered satd. or unsatd. carbocyclic group. Examples of such groups include naphthyl, 1,2,3,4 tetrahydronaphthyl, indenyt, indanyl, and the like. Unless stated or indicated otherwise, a described ring system is unsubstituted.

The term "halo" or "halogen", as used herein, unless otherwise indicated, includes fluoro, chloro, bromo or iodo. A preferred halo group is fluoro.

The term "protecting group" refers to a suitable chemical group that can be attached to a functional group and removed at a later stage to reveal the intact functional group. Examples of suitable protecting groups for various functional groups are described in T. W. Greene and P. G. M. Wuts, Protective Groups in Organic Synthesis, 2d Ed., John Wiley and Sons (1991 and later editions); L. Fieser and M. Fieser, Fieser and Fieser's Reagents for Organic Synthesis, John Wiley and Sons (1994); and L. Paquette, ed. Encyclopedia of Reagents for Organic Synthesis, John Wiley and Sons (1995). The term "hydroxy protecting group", as used herein, unless otherwise indicated, includes Ac, CBZ, and various hydroxy protecting groups familiar to those skilled in the art including the groups referred to in Greene.

The terms "treat," "treatment," and "treating", as used herein in the context of using the compounds of the present invention, unless otherwise indicated, means reversing, alleviating, inhibiting the progress of, or partially or completely preventing the disorder or condition to which such term applies, or one or more symptoms of such disorder or condition. "Preventing" means treating before an infection occurs.

The term "pharmaceutical composition" refers to an active compound in any form suitable for effective administration to a subject, e.g., a mixture of the compound and at least one pharmaceutically acceptable carrier.

The term "pharmaceutically acceptable carrier" refers to a material that can be administered to a subject together with a compound in a pharmaceutical composition. The carrier should not destroy the pharmacological activity of the compound and should be non-toxic when administered in doses sufficient to deliver a therapeutic amount of the compound.

| Abbreviations: Unless otherwise indicated, the following abbreviations apply throughout this document: | |
|---|---|
| Ac: | acetyl |
| AUC: | area under curve |
| Bn: | benzyl |
| Bz: | benzoyl |
| Bzh: | benzhydryl |
| BOC: | tert-butyloxycarbonyl |
| CBZ: | benzyloxycarbonyl |
| CDI: | carbonyldiimidazole |
| DAST: | (diethylamino)sulfur trifluoride |
| DBU: | 1,8-diazabicyclo[5.4.0]]undec-7-ene |
| DCM: | dichloromethane |
| DIEA: | diisopropylethylamine |
| DMAP: | dimethylaminopyridine |
| DMF: | dimethylformamide |
| DMSO: | dimethylsulfoxide |
| EDC: | 1-(3-dimethylaminopropyl)-3-ethylcarbodiimide hydrochloride |
| eq. | equivalents |

| -continued | |
|---|---|
| Abbreviations: Unless otherwise indicated, the following abbreviations apply throughout this document: | |
| EtOAc: | EtOAc |
| EtOH: | ethanol |
| HCl: | hydrochloric acid |
| HOBT: | N-hydroxybenzotriazole |
| HPLC: | high performance liquid chromatography |
| IBX: | 1-hydroxy-1,2-benziodoxol-3(1H)-one 1-oxide |
| IPA: | isopropyl alcohol |
| IPE: | diisopropyl ether |
| KHMDS: | potassium hexamethyldisilazide |
| LCMS: | liquid chromatography mass spectrometry |
| MeCN: | acetonitrile |
| MeOH: | methanol |
| MIC: | minimum inhibitory concentration |
| MS: | Mass Spectrometry. All samples herein were analyzed either by LCMS-electrospray (gradient elution using acetonitrile, water, formic acid mixtures) or probe APCI methods. |
| NaHCO$_3$: | sodium bicarbonate |
| Na$_2$SO$_4$: | sodium sulfate |
| NH$_4$OH: | concentrated aqueous ammonium hydroxide solution of 28-30% |
| NMP: | N-methylpyrrolidinone |
| NMR: | nuclear magnetic resonance spectroscopy. All samples herein were run at 400 MHz (Varian instruments) |
| PCR: | polymerase chain reaction |
| RP-HPLC: | reverse phase high performance liquid chromatography |
| RT: | RT or about RT |
| SGC: | silica gel chromatography |
| TEA: | triethylamine |
| TFA: | trifluoroacetic acid |
| THF: | tetrahydrofuran |

The invention claimed is:

1. A compound of the formula:

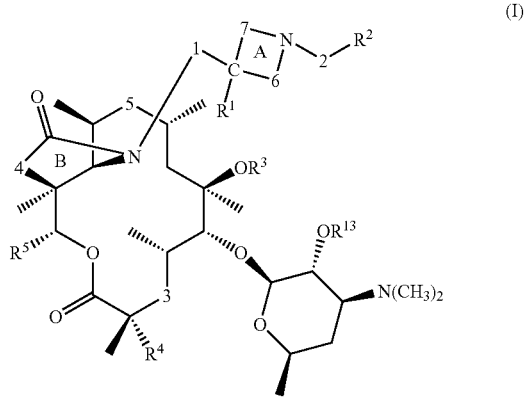

(I)

wherein:

diradical 1 is absent;

diradical 2 is >CH(R$^6$);

diradical 3 is >C(O), >CH(OC(O)R$^{14}$), >CH(OC(O)N(R$^{14}$)R$^{15}$), >CH(OC(O)OR$^{14}$), >CH(OC(O)CH(N(R$^{14}$)R$^{15}$)(CR$^a$R$^b$)$_n$Ar), >CH(OC(O)CH(N(R$^{14}$)R$^{15}$)R$^{14}$), >CH(OC(O)C(=NOR$^{14}$)(CR$^a$R$^b$)$_n$Ar), >CH(OC(O)C(=NOR$^{14}$)R$^{14}$), >CH(OC(O)(CR$^a$R$^b$)$_n$Ar), >CH(OC(O)(CR$^a$R$^b$)$_n$N(CR$^a$R$^b$)$_n$Ar)R$^{14}$), or:

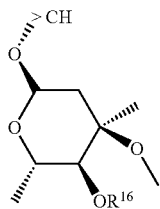

wherein n is an integer from 0 to 5;
diradical 4 is >O or >NR$^{10}$, with the proviso that when diradical 3 is not >C(O), diradical 4 is >O;
diradical 5 is >C(O);
diradical 6 is methylene;
diradical 7 is methylene;
R$^1$ is H;
R$^2$ is (a) 9-10 membered heterocyclic or carbocyclic, or (b) 4-6 membered heterocyclic or carbocyclic, wherein (b) can be substituted by 4-6 membered heterocyclic or carbocyclic; and R$^2$ can be substituted by 1 to 2 of: SO$_2$R$^{11}$, hydroxy-substituted (C$_1$-C$_3$)alkyl, (C$_1$-C$_3$)alkyl, CN, CHO, nitro, F, Cl, Br, CF$_3$, OCF$_3$, OCHF$_2$, CHF$_2$, hydroxy, (C$_1$-C$_3$)alkoxy-(C$_1$-C$_3$)alkoxy, oxo, (C$_1$-C$_3$)alkanoyl, (C$_2$-C$_6$)alkenyl, (C$_2$-C$_6$)alkynyl, or (C$_1$-C$_3$)alkoxy optionally substituted by CN;
R$^3$ is methyl;
R$^4$ is H or F, with the proviso that when diradical 3 is not >C(O), R$^4$ is H;
R$^5$ is ethyl;
R$^6$ is H or methyl;
R$^{10}$ is H or (C$_1$-C$_6$)alkyl;
each R$^{11}$ and R$^{12}$ is independently (a) H, (C$_1$-C$_{12}$)alkyl, (C$_2$-C$_{12}$)alkenyl, (C$_2$-C$_{12}$)alkynyl, any of which, except H, can have one carbon replaced by —NH—, —N(CH$_3$)—, —N(4-10 membered carbo- or heterocyclic), —O—, —S—, —S(O)$_2$—, or —S(O)$_2$—, and wherein the foregoing R$^{11}$ and R$^{12}$, together with the atom to which they are attached, can form a 3 to 8 membered ring, or (b) 9-10 membered heterocyclic, 9-10 membered carbocyclic, 4-6 membered heterocyclic, or 4-6 membered carbocyclic, wherein any of (a) and (b), except H, can independently be substituted by 1 to 3 of: F, Cl, OH, (C$_1$-C$_3$)alkoxy, (C$_1$-C$_3$)alkoxy-(C$_1$-C$_3$)alkoxy, oxo, (C$_1$-C$_3$)alkyl, halo-substituted (C$_1$-C$_3$)alkyl, or (C$_1$-C$_3$)alkoxy-(C$_1$-C$_3$)alkyl;
each R$^{14}$ and R$^{15}$ is independently H or (C$_1$-C$_{10}$)alkyl; wherein the alkyl can be substituted by 1 to 3 of the Group S substituents; independently wherein 1 to 2 carbons of the alkyl can be replaced by Group T diradicals; and independently wherein each R$^{14}$/R$^{15}$ pair can, together with the atom to which they are attached, form a 3 to 8 membered ring;
R$^{17}$ is OR$^{19}$, —C(O)(C$_1$-C$_6$ alkyl), or —C(O)(4-10 membered carbo- or heterocyclic);
R$^{19}$ is H, 4-10 membered carbo- or heterocyclic, —(C$_1$-C$_6$)alkyl, or —(C$_1$-C$_6$)alkyl-(4-10 membered carbo- or heterocyclic), any of which can have one alkyl carbon replaced by —NH—, —N(CH$_3$)—, —N(4-10 membered carbo- or heterocyclic), —O—, —S—, —S(O)—, or —(O)$_2$—; and independently which, except H, can be substituted by 1 to 3 of: F, Cl, OH, (C$_1$-C$_3$)alkoxy, (C$_1$-C$_3$)alkoxy-(C$_1$-C$_3$)alkoxy, oxo, (C$_1$-C$_3$)alkyl, halo-substituted (C$_1$-C$_3$)alkyl, or (C$_1$-C$_3$)alkoxy-(C$_1$-C$_3$)alkyl;

each R$^a$ and R$^b$ is independently H or (C$_1$-C$_6$)alkyl; wherein the alkyl can be substituted by 1 to 3 of the Group S substituents; independently wherein 1 to 2 carbons of the alkyl can be replaced by Group T diradicals; and independently wherein each R$^a$/R$^b$ pair together with the carbon to which they are attached can form a 3 to 10 membered ring;
each Ar is independently (a) 9-10 membered heterocyclic, (b) 9-10 membered carbocyclic, (c) 4-6 membered heterocyclic, or (d) 4-6 membered carbocyclic, wherein (c) or (d) can be substituted by 4-6 membered heterocyclic or 4-6 membered carbocyclic; wherein any of the foregoing Ar ring systems can be substituted by 1 to 3 of the Group S substituents;
the Group S substituents are: nitro, halo, hydroxy, CF$_3$, OCF$_3$, OCHF$_2$, CHF$_2$, CN, CHO, (C$_1$-C$_3$)alkoxy-(C$_1$-C$_3$)alkoxy, (C$_1$-C$_3$)alkoxy-(C$_1$-C$_3$)alkyl, oxo, (C$_1$-C$_{10}$)alkanoyl, (C$_1$-C$_{10}$)alkyl, (C$_2$-C$_{10}$)alkenyl, (C$_2$-C$_{10}$)alkynyl, 4-10 membered heterocyclic or carbocylic, hydroxy-substituted (C$_1$-C$_6$)alkyl, —C(O)R$^{11}$, —C(O)(4-10 membered heterocyclic), —C(O)(4-10 membered carbocyclic), —C(O)$_2$(4-10 membered heterocyclic), —O(4-10 membered carbocyclic), —O(4-10 membered heterocyclic), —C(O)$_2$(4-10 membered carbocyclic), —C(O)OR$^{11}$, —OC(O)R$^{11}$, —C(O)NR$^{11}$R$^{12}$, —OC(O)NR$^{11}$R$^{12}$, —NR$^{11}$R$^{12}$, —SO$_2$NR$^{11}$R$^{12}$, —S(O)$_p$R$^{11}$, wherein p is 0 to 2, and (C$_1$-C$_{10}$)alkoxy optionally substituted by CN; and in cases where the Group S substituent substitutes a non-aromatic carbon, Group S can also be =N—NR$^{11}$R$^{12}$, =N-(4-10 membered heterocyclic), =N-(4-10 membered carbocyclic), =N—NHC(O)R$^{11}$, =N—NHC(O)NR$^{11}$R$^{12}$, —N(R$^{11}$)SO$_2$R$^{12}$, or =N—R$^{17}$; wherein any of the heterocyclic and carbocyclic groups can be substituted by Cl, F, (C$_1$-C$_{10}$)alkyl, (C$_1$-C$_{10}$)alkoxy, oxo, or CN; and
the Group T diradicals are: —O—, —S—, —S(O)—, —S(O)$_2$—, —N((C$_1$-C$_6$)alkyl)-, —NH—, —C(O)—, —OC(O)—, —C(O)—, —N(Ar)—, and —OC(O)O—.

2. The compound of claim 1, wherein:
R$^2$ is (a) 9-10 membered heterocyclic, or (b) 5-6 membered heterocyclic or carbocyclic, wherein (b) is substituted by 5-6 membered heterocyclic or carbocyclic, and wherein R$^2$ can be substituted by 1 to 2 of: SO$_2$R$^{11}$, hydroxy-substituted (C$_1$-C$_3$)alkyl, (C$_1$-C$_3$)alkyl, CN, CHO, Br, Cl, F, CF$_3$, OCF$_3$, OCHF$_2$, CHF$_2$, nitro, hydroxy, (C$_1$-C$_3$)alkoxy-(C$_1$-C$_3$)alkoxy, oxo, (C$_1$-C$_3$)alkanoyl, (C$_2$-C$_6$)alkenyl, (C$_2$-C$_6$)alkynyl, or (C$_1$-C$_3$)alkoxy optionally substituted by CN.

3. The compound of claim 1, wherein:
R$^2$ is 9-10 membered heteroaryl containing 1 to 3 heteroatoms, which can be substituted by 1 to 2 of SO$_2$R$^{11}$, hydroxy-substituted (C$_1$-C$_3$)alkyl, (C$_1$-C$_3$)alkyl, CN, CHO, Cl, F, CF$_3$, nitro, hydroxy, (C$_1$-C$_3$)alkoxy-(C$_1$-C$_3$)alkoxy, oxo, (C$_1$-C$_3$)alkanoyl, (C$_2$-C$_6$)alkenyl, (C$_2$-C$_6$)alkynyl, or (C$_1$-C$_3$)alkoxy optionally substituted by CN.

4. The compound of claim 1, wherein:
R$^2$ is quinolinyl, isoquinolinyl, quinazolinyl, 4H-quinolizinyl, quinoxalinyl, 1,5-naphthyridinyl, 1,6-naphthyridinyl, 1,7-naphthyridinyl, 1,8-naphthyridinyl, cinnolinyl, phthalazinyl, pyrido[2,3-b]pyrazinyl, pyrido[3,4-b]pyrazinyl, pyrido[3,2-b]pyrazinyl, pyrido[2,3-d]pyrimidinyl, pyrido[2,3-c]pyridazinyl, benzimidazolyl, indolyl, indazolyl, 1H-benzotriazolyl, 1H-pyrrolo[3,2-b]pyridinyl, 1H-pyrrolo[3,2-c]pyridinyl, 1H-pyrrolo[2,3-c]pyridinyl, 1H-pyrrolo[2,3-b]pyridinyl, 1H-imidazo[4,5-b]pyridinyl, 3H-imidazo[4,5-b]pyridinyl, 1H-imidazo[4,5-c]pyridinyl, 1H-[1,2,3]triazolo[4,5-b]

pyridinyl, 1H-[1,2,3]triazolo[4,5-c]pyridinyl, pyrazolo[1,5-a]pyridinyl, imidazo[1,5-a]pyridinyl, imidazo[1,2-a]pyridinyl, pyrrolo[1,2-a]pyridinyl, pyrrolo[1,2-a]pyrazinyl, pyrrolo[1,2-c]pyrimidinyl, pyrrolo[1,2-b]pyridazinyl, pyrrolo[1,5-a]pyrimidinyl, imidazo[1,5-a]pyrimidinyl, imidazo[1,2-a]pyrimidinyl, benzo[d][1.3]dioxolyl, or 1H-inden-2(3H)-sulfonyl, any of which can be substituted by 1 to 2 of $(C_1-C_3)$alkyl, CN, CHO, Cl, F, $CF_3$, nitro, hydroxy, oxo, $(C_1-C_3)$alkanoyl, $(C_2-C_3)$alkenyl, $(C_2-C_3)$alkynyl, or $(C_1-C_3)$alkoxy.

5. A compound of the formula

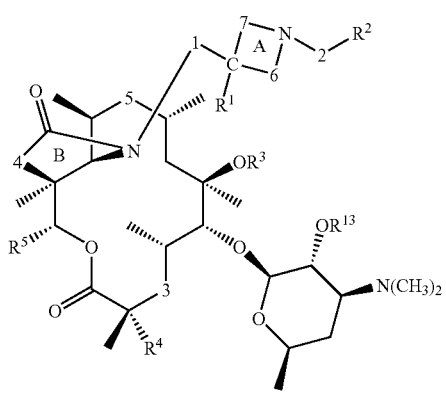

(I)

wherein:
diradical 1 is absent, >$CH_2$ or >$C(CH_3)H$;
diradical 2 is >$SO_2$;
diradical 3 is >C(O), >CH(OC(O)$R^{14}$), >CH(OC(O)N($R^{14}$)$R^{15}$), >CH(OC(O)O$R^{14}$), >CH(OC(O)CH(N($R^{14}$)$R^{15}$)(C$R^aR^b$)$_n$Ar), >CH(OC(O)CH(N($R^{14}$)$R^{15}$)$R^{14}$), >CH(OC(O)C(=NO$R^{14}$)(C$R^aR^b$)$_n$Ar), >CH(OC(O)C(=NO$R^{14}$)$R^{14}$), >CH(OC(O)(C$R^aR^b$)$_n$Ar), >CH(OC(O)(C$R^aR^b$)$_n$N(C$R^aR^b$)$_n$Ar)$R^{14}$), or:

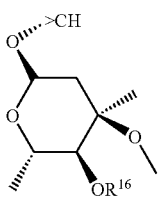

wherein n is an integer from 0 to 5;
diradical 4 is >O or >N$R^{10}$, with the proviso that when diradical 3 is not >C(O), diradical 4 is >O;
diradical 5 is >C(O);
diradical 6 is —(C($R^c$)($R^d$))$_x$—, wherein x is an integer from 0 to 5;
diradical 7 is —(C($R^c$)($R^e$))$_y$—, wherein y is an integer from 0 to 5; with the proviso that the sum of x+y is from 1 to 5;
$R^1$ is H, OH, F, or $(C_1-C_6)$alkyl, with the proviso that when diradical 1 is absent, $R^1$ is H;
$R^2$ is H or Ar;
$R^3$ is methyl;
$R^4$ is H or F, with the proviso that when diradical 3 is not >C(O), $R^4$ is H;
$R^5$ is ethyl;
$R^{20}$ is independently $(C_1-C_6)$alkyl;

$R^{10}$ is H or $(C_1-C_6)$alkyl;
each $R^{11}$ and $R^{12}$ is independently (a) H, $(C_1-C_{12})$alkyl, $(C_2-C_{12})$alkenyl, $(C_2-C_{12})$alkynyl, any of which, except H, can have one carbon replaced by —NH—, —N($CH_3$)—, —N(4-10 membered carbo- or heterocyclic), —O—, —S—, —S(O)—, or —S(O)$_2$—, and wherein the foregoing $R^{11}$ and $R^{12}$, together with the atom to which they are attached, can form a 3 to 8 membered ring, or (b) 9-10 membered heterocyclic, 9-10 membered carbocyclic, 4-6 membered heterocyclic, or 4-6 membered carbocyclic, wherein any of (a) and (b), except H, can independently be substituted by 1 to 3 of: F, Cl, OH, $(C_1-C_3)$alkoxy, $(C_1-C_3)$alkoxy-$(C_1-C_3)$alkoxy, oxo, $(C_1-C_3)$alkyl, halo-substituted $(C_1-C_3)$alkyl, or $(C_1-C_3)$alkoxy-$(C_1-C_3)$alkyl;
each $R^{14}$ and $R^{15}$ is independently H or $(C_1-C_{10})$alkyl; wherein the alkyl can be substituted by 1 to 3 of the Group S substituents; independently wherein 1 to 2 carbons of the alkyl can be replaced by Group T diradicals; and independently wherein each $R^{14}/R^{15}$ pair can, together with the atom to which they are attached, form a 3 to 8 membered ring;
$R^{17}$ is O$R^{19}$, —C(O)($C_1-C_6$ alkyl), or —C(O)(4-10 membered carbo- or heterocyclic);
$R^{19}$ is H, 4-10 membered carbo- or heterocyclic, —($C_1-C_6$)alkyl, or —($C_1-C_6$)alkyl-(4-10 membered carbo- or heterocyclic), any of which can have one alkyl carbon replaced by —NH—, —N($CH_3$)—, —N(4-10 membered carbo- or heterocyclic), —O—, —S—, —S(O)—, or —S(O)$_2$—; and independently which, except H, can be substituted by 1 to 3 of: F, Cl, OH, $(C_1-C_3)$alkoxy, $(C_1-C_3)$alkoxy-$(C_1-C_3)$alkoxy, oxo, $(C_1-C_3)$alkyl, halo-substituted $(C_1-C_3)$alkyl, or $(C_1-C_3)$alkyl;
each $R^a$ and $R^b$ is independently H or $(C_1-C_6)$alkyl; wherein the alkyl can be substituted by 1 to 3 of the Group S substituents; independently wherein 1 to 2 carbons of the alkyl can be replaced by Group T diradicals; and independently wherein each $R^a/R^b$ pair together with the carbon to which they are attached can form a 3 to 10 membered ring;
each $R^c$ group is independently H, F, Cl, $(C_1-C_3)$alkyl, hydroxy, $(C_1-C_3)$alkoxy, or CN, with the proviso that when x of diradical 6 is from 2 to 5, only one $R^c$ group can be other than H;
each $R^d$ and $R^e$ group is H, except that up to one $R^d$ group together with one $R^e$ group can form a bridging single carbon-carbon bond or bridging $(C_1-C_3)$alkyl diradical such that Ring A is bicyclic;
each Ar is independently (a) 9-10 membered heterocyclic, (b) 9-10 membered carbocyclic, (c) 4-6 membered heterocyclic, or (d) 4-6 membered carbocyclic, wherein (c) or (d) can be substituted by 4-6 membered heterocyclic or 4-6 membered carbocyclic; wherein any of the foregoing Ar ring systems can be substituted by 1 to 3 of the Group S substituents;
the Group S substituents are: nitro, halo, hydroxy, $CF_3$, $OCF_3$, $OCHF_2$, $CHF_2$, CN, CHO, $(C_1-C_3)$alkoxy-$(C_1-C_3)$alkoxy, $(C_1-C_3)$alkoxy-$(C_1-C_3)$alkyl, oxo, $(C_1-C_{10})$alkanoyl, $(C_1-C_{10})$alkyl, $(C_2-C_{10})$alkenyl, $(C_2-C_{10})$alkynyl, 4-10 membered heterocyclic or carbocyclic, hydroxy-substituted $(C_1-C_6)$alkyl, —C(O)$R^{11}$, —C(O)(4-10 membered heterocyclic), —C(O)(4-10 membered carbocyclic), —C(O)$_2$(4-10 membered heterocyclic), —O(4-10 membered carbocyclic), —O(4-10 membered heterocyclic), —C(O)$_2$(4-10 membered carbocyclic), —C(O)O$R^{11}$, —OC(O)$R^{11}$, —C(O)N$R^{11}R^{12}$, —OC(O)N$R^{11}R^{12}$, —SO$_2$N$R^{11}R^{12}$, —S(O)$_p R^{11}$, wherein p is 0 to 2, and ($C_1$-$C_{10}$)alkoxy optionally substituted by CN; and in cases where the Group S substituent substitutes a non-aromatic carbon, Group S can also be =N—$NR^{11}R^{12}$, =N—(4-10 membered heterocyclic), =N—(4-10 membered carbocyclic), =N—NHC(O) $R^{11}$, =N—NHC(O)$NR^{11}R^{12}$, —N($R^{11}$)$SO_2R^{12}$, or =NR—$R^{17}$; wherein any of the heterocyclic and carbocyclic groups can be substituted by Cl, F, ($C_1$-$C_{10}$)alkyl, ($C_1$-$C_{10}$)alkoxy, oxo, or CN; and the Group T diradicals are: —O—, —S—, —S(O)—, —S(O)$_2$—, —N(((C$_1$-C$_6$))alkyl)-, —NH—, —C(O)—, —OC(O)—, —C(O)O—, —N(Ar)—, and —OC(O)O—.

6. A compound according to claim 5, which has an in vitro MIC of about 8 μg/mL or less against *S. pyogenes* 1079.

7. The compound of claim 5, wherein:
diradical 1 is absent or is methylene;
diradical 6 is —(CH$_2$)$_x$—, wherein x is from 0 to 3;
diradical 7 is —(CH$_2$)$_y$—, wherein y is from 0 to 3; and wherein the sum of x+y is 2 to 3; and
$R^1$ is H.

8. The compound of claim 7, wherein:
diradical 1 is absent;
$R^2$ is (a) 9-10 membered heterocyclic, or carbocyclic, or (b) 4-6 membered heterocyclic or carbocyclic, wherein (b) can be substituted by 4-6 membered heterocyclic or carbocyclic; and $R^2$ can be substituted by 1 to 2 of $SO_2$, hydroxy-substituted ($C_1$-$C_3$)alkyl, ($C_1$-$C_3$)alkyl, CN, CHO, Br, Cl, F, $CF_3$, $OCF_3$, $OCHF_2$, $CHF_2$, nitro, hydroxy, ($C_1$-$C_3$)alkoxy-($C_1$-$C_3$)alkoxy, oxo, ($C_1$-$C_3$)alkanoyl, ($C_2$-$C_6$)alkenyl, ($C_2$-$C_6$)alkynyl, or ($C_1$-$C_3$)alkoxy optionally substituted by CN.

9. The compound of claim 8, wherein diradicals 6 and 7 are both methylene.

10. The compound of claim 9, wherein:
$R^2$ is (a) 9-10 membered heterocyclic, or (b) 5-6 membered heterocyclic or carbocyclic, wherein (b) is substituted by 5-6 membered heterocyclic or carbocyclic, and wherein $R^2$ can be substituted by 1 to 2 of $SO_2$, hydroxy-substituted ($C_1$-$C_3$)alkyl, ($C_1$-$C_3$)alkyl, CN, CHO, Br, Cl, F, $CF_3$, $OCF_3$, $OCHF_2$, $CHF_2$, nitro, hydroxy, ($C_1$-$C_3$)alkoxy-($C_1$-$C_3$)alkoxy, oxo, ($C_1$-$C_3$)alkanoyl, ($C_2$-$C_6$)alkenyl, ($C_2$-$C_6$)alkynyl, or ($C_1$-$C_3$)alkoxy optionally substituted by CN.

11. The compound of claim 9, wherein:
$R^2$ is 9-10 membered heteroaryl containing 1 to 3 heteroatoms, which can be substituted by 1 to 2 of $SO_2R^{11}$, hydroxy-substituted ($C_1$-$C_3$)alkyl, ($C_1$-$C_3$)alkyl, CN, CHO, Cl, F, $CF_3$, nitro, hydroxy, ($C_1$-$C_3$)alkoxy-($C_1$-$C_3$)alkoxy, oxo, ($C_1$-$C_3$)alkanoyl, ($C_2$-$C_6$)alkenyl, ($C_2$-$C_6$)alkynyl, or ($C_1$-$C_3$)alkoxy optionally substituted by CN.

12. The compound of claim 9 wherein:
$R^2$ is quinolinyl, isoquinolinyl, cinnolinyl, quinoxalinyl, quinazolinyl, 1,8-naphthyridinyl, 1,7-naphthyridinyl, 1,6-naphthyridinyl, 1,5-naphthyridinyl, phthalazinyl, benzo[d]thiazolyl, 2,1,3-benzothiadiazol-2,2-dioxidyl, benzo[c][1,2,5]oxadiazolyl, benzo[d]isooxazolyl, benzo[d]oxazolyl, benzo[d]isothiazolyl, imidazo[2,1-b]thiazolyl, 5-phenylthiazolyl, 2-phenyl-1,3,4-thiadiazolyl, 4-phenylthiazolyl, 4-phenyl-1,2,3-thiadiazolyl, 5-phenyloxazolyl, 2-phenyl-1,3,4-oxadiazolyl, 5-phenyl-1,2,4-oxadiazolyl, 3-phenyl-1,2,4-oxadiazolyl, 1-phenyl-1H-pyrazolyl, 4-phenyl-4H-1,2,4-triazolyl, 1-phenyl-1H-1,2,4-triazolyl, 2-(1H-1,2,4-triazol-1-yl)pyridinyl, 2-(1H-pyrazol-1-yl)pyridinyl, 2-(4H-1,2,4-triazol-4-yl)pyridinyl, 1H-indazolyl, 1,3-dihydrobenzo-2,2-dioxo[c]thiophenyl, 4-(2-oxooxazolidin-3-yl) phenyl, or 2H-indazolyl, any of which can be substituted by 1 to 2 of ($C_1$-$C_3$)alkyl, CN, CHO, Cl, F, $CF_3$, nitro, hydroxy, oxo, ($C_1$-$C_3$)alkanoyl, ($C_2$-$C_3$)alkenyl, ($C_2$-$C_3$)alkynyl, or ($C_1$-$C_3$)alkoxy.

13. A compound of the formula (I)

wherein:
diradical 1 is absent or >$CH_2$;
diradical 2 is >C(O), —C(O)N($R^6$)—, or —C(O)O—;
diradical 3 is >C(O);
diradical 4 is >O;
diradical 5 is >C(O);
diradical 6 is —(CH$_2$)$_x$—, wherein x is from 0 to 4;
diradical 7 is —(CH$_2$)$_y$—, wherein y is from 0 to 4; with the proviso that the sum of x+y is 2 to 4;
$R^1$ is H, OH, or methyl;
$R^2$ is Ar;
$R^3$ is methyl;
$R^4$ is H or F, with the proviso that when diradical 3 is not >C(O), $R^4$ H;
$R^5$ is ethyl;
$R^{20}$ is ($C_1$-$C_6$)alkyl;
$R^6$ is H or methyl; and
each Ar is independently (a) 9-10 membered heterocyclic, (b) 9-10 membered carbocyclic, (c) 4-6 membered heterocyclic, or (d) 4-6 membered carbocyclic, wherein (c) or (d) can be substituted by 4-6 membered heterocyclic or 4-6 membered carbocyclic; wherein the foregoing ring system can be substituted by 1 to 2 of: $CF_3$, $OCF_3$, $OCHF_2$, $CHF_2$, nitro, Cl, F, Br, hydroxy, ($C_1$-$C_6$)alkyl, CN, CHO, ($C_1$-$C_3$)alkoxy-($C_1$-$C_3$)alkoxy, ($C_1$-$C_3$)alkoxy-($C_1$-$C_3$)alkyl, oxo, ($C_1$-$C_6$)alkanoyl, ($C_2$-$C_6$)alkenyl, ($C_2$-$C_6$)alkynyl, hydroxy-substituted ($C_1$-$C_6$)alkyl, —C(O)$R^{11}$, —OC(O)$R^{11}$, —C(O)O$R^{11}$, C(O)N($R^{11}$)$R^{12}$—, —OC(O)N($R^{11}$)$R^{12}$—, —NHC(O)$R^{11}$, —N($R^{11}$)$R^{12}$, —N($R^{11}$)$SO_2R^{12}$, —$SO_2$N($R^{11}$)$R^{12}$, —S(O)$_p$$R^{11}$, wherein p is 0 to 2, or ($C_1$-$C_6$)alkoxy optionally substituted by CN.

14. The compound of 13, wherein:
diradical 1 is absent or is methyl;
diradical 6 is —(CH$_2$)$_x$—, wherein x is from 0 to 3;
diradical 7 is —(CH$_2$)$_y$—, wherein y is from 0 to 3; wherein the sum of x+y is 2 to 3; and
$R^6$ is H or methyl.

15. A compound according to claim 13, which has an in vitro MIC of about 8 μg/mL or less against *S. pyogenes* 1079.

16. The compound of claim 14, wherein:
diradical 1 is absent;
$R^2$ is (a) 9-10 membered heterocyclic, or (b) 5-6 membered heterocyclic or carbocyclic, wherein (b) is substituted by 5-6 membered heterocyclic or carbocyclic, and wherein $R^2$ can be substituted by 1 to 2 of $SO_2$, hydroxy-substituted $(C_1-C_3)$alkyl, $(C_1-C_3)$alkyl, CN, CHO, Br, Cl, F, $CF_3$, $OCF_3$, $OCHF_2$, $CHF_2$, nitro, hydroxy, $(C_1-C_3)$ alkoxy-$(C_1-C_3)$alkoxy, oxo, $(C_1-C_3)$alkanoyl, $(C_2-C_6)$ alkenyl, $(C_2-C_6)$alkynyl, or $(C_1-C_3)$alkoxy optionally substituted by CN.

17. A compound according to claim 1, which has an in vitro MIC of 4 μg/mL or less against *S. pyogenes* that is resistant to clarithromycin by an erm B mechanism and an in vitro MIC of about 0.5 μg/mL or less against *S. pneumo* that is resistant to clarithromycin by an efflux mechanism.

18. 3-descladinosyl-11,12-dideoxy-6-O-methyl-3-oxo-12,11-(oxycarbonyl-(1-(1R-(1,8-naphthyridin-4-yl)-ethyl)-azetidin-3-yl)-imino)-erythromycin A.

19. A compound selected from:
3-descladinosyl-11,12-dideoxy-6-O-methyl-3-oxo-12,11-(oxycarbonyl-(1-((quinolin-5-yl)-methyl)-azetidin-3-yl)-imino)-erythromycin A,
3-descladinosyl-11,12-dideoxy-6-O-methyl-3-oxo-12,11-(oxycarbonyl-(1-((quinolin-4-yl)-methyl)-azetidin-3-yl)-imino)-erythromycin A,
3-descladinosyl11,12-dideoxy-6-O-methyl-3-oxo-12,11-(oxycarbonyl-(1-((1,8-naphthyridin-4-yl)-methyl)-azetidin-3-yl)-imino)-erythromycin A,
3-descladinosyl-11,12-dideoxy-6-O-methyl-3-oxo-12,11-(oxycarbonyl-(1-((1,5-naphthyridin-4-yl)-methyl)-azetidin-3-yl)-imino)-erythromycin A,
3-descladinosyl-11,12-dideoxy-2-fluoro-6-O-methyl-3-oxo-12,11-(oxycarbonyl-(1-(1R-(1,8-naphthyridin-4-yl)-ethyl)-azetidin-3-yl)-imino)-erythromycin A,
3-descladinosyl-11,12-dideoxy-6-O-methyl-3-oxo-12,11-(oxycarbonyl-(1-(1-(quinolin-4-yl)-butyl)-azetidin-3-yl)-imino)-erythromycin A,
3-descladinosyl-11,12-dideoxy-6-O-methyl-3-oxo-12,11-(oxycarbonyl-(1-(8-methoxyquinoline-5-methyl)-azetidin-3-yl)-imino)-erythromycin A,
3-descladinosyl-11,12-dideoxy-6-O-methyl-3-oxo-12,11-(oxycarbonyl-(1-(3-methoxyquinoline-4-methyl)-azetidin-3-yl)-imino)-erythromycin A,
3-descladinosyl 11,12-dideoxy-6-O-methyl-3-oxo-12,11-(oxycarbonyl-(1-(3-methoxy-1,8-naphthyridine-4-methyl)-azetidin-3-yl)-imino)-erythromycin A,
3-descladinosyl-11,12-dideoxy-6-O-methyl-3-oxo-12,11-(oxycarbonyl-(1-(3-bromo-1,8-naphthyridine-4-methyl)-azetidin-3-yl)-imino)-erythromycin A,
3-descladinosyl-11,12-dideoxy-6-O-methyl-3-oxo-12,11-(oxycarbonyl-(1-(3-chloro-1,8-naphthyridine-4-methyl)-azetidin-3-yl)-imino)-erythromycin A,
3-descladinosyl-11,12-dideoxy-6-O-methyl-3-oxo-12,11-(oxycarbonyl-(1-(3-ethoxy-1,8-naphthyridine-4-methyl)-azetidin-3-yl)-imino)-erythromycin A,
3-descladinosyl-11,12-dideoxy-6-O-methyl-3-oxo-12,11-(oxycarbonyl-(1-(4-(oxazol-5-yl)-benzenesulfonyl)-azetidin-3-yl)-imino)-erythromycin A,
3-descladinosyl-11,12-dideoxy-6-O-methyl-3-oxo-12,11-(oxycarbonyl-(1-(3-(1H-pyrazol-3-yl)benzenesulfonyl)-azetidin-3-yl)-imino)-erythromycin A,
3-descladinosyl-11,12-dideoxy-6-O-methyl-3-oxo-12,11-(oxycarbonyl-(1-(3-(1,2,3-thiadiazol-4-yl)benzenesulfonyl)-azetidin-3-yl)-imino)-erythromycin A,
3-descladinosyl-11,12-dideoxy-6-O-methyl-3-oxo-12,11-(oxycarbonyl-(1-(quinoxaline-5-sulfonyl)-azetidin-3-yl)-imino)-erythromycin A,
3-descladinosyl-11,12-dideoxy-6-O-methyl-3-oxo-12,11-(oxycarbonyl-(1-(1,3dihydrobenzo-2,2-dioxo-[c]thiophene-5-sulfonyl)-azetidin-3-yl)-imino)-erythromycin A,
3-descladinosyl-11,12-dideoxy-6-O-methyl-3-oxo-12,11-(oxycarbonyl-(1-(8-methoxyquinoline-5-sulfonyl)-azetidin-3-yl)-imino)-erythromycin A,
3-descladinosyl-11,12-dideoxy-6-O-methyl-3-oxo-12,11-(oxycarbonyl-(1-(8-ethoxyquinoline-5-sulfonyl)-azetidin-3-yl)-imino)-erythromycin A,
3-descladinosyl-11,12-dideoxy-2-fluoro-6-O-methyl-3-oxo-12,11-(oxycarbonyl-(1-(3-cyano-4-ethoxybenzene-1-sulfonyl)-azetidin-3-yl)-imino)-erythromycin A,
3-descladinosyl-11,12-dideoxy-6-O-methyl-3-oxo-12,11-(oxycarbonyl-(1-(4-ethoxy-3-methoxybenzene-1-sulfonyl)-azetidin-3-yl)-imino)-erythromycin A, or
3-descladinosyl-11,12-dideoxy-6-O-methyl-3-oxo-12,11-(oxycarbonyl-(1-(8-methoxyquinoxaline-5-sulfonyl)-azetidin-3-yl)-imino)-erythromycin A.

20. A pharmaceutical composition comprising the compound of claim 1, which is formulated with or without one or more excipients.

21. A pharmaceutical composition comprising the compound of claim 18, which is formulated with or without one or more excipients.

22. A method of treating bacterial infection comprising administering a therapeutically effective amount of the compound of claim 1 to a mammalian subject in need thereof.

23. A method of treating protozoal infection comprising administering a therapeutically effective amount of the compound of claim 1 to a mammalian subject in need thereof.

24. A method of treating bacterial infection comprising administering a therapeutically effective amount of the compound of claim 18 to a mammalian subject in need thereof.

25. A method of treating bacterial infection that is resistant to clarithromycin comprising administering a therapeutically effective amount of the compound of claim 1 to a mammalian subject in need thereof.

26. A method of treating infection by at least one of *S. pyogenes* or *S. pneumo* that is resistant to clarithromycin comprising administering a therapeutically effective amount of the compound of claim 1 to a mammalian subject in need thereof.

27. A method of treating infection caused by at least one of *S. pyogenes, S. pneumo,* or *H. influenzae,* comprising administering a therapeutically effective amount of the compound of claim 1 to a mammalian subject in need thereof.

28. A method of treating infection caused by at least one of *S. pyogenes, S. pneumo,* or *H. influenzae,* comprising administering a therapeutically effective amount of the compound of claim 18 to a mammalian subject in need thereof.

29. A compound selected from 3-descladinosyl-11,12-dideoxy-6-O-methyl-3-oxo-12,11-(oxycarbonyl-(azetidin-3-yl)-imino)-erythromycin A or 3-descladinosyl-11,12-dideoxy-6-O-methyl-3-oxo-12,11-(oxycarbonyl-((1-benzhydryl)-azetidin-3-yl)-imino)-erythromycin A.

30. A compound selected from 1-[1,8]naphthyridin-4-yl-ethanol or 1-[1,8]naphthyridin-4-yl-ethanone.

* * * * *